US012453766B2

(12) United States Patent
Ciaramella et al.

(10) Patent No.: US 12,453,766 B2
(45) Date of Patent: *Oct. 28, 2025

(54) RSV RNA VACCINES

(71) Applicant: ModernaTX, Inc., Cambridge, MA (US)

(72) Inventors: Giuseppe Ciaramella, Sudbury, MA (US); Kapil Bahl, Medford, MA (US); Amy Espeseth, Chalfont, PA (US); Andrew J. Bett, Lansdale, PA (US); Pedro Cejas, Oreland, PA (US); Lan Zhang, Chalfont, PA (US); Christine Shaw, Reading, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/418,127

(22) Filed: Jan. 19, 2024

(65) Prior Publication Data

US 2024/0299525 A1 Sep. 12, 2024

Related U.S. Application Data

(63) Continuation of application No. 16/965,589, filed as application No. PCT/US2019/015412 on Jan. 28, 2019, now Pat. No. 11,911,453.

(60) Provisional application No. 62/623,240, filed on Jan. 29, 2018.

(51) Int. Cl.

| | |
|---|---|
| ***A61K 39/12*** | (2006.01) |
| ***A61K 9/00*** | (2006.01) |
| ***A61K 39/00*** | (2006.01) |

(52) U.S. Cl.

CPC ............ *A61K 39/12* (2013.01); *A61K 9/0019* (2013.01); *A61K 2039/53* (2013.01); *A61K 2039/55555* (2013.01)

(58) Field of Classification Search

None

See application file for complete search history.

(56) References Cited

U.S. PATENT DOCUMENTS

| | | | |
|---|---|---|---|
| 6,040,427 | A | 3/2000 | Locht et al. |
| 6,500,419 | B1 | 12/2002 | Hone et al. |
| 6,514,948 | B1 | 2/2003 | Raz et al. |
| 6,610,044 | B2 | 8/2003 | Mathiesen |
| 7,001,890 | B1 | 2/2006 | Wagner et al. |

(Continued)

FOREIGN PATENT DOCUMENTS

| | | | |
|---|---|---|---|
| AU | 652831 | B2 | 9/1994 |
| AU | 2015210364 | A1 | 3/2017 |

(Continued)

OTHER PUBLICATIONS

Geneseq database accession No. BCI53556 Jan. 2016 sequence alignment with SEQ ID No. 5.*

(Continued)

*Primary Examiner* — Shanon A. Foley

(74) *Attorney, Agent, or Firm* — Wolf, Greenfield & Sacks, P.C.

(57) ABSTRACT

The disclosure relates to respiratory syncytial virus (RSV) ribonucleic acid (RNA) vaccines as well as methods of using the vaccines and compositions comprising the vaccines. The vaccine can be formulated in a lipid nanoparticle.

14 Claims, 9 Drawing Sheets

Specification includes a Sequence Listing.

(56) References Cited

U.S. PATENT DOCUMENTS 8,569,256 B2 10/2013 Heyes et al.
8,609,142 B2 12/2013 Troiano et al.
8,613,954 B2 12/2013 Zale et al.
8,617,608 B2 12/2013 Zale et al.
8,691,966 B2 4/2014 Kariko et al.
8,710,200 B2 4/2014 Schrum et al.
8,734,832 B2 5/2014 O'Hagan et al.
8,734,853 B2 5/2014 Sood et al.
8,754,062 B2 6/2014 De Fougerolles et al.
8,822,663 B2 9/2014 Schrum et al.
8,980,864 B2 3/2015 Hoge et al.
8,999,380 B2 4/2015 Bancel et al.
9,221,891 B2 12/2015 Bancel et al.
9,283,287 B2 3/2016 Bancel et al.
9,303,079 B2 4/2016 Bancel et al.
9,464,124 B2 10/2016 Bancel et al.
9,512,456 B2 12/2016 Wang et al.
9,533,047 B2 1/2017 de Fougerolles et al.
9,572,896 B2 2/2017 Bancel et al.
9,597,380 B2 3/2017 Chakraborty et al.
9,675,668 B2 6/2017 Bancel et al.
9,803,199 B2 10/2017 Koizumi et al.
9,868,691 B2 1/2018 Benenato et al.
9,872,900 B2 1/2018 Ciaramella et al.
10,023,626 B2 7/2018 Bolen et al.
10,064,934 B2 9/2018 Ciaramella et al.
10,064,935 B2 9/2018 Ciaramella et al.
10,124,055 B2 11/2018 Ciaramella et al.
10,207,010 B2 2/2019 Besin et al.
10,232,055 B2 3/2019 Kariko et al.
10,273,269 B2 4/2019 Ciaramella
10,286,086 B2 5/2019 Roy et al.
10,323,076 B2 6/2019 Ellsworth et al.
10,385,088 B2 8/2019 Fraley et al.
10,449,244 B2 10/2019 Ciaramella et al.
10,465,190 B1 11/2019 Chen et al.
10,493,143 B2 12/2019 Ciaramella et al.
10,526,629 B2 1/2020 Rabideau et al.
10,653,712 B2 5/2020 Hoge
10,653,767 B2 5/2020 Ciaramella et al.
10,695,419 B2 6/2020 Ciaramella et al.
10,857,105 B2 12/2020 Benenato et al.
10,925,958 B2 2/2021 Ciaramella
11,027,025 B2 6/2021 Hoge et al.
11,045,540 B2 6/2021 Ciaramella
11,103,578 B2 8/2021 Ciaramella et al.
11,266,735 B2 3/2022 Kallen et al.
11,351,242 B1 6/2022 Lori et al.
11,384,352 B2 7/2022 Miracco
11,406,703 B2 8/2022 Kramarczyk et al.
11,464,848 B2 * 10/2022 Ciaramella .......... A61K 9/0019
11,485,960 B2 11/2022 Dousis et al.
11,497,807 B2 11/2022 Ciaramella et al.
11,564,893 B2 1/2023 Smith
11,566,051 B2 1/2023 Zhang et al.
11,576,961 B2 2/2023 Ciaramella et al.
11,638,693 B2 5/2023 Geall
11,638,694 B2 5/2023 Geall
11,643,441 B1 5/2023 Ciaramella et al.
11,666,534 B2 6/2023 Geall
11,696,946 B2 7/2023 Ciaramella
11,752,206 B2 9/2023 Ciaramella et al.
11,766,401 B2 9/2023 Geall
11,786,467 B2 10/2023 Geall
11,786,607 B2 10/2023 Hoge et al.
11,851,694 B1 12/2023 Mauger et al.
11,866,696 B2 1/2024 Issa et al.
11,872,278 B2 1/2024 Ciaramella et al.
11,905,525 B2 2/2024 Brito et al.
11,911,453 B2 * 2/2024 Ciaramella ........ A61K 31/7115
11,912,982 B2 2/2024 Issa et al.
2001/0001066 A1 5/2001 Cezayirli et al.
2003/0032615 A1 2/2003 Felgner et al.
2005/0032730 A1 2/2005 Von Der Mulbe et al.
2005/0059624 A1 3/2005 Hoerr et al.
2005/0250723 A1 11/2005 Hoerr et al.
2005/0287540 A1 12/2005 Murphy et al.
2006/0172003 A1 8/2006 Meers et al.
2006/0172966 A1 8/2006 Lipford et al.
2007/0280929 A1 12/2007 Hoerr et al.
2010/0068226 A1 3/2010 Taylor et al.
2010/0130588 A1 5/2010 Yaworski et al.
2010/0189729 A1 7/2010 Hoerr et al.
2010/0203076 A1 8/2010 Fotin-Mleczek et al.
2010/0239608 A1 9/2010 Von Der Mulbe et al.
2010/0303851 A1 12/2010 Hoerr et al.
2011/0250225 A1 10/2011 Fotin-Mleczek et al.
2011/0269950 A1 11/2011 Von Der Mulbe et al.
2011/0311472 A1 12/2011 Hoerr et al.
2012/0101148 A1 4/2012 Aking et al.
2012/0189700 A1 7/2012 Aguilar et al.
2012/0258046 A1 10/2012 Mutske
2012/0263648 A1 10/2012 Shapiro et al.
2013/0102034 A1 4/2013 Schrum et al.
2013/0121988 A1 5/2013 Hoerr et al.
2013/0142818 A1 6/2013 Baumhof et al.
2013/0171241 A1 7/2013 Geall
2013/0183355 A1 7/2013 Jain et al.
2013/0189351 A1 7/2013 Geall
2013/0195867 A1 8/2013 Hoerr et al.
2013/0195968 A1 8/2013 Geall et al.
2013/0195969 A1 8/2013 Geall et al.
2013/0202684 A1 8/2013 Geall et al.
2013/0236533 A1 9/2013 Von Andrian et al.
2013/0236974 A1 9/2013 De Fougerolles
2013/0245103 A1 9/2013 de Fougerolles et al.
2013/0245107 A1 9/2013 De Fougerolles et al.
2013/0259923 A1 10/2013 Bancel et al.
2013/0266640 A1 10/2013 De Fougerolles et al.
2013/0295043 A1 11/2013 Kallen et al.
2013/0336998 A1 12/2013 Kallen et al.
2014/0065228 A1 3/2014 Yarowoski et al.
2014/0134201 A1 5/2014 Tureci et al.
2014/0147432 A1 5/2014 Bancel et al.
2014/0148502 A1 5/2014 Bancel et al.
2014/0193482 A1 7/2014 Bancel et al.
2014/0206752 A1 7/2014 Afeyan et al.
2014/0248314 A1 9/2014 Swanson et al.
2014/0271699 A1 9/2014 Kwong et al.
2014/0271829 A1 9/2014 Lilja et al.
2014/0308304 A1 10/2014 Manoharan et al.
2014/0378538 A1 12/2014 Bancel
2015/0030622 A1 1/2015 Marshall et al.
2015/0051268 A1 2/2015 Bancel et al.
2015/0056253 A1 2/2015 Bancel et al.
2015/0079121 A1 3/2015 Weiner et al.
2015/0141499 A1 5/2015 Bancel et al.
2015/0307542 A1 10/2015 Roy et al.
2015/0315541 A1 11/2015 Bancel et al.
2015/0376115 A1 12/2015 Ansell et al.
2016/0022580 A1 1/2016 Ramsay et al.
2016/0024140 A1 1/2016 Issa et al.
2016/0024141 A1 1/2016 Issa et al.
2016/0032273 A1 2/2016 Shahrokh et al.
2016/0038612 A1 2/2016 Hoge et al.
2016/0046675 A1 2/2016 Kwong et al.
2016/0151284 A1 6/2016 Heyes et al.
2016/0194368 A1 7/2016 Hoge et al.
2016/0194625 A1 7/2016 Hoge et al.
2016/0243221 A1 8/2016 Hoge et al.
2016/0317647 A1 * 11/2016 Ciaramella ............. A61P 31/16
2016/0376224 A1 12/2016 Du et al.
2017/0043037 A1 2/2017 Kariko et al.
2017/0130255 A1 5/2017 Wang et al.
2017/0202979 A1 7/2017 Chakraborty et al.
2017/0204152 A1 7/2017 Nelson et al.
2017/0239371 A1 8/2017 Guild et al.
2017/0340724 A1 11/2017 Ciaramella et al.
2018/0000953 A1 1/2018 Almarsson et al.
2018/0002393 A1 1/2018 Bancel et al.
2018/0028664 A1 2/2018 Besin et al.
2018/0237849 A1 8/2018 Thompson
2018/0243225 A1 8/2018 Ciaramella
2018/0243230 A1 8/2018 Smith

(56) References Cited

U.S. PATENT DOCUMENTS

| | | | |
|---|---|---|---|
| 2018/0256628 | A1 | 9/2018 | Hoge et al. |
| 2018/0271795 | A1 | 9/2018 | Martini et al. |
| 2018/0271970 | A1 | 9/2018 | Ciaramella et al. |
| 2018/0273977 | A1 | 9/2018 | Mousavi et al. |
| 2018/0274009 | A1 | 9/2018 | Marquardt et al. |
| 2018/0296663 | A1 | 10/2018 | Hipp et al. |
| 2018/0303925 | A1 | 10/2018 | Weissman et al. |
| 2018/0303929 | A1 | 10/2018 | Ciaramella et al. |
| 2018/0311336 | A1 | 11/2018 | Ciaramella et al. |
| 2018/0311343 | A1 | 11/2018 | Huang et al. |
| 2018/0318409 | A1 | 11/2018 | Valiante et al. |
| 2018/0326039 | A1 | 11/2018 | Haruta |
| 2018/0363019 | A1 | 12/2018 | Hoge |
| 2018/0369374 | A1 | 12/2018 | Frederick et al. |
| 2018/0371047 | A1 | 12/2018 | Ticho et al. |
| 2019/0002890 | A1 | 1/2019 | Martini et al. |
| 2019/0008938 | A1 | 1/2019 | Ciaramella et al. |
| 2019/0085368 | A1 | 3/2019 | Bancel et al. |
| 2019/0099481 | A1 | 4/2019 | Ciaramella et al. |
| 2019/0125839 | A1 | 5/2019 | Frederick et al. |
| 2019/0175517 | A1 | 6/2019 | Martini et al. |
| 2019/0175727 | A1 | 6/2019 | Huang et al. |
| 2019/0192646 | A1 | 6/2019 | Cohen et al. |
| 2019/0192653 | A1 | 6/2019 | Hoge et al. |
| 2019/0275170 | A1 | 9/2019 | Benenato et al. |
| 2019/0298657 | A1 | 10/2019 | Martini et al. |
| 2019/0298658 | A1 | 10/2019 | Benenato |
| 2019/0300906 | A1 | 10/2019 | Martini et al. |
| 2019/0314292 | A1 | 10/2019 | Benenato et al. |
| 2019/0314493 | A1 | 10/2019 | Ciaramella et al. |
| 2019/0336452 | A1 | 11/2019 | Brader |
| 2019/0336595 | A1 | 11/2019 | Ciaramella |
| 2019/0351040 | A1 | 11/2019 | Valiante et al. |
| 2019/0382774 | A1 | 12/2019 | Hoge et al. |
| 2019/0390181 | A1 | 12/2019 | Benenato et al. |
| 2020/0030432 | A1 | 1/2020 | Ciaramella et al. |
| 2020/0032274 | A1 | 1/2020 | Mauger et al. |
| 2020/0038499 | A1 | 2/2020 | Narayanan et al. |
| 2020/0054737 | A1 | 2/2020 | Ciaramella et al. |
| 2020/0069599 | A1 | 3/2020 | Smith et al. |
| 2020/0069793 | A1 | 3/2020 | Ciaramella |
| 2020/0069794 | A1 | 3/2020 | Ciaramella et al. |
| 2020/0071689 | A1 | 3/2020 | Miracco |
| 2020/0085916 | A1 | 3/2020 | Martini et al. |
| 2020/0109420 | A1 | 4/2020 | Brito et al. |
| 2020/0129445 | A1 | 4/2020 | Patel et al. |
| 2020/0129608 | A1 | 4/2020 | Ciaramella et al. |
| 2020/0129615 | A1 | 4/2020 | Ciaramella et al. |
| 2020/0163878 | A1 | 5/2020 | Baumhof et al. |
| 2020/0239869 | A1 | 7/2020 | Issa et al. |
| 2020/0254086 | A1 | 8/2020 | Hoge et al. |
| 2020/0282047 | A1 | 9/2020 | Ciaramella et al. |
| 2020/0297634 | A1 | 9/2020 | Karmali et al. |
| 2020/0306191 | A1 | 10/2020 | Schariter et al. |
| 2020/0338004 | A1 | 10/2020 | Hansson et al. |
| 2020/0368162 | A1 | 11/2020 | Martini |
| 2020/0399322 | A1 | 12/2020 | Baumhof et al. |
| 2021/0046173 | A1 | 2/2021 | Ciaramella et al. |
| 2021/0060175 | A1 | 3/2021 | Baumhof et al. |
| 2021/0087135 | A1 | 3/2021 | Benenato et al. |
| 2021/0163919 | A1 | 6/2021 | Issa et al. |
| 2021/0187097 | A1 | 6/2021 | Ciaramella et al. |
| 2021/0206818 | A1 | 7/2021 | Huang et al. |
| 2021/0217484 | A1 | 7/2021 | Giessel et al. |
| 2021/0228707 | A1 | 7/2021 | Mektar et al. |
| 2021/0268086 | A1 | 9/2021 | Zhong et al. |
| 2021/0378980 | A1 | 12/2021 | Horhota et al. |
| 2022/0031631 | A1 | 2/2022 | Almarsson et al. |
| 2022/0047518 | A1 | 2/2022 | Hennessy et al. |
| 2022/0054653 | A1 | 2/2022 | Martini et al. |
| 2022/0062175 | A1 | 3/2022 | Smith et al. |
| 2022/0125899 | A1 | 4/2022 | Ashburn et al. |
| 2022/0145381 | A1 | 5/2022 | Elich et al. |
| 2022/0236253 | A1 | 7/2022 | Hopson |
| 2022/0241399 | A1 | 8/2022 | Lusso et al. |
| 2022/0347292 | A1 | 11/2022 | Panther et al. |
| 2022/0348900 | A1 | 11/2022 | Shamashkin et al. |
| 2022/0349006 | A1 | 11/2022 | Amato et al. |
| 2023/0000970 | A1 | 1/2023 | Nachbagauer et al. |
| 2023/0141153 | A1 | 5/2023 | Zhang et al. |
| 2023/0142529 | A1 | 5/2023 | White et al. |
| 2023/0181481 | A1 | 6/2023 | White et al. |
| 2023/0190761 | A1 | 6/2023 | Brader et al. |
| 2023/0212645 | A1 | 7/2023 | Marquardt et al. |
| 2023/0287437 | A1 | 9/2023 | Smith et al. |
| 2023/0338506 | A1 | 10/2023 | Shaw et al. |
| 2023/0346914 | A1 | 11/2023 | Stewart-Jones et al. |
| 2023/0355743 | A1 | 11/2023 | Stewart-Jones et al. |
| 2024/0100145 | A1 | 3/2024 | Bollman et al. |
| 2024/0100151 | A1 | 3/2024 | Carfi et al. |
| 2024/0139309 | A1 | 5/2024 | Carfi et al. |

FOREIGN PATENT DOCUMENTS

| | | | |
|---|---|---|---|
| CA | 2473135 | A1 | 6/2003 |
| CA | 3194325 | A1 | 5/2022 |
| CN | 102548578 | A | 7/2012 |
| CN | 110603262 | A | 12/2019 |
| CN | 110974954 | A | 4/2020 |
| EP | 1083232 | B1 | 2/2005 |
| EP | 1301614 | B1 | 11/2006 |
| EP | 1383556 | B1 | 10/2007 |
| EP | 1905844 | A2 | 2/2008 |
| EP | 1026253 | B2 | 12/2012 |
| EP | 2188379 | B1 | 1/2013 |
| WO | WO 1990/011092 | A1 | 10/1990 |
| WO | WO 1996/040945 | A2 | 12/1996 |
| WO | WO 1999/052503 | A2 | 10/1999 |
| WO | WO 2001/021810 | A1 | 3/2001 |
| WO | WO 2004/058166 | A2 | 7/2004 |
| WO | WO 2005/007689 | A1 | 1/2005 |
| WO | WO 2005/120152 | | 12/2005 |
| WO | WO 2006/050280 | A2 | 5/2006 |
| WO | WO 2008/014979 | A3 | 2/2008 |
| WO | WO 2008/052770 | A2 | 5/2008 |
| WO | WO 2008/083949 | A2 | 7/2008 |
| WO | WO 2008/103276 | A2 | 8/2008 |
| WO | WO 2010/037408 | A1 | 4/2010 |
| WO | WO 2010/042877 | A1 | 4/2010 |
| WO | WO 2010/054401 | A1 | 5/2010 |
| WO | WO 2010/054406 | A1 | 5/2010 |
| WO | WO 2010/077717 | A1 | 7/2010 |
| WO | WO 2010/088927 | A1 | 8/2010 |
| WO | WO 2010/115046 | A2 | 10/2010 |
| WO | WO 2011/005799 | A2 | 1/2011 |
| WO | WO 2011/069529 | A1 | 6/2011 |
| WO | WO 2011/069586 | A1 | 6/2011 |
| WO | WO 2011/140627 | A1 | 11/2011 |
| WO | WO 2011/144358 | A1 | 11/2011 |
| WO | WO 2012/006369 | A2 | 1/2012 |
| WO | WO 2012/006376 | A2 | 1/2012 |
| WO | WO 2012/006378 | A1 | 1/2012 |
| WO | WO 2012/006380 | A2 | 1/2012 |
| WO | WO 2012/019630 | A1 | 2/2012 |
| WO | WO 2012/019780 | A1 | 2/2012 |
| WO | WO 2012/030901 | A1 | 3/2012 |
| WO | WO 2012/075040 | A2 | 6/2012 |
| WO | WO 2012/089225 | A1 | 7/2012 |
| WO | WO 2012/113513 | A1 | 8/2012 |
| WO | WO 2012/116714 | A1 | 9/2012 |
| WO | WO 2012/116715 | A1 | 9/2012 |
| WO | WO 2012/116810 | A1 | 9/2012 |
| WO | WO 2012/116811 | A1 | 9/2012 |
| WO | WO 2013/006825 | A1 | 1/2013 |
| WO | WO 2013/006837 | A1 | 1/2013 |
| WO | WO 2013/006838 | A1 | 1/2013 |
| WO | WO 2013/006842 | A2 | 1/2013 |
| WO | WO 2013/030778 | A2 | 3/2013 |
| WO | WO 2013/052167 | A2 | 4/2013 |
| WO | WO 2013/056132 | A2 | 4/2013 |
| WO | WO 2013/059496 | A1 | 4/2013 |
| WO | WO 2013/090648 | A1 | 6/2013 |
| WO | WO 2013/113502 | A1 | 8/2013 |
| WO | WO 2013/174409 | A1 | 11/2013 |

(56) References Cited

FOREIGN PATENT DOCUMENTS

| | | | |
|---|---|---|---|
| WO | WO 2013/185069 A1 | 12/2013 | |
| WO | WO 2014/071963 A1 | 5/2014 | |
| WO | WO 2014/072061 A1 | 5/2014 | |
| WO | WO 2014/089239 A1 | 6/2014 | |
| WO | WO 2014/089486 A1 | 6/2014 | |
| WO | WO 2014/127917 A1 | 8/2014 | |
| WO | WO 2014/136086 A1 | 9/2014 | |
| WO | WO 2014/144196 A1 | 9/2014 | |
| WO | WO 2014/152027 A1 | 9/2014 | |
| WO | WO 2014/152774 A1 | 9/2014 | |
| WO | WO 2014/159813 A1 | 10/2014 | |
| WO | WO 2014/160243 A1 | 10/2014 | |
| WO | WO 2014/160463 A1 | 10/2014 | |
| WO | WO 2014/174018 A1 | 10/2014 | |
| WO | WO 2014/202570 A1 | 12/2014 | |
| WO | WO 2015/005253 A1 | 1/2015 | |
| WO | WO 2015/013551 A1 | 1/2015 | |
| WO | WO 2015/024667 A1 | 2/2015 | |
| WO | WO 2015/024668 A2 | 2/2015 | |
| WO | WO 2015/024669 A1 | 2/2015 | |
| WO | WO 2015/095340 A1 | 6/2015 | |
| WO | WO 2015/095346 A1 | 6/2015 | |
| WO | WO 2015/130584 A2 | 9/2015 | |
| WO | WO 2015/177312 A1 | 11/2015 | |
| WO | WO 2015/189425 A1 | 12/2015 | |
| WO | WO 2015/199952 A1 | 12/2015 | |
| WO | WO 2016/037053 A1 | 3/2016 | |
| WO | WO 2016/164762 A1 | 10/2016 | |
| WO | WO 2016/176330 A1 | 11/2016 | |
| WO | WO 2016/201377 A1 | 12/2016 | |
| WO | WO 2016/203025 A1 | 12/2016 | |
| WO | WO 2017/011773 A2 | 1/2017 | |
| WO | WO 2017/015457 A1 | 1/2017 | |
| WO | WO 2017/015463 A1 | 1/2017 | |
| WO | WO 2017/019935 A1 | 2/2017 | |
| WO | WO 2017/020026 A1 | 2/2017 | |
| WO | WO 2017/153936 | 3/2017 | |
| WO | WO 2017/172890 A1 | 3/2017 | |
| WO | WO 2017/062513 A1 | 4/2017 | |
| WO | WO 2017/066789 A1 | 4/2017 | |
| WO | WO 2017/070601 A1 | 4/2017 | |
| WO | WO 2017/070616 A1 | 4/2017 | |
| WO | WO 2017/070618 A1 | 4/2017 | |
| WO | WO 2017/070620 A1 | 4/2017 | |
| WO | WO 2017/070622 A1 | 4/2017 | |
| WO | WO 2017/070623 A1 | 4/2017 | |
| WO | WO 2017/070626 A2 | 4/2017 | |
| WO | WO 2017/075038 A1 | 5/2017 | |
| WO | WO 2017/075531 A1 | 5/2017 | |
| WO | WO 2017/081082 A1 | 5/2017 | |
| WO | WO 2017/112865 A1 | 6/2017 | |
| WO | WO 2017/127750 A1 | 7/2017 | |
| WO | WO 2017/174564 A1 | 10/2017 | |
| WO | WO 2017/201333 A1 | 11/2017 | |
| WO | WO 2017/201340 A1 | 11/2017 | |
| WO | WO 2017/201342 A1 | 11/2017 | |
| WO | WO 2017/201347 A1 | 11/2017 | |
| WO | WO 2017/201349 A1 | 11/2017 | |
| WO | WO 2018/053209 A1 | 3/2018 | |
| WO | WO 2018/075980 A1 | 4/2018 | |
| WO | WO 2018/078053 A1 | 5/2018 | |
| WO | WO 2018/081459 A1 | 5/2018 | |
| WO | WO 2018/081462 A1 | 5/2018 | |
| WO | WO 2018/081638 A1 | 5/2018 | |
| WO | WO 2018/089801 A1 | 5/2018 | |
| WO | WO 2018/089851 A1 | 5/2018 | |
| WO | WO-2018089851 A2 * | 5/2018 | ............ A61K 39/12 |
| WO | WO 2018/107088 A1 | 6/2018 | |
| WO | WO 2018/111967 A1 | 6/2018 | |
| WO | WO 2018/144082 A1 | 8/2018 | |
| WO | WO 2018/144778 A1 | 8/2018 | |
| WO | WO 2018/151816 A1 | 8/2018 | |
| WO | WO 2018/157009 A1 | 8/2018 | |
| WO | WO 2018/170245 A1 | 9/2018 | |
| WO | WO 2018/170256 A1 | 9/2018 | |
| WO | WO 2018/170260 A1 | 9/2018 | |
| WO | WO 2018/170270 A1 | 9/2018 | |
| WO | WO 2018/170347 A1 | 9/2018 | |
| WO | WO 2018/175783 A1 | 9/2018 | |
| WO | WO 2018/187590 A2 | 10/2018 | |
| WO | WO 2018/200737 A1 | 11/2018 | |
| WO | WO 2018/232355 A1 | 12/2018 | |
| WO | WO 2018/232357 A1 | 12/2018 | |
| WO | WO 2019/018765 A1 | 1/2019 | |
| WO | WO 2019/036670 A1 | 2/2019 | |
| WO | WO 2019/036683 A1 | 2/2019 | |
| WO | WO 2019/036685 A1 | 2/2019 | |
| WO | WO 2019/103993 A1 | 5/2019 | |
| WO | WO 2019/148101 A1 | 8/2019 | |
| WO | WO 2019/202035 A1 | 10/2019 | |
| WO | WO 2020/006242 A1 | 1/2020 | |
| WO | WO 2020/056370 A1 | 3/2020 | |
| WO | WO 2020/061284 A1 | 3/2020 | |
| WO | WO 2020/061295 A1 | 3/2020 | |
| WO | WO 2020/061367 A1 | 3/2020 | |
| WO | WO 2020/097291 A1 | 5/2020 | |
| WO | WO 2020/163719 A2 | 8/2020 | |
| WO | WO 2020/172239 A1 | 8/2020 | |
| WO | WO 2020/185811 A1 | 9/2020 | |
| WO | WO 2020/190750 A1 | 9/2020 | |
| WO | WO 2020/243561 A1 | 12/2020 | |
| WO | WO 2021/016430 A1 | 1/2021 | |
| WO | WO 2021/030533 A1 | 2/2021 | |
| WO | WO 2021/050864 A1 | 3/2021 | |
| WO | WO 2021/055811 A1 | 3/2021 | |
| WO | WO 2021/155243 A1 | 8/2021 | |
| WO | WO 2021/155274 A1 | 8/2021 | |
| WO | WO 2021/159040 A2 | 8/2021 | |
| WO | WO 2021/159130 A2 | 8/2021 | |
| WO | WO 2021/204175 A1 | 10/2021 | |
| WO | WO 2021/211343 A1 | 10/2021 | |
| WO | WO 2021/222304 A1 | 11/2021 | |
| WO | WO 2021/231929 A1 | 11/2021 | |
| WO | WO 2021/231963 A1 | 11/2021 | |
| WO | WO 2021/237084 A1 | 11/2021 | |
| WO | WO 2021/239880 A1 | 12/2021 | |
| WO | WO 2021/247817 A1 | 12/2021 | |
| WO | WO 2022/032154 A2 | 2/2022 | |
| WO | WO 2022/067010 A1 | 3/2022 | |
| WO | WO 2022/076562 A1 | 4/2022 | |
| WO | WO 2022/099003 A1 | 5/2022 | |
| WO | WO 2022/101469 A1 | 5/2022 | |
| WO | WO 2022/155524 A1 | 7/2022 | |
| WO | WO 2022/155530 A1 | 7/2022 | |
| WO | WO 2022/187698 A1 | 9/2022 | |
| WO | WO 2022/197624 A1 | 9/2022 | |
| WO | WO 2022/204491 A1 | 9/2022 | |
| WO | WO 2022/212191 A1 | 10/2022 | |
| WO | WO 2022/212442 A1 | 10/2022 | |
| WO | WO 2022/212711 A2 | 10/2022 | |
| WO | WO 2022/221335 A1 | 10/2022 | |
| WO | WO 2022/221336 A1 | 10/2022 | |
| WO | WO 2022/221359 A1 | 10/2022 | |
| WO | WO 2022/221440 A1 | 10/2022 | |
| WO | WO 2022/226277 A1 | 10/2022 | |
| WO | WO 2022/226318 A1 | 10/2022 | |
| WO | WO 2022/232585 A1 | 11/2022 | |
| WO | WO 2022/241103 A1 | 11/2022 | |
| WO | WO 2022/245888 A1 | 11/2022 | |
| WO | WO 2022/266010 A1 | 12/2022 | |
| WO | WO 2022/266012 A1 | 12/2022 | |
| WO | WO 2022/266389 A1 | 12/2022 | |
| WO | WO 2023/283642 A2 | 1/2023 | |
| WO | WO 2023/283645 A1 | 1/2023 | |
| WO | WO 2023/283651 A1 | 1/2023 | |
| WO | WO 2023/014649 A1 | 2/2023 | |
| WO | WO 2023/018773 A1 | 2/2023 | |
| WO | WO 2023/018923 A1 | 2/2023 | |
| WO | WO 2023/019181 A1 | 2/2023 | |
| WO | WO 2023/056401 A1 | 4/2023 | |
| WO | WO 2023/069625 A1 | 4/2023 | |
| WO | WO 2023/069895 A1 | 4/2023 | |
| WO | WO 2023/069900 A1 | 4/2023 | |
| WO | WO 2023/076658 A1 | 5/2023 | |

(56) References Cited

FOREIGN PATENT DOCUMENTS

| | | | |
|---|---|---|---|
| WO | WO 2023/081311 | A1 | 5/2023 |
| WO | WO 2023/092069 | A1 | 5/2023 |
| WO | WO 2023/107999 | A2 | 6/2023 |
| WO | WO 2023/114307 | A1 | 6/2023 |
| WO | WO 2023/132885 | A1 | 7/2023 |
| WO | WO 2023/137149 | A1 | 7/2023 |
| WO | WO 2023/150256 | A1 | 8/2023 |
| WO | WO 2023/154818 | A1 | 8/2023 |
| WO | WO 2023/196914 | A1 | 10/2023 |
| WO | WO 2023/201204 | A1 | 10/2023 |
| WO | WO 2023/201294 | A1 | 10/2023 |
| WO | WO 2023/201296 | A1 | 10/2023 |
| WO | WO 2023/212696 | A1 | 11/2023 |
| WO | WO 2023/225524 | A1 | 11/2023 |
| WO | WO 2023/250119 | A1 | 12/2023 |
| WO | WO 2024/010993 | A1 | 1/2024 |
| WO | WO 2024/015890 | A1 | 1/2024 |
| WO | WO 2024/026005 | A1 | 2/2024 |
| WO | WO 2024/030369 | A1 | 2/2024 |
| WO | WO 2024/050483 | A1 | 3/2024 |
| WO | WO 2024/097874 | A1 | 5/2024 |

OTHER PUBLICATIONS

International Search Report and Written Opinion for Application No. PCT/US2019/015412, mailed Apr. 16, 2019.

[No Author Listed], Clinical trial NCT04528719: A Dose Escalation Study to Evaluate Safety, Reactogenicity, and Immunogenicity of mRNA-1345 in Healthy Adults and in Children who are Respiratory Syncytial Virus Seropositive (ModernaTX, Inc.) First Posted Aug. 27, 2020. Retrieved online on Mar. 15, 2021 at https://www.clinicaltrials.gov/ct2/show/NCT04528719?term=NCT04528719&draw=2&rank=1. 9 pages.

[No Author Listed], Geneseq Accession No. BC153556. First entry: Jan. 14, 2016. 3 pages.

[No Author Listed], Geneseq Accession No. BGP67180. First entry: Sep. 19, 2019. 3 pages.

Aliprantis et al., A phase 1, randomized, placebo-controlled study to evaluate the safety and immunogenicity of an mRNA-based RSV prefusion F protein vaccine in healthy younger and older adults. Hum Vaccin Immunother. May 4, 2021;17(5):1248-1261. doi: 10.1080/21645515.2020.1829899. Epub Oct. 29, 2020.

Anderson et al., Incorporation of pseudouridine into mRNA enhances translation by diminishing PKR activation, Nucleic Acids Res. Sep. 2010;38(17):5884-92. doi: 10.1093/nar/gkq347. Epub May 10, 2010.

Ausar et al., High-throughput screening of stabilizers for respiratory syncytial virus: identification of stabilizers and their effects on the conformational thermostability of viral particles. Hum Vaccin. May-Jun. 2007;3(3):94-103. Epub May 15, 2007.

Austin et al., Split-Dose Administration Enhances Immune Responses Elicited by a mRNA/Lipid Nanoparticle Vaccine Expressing Respiratory Syncytial Virus F Protein. Mol Pharm. Jan. 2, 2023;20(1):279-289. doi: 10.1021/acs.molpharmaceut.2c00635. Epub Oct. 17, 2022.

Bahl et al., Preclinical and Clinical Demonstration of Immunogenicity by mRNA Vaccines against H10N8 and H7N9 Influenza Viruses. Mol Ther. Jun. 7, 2017;25(6):1316-1327. doi: 10.1016/j.ymthe.2017.03.035. Epub Apr. 27, 2017.

Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.

Buschmann et al., Nanomaterial Delivery Systems for mRNA Vaccines. Vaccines (Basel). Jan. 19, 2021;9(1):65. doi: 10.3390/vaccines9010065.

Chaudhary et al., mRNA vaccines for infectious diseases: principles, delivery and clinical translation. Nature Reviews Drug Discovery vol. 20, pp. 817-838 (2021).

Cheng et al., Multifunctional triblock copolymers for intracellular messenger RNA delivery. Biomaterials. Oct. 2012; 33(28): 6868-6876.

Cross et al., Can mRNA disrupt the drug industry? C&EN, 2018: 96(35);35-40.

Cross, Without these lipid shells, there would be no mRNA vaccines for COVID-19. C&EN. Mar. 6, 2021;99(8):1-8.

Cross, Without these lipid shells, there would be no mRNA vaccines for COVID-19. Chem Eng News. Mar. 6, 2021; 99(8). 4 pages.

Cu et al., Enhanced Delivery and Potency of Self-Amplifying mRNA Vaccines by Electroporation in Situ, Vaccines, 2013, 1, 367-383. Abstract Only.

Deering et al., Nucleic acid vaccines: prospects for non-viral delivery of mRNA vaccines. Expert Opin Drug Deliv. Jun. 2014;11(6):885-99. doi: 10.1517/17425247.2014.901308. Epub Mar. 26, 2014.

DiCaro et al., In Vivo Delivery of Nucleic Acid-Formulated Microparticles as a Potential Tolerogenic Vaccine for Type 1 Diabetes. Rev Diabet Stud. 2012 Winter;9(4):348-56.

Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.

Espeseth et al., Modified mRNA/lipid nanoparticle-based vaccines expressing respiratory syncytial virus F protein variants are immunogenic and protective in rodent models of RSV infection. NPJ Vaccines. Feb. 14, 2020;5:16. doi: 10.1038/s41541-020-0163-z. eCollection 2020.

Ewert et al., Cationic liposome-nucleic acid complexes for gene delivery and silencing: pathways and mechanisms for plasmid DNA and siRNA. Top Curr Chem. 2010;296:191-226.

Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.

Furuichi et al., Viral and cellular mRNA capping: past and prospects. Adv Virus Res. 2000;55:135-84. doi: 10.1016/s0065-3527(00)55003-9.

Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.

Geall et al., RNA: the new revolution in nucleic acid vaccines. Semin Immunol. Apr. 2013;25(2):152-9. doi: 10.1016/j.smim.2013.05.001. Epub Jun. 2, 2013.

Gjetting et al., In vitro and in vivo effects of polyethylene glycol (PEG)-modified lipid in DOTAP/cholesterol-mediated gene transfection. Int J Nanomedicine. Aug. 9, 2010;5:371-83.

Graham et al., Novel antigens for RSV vaccines. Curr Opin Immunol. Aug. 2015;35:30-8. doi: 10.1016/j.coi.2015.04.005. Epub Jun. 10, 2015.

Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.

Hassett et al., Optimization of Lipid Nanoparticles for Intramuscular Administration of mRNA Vaccines. Mol Ther Nucleic Acids. Apr. 15, 2019;15:1-11. Epub Feb. 7, 2019.

Holtkamp et al., Modification of antigen-encoding RNA increases stability, translational efficacy, and T-cell stimulatory capacity of dendritic cells. Blood. Dec. 15, 2006;108(13):4009-17.

Hou et al., Lipid nanoparticles for mRNA delivery. Nature Reviews Materials vol. 6, pp. 1078-1094 (2021).

Jorquera et al., Nanoparticle vaccines encompassing the respiratory syncytial virus (RSV) G protein CX3C chemokine motif induce robust immunity protecting from challenge and disease. PLoS One. Sep. 10, 2013;8(9):e74905. doi: 10.1371/journal.pone.0074905. eCollection 2013.

Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.

Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.

(56) References Cited

OTHER PUBLICATIONS

Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.
Kowalski et al., Delivering the Messenger: Advances in Technologies for Therapeutic mRNA Delivery. Molecular Therapy vol. 27 No. 4 Apr. 2019.
Kramps et al., Messenger RNA-based vaccines: progress, challenges, applications. Wiley Interdiscip Rev RNA. Nov.-Dec. 2013;4(6):737-49. doi: 10.1002/wrna.1189. Epub Jul. 25, 2013.
Kuhn et al., mRNA as a versatile tool for exogenous protein expression. Current Gene Therapy. Oct. 2012; 12 (5): 347-361.
Kulkarni et al., Lipid Nanoparticles Enabling Gene Therapies: From Concepts to Clinical Utility. Nucleic Acid Ther. Jun. 2018;28(3):146-157. doi: 10.1089/nat.2018.0721. Epub Apr. 23, 2018.
Leitner et al., DNA and RNA-based vaccines: principles, progress and prospects. Vaccine. Dec. 10, 1999;18 (9-10):765-77.
Li et al., Lipid-based nanoparticles for nucleic acid delivery. Pharm Res. Mar. 2007;24(3):438-49. doi: 10.1007/s11095-006-9180-5.
Lian et al., Trends and developments in liposome drug delivery systems. J Pharm Sci. Jun. 2001;90(6):667-80.
Liang et al., Efficient Targeting and Activation of Antigen-Presenting Cells In Vivo after Modified mRNA Vaccine Administration in Rhesus Macaques. Mol Ther. Dec. 6, 2017;25(12):2635-2647. doi: 10.1016/j.ymthe.2017.08.006. Epub Aug. 12, 2017.
Liang et al., Enhanced Neutralizing Antibody Response Induced by Respiratory Syncytial Virus Prefusion F Protein Expressed by a Vaccine Candidate. J Virol. Sep. 2015;89(18):9499-510. doi: 10.1128/JVI.01373-15. Epub Jul. 8, 2015.
Lindgren et al., Induction of Robust B Cell Responses after Influenza mRNA Vaccination is Accompanied by Circulating Hemagglutinin-Specific ICOS+ PD-1+ CXCR3+ T Follicular Helper Cells. Front Immunol. Nov. 13, 2017;8:1539. doi: 10.3389/fimmu.2017.01539. eCollection 2017.
Lorenzi et al., Intranasal vaccination with messenger RNA as a new approach in gene therapy: Use against tuberculosis. BMC Biotechnol. Oct. 2010; 10(77): 1-11.
MacLachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016.
Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.
Martinon et al., Induction of virus-specific cytotoxic T lymphocytes in vivo by liposome-entrapped mRNA. EurJ Immunol. Jul. 1993;23(7):1719-22.
Maruggi et al., mRNA as a Transformative Technology for Vaccine Development to Control Infectious Diseases. Mol Ther. Apr. 10, 2019;27(4):757-772. doi: 10.1016/j.ymthe.2019.01.020. Epub Feb. 7, 2019.
McKenzie et al., Nucleic acid vaccines: tasks and tactics. Immunol Res. 2001 ;24(3):225-44.
McLellan et al., Structure of respiratory syncytial virus fusion glycoprotein in the postfusion conformation reveals preservation of neutralizing epitopes. J Virol. Aug. 2011;85(15):7788-96. doi: 10.1128/JVI.00555-11. Epub May 25, 2011.
McLellan et al., Structure-based design of a fusion glycoprotein vaccine for respiratory syncytial virus. Science. Nov. 1, 2013;342(6158):592-8. doi: 10.1126/science.1243283.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Mitchell et al., RNA transfected dendritic cells as cancer vaccines. Curr Opin Mol Ther. Apr. 2000;2(2):176-81.
Mockey et al., mRNA-based cancer vaccine: prevention of B16 melanoma progression and metastasis by systemic injection of MART1 mRNA histidylated lipopolyplexes. Cancer Gene Ther. Sep. 2007;14(9):802-14. Epub Jun. 22, 2007.
Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.
Pardi et al., mRNA vaccines—a new era in vaccinology. Nat Rev Drug Discov. Apr. 2018;17(4):261-279. doi: 10.1038/nrd.2017.243. Epub Jan. 12, 2018.
Patel et al., Naturally-occurring cholesterol analogues in lipid nanoparticles induce polymorphic shape and enhance intracellular delivery of mRNA. Nat Commun. Feb. 20, 2020;11(1):983. doi: 10.1038/s41467-020-14527-2.
Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
Pollard et al., Type I IFN counteracts the induction of antigen-specific immune responses by lipid-based delivery of mRNA vaccines. Mol Ther. Jan. 2013; 21 (1): 251-259.
Reichmuth et al., mRNA Vaccine Delivery Using Lipid Nanoparticles. Ther Deliv. 2016;7(5):319-34. doi: 10.4155/tde-2016-0006.
Rosa et al., mRNA vaccines manufacturing: Challenges and bottlenecks. Vaccine. Apr. 15, 2021;39(16):2190-2200.
Schirrmacher et al., Intra-pinna anti-tumor vaccination with self-replicating infectious RNA or with DNA encoding a model tumor antigen and a cytokine. Gene Ther. Jul. 2000;7(13):1137-47.
Schlake et al., Developing mRNA-vaccine technologies. RNA Biol. Nov. 2012;9(11):1319-30. doi: 10.4161/rna.22269. Epub Oct. 12, 2012.
Schott et al., Viral and non-viral approaches for transient delivery of mRNA and proteins. Current Gene Ther. 2011; 11 (5): 382-398.
Schwendener, Liposomes as vaccine delivery systems: a review of the recent advances. Ther Adv Vaccines. Nov. 2014;2(6):159-82. doi: 10.1177/2051013614541440.
Shin et al., Recent Advances in RNA Therapeutics and RNA Delivery Systems Based on Nanoparticles. Adv. Therap., Nov. 2018;1(7):1800065. Review.
Stab et al., Protective efficacy and immunogenicity of a combinatory DNA vaccine against Influenza A Virus and the Respiratory Syncytial Virus. PLoS One. Aug. 14, 2013;8(8):e72217. doi: 10.1371/journal.pone.0072217. eCollection 2013.
Terada et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir.0c03039. Epub Jan. 13, 2021.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
To et al., An overview of rational design of mRNA-based therapeutics and vaccines. Expert Opin Drug Discov. Nov. 2021;16(11):1307-1317. doi: 10.1080/17460441.2021.1935859. Epub Jul. 19, 2021.
Vassilev et al., Microparticle-mediated RNA immunization against bovine viral diarrhea virus. Vaccine. Feb. 28, 2001;19(15-16):2012-9.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.
Wong et al., An mRNA vaccine for influenza. Nat Biotechnol. Dec. 2012;30(12):1202-4. doi: 10.1038/nbt.2439.
Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.
Ying et al., Cancer therapy using a self-replicating RNA vaccine. Nat Med. Jul. 1999;5(7):823-7.

(56) References Cited

OTHER PUBLICATIONS

Youn et al., Modified mRNA as an alternative to plasmid DNA (pDNA) for transcript replacement and vaccination therapy. Expert Opin Biol Ther. 2015;15(9):1337-48. doi: 10.1517/14712598.2015.1057563. Epub Jun. 30, 2015.
Zeng et al., Formulation and Delivery Technologies for mRNA Vaccines. Curr Top Microbiol Immunol. Jun. 2, 2020;10.1007/82_2020_217. doi: 10.1007/82_2020_217.
Zhao et al., Nanoparticle vaccines. Vaccine. Jan. 9, 2014;32(3):327-37. doi: 10.1016/j.vaccine.2013.11.069. Epub Dec. 2, 2013.
Allen et al., Liposomal drug delivery systems: from concept to clinical applications. Adv Drug Deliv Rev. Jan. 2013;65(1):36-48. doi: 10.1016/j.addr.2012.09.037. Epub Oct. 1, 2012.
Karikó, Modified uridines are the key to a successful message. Nat Rev Immunol. Oct. 2021;21(10):619. doi: 10.1038/s41577-021-00608-w.
Kutikuppala et al., Prospects and Challenges in Developing mRNA Vaccines for Infectious Diseases and Oncogenic Viruses. Med Sci (Basel). May 22, 2024;12(2):28. doi: 10.3390/medsci12020028.

* cited by examiner

SEQUENCE LISTING

```
Sequence total quantity: 100
SEQ ID NO: 1           moltype = RNA  length = 1771
FEATURE                Location/Qualifiers
misc_feature           1..1771
                       note = Synthetic Polynucleotide
source                 1..1771
                       mol_type = other RNA
                       organism = synthetic construct
SEQUENCE: 1
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataaaaa cgctgtgacc gagctgcagt tattgatgca gagtacacct gccaccgggt  360
cgggctctgc catttgctcc ggcgtggctg tatgtaaagt tctccacctc gagggagagg  420
ttaataagat taagtcggcc ctgctgagta ctaacaaagc agtggtgtcg ctgagtaacg  480
gagtaagtgt gttaacattt aaggtgctgg acctcaagaa ttatattgac aaacagttgc  540
ttcctattct aaacaaacag agctgttcaa taagtaatat tgaaactgtt attgagtttc  600
agcagaagaa caacaggctt cttgagatta cacgcgagtt cagtgtcaat gccggcgtta  660
caacacccgt gtctacctac atgctgacga attctgagct tctctctctc ataaacgaca  720
tgcccattac gaatgaccaa aaaaaactta tgtccaacaa cgtgcagatt gtgcgacagc  780
aatcctatag cattatgtgt atcatcaagg aagaggtact cgcttatgtt gtgcagctac  840
cactctatgg tgtgattgac accccctgtt ggaagctgca taccagtcca ctctgcacca  900
ctaacacaaa ggaagggagc aatatttgcc tcactcgaac cgacaggggg tggtattgcg  960
ataatgcggg ctccgtgtcc ttctttccac aggctgaaac ttgtaaggta cagtcaaacc  1020
gcgtgttctg tgatactatg aattctcgta ctcttcccag cgaggttaat ctctgcaacg  1080
tcgacatttt caatcctaaa tatgactgca agatcatgac cagcaagacc gacgtctcca  1140
gctcagtaat cactagccta ggggccattg taagctgcta tggcaaaacc aagtgtactg  1200
cctctaataa gaacagaggc ataattaaaa ccttttcaaa tggctgtgac tatgtgtcga  1260
ataagggcgt cgacacggtc tcagtaggga ataccctcta ctgcgttaac aaacaggaag  1320
gcaaatccct ttatgtaaag ggcgagccca tcataaattt ctacgaccca cttgtgttcc  1380
ccagtgatga attcgatgca tcaatctccc aggtgaacga aaagatcaat caatcccttg  1440
cttttatacg aaagtcagat gaactcctgc ataacgtgaa tgctgggaaa tctacaacca  1500
acatcatgat cactaccatc attattgtga ttatcgtaat tctgctatcc ttgattgctg  1560
tcgggctgct tctgtactgt aaggccagat cgacgcctgt gaccctttca aaagaccaac  1620
ttagcggtat caataatatt gcctttagca attgataata ggctggagcc tcggtggcca  1680
tgcttcttgc cccttgggcc tccccccagc ccctcctccc cttcctgcac ccgtaccccc  1740
gtggtctttg aataaagtct gagtgggcgg c                                  1771

SEQ ID NO: 2           moltype = RNA  length = 47
FEATURE                Location/Qualifiers
misc_feature           1..47
                       note = Synthetic Polynucleotide
source                 1..47
                       mol_type = other RNA
                       organism = synthetic construct
SEQUENCE: 2
gggaaataag agagaaaaga agagtaagaa gaaatataag agccacc                 47

SEQ ID NO: 3           moltype = RNA  length = 1605
FEATURE                Location/Qualifiers
misc_feature           1..1605
                       note = Synthetic Polynucleotide
source                 1..1605
                       mol_type = other RNA
                       organism = synthetic construct
SEQUENCE: 3
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
```

```
caggaactcg acaaatataa aaacgctgtg accgagctgc agttattgat gcagagtaca  300
cctgccaccg ggtcgggctc tgccatttgc tccggcgtgg ctgtatgtaa agttctccac  360
ctcgagggag aggttaataa gattaagtcg gccctgctga gtactaacaa agcagtggtg  420
tcgctgagta acggagtaag tgtgttaaca tttaaggtgc tggacctcaa gaattatatt  480
gacaaacagt tgcttcctat tctaaacaaa cagagctgtt caataagtaa tattgaaact  540
gttattgagt ttcagcagaa gaacaacagg cttcttgaga ttacacgcga gttcagtgtc  600
aatgccggcg ttacaacacc cgtgtctacc tacatgctga cgaattctga gcttctctct  660
ctcataaacg acatgcccat tacgaatgac caaaaaaaac ttatgtccaa caacgtgcag  720
attgtgcgac agcaatccta tagcattatg tgtatcatca aggaagaggt actcgcttat  780
gttgtgcagc taccactcta tggtgtgatt gacacccccct gttggaagct gcataccagt  840
ccactctgca ccactaacac aaaggaaggg agcaatattt gcctcactcg aaccgacagg  900
gggtggtatt gcgataatgc gggctccgtg tccttctttc cacaggctga aacttgtaag  960
gtacagtcaa accgcgtgtt ctgtgatact atgaattctc gtactcttcc cagcgaggtt  1020
aatctctgca acgtcgacat tttcaatcct aaatatgact gcaagatcat gaccagcaag  1080
accgacgtct ccagctcagt aatcactagc ctaggggcca ttgtaagctg ctatggcaaa  1140
accaagtgta ctgcctctaa taagaacaga ggcataatta aaacctttttc aaatggctgt  1200
gactatgtgt cgaataaggg cgtcgacacg gtctcagtag ggaataccct ctactgcgtt  1260
aacaaacagg aaggcaaatc cctttatgta aagggcgagc ccatcataaa tttctacgac  1320
ccacttgtgt tccccagtga tgaattcgat gcatcaatct cccaggtgaa cgaaaagatc  1380
aatcaatccc ttgcttttat acgaaagtca gatgaactcc tgcataacgt gaatgctggg  1440
aaatctacaa ccaacatcat gatcactacc atcattattg tgattatcgt aattctgcta  1500
tccttgattg ctgtcgggct gcttctgtac tgtaaggcca gatcgacgcc tgtgaccctt  1560
tcaaaagacc aacttagcgg tatcaataat attgccttta gcaat                  1605
```

```
SEQ ID NO: 4            moltype = RNA  length = 119
FEATURE                 Location/Qualifiers
misc_feature            1..119
                        note = Synthetic Polynucleotide
source                  1..119
                        mol_type = other RNA
                        organism = synthetic construct
SEQUENCE: 4
tgataatagg ctggagcctc ggtggccatg cttcttgccc cttgggcctc cccccagccc  60
ctcctcccct tcctgcaccc gtacccccgt ggtctttgaa taaagtctga gtgggcggc   119
```

```
SEQ ID NO: 5            moltype = AA  length = 535
FEATURE                 Location/Qualifiers
REGION                  1..535
                        note = Synthetic Polypeptide
source                  1..535
                        mol_type = protein
                        organism = synthetic construct
SEQUENCE: 5
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATGSGSAIC SGVAVCKVLH  120
LEGEVNKIKS ALLSTNKAVV SLSNGVSVLT FKVLDLKNYI DKQLLPILNK QSCSISNIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGKSLYV KGEPIINFYD PLVFPSDEFD ASISQVNEKI NQSLAFIRKS DELLHNVNAG  480
KSTTNIMITT IIIVIIVILL SLIAVGLLLY CKARSTPVTL SKDQLSGINN IAFSN       535
```

```
SEQ ID NO: 6            moltype = RNA  length = 1774
FEATURE                 Location/Qualifiers
misc_feature            1..1774
                        note = Synthetic Polynucleotide
source                  1..1774
                        mol_type = other RNA
                        organism = synthetic construct
SEQUENCE: 6
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataaaaa cgctgtgacc gagctgcagt tattgatgca gagtacacct gccaccgggt  360
cgggctctgc cattgcttcc ggcgtggctg tatgtaaagt tctccacctc gagggagagg  420
ttaataagat taagtcggcc ctgctgagta ctaacaaagc agtggtgtcg ctgagtggct  480
gcggagtaag tgtgttaaca tttaaggtgc tggacctcaa gaattatatt gacaaacagt  540
tgcttcctat tctaaacaaa cagagctgtt caataagtaa tattgaaact gttattgagt  600
ttcagcagaa gaacaacagg cttcttgaga ttacacgcga gttcagtgtc aatgccggcg  660
ttacaacacc cgtgtctacc tacatgctga cgaattctga gcttctctct ctcataaacg  720
acatgcccat tacgaatgac caaaaaaaac ttatgtccaa caacgtgcag attgtgcgac  780
agcaatccta tagcattatg tgtatcatca aggaagaggt actcgcttat gttgtgcagc  840
taccactcta tggtgtgatt gacaccccct gttggaagct gcataccagt ccactctgca  900
ccactaacac aaaggaaggg agcaatattt gcctcactcg aaccgacagg gggtggtatt  960
gcgataatgc gggctccgtg tccttctttc cacaggctga aacttgtaag gtacagtcaa  1020
accgcgtgtt ctgtgatact atgaattctc gtactcttcc cagcgaggtt aatctctgca  1080
```

-continued

```
acgtcgacat tttcaatcct aaatatgact gcaagatcat gaccagcaag accgacgtct  1140
ccagctcagt aatcactagc ctaggggcca ttgtaagctg ctatggcaaa accaagtgta  1200
ctgcctctaa taagtgcaga ggcataatta aaaccttttc aaatggctgt gactatgtgt  1260
cgaataaggg cgtcgacacg gtctcagtag ggaataccct ctactacgtt aacaaacagg  1320
aaggcaaatc cctttatgta aagggcgagc ccatcataaa tttctacgac ccacttgtgt  1380
tccccagtga tgaattcgat gcatcaatct cccaggtgaa cgaaaagatc aatcaatccc  1440
ttgcttttat acgaaagtca gatgaactcc tgcataacgt gaatgctggg aaatctacaa  1500
ccaacatcat gatcactacc atcattattg tgattatcgt aattctgcta tccttgattg  1560
ctgtcgggct gcttctgtac tgtaaggcca gatcgacgcc tgtgaccctt tcaaaagacc  1620
aacttagcgg tatcaataat attgccttta gcaattgata ataggctgga gcctcggtgg  1680
ccatgcttct tgccccttgg gcctccccc  agcccctcct ccccttcctg cacccgtacc  1740
cccgtggtct ttgaataaag tctgagtggg cggc                              1774
```

```
SEQ ID NO: 7           moltype = RNA  length = 1608
FEATURE                Location/Qualifiers
misc_feature           1..1608
                       note = Synthetic Polynucleotide
source                 1..1608
                       mol_type = other RNA
                       organism = synthetic construct
SEQUENCE: 7
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa aaacgctgtg accgagctgc agttattgat gcagagtaca  300
cctgccaccg ggtcgggctc tgccattgct tccggcgtgg ctgtatgtaa agttctccac  360
ctcgagggag aggttaataa gattaagtcg gccctgctga gtactaacaa agcagtggtg  420
tcgctgagtg gctgcggagt aagtgtgtta acatttaagg tgctggacct caagaattat  480
attgacaaac agttgcttcc tattctaaac aaacagagct gttcaataag taatattgaa  540
actgttattg agtttcagca gaagaacaac aggcttcttg agattacacg cgagttcagt  600
gtcaatgccg gcgttacaac acccgtgtct acctacatgc tgacgaattc tgagcttctc  660
tctctcataa acgacatgcc cattacgaat gaccaaaaaa aacttatgtc caacaacgtg  720
cagattgtgc gacagcaatc ctatagcatt atgtgtatca tcaaggaaga ggtactcgct  780
tatgttgtgc agctaccact ctatggtgtg attgacaccc cctgttggaa gctgcatacc  840
agtccactct gcaccactaa cacaaaggaa gggagcaata tttgcctcac tcgaaccgac  900
agggggtggt attgcgataa tgcgggctcc gtgtccttct ttccacaggc tgaaacttgt  960
aaggtacagt caaaccgcgt gttctgtgat actatgaatt ctcgtactct tcccagcgag  1020
gttaatctct gcaacgtcga cattttcaat cctaaatatg actgcaagat catgaccagc  1080
aagaccgacg tctccagctc agtaatcact agcctagggg ccattgtaag ctgctatggc  1140
aaaaccaagt gtactgcctc taataagtgc agaggcataa ttaaaacctt ttcaaatggc  1200
tgtgactatg tgtcgaataa gggcgtcgac acggtctcag tagggaatac cctctactac  1260
gttaacaaac aggaaggcaa atccctttat gtaaagggcg agcccatcat aaatttctac  1320
gacccacttg tgttccccag tgatgaattc gatgcatcaa tctcccaggt gaacgaaaag  1380
atcaatcaat cccttgcttt tatacgaaag tcagatgaac tcctgcataa cgtgaatgct  1440
gggaaatcta caaccaacat catgatcact accatcatta ttgtgattat cgtaattctg  1500
ctatccttga ttgctgtcgg gctgcttctg tactgtaagg ccagatcgac gcctgtgacc  1560
ctttcaaaag accaacttag cggtatcaat aatattgcct ttagcaat                1608
```

```
SEQ ID NO: 8           moltype = AA  length = 536
FEATURE                Location/Qualifiers
REGION                 1..536
                       note = Synthetic Polypeptide
source                 1..536
                       mol_type = protein
                       organism = synthetic construct
SEQUENCE: 8
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATGSGSAIA SGVAVCKVLH  120
LEGEVNKIKS ALLSTNKAVV SLSGCGVSVL TFKVLDLKNY IDKQLLPILN KQSCSISNIE  180
TVIEFQQKNN RLLEITREFS VNAGVTTPVS TYMLTNSELL SLINDMPITN DQKKLMSNNV  240
QIVRQQSYSI MCIIKEEVLA YVVQLPLYGV IDTPCWKLHT SPLCTTNTKE GSNICLTRTD  300
RGWYCDNAGS VSFFPQAETC KVQSNRVFCD TMNSRTLPSE VNLCNVDIFN PKYDCKIMTS  360
KTDVSSSVIT SLGAIVSCYG KTKCTASNKC RGIIKTFSNG CDYVSNKGVD TVSVGNTLYY  420
VNKQEGKSLY VKGEPIINFY DPLVFPSDEF DASISQVNEK INQSLAFIRK SDELLHNVNA  480
GKSTTNIMIT TIIIVIIVIL LSLIAVGLLL YCKARSTPVT LSKDQLSGIN NIAFSN      536
```

```
SEQ ID NO: 9           moltype = RNA  length = 1777
FEATURE                Location/Qualifiers
misc_feature           1..1777
                       note = Synthetic Polynucleotide
source                 1..1777
                       mol_type = other RNA
                       organism = synthetic construct
SEQUENCE: 9
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
```

-continued

```
aagagaacaa gtgcaatggt accgacgcta aagtcaaact tatcaagcag gaactcgaca  300
aatataaaaa cgctgtgacc gagctgcagt tattgatgca gagtacacct gccaccaata  360
acgggtcggg ctctgccatt gcttccggcg tggctgtatg taaagttctc cacctcgagg  420
gagaggttaa taagattaag tcggccctgc tgagtactaa caaagcagtg gtgtcgctga  480
gtaacggagt aagtgtgtta acatttaagg tgctggacct caagaattat attgacaaac  540
agttgcttcc tattctaaac aaacagagct gttcaataag taatattgaa actgttattg  600
agtttcagca gaagaacaac aggcttcttg agattacacg cgagttcagt gtcaatgccg  660
gcgttacaac acccgtgtct acctacatgc tgacgaattc tgagcttctc tctctcataa  720
acgacatgcc cattacgaat gaccaaaaaa aacttatgtc caacaacgtg cagattgtgc  780
gacagcaatc ctatagcatt atgtgtatca tcaaggaaga ggtactcgct tatgttgtgc  840
agctaccact ctatggtgtg attgacaccc cctgttggaa gctgcatacc agtccactct  900
gcaccactaa cacaaaggaa gggagcaata tttgcctcac tcgaaccgac agggggtggt  960
attgcgataa tgcgggctcc gtgtccttct ttccacaggc tgaaacttgt aaggtacagt  1020
caaaccgcgt gttctgtgat actatgaatt ctcgtactct tcccagcgag gttaatctct  1080
gcaacgtcga cattttcaat cctaaatatg actgcaagat catgaccagc aagaccgacg  1140
tctccagctc agtaatcact agcctagggg ccattgtaag ctgctatggc aaaaccaagt  1200
gtactgcctc taataagaac agaggcataa ttaaaacctt ttcaaatggc tgtgactatg  1260
tgtcgaataa gggcgtcgac acggtctcag tagggaatac cctctactac gttaacaaac  1320
aggaaggcaa atcccttat gtaaagggcg agcccatcat aaatttctac gacccacttg  1380
tgttccccag tgatgaattc gatgcatcaa tctcccaggt gaacgaaaag atcaatcaat  1440
cccttgcttt tatacgaaag tcagatgaac tcctgcataa cgtgaatgct gggaaatcta  1500
caaccaacat catgatcact accatcatta ttgtgattat cgtaattctg ctatccttga  1560
ttgctgtcgg gctgcttctg tactgtaagg ccagatcgac gcctgtgacc ctttcaaaag  1620
accaacttag cggtatcaat aatattgcct ttagcaattg ataataggct ggagcctcgg  1680
tggccatgct tcttgcccct tgggcctccc cccagcccct cctccccttc ctgcacccgt  1740
acccccgtgg tctttgaata aagtctgagt gggcggc                           1777

SEQ ID NO: 10          moltype = RNA  length = 1611
FEATURE                Location/Qualifiers
misc_feature           1..1611
                       note = Synthetic Polynucleotide
source                 1..1611
                       mol_type = other RNA
                       organism = synthetic construct
SEQUENCE: 10
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa aaacgctgtg accgagctgc agttattgat gcagagtaca  300
cctgccacca ataacgggtc gggctctgcc attgcttccg gcgtggctgt atgtaaagtt  360
ctccacctcg agggagaggt taataagatt aagtcggccc tgctgagtac taacaaagca  420
gtggtgtcgc tgagtaacgg agtaagtgtg ttaacattta aggtgctgga cctcaagaat  480
tatattgaca aacagttgct tcctattcta aacaaacaga gctgttcaat aagtaatatt  540
gaaactgtta ttgagtttca gcagaagaac aacaggcttc ttgagattac acgcgagttc  600
agtgtcaatg ccggcgttac aacacccgtg tctacctaca tgctgacgaa ttctgagctt  660
ctctctctca taaacgacat gcccattacg aatgaccaaa aaaaacttat gtccaacaac  720
gtgcagattg tgcgacagca atcctatagc attatgtgta tcatcaagga agaggtactc  780
gcttatgttg tgcagctacc actctatggt gtgattgaca ccccctgttg gaagctgcat  840
accagtccac tctgcaccac taacacaaag gaagggagca atatttgcct cactcgaacc  900
gacagggggt ggtattgcga taatgcgggc tccgtgtcct tctttccaca ggctgaaact  960
tgtaaggtac agtcaaaccg cgtgttctgt gatactatga attctcgtac tcttcccagc  1020
gaggttaatc tctgcaacgt cgacattttc aatcctaaat atgactgcaa gatcatgacc  1080
agcaagaccg acgtctccag ctcagtaatc actagcctag gggccattgt aagctgctat  1140
ggcaaaacca agtgtactgc ctctaataag aacagaggca taattaaaac cttttcaaat  1200
ggctgtgact atgtgtcgaa taagggcgtc gacacggtct cagtagggaa taccctctac  1260
tacgttaaca aacaggaagg caaatccctt tatgtaaagg gcgagcccat cataaatttc  1320
tacgacccac ttgtgttccc cagtgatgaa ttcgatgcat caatctccca ggtgaacgaa  1380
aagatcaatc aatcccttgc ttttatacga aagtcagatg aactcctgca taacgtgaat  1440
gctgggaaat ctacaaccaa catcatgatc actaccatca ttattgtgat tatcgtaatt  1500
ctgctatcct tgattgctgt cggctgctt ctgtactgta aggccagatc gacgcctgtg  1560
accctttcaa aagaccaact tagcggtatc aataatattg cctttagcaa t           1611

SEQ ID NO: 11          moltype = AA  length = 537
FEATURE                Location/Qualifiers
REGION                 1..537
                       note = Synthetic Polypeptide
source                 1..537
                       mol_type = protein
                       organism = synthetic construct
SEQUENCE: 11
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNGSGSA IASGVAVCKV  120
LHLEGEVNKI KSALLSTNKA VVSLSNGVSV LTFKVLDLKN YIDKQLLPIL NKQSCSISNI  180
ETVIEFQQKN NRLLEITREF SVNAGVTTPV STYMLTNSEL LSLINDMPIT NDQKKLMSNN  240
VQIVRQQSYS IMCIIKEEVL AYVVQLPLYG VIDTPCWKLH TSPLCTTNTK EGSNICLTRT  300
DRGWYCDNAG SVSFFPQAET CKVQSNRVFC DTMNSRTLPS EVNLCNVDIF NPKYDCKIMT  360
SKTDVSSSVI TSLGAIVSCY GKTKCTASNK NRGIIKTFSN GCDYVSNKGV DTVSVGNTLY  420
YVNKQEGKSL YVKGEPIINF YDPLVFPSDE FDASISQVNE KINQSLAFIR KSDELLHNVN  480
```

```
AGKSTTNIMI TTIIIVIIVI LLSLIAVGLL LYCKARSTPV TLSKDQLSGI NNIAFSN     537

SEQ ID NO: 12          moltype = RNA  length = 1681
FEATURE                Location/Qualifiers
misc_feature           1..1681
                       note = Synthetic Polynucleotide
source                 1..1681
                       mol_type = other RNA
                       organism = synthetic construct
SEQUENCE: 12
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataaaaa cgctgtgacc gagctgcagt tattgatgca gagtacacct gccaccgggt  360
cgggctctgc catttgctcc ggcgtggctg tatgtaaagt tctccacctc gagggagagg  420
ttaataagat taagtcggcc ctgctgagta ctaacaaagc agtggtgtcg ctgagtaacg  480
gagtaagtgt gttaacattt aaggtgctgg acctcaagaa ttatattgac aaacagttgc  540
ttcctattct aaacaaacag agctgttcaa taagtaatat tgaaactgtt attgagtttc  600
agcagaagaa caacaggctt cttgagatta cacgcgagtt cagtgtcaat gccggcgtta  660
caacacccgt gtctacctac atgctgacga attctgagct tctctctctc ataaacgaca  720
tgcccattac gaatgaccaa aaaaaactta tgtccaacaa cgtgcagatt gtgcgacagc  780
aatcctatag cattatgtgt atcatcaagg aagaggtact cgcttatgtt gtgcagctac  840
cactctatgg tgtgattgac accccctgtt ggaagctgca taccagtcca ctctgcacca  900
ctaacacaaa ggaagggagc aatatttgcc tcactcgaac cgacaggggg tggtattgcg  960
ataatgcggg ctccgtgtcc ttctttccac aggctgaaac ttgtaaggta cagtcaaacc  1020
gcgtgttctg tgatactatg aattctcgta ctcttcccag cgaggttaat ctctgcaacg  1080
tcgacatttt caatcctaaa tatgactgca agatcatgac cagcaagacc gacgtctcca  1140
gctcagtaat cactagccta ggggccattg taagctgcta tggcaaaacc aagtgtactg  1200
cctctaataa gaacagaggc ataattaaaa ccttttcaaa tggctgtgac tatgtgtcga  1260
ataagggcgt cgacacggtc tcagtaggga ataccctcta ctgcgttaac aaacaggaag  1320
gcaaatccct ttatgtaaag ggcgagccca tcataaattt ctacgaccca cttgtgttcc  1380
ccagtgatga attcgatgca tcaatctccc aggtgaacga aaagatcaat caatcccttg  1440
cttttatacg aaagtcagat gaactcctgt ccgccatcgg tggctatatc ccagaagccc  1500
caagagacgg acaagcgtac gtccggaaag atggtgagtg ggtcctcctc tctacctttc  1560
tttgataata ggctggagcc tcggtggcca tgcttcttgc cccttgggcc tccccccagc  1620
ccctcctccc cttcctgcac ccgtaccccc gtggtctttg aataaagtct gagtgggcgg  1680
c                                                                   1681

SEQ ID NO: 13          moltype = RNA  length = 1515
FEATURE                Location/Qualifiers
misc_feature           1..1515
                       note = Synthetic Polynucleotide
source                 1..1515
                       mol_type = other RNA
                       organism = synthetic construct
SEQUENCE: 13
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa aaacgctgtg accgagctgc agttattgat gcagagtaca  300
cctgccaccg ggtcgggctc tgccatttgc tccggcgtgg ctgtatgtaa agttctccac  360
ctcgagggag aggttaataa gattaagtcg gccctgctga gtactaacaa agcagtggtg  420
tcgctgagta acggagtaag tgtgttaaca tttaaggtgc tggacctcaa gaattatatt  480
gacaaacagt tgcttcctat tctaaacaaa cagagctgtt caataagtaa tattgaaact  540
gttattgagt ttcagcagaa gaacaacagg cttcttgaga ttacacgcga gttcagtgtc  600
aatgccggcg ttacaacacc cgtgtctacc tacatgctga cgaattctga gcttctctct  660
ctcataaacg acatgcccat tacgaatgac caaaaaaaac ttatgtccaa caacgtgcag  720
attgtgcgac agcaatccta tagcattatg tgtatcatca aggaagaggt actcgcttat  780
gttgtgcagc taccactcta tggtgtgatt gacaccccct gttggaagct gcataccagt  840
ccactctgca ccactaacac aaaggaaggg agcaatattt gcctcactcg aaccgacagg  900
gggtggtatt gcgataatgc gggctccgtg tccttctttc cacaggctga aacttgtaag  960
gtacagtcaa accgcgtgtt ctgtgatact atgaattctc gtactcttcc cagcgaggtt  1020
aatctctgca acgtcgacat tttcaatcct aaatatgact gcaagatcat gaccagcaag  1080
accgacgtct ccagctcagt aatcactagc ctaggggcca ttgtaagctg ctatggcaaa  1140
accaagtgta ctgcctctaa taagaacaga ggcataatta aaaccttttc aaatggctgt  1200
gactatgtgt cgaataaggg cgtcgacacg gtctcagtag ggaataccct ctactgcgtt  1260
aacaaacagg aaggcaaatc cctttatgta aagggcgagc ccatcataaa tttctacgac  1320
ccacttgtgt tccccagtga tgaattcgat gcatcaatct cccaggtgaa cgaaaagatc  1380
aatcaatccc ttgcttttat acgaaagtca gatgaactcc tgtccgccat cggtggctat  1440
atcccagaag ccccaagaga cggacaagcg tacgtccgga aagatggtga gtgggtcctc  1500
ctctctacct ttctt                                                    1515

SEQ ID NO: 14          moltype = AA  length = 505
FEATURE                Location/Qualifiers
REGION                 1..505
                       note = Synthetic Polypeptide
```

-continued

```
source                  1..505
                        mol_type = protein
                        organism = synthetic construct
SEQUENCE: 14
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATGSGSAIC SGVAVCKVLH  120
LEGEVNKIKS ALLSTNKAVV SLSNGVSVLT FKVLDLKNYI DKQLLPILNK QSCSISNIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGKSLYV KGEPIINFYD PLVFPSDEFD ASISQVNEKI NQSLAFIRKS DELLSAIGGY  480
IPEAPRDGQA YVRKDGEWVL LSTFL                                       505

SEQ ID NO: 15           moltype = RNA  length = 1684
FEATURE                 Location/Qualifiers
misc_feature            1..1684
                        note = Synthetic Polynucleotide
source                  1..1684
                        mol_type = other RNA
                        organism = synthetic construct
SEQUENCE: 15
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataaaaa cgctgtgacc gagctgcagt tattgatgca gagtacacct gccaccgggt  360
cgggctctgc cattgcttcc ggcgtggctg tatgtaaagt tctccacctc gagggagagg  420
ttaataagat taagtcggcc ctgctgagta ctaacaaagc agtggtgtcg ctgagtggct  480
gcggagtaag tgtgttaaca tttaaggtgc tggacctcaa gaattatatt gacaaacagt  540
tgcttcctat tctaaacaaa cagagctgtt caataagtaa tattgaaact gttattgagt  600
ttcagcagaa gaacaacagg cttcttgaga ttacacgcga gttcagtgtc aatgccggcg  660
ttacaacacc cgtgtctacc tacatgctga cgaattctga gcttctctct ctcataaacg  720
acatgcccat tacgaatgac caaaaaaaac ttatgtccaa caacgtgcag attgtgcgac  780
agcaatccta tagcattatg tgtatcatca aggaagaggt actcgcttat gttgtgcagc  840
taccactcta tggtgtgatt gacacccccct gttggaagct gcataccagt ccactctgca  900
ccactaacac aaaggaaggg agcaatattt gcctcactcg aaccgacagg gggtggtatt  960
gcgataatgc gggctccgtg tccttctttc cacaggctga aacttgtaag gtacagtcaa  1020
accgcgtgtt ctgtgatact atgaattctc gtactcttcc cagcgaggtt aatctctgca  1080
acgtcgacat tttcaatcct aaatatgact gcaagatcat gaccagcaag accgacgtct  1140
ccagctcagt aatcactagc ctaggggcca ttgtaagctg ctatggcaaa accaagtgta  1200
ctgcctctaa taagtgcaga ggcataatta aaacctttc aaatggctgt gactatgtgt  1260
cgaataaggg cgtcgacacg gtctcagtag ggaataccct ctactacgtt aacaaacagg  1320
aaggcaaatc cctttatgta aagggcgagc ccatcataaa tttctacgac ccacttgtgt  1380
tccccagtga tgaattcgat gcatcaatct cccaggtgaa cgaaaagatc aatcaatccc  1440
ttgcttttat acgaaagtca gatgaactcc tgtccgccat cggtggctat atcccagaag  1500
ccccaagaga cggacaagcg tacgtccgga aagatggtga gtgggtcctc ctctctacct  1560
ttctttgata ataggctgga gcctcggtgg ccatgcttct tgccccttgg gcctcccccc  1620
agcccctcct ccccttcctg cacccgtacc cccgtggtct ttgaataaag tctgagtggg  1680
cggc                                                              1684

SEQ ID NO: 16           moltype = RNA  length = 1518
FEATURE                 Location/Qualifiers
misc_feature            1..1518
                        note = Synthetic Polynucleotide
source                  1..1518
                        mol_type = other RNA
                        organism = synthetic construct
SEQUENCE: 16
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa aaacgctgtg accgagctgc agttattgat gcagagtaca  300
cctgccaccg ggtcgggctc tgccattgct tccggcgtgg ctgtatgtaa agttctccac  360
ctcgagggag aggttaataa gattaagtcg gccctgctga gtactaacaa agcagtggtg  420
tcgctgagtg gctgcggagt aagtgtgtta acatttaagg tgctggacct caagaattat  480
attgacaaac agttgcttcc tattctaaac aaacagagct gttcaataag taatattgaa  540
actgttattg agtttcagca gaagaacaac aggcttcttg agattacacg cgagttcagt  600
gtcaatgccg gcgttacaac acccgtgtct acctacatgc tgacgaattc tgagcttctc  660
tctctcataa acgacatgcc cattacgaat gaccaaaaaa aacttatgtc caacaacgtg  720
cagattgtgc gacagcaatc ctatagcatt atgtgtatca tcaaggaaga ggtactcgct  780
tatgttgtgc agctaccact ctatggtgtg attgacaccc cctgttggaa gctgcatacc  840
agtccactct gcaccactaa cacaaaggaa gggagcaata tttgcctcac tcgaaccgac  900
agggggtggt attgcgataa tgcgggctcc gtgtccttct ttccacaggc tgaaacttgt  960
aaggtacagt caaaccgcgt gttctgtgat actatgaatt ctcgtactct tcccagcgag  1020
gttaatctct gcaacgtcga cattttcaat cctaaatatg actgcaagat catgaccagc  1080
aagaccgacg tctccagctc agtaatcact agcctagggg ccattgtaag ctgctatggc  1140
```

```
aaaaccaagt gtactgcctc taataagtgc agaggcataa ttaaaacctt ttcaaatggc  1200
tgtgactatg tgtcgaataa gggcgtcgac acggtctcag tagggaatac cctctactac  1260
gttaacaaac aggaaggcaa atccctttat gtaaagggcg agcccatcat aaatttctac  1320
gacccacttg tgttccccag tgatgaattc gatgcatcaa tctcccaggt gaacgaaaag  1380
atcaatcaat cccttgcttt tatacgaaag tcagatgaac tcctgtccgc catcggtggc  1440
tatatcccag aagccccaag agacggacaa gcgtacgtcc ggaaagatgg tgagtgggtc  1500
ctcctctcta cctttctt                                                 1518

SEQ ID NO: 17          moltype = AA  length = 506
FEATURE                Location/Qualifiers
REGION                 1..506
                       note = Synthetic Polypeptide
source                 1..506
                       mol_type = protein
                       organism = synthetic construct
SEQUENCE: 17
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATGSGSAIA SGVAVCKVLH  120
LEGEVNKIKS ALLSTNKAVV SLSGCGVSVL TFKVLDLKNY IDKQLLPILN KQSCSISNIE  180
TVIEFQQKNN RLLEITREFS VNAGVTTPVS TYMLTNSELL SLINDMPITN DQKKLMSNNV  240
QIVRQQSYSI MCIIKEEVLA YVVQLPLYGV IDTPCWKLHT SPLCTTNTKE GSNICLTRTD  300
RGWYCDNAGS VSFFPQAETC KVQSNRVFCD TMNSRTLPSE VNLCNVDIFN PKYDCKIMTS  360
KTDVSSSVIT SLGAIVSCYG KTKCTASNKC RGIIKTFSNG CDYVSNKGVD TVSVGNTLYY  420
VNKQEGKSLY VKGEPIINFY DPLVFPSDEF DASISQVNEK INQSLAFIRK SDELLSAIGG  480
YIPEAPRDGQ AYVRKDGEWV LLSTFL                                        506

SEQ ID NO: 18          moltype = RNA  length = 1687
FEATURE                Location/Qualifiers
misc_feature           1..1687
                       note = Synthetic Polynucleotide
source                 1..1687
                       mol_type = other RNA
                       organism = synthetic construct
SEQUENCE: 18
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataaaaa cgctgtgacc gagctgcagt tattgatgca gagtacacct gccaccaata  360
acgggtcggg ctctgccatt gcttccggcg tggctgtatg taaagttctc cacctcgagg  420
gagaggttaa taagattaag tcggccctgc tgagtactaa caaagcagtg gtgtcgctga  480
gtaacggagt aagtgtgtta acatttaagg tgctggacct caagaattat attgacaaac  540
agttgcttcc tattctaaac aaacagagct gttcaataag taatattgaa actgttattg  600
agtttcagca gaagaacaac aggcttcttg agattacacg cgagttcagt gtcaatgccg  660
gcgttacaac acccgtgtct acctacatgc tgacgaattc tgagcttctc tctctcataa  720
acgacatgcc cattacgaat gaccaaaaaa aacttatgtc caacaacgtg cagattgtgc  780
gacagcaatc ctatagcatt atgtgtatca tcaaggaaga ggtactcgct tatgttgtgc  840
agctaccact ctatggtgtg attgacaccc cctgttggaa gctgcatacc agtccactct  900
gcaccactaa cacaaaggaa gggagcaata tttgcctcac tcgaaccgac agggggtggt  960
attgcgataa tgcgggctcc gtgtccttct ttccacaggc tgaaacttgt aaggtacagt  1020
caaaccgcgt gttctgtgat actatgaatt ctcgtactct tcccagcgag gttaatctct  1080
gcaacgtcga cattttcaat cctaaatatg actgcaagat catgaccagc aagaccgacg  1140
tctccagctc agtaatcact agcctagggg ccattgtaag ctgctatggc aaaaccaagt  1200
gtactgcctc taataagaac agaggcataa ttaaaacctt ttcaaatggc tgtgactatg  1260
tgtcgaataa gggcgtcgac acggtctcag tagggaatac cctctactac gttaacaaac  1320
aggaaggcaa atccctttat gtaaagggcg agcccatcat aaatttctac gacccacttg  1380
tgttccccag tgatgaattc gatgcatcaa tctcccaggt gaacgaaaag atcaatcaat  1440
cccttgcttt tatacgaaag tcagatgaac tcctgtccgc catcggtggc tatatcccag  1500
aagccccaag agacggacaa gcgtacgtcc ggaaagatgg tgagtgggtc ctcctctcta  1560
cctttctttg ataataggct ggagcctcgg tggccatgct tcttgcccct tgggcctccc  1620
cccagcccct cctccccttc ctgcacccgt acccccgtgg tctttgaata aagtctgagt  1680
gggcggc                                                             1687

SEQ ID NO: 19          moltype = RNA  length = 1521
FEATURE                Location/Qualifiers
misc_feature           1..1521
                       note = Synthetic Polynucleotide
source                 1..1521
                       mol_type = other RNA
                       organism = synthetic construct
SEQUENCE: 19
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa aaacgctgtg accgagctgc agttattgat gcagagtaca  300
cctgccacca ataacgggtc gggctctgcc attgcttccg gcgtggctgt atgtaaagtt  360
ctccacctcg agggagaggt taataagatt aagtcggccc tgctgagtac taacaaagca  420
```

-continued

```
gtggtgtcgc tgagtaacgg agtaagtgtg ttaacattta aggtgctgga cctcaagaat  480
tatattgaca aacagttgct tcctattcta aacaaacaga gctgttcaat aagtaatatt  540
gaaactgtta ttgagtttca gcagaagaac aacaggcttc ttgagattac acgcgagttc  600
agtgtcaatg ccggcgttac aacacccgtg tctacctaca tgctgacgaa ttctgagctt  660
ctctctctca taaacgacat gcccattacg aatgaccaaa aaaaacttat gtccaacaac  720
gtgcagattg tgcgacagca atcctatagc attatgtgta tcatcaagga agaggtactc  780
gcttatgttg tgcagctacc actctatggt gtgattgaca ccccctgttg gaagctgcat  840
accagtccac tctgcaccac taacacaaag gaagggagca atatttgcct cactcgaacc  900
gacaggggt ggtattgcga taatgcgggc tccgtgtcct tctttccaca ggctgaaact  960
tgtaaggtac agtcaaaccg cgtgttctgt gatactatga attctcgtac tcttcccagc  1020
gaggttaatc tctgcaacgt cgacattttc aatcctaaat atgactgcaa gatcatgacc  1080
agcaagaccg acgtctccag ctcagtaatc actagcctag gggccattgt aagctgctat  1140
ggcaaaacca agtgtactgc ctctaataag aacagaggca taattaaaac cttttcaaat  1200
ggctgtgact atgtgtcgaa taagggcgtc gacacggtct cagtagggaa taccctctac  1260
tacgttaaca aacaggaagg caaatccctt tatgtaaagg gcgagcccat cataaatttc  1320
tacgacccac ttgtgttccc cagtgatgaa ttcgatgcat caatctccca ggtgaacgaa  1380
aagatcaatc aatcccttgc ttttatacga aagtcagatg aactcctgtc cgccatcggt  1440
ggctatatcc cagaagcccc aagagacgga caagcgtacg tccggaaaga tggtgagtgg  1500
gtcctcctct ctacctttct t                                            1521

SEQ ID NO: 20          moltype = AA  length = 507
FEATURE                Location/Qualifiers
REGION                 1..507
                       note = Synthetic Polypeptide
source                 1..507
                       mol_type = protein
                       organism = synthetic construct
SEQUENCE: 20
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNGSGSA IASGVAVCKV  120
LHLEGEVNKI KSALLSTNKA VVSLSNGVSV LTFKVLDLKN YIDKQLLPIL NKQSCSISNI  180
ETVIEFQQKN NRLLEITREF SVNAGVTTPV STYMLTNSEL LSLINDMPIT NDQKKLMSNN  240
VQIVRQQSYS IMCIIKEEVL AYVVQLPLYG VIDTPCWKLH TSPLCTTNTK EGSNICLTRT  300
DRGWYCDNAG SVSFFPQAET CKVQSNRVFC DTMNSRTLPS EVNLCNVDIF NPKYDCKIMT  360
SKTDVSSSVI TSLGAIVSCY GKTKCTASNK NRGIIKTFSN GCDYVSNKGV DTVSVGNTLY  420
YVNKQEGKSL YVKGEPIINF YDPLVFPSDE FDASISQVNE KINQSLAFIR KSDELLSAIG  480
GYIPEAPRDG QAYVRKDGEW VLLSTFL                                      507

SEQ ID NO: 21          moltype = RNA  length = 1771
FEATURE                Location/Qualifiers
misc_feature           1..1771
                       note = Synthetic Polynucleotide
source                 1..1771
                       mol_type = other RNA
                       organism = synthetic construct
SEQUENCE: 21
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatgca gagtacacct gccaccgggt  360
cgggctctgc catttgctcc ggcgtggctg tatgtaaagt tctccacctc gagggagagg  420
ttaataagat taagtcggcc ctgctgagta ctaacaaagc agtggtgtcg ctgagtaacg  480
gagtaagtgt gttaacattt aaggtgctgg acctcaagaa ttatattgac aaacagttgc  540
ttcctattct aaacaaacag agctgttcaa taagtaatat tgaaactgtt attgagtttc  600
agcagaagaa caacaggctt cttgagatta cacgcgagtt cagtgtcaat gccggcgtta  660
caacacccgt gtctacctac atgctgacga attctgagct tctctctctc ataaacgaca  720
tgcccattac gaatgaccaa aagaaactta tgtccaacaa cgtgcagatt gtgcgacagc  780
aatcctatag cattatgtgt atcatcaagg aagaggtact cgcttatgtt gtgcagctac  840
cactctatgg tgtgattgac accccctgtt ggaagctgca taccagtcca ctctgcacca  900
ctaacacaaa ggaagggagc aatatttgcc tcactcgaac cgacaggggg tggtattgcg  960
ataatgcggg ctccgtgtcc ttctttccac aggctgaaac ttgtaaggta cagtcaaacc  1020
gcgtgttctg tgatactatg aattctcgta ctcttcccag cgaggttaat ctctgcaacg  1080
tcgacatttt caatcctaaa tatgactgca agatcatgac cagcaagacc gacgtctcca  1140
gctcagtaat cactagccta ggggccattg taagctgcta tggcaaaacc aagtgtactg  1200
cctctaataa gaacagaggc ataattaaaa ccttttcaaa tggctgtgac tatgtgtcga  1260
ataagggcgt cgacacggtc tcagtaggga ataccctcta ctacgttaac aaacaggaag  1320
gcaaatccct ttatgtaaag ggcgagccca tcataaattt ctacgaccca cttgtgttcc  1380
ccagtgatga attcgatgca tcaatctccc aggtgaacga aaagatcaat caatcccttg  1440
cttttatacg aaagtcagat gaactcctgc ataacgtgaa tgctgggaaa tctacaacca  1500
acatcatgat cactaccatc attattgtga ttatcgtaat tctgctatcc ttgattgctg  1560
tcgggctgct tctgtactgt aaggccagat cgacgcctgt gaccctttca aaagaccaac  1620
ttagcggtat caataatatt gcctttagca attgataata ggctggagcc tcggtggcca  1680
tgcttcttgc cccttgggcc tcccccagc ccctcctccc cttcctgcac ccgtaccccc  1740
gtggtctttg aataaagtct gagtgggcgg c                                 1771

SEQ ID NO: 22          moltype = RNA  length = 1605
FEATURE                Location/Qualifiers
```

-continued

```
misc_feature            1..1605
                        note = Synthetic Polynucleotide
source                  1..1605
                        mol_type = other RNA
                        organism = synthetic construct
SEQUENCE: 22
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gcagagtaca  300
cctgccaccg ggtcgggctc tgccatttgc tccggcgtgg ctgtatgtaa agttctccac  360
ctcgagggag aggttaataa gattaagtcg gccctgctga gtactaacaa agcagtggtg  420
tcgctgagta acggagtaag tgtgttaaca tttaaggtgc tggacctcaa gaattatatt  480
gacaaacagt tgcttcctat tctaaacaaa cagagctgtt caataagtaa tattgaaact  540
gttattgagt ttcagcagaa gaacaacagg cttcttgaga ttacacgcga gttcagtgtc  600
aatgccggcg ttacaacacc cgtgtctacc tacatgctga cgaattctga gcttctctct  660
ctcataaacg acatgcccat tacgaatgac caaaagaaac ttatgtccaa caacgtgcag  720
attgtgcgac agcaatccta tagcattatg tgtatcatca aggaagaggt actcgcttat  780
gttgtgcagc taccactcta tggtgtgatt gacacccccct gttggaagct gcataccagt  840
ccactctgca ccactaacac aaaggaaggg agcaatattt gcctcactcg aaccgacagg  900
gggtggtatt gcgataatgc gggctccgtg tccttctttc cacaggctga aacttgtaag  960
gtacagtcaa accgcgtgtt ctgtgatact atgaattctc gtactcttcc cagcgaggtt  1020
aatctctgca acgtcgacat tttcaatcct aaatatgact gcaagatcat gaccagcaag  1080
accgacgtct ccagctcagt aatcactagc ctaggggcca ttgtaagctg ctatggcaaa  1140
accaagtgta ctgcctctaa taagaacaga ggcataatta aaacctttc aaatggctgt  1200
gactatgtgt cgaataaggg cgtcgacacg gtctcagtag ggaataccct ctactgcgtt  1260
aacaaacagg aaggcaaatc cctttatgta aagggcgagc ccatcataaa tttctacgac  1320
ccacttgtgt tccccagtga tgaattcgat gcatcaatct cccaggtgaa cgaaaagatc  1380
aatcaatccc ttgcttttat acgaaagtca gatgaactcc tgcataacgt gaatgctggg  1440
aaatctacaa ccaacatcat gatcactacc atcattattg tgattatcgt aattctgcta  1500
tccttgattg ctgtcgggct gcttctgtac tgtaaggcca gatcgacgcc tgtgaccctt  1560
tcaaaagacc aacttagcgg tatcaataat attgccttta gcaat                  1605

SEQ ID NO: 23           moltype = RNA  length = 1774
FEATURE                 Location/Qualifiers
misc_feature            1..1774
                        note = Synthetic Polynucleotide
source                  1..1774
                        mol_type = other RNA
                        organism = synthetic construct
SEQUENCE: 23
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatgca gagtacacct gccaccgggt  360
cgggctctgc cattgcttcc ggcgtggctg tatgtaaagt tctccacctc gagggagagg  420
ttaataagat taagtcggcc ctgctgagta ctaacaaagc agtggtgtcg ctgagtggct  480
gcggagtaag tgtgttaaca tttaaggtgc tggacctcaa gaattatatt gacaaacagt  540
tgcttcctat tctaaacaaa cagagctgtt caataagtaa tattgaaact gttattgagt  600
ttcagcagaa gaacaacagg cttcttgaga ttacacgcga gttcagtgtc aatgccggcg  660
ttacaacacc cgtgtctacc tacatgctga cgaattctga gcttctctct ctcataaacg  720
acatgcccat tacgaatgac caaaagaaac ttatgtccaa caacgtgcag attgtgcgac  780
agcaatccta tagcattatg tgtatcatca aggaagaggt actcgcttat gttgtgcagc  840
taccactcta tggtgtgatt gacacccccct gttggaagct gcataccagt ccactctgca  900
ccactaacac aaaggaaggg agcaatattt gcctcactcg aaccgacagg gggtggtatt  960
gcgataatgc gggctccgtg tccttctttc cacaggctga aacttgtaag gtacagtcaa  1020
accgcgtgtt ctgtgatact atgaattctc gtactcttcc cagcgaggtt aatctctgca  1080
acgtcgacat tttcaatcct aaatatgact gcaagatcat gaccagcaag accgacgtct  1140
ccagctcagt aatcactagc ctaggggcca ttgtaagctg ctatggcaaa accaagtgta  1200
ctgcctctaa taagtgcaga ggcataatta aaacctttc aaatggctgt gactatgtgt  1260
cgaataaggg cgtcgacacg gtctcagtag ggaataccct ctactacgtt aacaaacagg  1320
aaggcaaatc cctttatgta aagggcgagc ccatcataaa tttctacgac ccacttgtgt  1380
tccccagtga tgaattcgat gcatcaatct cccaggtgaa cgaaaagatc aatcaatccc  1440
ttgcttttat acgaaagtca gatgaactcc tgcataacgt gaatgctggg aaatctacaa  1500
ccaacatcat gatcactacc atcattattg tgattatcgt aattctgcta tccttgattg  1560
ctgtcgggct gcttctgtac tgtaaggcca gatcgacgcc tgtgaccctt tcaaaagacc  1620
aacttagcgg tatcaataat attgccttta gcaattgata ataggctgga gcctcggtgg  1680
ccatgcttct tgccccttgg gcctcccccc agcccctcct ccccttcctg cacccgtacc  1740
cccgtggtct ttgaataaag tctgagtggg cggc                              1774

SEQ ID NO: 24           moltype = RNA  length = 1608
FEATURE                 Location/Qualifiers
misc_feature            1..1608
                        note = Synthetic Polynucleotide
source                  1..1608
                        mol_type = other RNA
```

```
                        organism = synthetic construct
SEQUENCE: 24
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gcagagtaca  300
cctgccaccg ggtcgggctc tgccattgct tccggcgtgg ctgtatgtaa agttctccac  360
ctcgagggag aggttaataa gattaagtcg gccctgctga gtactaacaa agcagtggtg  420
tcgctgagtg gctgcggagt aagtgtgtta acatttaagg tgctggacct caagaattat  480
attgacaaac agttgcttcc tattctaaac aaacagagct gttcaataag taatattgaa  540
actgttattg agtttcagca gaagaacaac aggcttcttg agattacacg cgagttcagt  600
gtcaatgccg gcgttacaac acccgtgtct acctacatgc tgacgaattc tgagcttctc  660
tctctcataa acgacatgcc cattacgaat gaccaaaaga aacttatgtc caacaacgtg  720
cagattgtgc gacagcaatc ctatagcatt atgtgtatca tcaaggaaga ggtactcgct  780
tatgttgtgc agctaccact ctatggtgtg attgacaccc cctgttggaa gctgcatacc  840
agtccactct gcaccactaa cacaaaggaa gggagcaata tttgcctcac tcgaaccgac  900
agggggtggt attgcgataa tgcgggctcc gtgtccttct ttccacaggc tgaaacttgt  960
aaggtacagt caaaccgcgt gttctgtgat actatgaatt ctcgtactct tcccagcgag  1020
gttaatctct gcaacgtcga cattttcaat cctaaatatg actgcaagat catgaccagc  1080
aagaccgacg tctccagctc agtaatcact agcctagggg ccattgtaag ctgctatggc  1140
aaaaccaagt gtactgcctc taataagtgc agaggcataa ttaaaacctt ttcaaatggc  1200
tgtgactatg tgtcgaataa gggcgtcgac acggtctcag tagggaatac cctctactac  1260
gttaacaaac aggaaggcaa atccctttat gtaaagggcg agcccatcat aaatttctac  1320
gacccacttg tgttccccag tgatgaattc gatgcatcaa tctcccaggt gaacgaaaag  1380
atcaatcaat cccttgcttt tatacgaaag tcagatgaac tcctgcataa cgtgaatgct  1440
gggaaatcta caaccaacat catgatcact accatcatta ttgtgattat cgtaattctg  1500
ctatccttga ttgctgtcgg gctgcttctg tactgtaagg ccagatcgac gcctgtgacc  1560
ctttcaaaag accaacttag cggtatcaat aatattgcct ttagcaat             1608

SEQ ID NO: 25           moltype = RNA  length = 1777
FEATURE                 Location/Qualifiers
misc_feature            1..1777
                        note = Synthetic Polynucleotide
source                  1..1777
                        mol_type = other RNA
                        organism = synthetic construct
SEQUENCE: 25
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatgca gagtacacct gccaccaata  360
acgggtcggg ctctgccatt gcttccggcg tggctgtatg taaagttctc cacctcgagg  420
gagaggttaa taagattaag tcggccctgc tgagtactaa caaagcagtg gtgtcgctga  480
gtaacggagt aagtgtgtta acatttaagg tgctggacct caagaattat attgacaaac  540
agttgcttcc tattctaaac aaacagagct gttcaataag taatattgaa actgttattg  600
agtttcagca gaagaacaac aggcttcttg agattacacg cgagttcagt gtcaatgccg  660
gcgttacaac acccgtgtct acctacatgc tgacgaattc tgagcttctc tctctcataa  720
acgacatgcc cattacgaat gaccaaaaga aacttatgtc caacaacgtg cagattgtgc  780
gacagcaatc ctatagcatt atgtgtatca tcaaggaaga ggtactcgct tatgttgtgc  840
agctaccact ctatggtgtg attgacaccc cctgttggaa gctgcatacc agtccactct  900
gcaccactaa cacaaaggaa gggagcaata tttgcctcac tcgaaccgac agggggtggt  960
attgcgataa tgcgggctcc gtgtccttct ttccacaggc tgaaacttgt aaggtacagt  1020
caaaccgcgt gttctgtgat actatgaatt ctcgtactct tcccagcgag gttaatctct  1080
gcaacgtcga cattttcaat cctaaatatg actgcaagat catgaccagc aagaccgacg  1140
tctccagctc agtaatcact agcctagggg ccattgtaag ctgctatggc aaaaccaagt  1200
gtactgcctc taataagaac agaggcataa ttaaaacctt ttcaaatggc tgtgactatg  1260
tgtcgaataa gggcgtcgac acggtctcag tagggaatac cctctactac gttaacaaac  1320
aggaaggcaa atccctttat gtaaagggcg agcccatcat aaatttctac gacccacttg  1380
tgttccccag tgatgaattc gatgcatcaa tctcccaggt gaacgaaaag atcaatcaat  1440
cccttgcttt tatacgaaag tcagatgaac tcctgcataa cgtgaatgct gggaaatcta  1500
caaccaacat catgatcact accatcatta ttgtgattat cgtaattctg ctatccttga  1560
ttgctgtcgg gctgcttctg tactgtaagg ccagatcgac gcctgtgacc ctttcaaaag  1620
accaacttag cggtatcaat aatattgcct ttagcaattg ataataggct ggagcctcgg  1680
tggccatgct tcttgcccct tgggcctccc cccagcccct cctccccttc ctgcacccgt  1740
acccccgtgg tctttgaata aagtctgagt gggcggc                         1777

SEQ ID NO: 26           moltype = RNA  length = 1611
FEATURE                 Location/Qualifiers
misc_feature            1..1611
                        note = Synthetic Polynucleotide
source                  1..1611
                        mol_type = other RNA
                        organism = synthetic construct
SEQUENCE: 26
atggaactgc tcattttgaa ggcaaacgct atcacgacaa tactcactgc agtgaccttc  60
tgttttgcct caggccagaa cataaccgag gagttttatc aatctacatg cagcgctgta  120
```

```
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gcagagtaca  300
cctgccacca ataacgggtc gggctctgcc attgcttccg gcgtggctgt atgtaaagtt  360
ctccacctcg agggagaggt taataagatt aagtcggccc tgctgagtac taacaaagca  420
gtggtgtcgc tgagtaacgg agtaagtgtg ttaacattta aggtgctgga cctcaagaat  480
tatattgaca aacagttgct tcctattcta aacaaacaga gctgttcaat aagtaatatt  540
gaaactgtta ttgagtttca gcagaagaac aacaggcttc ttgagattac acgcgagttc  600
agtgtcaatg ccggcgttac aacacccgtg tctacctaca tgctgacgaa ttctgagctt  660
ctctctctca taaacgacat gcccattacg aatgaccaaa agaaacttat gtccaacaac  720
gtgcagattg tgcgacagca atcctatagc attatgtgta tcatcaagga agaggtactc  780
gcttatgttg tgcagctacc actctatggt gtgattgaca ccccctgttg gaagctgcat  840
accagtccac tctgcaccac taacacaaag gaagggagca atatttgcct cactcgaacc  900
gacaggggt ggtattgcga taatgcgggc tccgtgtcct tctttccaca ggctgaaact  960
tgtaaggtac agtcaaaccg cgtgttctgt gatactatga attctcgtac tcttcccagc  1020
gaggttaatc tctgcaacgt cgacattttc aatcctaaat atgactgcaa gatcatgacc  1080
agcaagaccg acgtctccag ctcagtaatc actagcctag gggccattgt aagctgctat  1140
ggcaaaacca agtgtactgc ctctaataag aacagaggca taattaaaac cttttcaaat  1200
ggctgtgact atgtgtcgaa taagggcgtc gacacggtct cagtagggaa taccctctac  1260
tacgttaaca aacaggaagg caaatccctt tatgtaaagg gcgagcccat cataaatttc  1320
tacgacccac ttgtgttccc cagtgatgaa ttcgatgcat caatctccca ggtgaacgaa  1380
aagatcaatc aatcccttgc ttttatacga aagtcagatg aactcctgca taacgtgaat  1440
gctgggaaat ctacaaccaa catcatgatc actaccatca ttattgtgat tatcgtaatt  1500
ctgctatcct tgattgctgt cggcctgctt ctgtactgta aggccagatc gacgcctgtg  1560
accctttcaa aagaccaact tagcggtatc aataatattg cctttagcaa t            1611

SEQ ID NO: 27          moltype = RNA  length = 1681
FEATURE                Location/Qualifiers
misc_feature           1..1681
                       note = Synthetic Polynucleotide
source                 1..1681
                       mol_type = other RNA
                       organism = synthetic construct
SEQUENCE: 27
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatgca gagtacacct gccaccgggt  360
cgggctctgc catttgctcc ggcgtggctg tatgtaaagt tctccacctc gagggagagg  420
ttaataagat taagtcggcc ctgctgagta ctaacaaagc agtggtgtcg ctgagtaacg  480
gagtaagtgt gttaacattt aaggtgctgg acctcaagaa ttatattgac aaacagttgc  540
ttcctattct aaacaaacag agctgttcaa taagtaatat tgaaactgtt attgagtttc  600
agcagaagaa caacaggctt cttgagatta cacgcgagtt cagtgtcaat gccggcgtta  660
caacacccgt gtctacctac atgctgacga attctgagct tctctctctc ataaacgaca  720
tgcccattac gaatgaccaa aagaaactta tgtccaacaa cgtgcagatt gtgcgacagc  780
aatcctatag cattatgtgt atcatcaagg aagaggtact cgcttatgtt gtgcagctac  840
cactctatgg tgtgattgac accccctgtt ggaagctgca taccagtcca ctctgcacca  900
ctaacacaaa ggaagggagc aatatttgcc tcactcgaac cgacaggggg tggtattgcg  960
ataatgcggg ctccgtgtcc ttctttccac aggctgaaac ttgtaaggta cagtcaaacc  1020
gcgtgttctg tgatactatg aattctcgta ctcttcccag cgaggttaat ctctgcaacg  1080
tcgacatttt caatcctaaa tatgactgca agatcatgac cagcaagacc gacgtctcca  1140
gctcagtaat cactagccta ggggccattg taagctgcta tggcaaaacc aagtgtactg  1200
cctctaataa gaacagaggc ataattaaaa ccttttcaaa tggctgtgac tatgtgtcga  1260
ataagggcgt cgacacggtc tcagtaggga ataccctcta ctacgttaac aaacaggaag  1320
gcaaatccct ttatgtaaag ggcgagccca tcataaattt ctacgaccca cttgtgttcc  1380
ccagtgatga attcgatgca tcaatctccc aggtgaacga aaagatcaat caatcccttg  1440
cttttatacg aaagtcagat gaactcctgt ccgccatcgg tggctatatc ccagaagccc  1500
caagagacgg acaagcgtac gtccggaaag atggtgagtg ggtcctcctc tctacctttc  1560
tttgataata ggctggagcc tcggtggcca tgcttcttgc cccttgggcc tccccccagc  1620
ccctcctccc cttcctgcac ccgtaccccc gtggtctttg aataaagtct gagtgggcgg  1680
c                                                                  1681

SEQ ID NO: 28          moltype = RNA  length = 1515
FEATURE                Location/Qualifiers
misc_feature           1..1515
                       note = Synthetic Polynucleotide
source                 1..1515
                       mol_type = other RNA
                       organism = synthetic construct
SEQUENCE: 28
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gcagagtaca  300
cctgccaccg ggtcgggctc tgccatttgc tccggcgtgg ctgtatgtaa agttctccac  360
ctcgagggag aggttaataa gattaagtcg gccctgctga gtactaacaa agcagtggtg  420
```

```
tcgctgagta acggagtaag tgtgttaaca tttaaggtgc tggacctcaa gaattatatt  480
gacaaacagt tgcttcctat tctaaacaaa cagagctgtt caataagtaa tattgaaact  540
gttattgagt ttcagcagaa gaacaacagg cttcttgaga ttacacgcga gttcagtgtc  600
aatgccggcg ttacaacacc cgtgtctacc tacatgctga cgaattctga gcttctctct  660
ctcataaacg acatgcccat tacgaatgac caaaagaaac ttatgtccaa caacgtgcag  720
attgtgcgac agcaatccta tagcattatg tgtatcatca aggaagaggt actcgcttat  780
gttgtgcagc taccactcta tggtgtgatt gacacccccct gttggaagct gcataccagt  840
ccactctgca ccactaacac aaaggaaggg agcaatattt gcctcactcg aaccgacagg  900
gggtggtatt gcgataatgc gggctccgtg tccttctttc cacaggctga aacttgtaag  960
gtacagtcaa accgcgtgtt ctgtgatact atgaattctc gtactcttcc cagcgaggtt  1020
aatctctgca acgtcgacat tttcaatcct aaatatgact gcaagatcat gaccagcaag  1080
accgacgtct ccagctcagt aatcactagc ctaggggcca ttgtaagctg ctatggcaaa  1140
accaagtgta ctgcctctaa taagaacaga ggcataatta aaaccttttc aaatggctgt  1200
gactatgtgt cgaataaggg cgtcgacacg gtctcagtag ggaataccct ctactgcgtt  1260
aacaaacagg aaggcaaatc cctttatgta aagggcgagc ccatcataaa tttctacgac  1320
ccacttgtgt tccccagtga tgaattcgat gcatcaatct cccaggtgaa cgaaaagatc  1380
aatcaatccc ttgcttttat acgaaagtca gatgaactcc tgtccgccat cggtggctat  1440
atcccagaag ccccaagaga cggacaagcg tacgtccgga aagatggtga gtgggtcctc  1500
ctctctacct ttctt                                                  1515
```

```
SEQ ID NO: 29          moltype = RNA  length = 1684
FEATURE                Location/Qualifiers
misc_feature           1..1684
                       note = Synthetic Polynucleotide
source                 1..1684
                       mol_type = other RNA
                       organism = synthetic construct
SEQUENCE: 29
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatgca gagtacacct gccaccgggt  360
cgggctctgc cattgcttcc ggcgtggctg tatgtaaagt tctccacctc gagggagagg  420
ttaataagat taagtcggcc ctgctgagta ctaacaaagc agtggtgtcg ctgagtggct  480
gcggagtaag tgtgttaaca tttaaggtgc tggacctcaa gaattatatt gacaaacagt  540
tgcttcctat tctaaacaaa cagagctgtt caataagtaa tattgaaact gttattgagt  600
ttcagcagaa gaacaacagg cttcttgaga ttacacgcga gttcagtgtc aatgccggcg  660
ttacaacacc cgtgtctacc tacatgctga cgaattctga gcttctctct ctcataaacg  720
acatgcccat tacgaatgac caaaagaaac ttatgtccaa caacgtgcag attgtgcgac  780
agcaatccta tagcattatg tgtatcatca aggaagaggt actcgcttat gttgtgcagc  840
taccactcta tggtgtgatt gacacccccct gttggaagct gcataccagt ccactctgca  900
ccactaacac aaaggaaggg agcaatattt gcctcactcg aaccgacagg gggtggtatt  960
gcgataatgc gggctccgtg tccttctttc cacaggctga aacttgtaag gtacagtcaa  1020
accgcgtgtt ctgtgatact atgaattctc gtactcttcc cagcgaggtt aatctctgca  1080
acgtcgacat tttcaatcct aaatatgact gcaagatcat gaccagcaag accgacgtct  1140
ccagctcagt aatcactagc ctaggggcca ttgtaagctg ctatggcaaa accaagtgta  1200
ctgcctctaa taagtgcaga ggcataatta aaaccttttc aaatggctgt gactatgtgt  1260
cgaataaggg cgtcgacacg gtctcagtag ggaataccct ctactacgtt aacaaacagg  1320
aaggcaaatc cctttatgta aagggcgagc ccatcataaa tttctacgac ccacttgtgt  1380
tccccagtga tgaattcgat gcatcaatct cccaggtgaa cgaaaagatc aatcaatccc  1440
ttgcttttat acgaaagtca gatgaactcc tgtccgccat cggtggctat atcccagaag  1500
ccccaagaga cggacaagcg tacgtccgga aagatggtga gtgggtcctc ctctctacct  1560
ttctttgata ataggctgga gcctcggtgg ccatgcttct tgccccttgg gcctcccccc  1620
agcccctcct ccccttcctg cacccgtacc cccgtggtct ttgaataaag tctgagtggg  1680
cggc                                                              1684
```

```
SEQ ID NO: 30          moltype = RNA  length = 1518
FEATURE                Location/Qualifiers
misc_feature           1..1518
                       note = Synthetic Polynucleotide
source                 1..1518
                       mol_type = other RNA
                       organism = synthetic construct
SEQUENCE: 30
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gcagagtaca  300
cctgccaccg ggtcgggctc tgccattgct tccggcgtgg ctgtatgtaa agttctccac  360
ctcgagggag aggttaataa gattaagtcg gccctgctga gtactaacaa agcagtggtg  420
tcgctgagtg gctgcggagt aagtgtgtta acatttaagg tgctggacct caagaattat  480
attgacaaac agttgcttcc tattctaaac aaacagagct gttcaataag taatattgaa  540
actgttattg agtttcagca gaagaacaac aggcttcttg agattacacg cgagttcagt  600
gtcaatgccg gcgttacaac acccgtgtct acctacatgc tgacgaattc tgagcttctc  660
tctctcataa acgacatgcc cattacgaat gaccaaaaga aacttatgtc caacaacgtg  720
cagattgtgc gacagcaatc ctatagcatt atgtgtatca tcaaggaaga ggtactcgct  780
```

```
tatgttgtgc agctaccact ctatggtgtg attgacaccc cctgttggaa gctgcatacc  840
agtccactct gcaccactaa cacaaaggaa gggagcaata tttgcctcac tcgaaccgac  900
agggggtggt attgcgataa tgcgggctcc gtgtccttct ttccacaggc tgaaacttgt  960
aaggtacagt caaaccgcgt gttctgtgat actatgaatt ctcgtactct tcccagcgag  1020
gttaatctct gcaacgtcga cattttcaat cctaaatatg actgcaagat catgaccagc  1080
aagaccgacg tctccagctc agtaatcact agcctagggg ccattgtaag ctgctatggc  1140
aaaaccaagt gtactgcctc taataagtgc agaggcataa ttaaaacctt ttcaaatggc  1200
tgtgactatg tgtcgaataa gggcgtcgac acggtctcag tagggaatac cctctactac  1260
gttaacaaac aggaaggcaa atccctttat gtaaagggcg agcccatcat aaatttctac  1320
gacccacttg tgttccccag tgatgaattc gatgcatcaa tctcccaggt gaacgaaaag  1380
atcaatcaat cccttgcttt tatacgaaag tcagatgaac tcctgtccgc catcggtggc  1440
tatatcccag aagccccaag agacggacaa gcgtacgtcc ggaaagatgg tgagtgggtc  1500
ctcctctcta cctttctt                                                1518
```

```
SEQ ID NO: 31          moltype = RNA  length = 1687
FEATURE                Location/Qualifiers
misc_feature           1..1687
                       note = Synthetic Polynucleotide
source                 1..1687
                       mol_type = other RNA
                       organism = synthetic construct
SEQUENCE: 31
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatgca gagtacacct gccaccaata  360
acgggtcggg ctctgccatt gcttccggcg tggctgtatg taaagttctc cacctcgagg  420
gagaggttaa taagattaag tcggccctgc tgagtactaa caaagcagtg gtgtcgctga  480
gtaacggagt aagtgtgtta acatttaagg tgctggacct caagaattat attgacaaac  540
agttgcttcc tattctaaac aaacagagct gttcaataag taatattgaa actgttattg  600
agtttcagca gaagaacaac aggcttcttg agattacacg cgagttcagt gtcaatgccg  660
gcgttacaac acccgtgtct acctacatgc tgacgaattc tgagcttctc tctctcataa  720
acgacatgcc cattacgaat gaccaaaaga aacttatgtc caacaacgtg cagattgtgc  780
gacagcaatc ctatagcatt atgtgtatca tcaaggaaga ggtactcgct tatgttgtgc  840
agctaccact ctatggtgtg attgacaccc cctgttggaa gctgcatacc agtccactct  900
gcaccactaa cacaaaggaa gggagcaata tttgcctcac tcgaaccgac agggggtggt  960
attgcgataa tgcgggctcc gtgtccttct ttccacaggc tgaaacttgt aaggtacagt  1020
caaaccgcgt gttctgtgat actatgaatt ctcgtactct tcccagcgag gttaatctct  1080
gcaacgtcga cattttcaat cctaaatatg actgcaagat catgaccagc aagaccgacg  1140
tctccagctc agtaatcact agcctagggg ccattgtaag ctgctatggc aaaaccaagt  1200
gtactgcctc taataagaac agaggcataa ttaaaacctt ttcaaatggc tgtgactatg  1260
tgtcgaataa gggcgtcgac acggtctcag tagggaatac cctctactac gttaacaaac  1320
aggaaggcaa atccctttat gtaaagggcg agcccatcat aaatttctac gacccacttg  1380
tgttccccag tgatgaattc gatgcatcaa tctcccaggt gaacgaaaag atcaatcaat  1440
cccttgcttt tatacgaaag tcagatgaac tcctgtccgc catcggtggc tatatcccag  1500
aagccccaag agacggacaa gcgtacgtcc ggaaagatgg tgagtgggtc ctcctctcta  1560
cctttctttg ataataggct ggagcctcgg tggccatgct tcttgcccct tgggcctccc  1620
cccagcccct cctccccttc ctgcacccgt acccccgtgg tctttgaata aagtctgagt  1680
gggcggc                                                            1687
```

```
SEQ ID NO: 32          moltype = RNA  length = 1521
FEATURE                Location/Qualifiers
misc_feature           1..1521
                       note = Synthetic Polynucleotide
source                 1..1521
                       mol_type = other RNA
                       organism = synthetic construct
SEQUENCE: 32
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gcagagtaca  300
cctgccacca ataacgggtc gggctctgcc attgcttccg gcgtggctgt atgtaaagtt  360
ctccacctcg agggagaggt taataagatt aagtcggccc tgctgagtac taacaaagca  420
gtggtgtcgc tgagtaacgg agtaagtgtg ttaacattta aggtgctgga cctcaagaat  480
tatattgaca aacagttgct tcctattcta aacaaacaga gctgttcaat aagtaatatt  540
gaaactgtta ttgagtttca gcagaagaac aacaggcttc ttgagattac acgcgagttc  600
agtgtcaatg ccggcgttac aacacccgtg tctacctaca tgctgacgaa ttctgagctt  660
ctctctctca taaacgacat gcccattacg aatgaccaaa agaaacttat gtccaacaac  720
gtgcagattg tgcgacagca atcctatagc attatgtgta tcatcaagga agaggtactc  780
gcttatgttg tgcagctacc actctatggt gtgattgaca ccccctgttg gaagctgcat  840
accagtccac tctgcaccac taacacaaag gaagggagca atatttgcct cactcgaacc  900
gacagggggt ggtattgcga taatgcgggc tccgtgtcct tctttccaca ggctgaaact  960
tgtaaggtac agtcaaaccg cgtgttctgt gatactatga attctcgtac tcttcccagc  1020
gaggttaatc tctgcaacgt cgacattttc aatcctaaat atgactgcaa gatcatgacc  1080
agcaagaccg acgtctccag ctcagtaatc actagcctag ggccattgt aagctgctat  1140
```

```
ggcaaaacca agtgtactgc ctctaataag aacagaggca taattaaaac cttttcaaat  1200
ggctgtgact atgtgtcgaa taagggcgtc gacacggtct cagtagggaa taccctctac  1260
tacgttaaca aacaggaagg caaatccctt tatgtaaagg gcgagcccat cataaatttc  1320
tacgacccac ttgtgttccc cagtgatgaa ttcgatgcat caatctccca ggtgaacgaa  1380
aagatcaatc aatcccttgc ttttatacga aagtcagatg aactcctgtc cgccatcggt  1440
ggctatatcc cagaagcccc aagagacgga caagcgtacg tccggaaaga tggtgagtgg  1500
gtcctcctct ctacctttct t                                            1521

SEQ ID NO: 33          moltype = RNA  length = 1771
FEATURE                Location/Qualifiers
misc_feature           1..1771
                       note = Synthetic Polynucleotide
source                 1..1771
                       mol_type = other RNA
                       organism = synthetic construct
SEQUENCE: 33
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgggcgcgct ccgcacagga tggtacacct ccgtgatcac catcgagctc agcaatatta  240
aagagattaa gtgcaatggt accgacgcta aagtcaaact tatcaagcag gaactcgaca  300
aatataagaa cgctgtgacc gacctgcagt tattgatgca gagtacacct gccaccgggt  360
cgggctctgc catttgctcc ggcgtggctg tatgtaaagt tctccacctc gagggagagg  420
ttaataagat taagtcggcc ctgctgagta ctaacaaagc agtggtgtcg ctgagtaacg  480
gagtaagtgt gttaacattt aaggtgctgg acctcaagaa ttatattgac aaacagttgc  540
ttcctattct aaacaaacag agctgttcaa tacccaatat tgaaactgtt attgagtttc  600
agcagaagaa caacaggctt cttgagatta cacgcgagtt cagtgtcaat gccggcgtta  660
caacacccgt gtctacctac atgctgacga attctgagct tctctctctc ataaacgaca  720
tgcccattac gaatgaccaa aagaaactta tgtccaacaa cgtgcagatt gtgcgacagc  780
aatcctatag cattatgtgt atcatcaagg aagaggtact cgcttatgtt gtgcagctac  840
cactctatgg tgtgattgac accccctgtt ggaagctgca taccagtcca ctctgcacca  900
ctaacacaaa ggaagggagc aatatttgcc tcactcgaac cgacaggggg tggtattgcg  960
ataatgcggg ctccgtgtcc ttctttccac aggctgaaac ttgtaaggta cagtcaaacc  1020
gcgtgttctg tgatactatg aattctcgta ctcttcccag cgaggttaat ctctgcaacg  1080
tcgacatttt caatcctaaa tatgactgca agatcatgac cagcaagacc gacgtctcca  1140
gctcagtaat cactagccta ggggccattg taagctgcta tggcaaaacc aagtgtactg  1200
cctctaataa gaacagaggc ataattaaaa ccttttcaaa tggctgtgac tatgtgtcga  1260
ataagggcgt cgacacggtc tcagtaggga ataccctcta ctgcgttaac aaacaggaag  1320
gccagtccct ttatgtaaag ggcgagccca tcataaattt ctacgaccca cttgtgttcc  1380
ccagtgatga attcgatgca tcaatctccc aggtgaacga aaagatcaat caatcccttg  1440
cttttatacg aaagtcagat gaactcctgc ataacgtgaa tgctgggaaa tctacaacca  1500
acatcatgat cactaccatc attattgtga ttatcgtaat tctgctatcc ttgattgctg  1560
tcgggctgct tctgtactgt aaggccagat cgacgcctgt gaccctttca aaagaccaac  1620
ttagcggtat caataatatt gcctttagca attgataata ggctggagcc tcggtggcca  1680
tgcttcttgc cccttgggcc tccccccagc ccctcctccc cttcctgcac ccgtaccccc  1740
gtggtctttg aataaagtct gagtgggcgg c                                 1771

SEQ ID NO: 34          moltype = RNA  length = 1605
FEATURE                Location/Qualifiers
misc_feature           1..1605
                       note = Synthetic Polynucleotide
source                 1..1605
                       mol_type = other RNA
                       organism = synthetic construct
SEQUENCE: 34
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgggcgc gctccgcaca ggatggtaca cctccgtgat caccatcgag  180
ctcagcaata ttaaagagat taagtgcaat ggtaccgacg ctaaagtcaa acttatcaag  240
caggaactcg acaaatataa gaacgctgtg accgacctgc agttattgat gcagagtaca  300
cctgccaccg ggtcgggctc tgccatttgc tccggcgtgg ctgtatgtaa agttctccac  360
ctcgagggag aggttaataa gattaagtcg gccctgctga gtactaacaa agcagtggtg  420
tcgctgagta acggagtaag tgtgttaaca tttaaggtgc tggacctcaa gaattatatt  480
gacaaacagt tgcttcctat tctaaacaaa cagagctgtt caatacccaa tattgaaact  540
gttattgagt ttcagcagaa gaacaacagg cttcttgaga ttacacgcga gttcagtgtc  600
aatgccggcg ttacaacacc cgtgtctacc tacatgctga cgaattctga gcttctctct  660
ctcataaacg acatgcccat tacgaatgac caaaagaaac ttatgtccaa caacgtgcag  720
attgtgcgac agcaatccta tagcattatg tgtatcatca aggaagaggt actcgcttat  780
gttgtgcagc taccactcta tggtgtgatt gacaccccct gttggaagct gcataccagt  840
ccactctgca ccactaacac aaaggaaggg agcaatattt gcctcactcg aaccgacagg  900
gggtggtatt gcgataatgc gggctccgtg tccttctttc cacaggctga aacttgtaag  960
gtacagtcaa accgcgtgtt ctgtgatact atgaattctc gtactcttcc cagcgaggtt  1020
aatctctgca acgtcgacat tttcaatcct aaatatgact gcaagatcat gaccagcaag  1080
accgacgtct ccagctcagt aatcactagc ctaggggcca ttgtaagctg ctatggcaaa  1140
accaagtgta ctgcctctaa taagaacaga ggcataatta aaaccttttc aaatggctgt  1200
gactatgtgt cgaataaggg cgtcgacacg gtctcagtag ggaataccct ctactgcgtt  1260
aacaaacagg aaggccagtc cctttatgta aagggcgagc ccatcataaa tttctacgac  1320
ccacttgtgt tccccagtga tgaattcgat gcatcaatct cccaggtgaa cgaaaagatc  1380
aatcaatccc ttgcttttat acgaaagtca gatgaactcc tgcataacgt gaatgctggg  1440
```

```
aaatctacaa ccaacatcat gatcactacc atcattattg tgattatcgt aattctgcta  1500
tccttgattg ctgtcgggct gcttctgtac tgtaaggcca gatcgacgcc tgtgaccctt  1560
tcaaaagacc aacttagcgg tatcaataat attgccttta gcaat                  1605

SEQ ID NO: 35           moltype = AA  length = 535
FEATURE                 Location/Qualifiers
REGION                  1..535
                        note = Synthetic Polypeptide
source                  1..535
                        mol_type = protein
                        organism = synthetic construct
SEQUENCE: 35
MELLILKANA ITTILTAVTF CFASGQNITE EFYQSTCSAV SKGYLGALRT GWYTSVITIE  60
LSNIKEIKCN GTDAKVKLIK QELDKYKNAV TDLQLLMQST PATGSGSAIC SGVAVCKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSDEFD ASISQVNEKI NQSLAFIRKS DELLHNVNAG  480
KSTTNIMITT IIIVIIVILL SLIAVGLLLY CKARSTPVTL SKDQLSGINN IAFSN       535

SEQ ID NO: 36           moltype = RNA  length = 1774
FEATURE                 Location/Qualifiers
misc_feature            1..1774
                        note = Synthetic Polynucleotide
source                  1..1774
                        mol_type = other RNA
                        organism = synthetic construct
SEQUENCE: 36
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgggcgcgct ccgcacagga tggtacacct ccgtgatcac catcgagctc agcaatatta  240
aagagattaa gtgcaatggt accgacgcta aagtcaaact tatcaagcag gaactcgaca  300
aatataagaa cgctgtgacc gacctgcagt tattgatgca gagtacacct gccaccgggt  360
cgggctctgc cattgcttcc ggcgtggctg tatgtaaagt tctccacctc gagggagagg  420
ttaataagat taagtcggcc ctgctgagta ctaacaaagc agtggtgtcg ctgagtggct  480
gcggagtaag tgtgttaaca tttaaggtgc tggacctcaa gaattatatt gacaaacagt  540
tgcttcctat tctaaacaaa cagagctgtt caatacccaa tattgaaact gttattgagt  600
ttcagcagaa gaacaacagg cttcttgaga ttacacgcga gttcagtgtc aatgccggcg  660
ttacaacacc cgtgtctacc tacatgctga cgaattctga gcttctctct ctcataaacg  720
acatgcccat tacgaatgac caaaagaaac ttatgtccaa caacgtgcag attgtgcgac  780
agcaatccta tagcattatg tgtatcatca aggaagaggt actcgcttat gttgtgcagc  840
taccactcta tggtgtgatt gacacccccct gttggaagct gcataccagt ccactctgca  900
ccactaacac aaaggaaggg agcaatattt gcctcactcg aaccgacagg gggtggtatt  960
gcgataatgc gggctccgtg tccttctttc cacaggctga aacttgtaag gtacagtcaa  1020
accgcgtgtt ctgtgatact atgaattctc gtactcttcc cagcgaggtt aatctctgca  1080
acgtcgacat tttcaatcct aaatatgact gcaagatcat gaccagcaag accgacgtct  1140
ccagctcagt aatcactagc ctaggggcca ttgtaagctg ctatggcaaa accaagtgta  1200
ctgcctctaa taagtgcaga ggcataatta aaaccttttc aaatggctgt gactatgtgt  1260
cgaataaggg cgtcgacacg gtctcagtag ggaataccct ctactacgtt aacaaacagg  1320
aaggccagtc cctttatgta aagggcgagc ccatcataaa tttctacgac ccacttgtgt  1380
tccccagtga tgaattcgat gcatcaatct cccaggtgaa cgaaaagatc aatcaatccc  1440
ttgcttttat acgaaagtca gatgaactcc tgcataacgt gaatgctggg aaatctacaa  1500
ccaacatcat gatcactacc atcattattg tgattatcgt aattctgcta tccttgattg  1560
ctgtcgggct gcttctgtac tgtaaggcca gatcgacgcc tgtgaccctt tcaaaagacc  1620
aacttagcgg tatcaataat attgccttta gcaattgata ataggctgga gcctcggtgg  1680
ccatgcttct tgccccttgg gcctcccccc agcccctcct ccccttcctg cacccgtacc  1740
cccgtggtct ttgaataaag tctgagtggg cggc                              1774

SEQ ID NO: 37           moltype = RNA  length = 1608
FEATURE                 Location/Qualifiers
misc_feature            1..1608
                        note = Synthetic Polynucleotide
source                  1..1608
                        mol_type = other RNA
                        organism = synthetic construct
SEQUENCE: 37
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgggcgc gctccgcaca ggatggtaca cctccgtgat caccatcgag  180
ctcagcaata ttaaagagat taagtgcaat ggtaccgacg ctaaagtcaa acttatcaag  240
caggaactcg acaaatataa gaacgctgtg accgacctgc agttattgat gcagagtaca  300
cctgccaccg ggtcgggctc tgccattgct tccggcgtgg ctgtatgtaa agttctccac  360
ctcgagggag aggttaataa gattaagtcg gccctgctga gtactaacaa agcagtggtg  420
tcgctgagtg gctgcggagt aagtgtgtta acatttaagg tgctggacct caagaattat  480
attgacaaac agttgcttcc tattctaaac aaacagagct gttcaatacc caatattgaa  540
actgttattg agtttcagca gaagaacaac aggcttcttg agattacacg cgagttcagt  600
```

```
gtcaatgccg gcgttacaac acccgtgtct acctacatgc tgacgaattc tgagcttctc  660
tctctcataa acgacatgcc cattacgaat gaccaaaaga aacttatgtc caacaacgtg  720
cagattgtgc gacagcaatc ctatagcatt atgtgtatca tcaaggaaga ggtactcgct  780
tatgttgtgc agctaccact ctatggtgtg attgacaccc cctgttggaa gctgcatacc  840
agtccactct gcaccactaa cacaaaggaa gggagcaata tttgcctcac tcgaaccgac  900
agggggtggt attgcgataa tgcgggctcc gtgtccttct ttccacaggc tgaaacttgt  960
aaggtacagt caaaccgcgt gttctgtgat actatgaatt ctcgtactct tcccagcgag  1020
gttaatctct gcaacgtcga cattttcaat cctaaatatg actgcaagat catgaccagc  1080
aagaccgacg tctccagctc agtaatcact agcctagggg ccattgtaag ctgctatggc  1140
aaaaccaagt gtactgcctc taataagtgc agaggcataa ttaaaacctt ttcaaatggc  1200
tgtgactatg tgtcgaataa gggcgtcgac acggtctcag tagggaatac cctctactac  1260
gttaacaaac aggaaggcca gtccctttat gtaaagggcg agcccatcat aaatttctac  1320
gacccacttg tgttccccag tgatgaattc gatgcatcaa tctcccaggt gaacgaaaag  1380
atcaatcaat cccttgcttt tatacgaaag tcagatgaac tcctgcataa cgtgaatgct  1440
gggaaatcta caaccaacat catgatcact accatcatta ttgtgattat cgtaattctg  1500
ctatccttga ttgctgtcgg gctgcttctg tactgtaagg ccagatcgac gcctgtgacc  1560
ctttcaaaag accaacttag cggtatcaat aatattgcct ttagcaat              1608

SEQ ID NO: 38          moltype = AA  length = 536
FEATURE                Location/Qualifiers
REGION                 1..536
                       note = Synthetic Polypeptide
source                 1..536
                       mol_type = protein
                       organism = synthetic construct
SEQUENCE: 38
MELLILKANA ITTILTAVTF CFASGQNITE EFYQSTCSAV SKGYLGALRT GWYTSVITIE  60
LSNIKEIKCN GTDAKVKLIK QELDKYKNAV TDLQLLMQST PATGSGSAIA SGVAVCKVLH  120
LEGEVNKIKS ALLSTNKAVV SLSGCGVSVL TFKVLDLKNY IDKQLLPILN KQSCSIPNIE  180
TVIEFQQKNN RLLEITREFS VNAGVTTPVS TYMLTNSELL SLINDMPITN DQKKLMSNNV  240
QIVRQQSYSI MCIIKEEVLA YVVQLPLYGV IDTPCWKLHT SPLCTTNTKE GSNICLTRTD  300
RGWYCDNAGS VSFFPQAETC KVQSNRVFCD TMNSRTLPSE VNLCNVDIFN PKYDCKIMTS  360
KTDVSSSVIT SLGAIVSCYG KTKCTASNKC RGIIKTFSNG CDYVSNKGVD TVSVGNTLYY  420
VNKQEGQSLY VKGEPIINFY DPLVFPSDEF DASISQVNEK INQSLAFIRK SDELLHNVNA  480
GKSTTNIMIT TIIIVIIVIL LSLIAVGLLL YCKARSTPVT LSKDQLSGIN NIAFSN      536

SEQ ID NO: 39          moltype = RNA  length = 1771
FEATURE                Location/Qualifiers
misc_feature           1..1771
                       note = Synthetic Polynucleotide
source                 1..1771
                       mol_type = other RNA
                       organism = synthetic construct
SEQUENCE: 39
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatgca gagtacacct gccaccgggt  360
cgggctctgc cattgcttcc ggcgtggctg tatgtaaagt tctccacctc gagggagagg  420
ttaataagat taagtcggcc ctgctgagta ctaacaaagc agtggtgtcg ctgagtaacg  480
gagtaagtgt gttaacattt aaggtgctgg acctcaagaa ttatattgac aaacagttgc  540
ttcctattct aaacaaacag agctgttcaa taagtaatat tgaaactgtt attgagtttc  600
agcagaagaa caacaggctt cttgagatta cacgcgagtt cagtgtcaat gccggcgtta  660
caacacccgt gtctacctac atgctgacga attctgagct tctctctctc ataaacgaca  720
tgcccattac gaatgaccaa aagaaactta tgtccaacaa cgtgcagatt gtgcgacagc  780
aatcctatag cattatgtgt atcatcaagg aagaggtact cgcttatgtt gtgcagctac  840
cactctatgg tgtgattgac accccctgtt ggaagctgca taccagtcca ctctgcacca  900
ctaacacaaa ggaagggagc aatatttgcc tcactcgaac cgacaggggg tggtattgcg  960
ataatgcggg ctccgtgtcc ttctttccac aggctgaaac ttgtaaggta cagtcaaacc  1020
gcgtgttctg tgatactatg aattctcgta ctcttcccag cgaggttaat ctctgcaacg  1080
tcgacatttt caatcctaaa tatgactgca agatcatgac cagcaagacc gacgtctcca  1140
gctcagtaat cactagccta ggggccattg taagctgcta tggcaaaacc aagtgtactg  1200
cctctaataa gaacagaggc ataattaaaa ccttttcaaa tggctgtgac tatgtgtcga  1260
ataagggcgt cgacacggtc tcagtaggga ataccctcta ctacgttaac aaacaggaag  1320
gcaaatccct ttatgtaaag ggcgagccca tcataaattt ctacgaccca cttgtgttcc  1380
ccagtgatga attcgatgca tcaatctccc aggtgaacga aaagatcaat caatcccttg  1440
cttttatacg aaagtcagat gaactcctgc ataacgtgaa tgctgggaaa tctacaacca  1500
acatcatgat cactaccatc attattgtga ttatcgtaat tctgctatcc ttgattgctg  1560
tcgggctgct tctgtactgt aaggccagat cgacgcctgt gaccctttca aaagaccaac  1620
ttagcggtat caataatatt gcctttagca attgataata ggctggagcc tcggtggcca  1680
tgcttcttgc cccttgggcc tccccccagc ccctcctccc cttcctgcac ccgtaccccc  1740
gtggtctttg aataaagtct gagtgggcgg c                                 1771

SEQ ID NO: 40          moltype = RNA  length = 1605
FEATURE                Location/Qualifiers
misc_feature           1..1605
                       note = Synthetic Polynucleotide
```

-continued

```
source                  1..1605
                        mol_type = other RNA
                        organism = synthetic construct
SEQUENCE: 40
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gcagagtaca  300
cctgccaccg ggtcgggctc tgccattgct tccggcgtgg ctgtatgtaa agttctccac  360
ctcgagggag aggttaataa gattaagtcg gccctgctga gtactaacaa agcagtggtg  420
tcgctgagta acggagtaag tgtgttaaca tttaaggtgc tggacctcaa gaattatatt  480
gacaaacagt tgcttcctat tctaaacaaa cagagctgtt caataagtaa tattgaaact  540
gttattgagt ttcagcagaa gaacaacagg cttcttgaga ttacacgcga gttcagtgtc  600
aatgccggcg ttacaacacc cgtgtctacc tacatgctga cgaattctga gcttctctct  660
ctcataaacg acatgcccat tacgaatgac caaaagaaac ttatgtccaa caacgtgcag  720
attgtgcgac agcaatccta tagcattatg tgtatcatca aggaagaggt actcgcttat  780
gttgtgcagc taccactcta tggtgtgatt gacaccccct gttggaagct gcataccagt  840
ccactctgca ccactaacac aaaggaaggg agcaatattt gcctcactcg aaccgacagg  900
gggtggtatt gcgataatgc gggctccgtg tccttctttc cacaggctga aacttgtaag  960
gtacagtcaa accgcgtgtt ctgtgatact atgaattctc gtactcttcc cagcgaggtt  1020
aatctctgca acgtcgacat tttcaatcct aaatatgact gcaagatcat gaccagcaag  1080
accgacgtct ccagctcagt aatcactagc ctaggggcca ttgtaagctg ctatggcaaa  1140
accaagtgta ctgcctctaa taagaacaga ggcataatta aaacctttc aaatggctgt  1200
gactatgtgt cgaataaggg cgtcgacacg gtctcagtag ggaataccct ctactacgtt  1260
aacaaacagg aaggcaaatc cctttatgta aagggcgagc ccatcataaa tttctacgac  1320
ccacttgtgt tccccagtga tgaattcgat gcatcaatct cccaggtgaa cgaaaagatc  1380
aatcaatccc ttgcttttat acgaaagtca gatgaactcc tgcataacgt gaatgctggg  1440
aaatctacaa ccaacatcat gatcactacc atcattattg tgattatcgt aattctgcta  1500
tccttgattg ctgtcgggct gcttctgtac tgtaaggcca gatcgacgcc tgtgaccctt  1560
tcaaaagacc aacttagcgg tatcaataat attgccttta gcaat                  1605

SEQ ID NO: 41           moltype = AA  length = 535
FEATURE                 Location/Qualifiers
REGION                  1..535
                        note = Synthetic Polypeptide
source                  1..535
                        mol_type = protein
                        organism = synthetic construct
SEQUENCE: 41
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATGSGSAIA SGVAVCKVLH  120
LEGEVNKIKS ALLSTNKAVV SLSNGVSVLT FKVLDLKNYI DKQLLPILNK QSCSISNIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGKSLYV KGEPIINFYD PLVFPSDEFD ASISQVNEKI NQSLAFIRKS DELLHNVNAG  480
KSTTNIMITT IIVIIVILL SLIAVGLLLY CKARSTPVTL SKDQLSGINN IAFSN       535

SEQ ID NO: 42           moltype = RNA  length = 1681
FEATURE                 Location/Qualifiers
misc_feature            1..1681
                        note = Synthetic Polynucleotide
source                  1..1681
                        mol_type = other RNA
                        organism = synthetic construct
SEQUENCE: 42
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgggcgcgct ccgcacagga tggtacacct ccgtgatcac catcgagctc agcaatatta  240
aagagattaa gtgcaatggt accgacgcta aagtcaaact tatcaagcag gaactcgaca  300
aatataagaa cgctgtgacc gacctgcagt tattgatgca gagtacacct gccaccgggt  360
cgggctctgc catttgctcc ggcgtggctg tatgtaaagt tctccacctc gagggagagg  420
ttaataagat taagtcggcc ctgctgagta ctaacaaagc agtggtgtcg ctgagtaacg  480
gagtaagtgt gttaacattt aaggtgctgg acctcaagaa ttatattgac aaacagttgc  540
ttcctattct aaacaaacag agctgttcaa tacccaatat tgaaactgtt attgagtttc  600
agcagaagaa caacaggctt cttgagatta cacgcgagtt cagtgtcaat gccggcgtta  660
caacacccgt gtctacctac atgctgacga attctgagct tctctctctc ataaacgaca  720
tgcccattac gaatgaccaa aagaaactta tgtccaacaa cgtgcagatt gtgcgacagc  780
aatcctatag cattatgtgt atcatcaagg aagaggtact cgcttatgtt gtgcagctac  840
cactctatgg tgtgattgac accccctgtt ggaagctgca taccagtcca ctctgcacca  900
ctaacacaaa ggaagggagc aatatttgcc tcactcgaac cgacaggggg tggtattgcg  960
ataatgcggg ctccgtgtcc ttctttccac aggctgaaac ttgtaaggta cagtcaaacc  1020
gcgtgttctg tgatactatg aattctcgta ctcttcccag cgaggttaat ctctgcaacg  1080
tcgacatttt caatcctaaa tatgactgca agatcatgac cagcaagacc gacgtctcca  1140
gctcagtaat cactagccta ggggccattg taagctgcta tggcaaaacc aagtgtactg  1200
cctctaataa gaacagaggc ataattaaaa ccttttcaaa tggctgtgac tatgtgtcga  1260
```

-continued

```
ataagggcgt cgacacggtc tcagtaggga ataccctcta ctgcgttaac aaacaggaag  1320
gccagtccct ttatgtaaag ggcgagccca tcataaattt ctacgaccca cttgtgttcc  1380
ccagtgatga attcgatgca tcaatctccc aggtgaacga aaagatcaat caatcccttg  1440
cttttatacg aaagtcagat gaactcctgt ccgccatcgg tggctatatc ccagaagccc  1500
caagagacgg acaagcgtac gtccggaaag atggtgagtg ggtcctcctc tctacctttc  1560
tttgataata ggctggagcc tcggtggcca tgcttcttgc cccttgggcc tcccccccagc  1620
ccctcctccc cttcctgcac ccgtaccccc gtggtctttg aataaagtct gagtgggcgg  1680
c                                                                  1681

SEQ ID NO: 43          moltype = RNA  length = 1515
FEATURE                Location/Qualifiers
misc_feature           1..1515
                       note = Synthetic Polynucleotide
source                 1..1515
                       mol_type = other RNA
                       organism = synthetic construct
SEQUENCE: 43
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgggcgc gctccgcaca ggatggtaca cctccgtgat caccatcgag  180
ctcagcaata ttaaagagat taagtgcaat ggtaccgacg ctaaagtcaa acttatcaag  240
caggaactcg acaaatataa gaacgctgtg accgacctgc agttattgat gcagagtaca  300
cctgccaccg ggtcgggctc tgccatttgc tccggcgtgg ctgtatgtaa agttctccac  360
ctcgagggag aggttaataa gattaagtcg gccctgctga gtactaacaa agcagtggtg  420
tcgctgagta acggagtaag tgtgttaaca tttaaggtgc tggacctcaa gaattatatt  480
gacaaacagt tgcttcctat tctaaacaaa cagagctgtt caatacccaa tattgaaact  540
gttattgagt ttcagcagaa gaacaacagg cttcttgaga ttacacgcga gttcagtgtc  600
aatgccggcg ttacaacacc cgtgtctacc tacatgctga cgaattctga gcttctctct  660
ctcataaacg acatgcccat tacgaatgac caaaagaaac ttatgtccaa caacgtgcag  720
attgtgcgac agcaatccta tagcattatg tgtatcatca aggaagaggt actcgcttat  780
gttgtgcagc taccactcta tggtgtgatt gacacccccct gttggaagct gcataccagt  840
ccactctgca ccactaacac aaaggaaggg agcaatattt gcctcactcg aaccgacagg  900
gggtggtatt gcgataatgc gggctccgtg tccttctttc cacaggctga aacttgtaag  960
gtacagtcaa accgcgtgtt ctgtgatact atgaattctc gtactcttcc cagcgaggtt  1020
aatctctgca acgtcgacat tttcaatcct aaatatgact gcaagatcat gaccagcaag  1080
accgacgtct ccagctcagt aatcactagc ctaggggcca ttgtaagctg ctatggcaaa  1140
accaagtgta ctgcctctaa taagaacaga ggcataatta aaacctttttc aaatggctgt  1200
gactatgtgt cgaataaggg cgtcgacacg gtctcagtag ggaataccct ctactgcgtt  1260
aacaaacagg aaggccagtc cctttatgta aagggcgagc ccatcataaa tttctacgac  1320
ccacttgtgt tccccagtga tgaattcgat gcatcaatct cccaggtgaa cgaaaagatc  1380
aatcaatccc ttgcttttat acgaaagtca gatgaactcc tgtccgccat cggtggctat  1440
atcccagaag ccccaagaga cggacaagcg tacgtccgga aagatggtga gtgggtcctc  1500
ctctctacct ttctt                                                  1515

SEQ ID NO: 44          moltype = AA  length = 505
FEATURE                Location/Qualifiers
REGION                 1..505
                       note = Synthetic Polypeptide
source                 1..505
                       mol_type = protein
                       organism = synthetic construct
SEQUENCE: 44
MELLILKANA ITTILTAVTF CFASGQNITE EFYQSTCSAV SKGYLGALRT GWYTSVITIE  60
LSNIKEIKCN GTDAKVKLIK QELDKYKNAV TDLQLLMQST PATGSGSAIC SGVAVCKVLH  120
LEGEVNKIKS ALLSTNKAVV SLSNGVSVLT FKVLDLKNYI DKQLLPILNK QSCSIPNIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGQSLYV KGEPIINFYD PLVFPSDEFD ASISQVNEKI NQSLAFIRKS DELLSAIGGY  480
IPEAPRDGQA YVRKDGEWVL LSTFL                                       505

SEQ ID NO: 45          moltype = RNA  length = 1684
FEATURE                Location/Qualifiers
misc_feature           1..1684
                       note = Synthetic Polynucleotide
source                 1..1684
                       mol_type = other RNA
                       organism = synthetic construct
SEQUENCE: 45
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgggcgcgct ccgcacagga tggtacacct ccgtgatcac catcgagctc agcaatatta  240
aagagattaa gtgcaatggt accgacgcta aagtcaaact tatcaagcag gaactcgaca  300
aatataagaa cgctgtgacc gacctgcagt tattgatgca gagtacacct gccaccgggt  360
cgggctctgc cattgcttcc ggcgtggctg tatgtaaagt tctccacctc gagggagagg  420
ttaataagat taagtcggcc ctgctgagta ctaacaaagc agtggtgtcg ctgagtggct  480
gcggagtaag tgtgttaaca tttaaggtgc tggacctcaa gaattatatt gacaaacagt  540
```

```
tgcttcctat tctaaacaaa cagagctgtt caatacccaa tattgaaact gttattgagt  600
ttcagcagaa gaacaacagg cttcttgaga ttacacgcga gttcagtgtc aatgccggcg  660
ttacaacacc cgtgtctacc tacatgctga cgaattctga gcttctctct ctcataaacg  720
acatgcccat tacgaatgac caaaagaaac ttatgtccaa caacgtgcag attgtgcgac  780
agcaatccta tagcattatg tgtatcatca aggaagaggt actcgcttat gttgtgcagc  840
taccactcta tggtgtgatt gacaccccct gttggaagct gcataccagt ccactctgca  900
ccactaacac aaaggaaggg agcaatattt gcctcactcg aaccgacagg gggtggtatt  960
gcgataatgc gggctccgtg tccttctttc cacaggctga aacttgtaag gtacagtcaa  1020
accgcgtgtt ctgtgatact atgaattctc gtactcttcc cagcgaggtt aatctctgca  1080
acgtcgacat tttcaatcct aaatatgact gcaagatcat gaccagcaag accgacgtct  1140
ccagctcagt aatcactagc ctaggggcca ttgtaagctg ctatggcaaa accaagtgta  1200
ctgcctctaa taagtgcaga ggcataatta aaaccttttc aaatggctgt gactatgtgt  1260
cgaataaggg cgtcgacacg gtctcagtag ggaataccct ctactacgtt aacaaacagg  1320
aaggccagtc cctttatgta aagggcgagc ccatcataaa tttctacgac ccacttgtgt  1380
tccccagtga tgaattcgat gcatcaatct cccaggtgaa cgaaaagatc aatcaatccc  1440
ttgcttttat acgaaagtca gatgaactcc tgtccgccat cggtggctat atcccagaag  1500
ccccaagaga cggacaagcg tacgtccgga aagatggtga gtgggtcctc ctctctacct  1560
ttctttgata ataggctgga gcctcggtgg ccatgcttct tgccccttgg gcctcccccc  1620
agcccctcct ccccttcctg cacccgtacc cccgtggtct ttgaataaag tctgagtggg  1680
cggc                                                               1684

SEQ ID NO: 46          moltype = RNA  length = 1518
FEATURE                Location/Qualifiers
misc_feature           1..1518
                       note = Synthetic Polynucleotide
source                 1..1518
                       mol_type = other RNA
                       organism = synthetic construct
SEQUENCE: 46
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgggcgc gctccgcaca ggatggtaca cctccgtgat caccatcgag  180
ctcagcaata ttaaagagat taagtgcaat ggtaccgacg ctaaagtcaa acttatcaag  240
caggaactcg acaaatataa gaacgctgtg accgacctgc agttattgat gcagagtaca  300
cctgccaccg ggtcgggctc tgccattgct tccggcgtgg ctgtatgtaa agttctccac  360
ctcgagggag aggttaataa gattaagtcg gccctgctga gtactaacaa agcagtggtg  420
tcgctgagtg gctgcggagt aagtgtgtta acatttaagg tgctggacct caagaattat  480
attgacaaac agttgcttcc tattctaaac aaacagagct gttcaatacc caatattgaa  540
actgttattg agtttcagca gaagaacaac aggcttcttg agattacacg cgagttcagt  600
gtcaatgccg gcgttacaac acccgtgtct acctacatgc tgacgaattc tgagcttctc  660
tctctcataa acgacatgcc cattacgaat gaccaaaaga aacttatgtc caacaacgtg  720
cagattgtgc gacagcaatc ctatagcatt atgtgtatca tcaaggaaga ggtactcgct  780
tatgttgtgc agctaccact ctatggtgtg attgacaccc cctgttggaa gctgcatacc  840
agtccactct gcaccactaa cacaaaggaa gggagcaata tttgcctcac tcgaaccgac  900
agggggtggt attgcgataa tgcgggctcc gtgtccttct ttccacaggc tgaaacttgt  960
aaggtacagt caaaccgcgt gttctgtgat actatgaatt ctcgtactct tcccagcgag  1020
gttaatctct gcaacgtcga cattttcaat cctaaatatg actgcaagat catgaccagc  1080
aagaccgacg tctccagctc agtaatcact agcctagggg ccattgtaag ctgctatggc  1140
aaaaccaagt gtactgcctc taataagtgc agaggcataa ttaaaacctt ttcaaatggc  1200
tgtgactatg tgtcgaataa gggcgtcgac acggtctcag tagggaatac cctctactac  1260
gttaacaaac aggaaggcca gtccctttat gtaaagggcg agcccatcat aaatttctac  1320
gacccacttg tgttccccag tgatgaattc gatgcatcaa tctcccaggt gaacgaaaag  1380
atcaatcaat cccttgcttt tatacgaaag tcagatgaac tcctgtccgc catcggtggc  1440
tatatcccag aagccccaag agacggacaa gcgtacgtcc ggaaagatgg tgagtgggtc  1500
ctcctctcta cctttctt                                                1518

SEQ ID NO: 47          moltype = AA  length = 506
FEATURE                Location/Qualifiers
REGION                 1..506
                       note = Synthetic Polypeptide
source                 1..506
                       mol_type = protein
                       organism = synthetic construct
SEQUENCE: 47
MELLILKANA ITTILTAVTF CFASGQNITE EFYQSTCSAV SKGYLGALRT GWYTSVITIE  60
LSNIKEIKCN GTDAKVKLIK QELDKYKNAV TDLQLLMQST PATGSGSAIA SGVAVCKVLH  120
LEGEVNKIKS ALLSTNKAVV SLSGCGVSVL TFKVLDLKNY IDKQLLPILN KQSCSIPNIE  180
TVIEFQQKNN RLLEITREFS VNAGVTTPVS TYMLTNSELL SLINDMPITN DQKKLMSNNV  240
QIVRQQSYSI MCIIKEEVLA YVVQLPLYGV IDTPCWKLHT SPLCTTNTKE GSNICLTRTD  300
RGWYCDNAGS VSFFPQAETC KVQSNRVFCD TMNSRTLPSE VNLCNVDIFN PKYDCKIMTS  360
KTDVSSSVIT SLGAIVSCYG KTKCTASNKC RGIIKTFSNG CDYVSNKGVD TVSVGNTLYY  420
VNKQEGQSLY VKGEPIINFY DPLVFPSDEF DASISQVNEK INQSLAFIRK SDELLSAIGG  480
YIPEAPRDGQ AYVRKDGEWV LLSTFL                                       506

SEQ ID NO: 48          moltype = RNA  length = 1681
FEATURE                Location/Qualifiers
misc_feature           1..1681
                       note = Synthetic Polynucleotide
source                 1..1681
```

```
                        mol_type = other RNA
                        organism = synthetic construct
SEQUENCE: 48
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatgca gagtacacct gccaccgggt  360
cgggctctgc cattgcttcc ggcgtggctg tatgtaaagt tctccacctc gagggagagg  420
ttaataagat taagtcggcc ctgctgagta ctaacaaagc agtggtgtcg ctgagtaacg  480
gagtaagtgt gttaacattt aaggtgctgg acctcaagaa ttatattgac aaacagttgc  540
ttcctattct aaacaaacag agctgttcaa taagtaatat tgaaactgtt attgagtttc  600
agcagaagaa caacaggctt cttgagatta cacgcgagtt cagtgtcaat gccggcgtta  660
caacacccgt gtctacctac atgctgacga attctgagct tctctctctc ataaacgaca  720
tgcccattac gaatgaccaa aagaaactta tgtccaacaa cgtgcagatt gtgcgacagc  780
aatcctatag cattatgtgt atcatcaagg aagaggtact cgcttatgtt gtgcagctac  840
cactctatgg tgtgattgac accccctgtt ggaagctgca taccagtcca ctctgcacca  900
ctaacacaaa ggaagggagc aatatttgcc tcactcgaac cgacaggggg tggtattgcg  960
ataatgcggg ctccgtgtcc ttctttccac aggctgaaac ttgtaaggta cagtcaaacc  1020
gcgtgttctg tgatactatg aattctcgta ctcttcccag cgaggttaat ctctgcaacg  1080
tcgacatttt caatcctaaa tatgactgca agatcatgac cagcaagacc gacgtctcca  1140
gctcagtaat cactagccta ggggccattg taagctgcta tggcaaaacc aagtgtactg  1200
cctctaataa gaacagaggc ataattaaaa ccttttcaaa tggctgtgac tatgtgtcga  1260
ataagggcgt cgacacggtc tcagtaggga ataccctcta ctacgttaac aaacaggaag  1320
gcaaatccct ttatgtaaag ggcgagccca tcataaattt ctacgaccca cttgtgttcc  1380
ccagtgatga attcgatgca tcaatctccc aggtgaacga aaagatcaat caatcccttg  1440
cttttatacg aaagtcagat gaactcctgt ccgccatcgg tggctatatc ccagaagccc  1500
caagagacgg acaagcgtac gtccggaaag atggtgagtg ggtcctcctc tctacctttc  1560
tttgataata ggctggagcc tcggtggcca tgcttcttgc cccttgggcc tccccccagc  1620
ccctcctccc cttcctgcac ccgtaccccc gtggtctttg aataaagtct gagtgggcgg  1680
c                                                                  1681

SEQ ID NO: 49           moltype = RNA  length = 1515
FEATURE                 Location/Qualifiers
misc_feature            1..1515
                        note = Synthetic Polynucleotide
source                  1..1515
                        mol_type = other RNA
                        organism = synthetic construct
SEQUENCE: 49
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gcagagtaca  300
cctgccaccg ggtcgggctc tgccattgct tccggcgtgg ctgtatgtaa agttctccac  360
ctcgagggag aggttaataa gattaagtcg gccctgctga gtactaacaa agcagtggtg  420
tcgctgagta acggagtaag tgtgttaaca tttaaggtgc tggacctcaa gaattatatt  480
gacaaacagt tgcttcctat tctaaacaaa cagagctgtt caataagtaa tattgaaact  540
gttattgagt ttcagcagaa gaacaacagg cttcttgaga ttacacgcga gttcagtgtc  600
aatgccggcg ttacaacacc cgtgtctacc tacatgctga cgaattctga gcttctctct  660
ctcataaacg acatgcccat tacgaatgac caaaagaaac ttatgtccaa caacgtgcag  720
attgtgcgac agcaatccta tagcattatg tgtatcatca aggaagaggt actcgcttat  780
gttgtgcagc taccactcta tggtgtgatt gacaccccct gttggaagct gcataccagt  840
ccactctgca ccactaacac aaaggaaggg agcaatattt gcctcactcg aaccgacagg  900
gggtggtatt gcgataatgc gggctccgtg tccttctttc cacaggctga aacttgtaag  960
gtacagtcaa accgcgtgtt ctgtgatact atgaattctc gtactcttcc cagcgaggtt  1020
aatctctgca acgtcgacat tttcaatcct aaatatgact gcaagatcat gaccagcaag  1080
accgacgtct ccagctcagt aatcactagc ctaggggcca ttgtaagctg ctatggcaaa  1140
accaagtgta ctgcctctaa taagaacaga ggcataatta aaaccttttc aaatggctgt  1200
gactatgtgt cgaataaggg cgtcgacacg gtctcagtag ggaataccct ctactacgtt  1260
aacaaacagg aaggcaaatc cctttatgta aagggcgagc ccatcataaa tttctacgac  1320
ccacttgtgt tccccagtga tgaattcgat gcatcaatct cccaggtgaa cgaaaagatc  1380
aatcaatccc ttgcttttat acgaaagtca gatgaactcc tgtccgccat cggtggctat  1440
atcccagaag ccccaagaga cggacaagcg tacgtccgga aagatggtga gtgggtcctc  1500
ctctctacct ttctt                                                   1515

SEQ ID NO: 50           moltype = AA  length = 505
FEATURE                 Location/Qualifiers
REGION                  1..505
                        note = Synthetic Polypeptide
source                  1..505
                        mol_type = protein
                        organism = synthetic construct
SEQUENCE: 50
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATGSGSAIA SGVAVCKVLH  120
LEGEVNKIKS ALLSTNKAVV SLSNGVSVLT FKVLDLKNYI DKQLLPILNK QSCSISNIET  180
```

-continued

```
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGKSLYV KGEPIINFYD PLVFPSDEFD ASISQVNEKI NQSLAFIRKS DELLSAIGGY  480
IPEAPRDGQA YVRKDGEWVL LSTFL                                        505

SEQ ID NO: 51          moltype = RNA  length = 1781
FEATURE                Location/Qualifiers
misc_feature           1..1781
                       note = Synthetic Polynucleotide
source                 1..1781
                       mol_type = other RNA
                       organism = synthetic construct
SEQUENCE: 51
gggaaataag agagaaaaga agagtaagaa gaaatataag accccggcgc cgccaccatg  60
gaactgctca ttttgaaggc aaacgctatc acgacaatac tcactgcagt gaccttctgt  120
tttgcctcag gccagaacat aaccgaggag ttttatcaat ctacatgcag cgctgtatct  180
aaaggctacc tgagtgcgct ccgcacagga tggtacacct ccgtgatcac catcgagctc  240
agcaatatta aagagaacaa gtgcaatggt accgacgcta aagtcaaact tatcaagcag  300
gaactcgaca aatataagaa cgctgtgacc gagctgcagt tattgatgca gagtacacct  360
gccaccgggt cgggctctgc catttgctcc ggcgtggctg tatgtaaagt tctccacctc  420
gagggagagg ttaataagat taagtcggcc ctgctgagta ctaacaaagc agtggtgtcg  480
ctgagtaacg gagtaagtgt gttaacattt aaggtgctgg acctcaagaa ttatattgac  540
aaacagttgc ttcctattct aaacaaacag agctgttcaa taagtaatat tgaaactgtt  600
attgagtttc agcagaagaa caacaggctt cttgagatta cacgcgagtt cagtgtcaat  660
gccggcgtta caacacccgt gtctacctac atgctgacga attctgagct tctctctctc  720
ataaacgaca tgcccattac gaatgaccaa aagaaactta tgtccaacaa cgtgcagatt  780
gtgcgacagc aatcctatag cattatgtgt atcatcaagg aagaggtact cgcttatgtt  840
gtgcagctac cactctatgg tgtgattgac accccctgtt ggaagctgca taccagtcca  900
ctctgcacca ctaacacaaa ggaagggagc aatatttgcc tcactcgaac cgacaggggg  960
tggtattgcg ataatgcggg ctccgtgtcc ttctttccac aggctgaaac ttgtaaggta  1020
cagtcaaacc gcgtgttctg tgatactatg aattctcgta ctcttcccag cgaggttaat  1080
ctctgcaacg tcgacatttt caatcctaaa tatgactgca agatcatgac cagcaagacc  1140
gacgtctcca gctcagtaat cactagccta ggggccattg taagctgcta tggcaaaacc  1200
aagtgtactg cctctaataa gaacagaggc ataattaaaa ccttttcaaa tggctgtgac  1260
tatgtgtcga ataagggcgt cgacacggtc tcagtaggga ataccctcta ctgcgttaac  1320
aaacaggaag gcaaatccct ttatgtaaag ggcgagccca tcataaattt ctacgaccca  1380
cttgtgttcc ccagtgatga attcgatgca tcaatctccc aggtgaacga aaagatcaat  1440
caatcccttg cttttatacg aaagtcagat gaactcctgc ataacgtgaa tgctgggaaa  1500
tctacaacca acatcatgat cactaccatc attattgtga ttatcgtaat tctgctatcc  1560
ttgattgctg tcgggctgct tctgtactgt aaggccagat cgacgcctgt gacccttca  1620
aaagaccaac ttagcggtat caataatatt gcctttagca attgataata ggctggagcc  1680
tcggtggcct agcttcttgc cccttgggcc tccccccagc ccctcctccc cttcctgcac  1740
ccgtaccccc gtggtctttg aataaagtct gagtgggcgg c                      1781

SEQ ID NO: 52          moltype = RNA  length = 1605
FEATURE                Location/Qualifiers
misc_feature           1..1605
                       note = Synthetic Polynucleotide
source                 1..1605
                       mol_type = other RNA
                       organism = synthetic construct
SEQUENCE: 52
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gcagagtaca  300
cctgccaccg ggtcgggctc tgccatttgc tccggcgtgg ctgtatgtaa agttctccac  360
ctcgagggag aggttaataa gattaagtcg gccctgctga gtactaacaa agcagtggtg  420
tcgctgagta acggagtaag tgtgttaaca tttaaggtgc tggacctcaa gaattatatt  480
gacaaacagt tgcttcctat tctaaacaaa cagagctgtt caataagtaa tattgaaact  540
gttattgagt ttcagcagaa gaacaacagg cttcttgaga ttacacgcga gttcagtgtc  600
aatgccggcg ttacaacacc cgtgtctacc tacatgctga cgaattctga gcttctctct  660
ctcataaacg acatgcccat tacgaatgac caaaagaaac ttatgtccaa caacgtgcag  720
attgtgcgac agcaatccta tagcattatg tgtatcatca aggaagaggt actcgcttat  780
gttgtgcagc taccactcta tggtgtgatt gacaccccct gttggaagct gcataccagt  840
ccactctgca ccactaacac aaaggaaggg agcaatattt gcctcactcg aaccgacagg  900
gggtggtatt gcgataatgc gggctccgtg tccttctttc cacaggctga aacttgtaag  960
gtacagtcaa accgcgtgtt ctgtgatact atgaattctc gtactcttcc cagcgaggtt  1020
aatctctgca acgtcgacat tttcaatcct aaatatgact gcaagatcat gaccagcaag  1080
accgacgtct ccagctcagt aatcactagc ctaggggcca ttgtaagctg ctatggcaaa  1140
accaagtgta ctgcctctaa taagaacaga ggcataatta aaaccttttc aaatggctgt  1200
gactatgtgt cgaataaggg cgtcgacacg gtctcagtag ggaataccct ctactgcgtt  1260
aacaaacagg aaggcaaatc cctttatgta aagggcgagc ccatcataaa tttctacgac  1320
ccacttgtgt tccccagtga tgaattcgat gcatcaatct cccaggtgaa cgaaaagatc  1380
aatcaatccc ttgcttttat acgaaagtca gatgaactcc tgcataacgt gaatgctggg  1440
aaatctacaa ccaacatcat gatcactacc atcattattg tgattatcgt aattctgcta  1500
```

```
tccttgattg ctgtcgggct gcttctgtac tgtaaggcca gatcgacgcc tgtgaccctt  1560
tcaaaagacc aacttagcgg tatcaataat attgccttta gcaat                   1605

SEQ ID NO: 53          moltype = RNA  length = 1781
FEATURE                Location/Qualifiers
misc_feature           1..1781
                       note = Synthetic Polynucleotide
source                 1..1781
                       mol_type = other RNA
                       organism = synthetic construct
SEQUENCE: 53
gggaaataag agagaaaaga agagtaagaa gaaatataag accccggcgc cgccaccatg  60
gagctgctga tcctcaaggc taacgccatc accaccatcc tgaccgccgt gaccttctgc  120
ttcgccagcg ggcagaacat caccgaggag ttctaccaga gcacttgcag cgccgtgagc  180
aagggctacc tgtcagccct gcggaccggc tggtacacca gcgtgatcac catcgagctg  240
agcaacatca aggagaacaa gtgcaacggc accgacgcca aggtgaagct gatcaagcag  300
gagctggaca agtacaagaa cgccgtgacc gagctgcagc tgctgatgca gtccacgccc  360
gctaccgggt caggcagcgc catctgctcc ggcgtggccg tgtgcaaggt gctgcacctg  420
gagggcgagg tgaacaagat caagagcgcc ctgctgagca ccaacaaggc cgtggtgagc  480
ctgagcaacg gcgtgagcgt gctgaccttc aaggtgctgg acctgaagaa ctacatcgac  540
aagcagctgc tgcccatcct gaacaagcag tcctgctcca tctccaacat cgaaactgtg  600
atcgagttcc agcagaagaa caaccgcctg ctggagatca cccgcgagtt cagcgtgaac  660
gccggcgtga ccaccccagt gagcacctac atgctgacca acagcgagct gctgagcctg  720
atcaacgaca tgcccatcac caacgaccag aagaagctga tgagcaacaa cgtgcagatc  780
gtgcgccagc agtcctactc tatcatgtgc atcatcaagg aggaggtgct ggcctacgtg  840
gtgcagctgc ccctgtacgg cgtgatcgac acaccctgct ggaagctgca cacctcccct  900
ctgtgcacca ctaacaccaa ggaggggagc aacatctgcc tgacccggac cgaccgcggc  960
tggtactgcg acaacgccgg cagcgtgagc ttcttccctc aggccgaaac ctgcaaggtg  1020
cagagcaaca gggtgttctg cgacaccatg aactcccgga ccctgcccag cgaggtgaac  1080
ctgtgcaacg tggacatctt caaccccaag tacgattgca agatcatgac ctccaagacc  1140
gacgtgagca gctccgtgat cacctccctg ggcgccatcg tgagttgcta cggcaagacc  1200
aagtgcaccg ccagcaacaa gaaccgcggc atcatcaaga ccttcagcaa cggctgcgac  1260
tacgtgtcca acaagggcgt ggacaccgtg agcgtgggca acaccctgta ctgcgtgaac  1320
aagcaggagg gcaagagcct gtacgtgaag ggcgagccca tcatcaactt ctacgatccg  1380
ctggtgttcc cctccgacga gttcgacgcc tccatcagcc aggtgaacga gaagatcaac  1440
cagagcctgg ccttcatccg caagtccgac gagctgctgc acaacgtcaa cgccggtaag  1500
agcaccacca acatcatgat caccacaatc atcatcgtga tcattgtgat cttgctctcc  1560
ttaatcgccg tgggcctgct gctgtactgc aaggcccgga gcaccccagt gaccctgagc  1620
aaagatcagc tgtccggcat caacaacatc gccttctcca actgataata ggctggagcc  1680
tcggtggcct agcttcttgc cccttgggcc tccccccagc ccctcctccc cttcctgcac  1740
ccgtaccccc gtggtctttg aataaagtct gagtgggcgg c                       1781

SEQ ID NO: 54          moltype = RNA  length = 1605
FEATURE                Location/Qualifiers
misc_feature           1..1605
                       note = Synthetic Polynucleotide
source                 1..1605
                       mol_type = other RNA
                       organism = synthetic construct
SEQUENCE: 54
atggagctgc tgatcctcaa ggctaacgcc atcaccacca tcctgaccgc cgtgaccttc  60
tgcttcgcca gcgggcagaa catcaccgag gagttctacc agagcacttg cagcgccgtg  120
agcaagggct acctgtcagc cctgcggacc ggctggtaca ccagcgtgat caccatcgag  180
ctgagcaaca tcaaggagaa caagtgcaac ggcaccgacg ccaaggtgaa gctgatcaag  240
caggagctgg acaagtacaa gaacgccgtg accgagctgc agctgctgat gcagtccacg  300
cccgctaccg ggtcaggcag cgccatctgc tccggcgtgg ccgtgtgcaa ggtgctgcac  360
ctggagggcg aggtgaacaa gatcaagagc gccctgctga gcaccaacaa ggccgtggtg  420
agcctgagca acggcgtgag cgtgctgacc ttcaaggtgc tggacctgaa gaactacatc  480
gacaagcagc tgctgcccat cctgaacaag cagtcctgct ccatctccaa catcgaaact  540
gtgatcgagt tccagcagaa gaacaaccgc ctgctggaga tcacccgcga gttcagcgtg  600
aacgccggcg tgaccacccc agtgagcacc tacatgctga ccaacagcga gctgctgagc  660
ctgatcaacg acatgcccat caccaacgac cagaagaagc tgatgagcaa caacgtgcag  720
atcgtgcgcc agcagtccta ctctatcatg tgcatcatca aggaggaggt gctggcctac  780
gtggtgcagc tgcccctgta cggcgtgatc gacacaccct gctggaagct gcacacctcc  840
cctctgtgca ccactaacac caaggagggg agcaacatct gcctgacccg gaccgaccgc  900
ggctggtact gcgacaacgc cggcagcgtg agcttcttcc ctcaggccga aacctgcaag  960
gtgcagagca acagggtgtt ctgcgacacc atgaactccc ggaccctgcc cagcgaggtg  1020
aacctgtgca acgtggacat cttcaacccc aagtacgatt gcaagatcat gacctccaag  1080
accgacgtga gcagctccgt gatcacctcc ctgggcgcca tcgtgagttg ctacggcaag  1140
accaagtgca ccgccagcaa caagaaccgc ggcatcatca agaccttcag caacggctgc  1200
gactacgtgt ccaacaaggg cgtggacacc gtgagcgtgg gcaacaccct gtactgcgtg  1260
aacaagcagg agggcaagag cctgtacgtg aagggcgagc ccatcatcaa cttctacgat  1320
ccgctggtgt tcccctccga cgagttcgac gcctccatca gccaggtgaa cgagaagatc  1380
aaccagagcc tggccttcat ccgcaagtcc gacgagctgc tgcacaacgt caacgccggt  1440
aagagcacca ccaacatcat gatcaccaca atcatcatcg tgatcattgt gatcttgctc  1500
tccttaatcg ccgtgggcct gctgctgtac tgcaaggccc ggagcacccc agtgaccctg  1560
agcaaagatc agctgtccgg catcaacaac atcgccttct ccaac                   1605

SEQ ID NO: 55          moltype = RNA  length = 1781
```

```
FEATURE                Location/Qualifiers
misc_feature           1..1781
                       note = Synthetic Polynucleotide
source                 1..1781
                       mol_type = other RNA
                       organism = synthetic construct
SEQUENCE: 55
gggaaataag agagaaaaga agagtaagaa gaaatataag accccggcgc cgccaccatg  60
gagctgctga ttctgaaggc caacgccatt accaccattc tgaccgccgt gaccttctgc  120
ttcgccagcg gccagaatat taccgaggag ttctaccagt caacctgcag cgccgtgagc  180
aagggctacc tgagcgccct acggaccggg tggtacacct ccgtgatcac cattgagctg  240
agcaatatta aggagaataa gtgcaacggg accgacgcca aggtgaagct catcaagcag  300
gagctggata agtacaagaa cgccgtgacc gagctgcagc tgctgatgca gagcacaccg  360
gccacgggct ccggcagcgc catttgctca ggcgtggccg tgtgcaaggt gctgcacctc  420
gagggcgagg tcaataagat taagagcgcc ctgttgagca ccaataaggc cgtggtgagc  480
ctgagcaacg gcgtgagcgt gctgaccttc aaggtgctgg atctcaagaa ttacattgat  540
aagcagctgc tgccaattct caataagcag agctgcagca ttagcaatat cgaaaccgtg  600
attgagttcc agcagaagaa taatcgcctg ctggagatta cccgcgagtt cagcgtcaac  660
gccggggtga ccaccccagt cagcacctac atgctgacca atagcgagct gctgagcctg  720
attaacgata tgcccattac caacgaccag aagaagctga tgagcaataa cgtgcagatt  780
gtgcgccagc agagctacag cattatgtgc attattaagg aggaggtgct ggcctacgtg  840
gtgcagctgc ccctctacgg cgtgattgat acgccctgct ggaagctgca caccagccca  900
ctgtgcacca ccaataccaa ggagggcagc aatatttgcc tgacccgcac cgatcgcggg  960
tggtactgcg ataacgccgg cagcgtgagc ttcttcccac aggccgaaac atgcaaggtg  1020
cagtccaatc gcgtgttctg cgataccatg aacagccgca ccctgcccag cgaggtgaat  1080
ctctgcaacg tggatatttt caatccaaag tacgattgca agattatgac cagcaagacc  1140
gacgtgagct ccagcgtgat tacctcactc ggcgccattg tgagctgcta cggcaagacc  1200
aagtgcaccg cctcaaataa gaatcgcggc attattaaga ccttcagcaa cggctgcgat  1260
tacgtgagca ataagggcgt ggataccgtg agcgtgggaa ataccctgta ctgcgtgaat  1320
aagcaggagg gcaagagcct gtacgtgaag ggcgagccaa ttattaattt ctacgatccc  1380
ctggtgttcc ccagcgacga gttcgacgcc agcattagcc aggtgaacga gaagattaat  1440
cagagcctgg ccttcattcg caagtccgac gagctcctgc acaacgtgaa cgccggcaag  1500
agcaccacca acatcatgat taccaccatc atcattgtga ttatcgtgat cctcctcagc  1560
ctcattgccg tgggcctcct cctgtactgc aaggcccgca gcactcctgt gaccctcagc  1620
aaggatcagc tgagcggcat caataatatc gccttcagca attgataata ggctggagcc  1680
tcggtggcct agcttcttgc cccttgggcc tccccccagc ccctcctccc cttcctgcac  1740
ccgtaccccc gtggtctttg aataaagtct gagtgggcgg c                        1781

SEQ ID NO: 56          moltype = RNA  length = 1605
FEATURE                Location/Qualifiers
misc_feature           1..1605
                       note = Synthetic Polynucleotide
source                 1..1605
                       mol_type = other RNA
                       organism = synthetic construct
SEQUENCE: 56
atggagctgc tgattctgaa ggccaacgcc attaccacca ttctgaccgc cgtgaccttc  60
tgcttcgcca gcggccagaa tattaccgag gagttctacc agtcaacctg cagcgccgtg  120
agcaagggct acctgagcgc cctacggacc gggtggtaca cctccgtgat caccattgag  180
ctgagcaata ttaaggagaa taagtgcaac gggaccgacg ccaaggtgaa gctcatcaag  240
caggagctgg ataagtacaa gaacgccgtg accgagctgc agctgctgat gcagagcaca  300
ccggccacgg gctccggcag cgccatttgc tcaggcgtgg ccgtgtgcaa ggtgctgcac  360
ctcgagggcg aggtcaataa gattaagagc gccctgttga gcaccaataa ggccgtggtg  420
agcctgagca acggcgtgag cgtgctgacc ttcaaggtgc tggatctcaa gaattacatt  480
gataagcagc tgctgccaat tctcaataag cagagctgca gcattagcaa tatcgaaacc  540
gtgattgagt tccagcagaa gaataatcgc ctgctggaga ttacccgcga gttcagcgtc  600
aacgccgggg tgaccacccc agtcagcacc tacatgctga ccaatagcga gctgctgagc  660
ctgattaacg atatgcccat taccaacgac cagaagaagc tgatgagcaa taacgtgcag  720
attgtgcgcc agcagagcta cagcattatg tgcattatta aggaggaggt gctggcctac  780
gtggtgcagc tgcccctcta cggcgtgatt gatacgccct gctggaagct gcacaccagc  840
ccactgtgca ccaccaatac caaggagggc agcaatattt gcctgacccg caccgatcgc  900
gggtggtact gcgataacgc cggcagcgtg agcttcttcc cacaggccga aacatgcaag  960
gtgcagtcca atcgcgtgtt ctgcgatacc atgaacagcc gcaccctgcc cagcgaggtg  1020
aatctctgca acgtggatat tttcaatcca aagtacgatt gcaagattat gaccagcaag  1080
accgacgtga gctccagcgt gattacctca ctcggcgcca ttgtgagctg ctacggcaag  1140
accaagtgca ccgcctcaaa taagaatcgc ggcattatta agaccttcag caacggctgc  1200
gattacgtga gcaataaggg cgtggatacc gtgagcgtgg gaaataccct gtactgcgtg  1260
aataagcagg agggcaagag cctgtacgtg aagggcgagc caattattaa tttctacgat  1320
cccctggtgt tccccagcga cgagttcgac gccagcatta gccaggtgaa cgagaagatt  1380
aatcagagcc tggccttcat tcgcaagtcc gacgagctcc tgcacaacgt gaacgccggc  1440
aagagcacca ccaacatcat gattaccacc atcatcattg tgattatcgt gatcctcctc  1500
agcctcattg ccgtgggcct cctcctgtac tgcaaggccc gcagcactcc tgtgaccctc  1560
agcaaggatc agctgagcgg catcaataat atcgccttca gcaat                    1605

SEQ ID NO: 57          moltype = RNA  length = 1781
FEATURE                Location/Qualifiers
misc_feature           1..1781
                       note = Synthetic Polynucleotide
source                 1..1781
```

```
                         mol_type = other RNA
                         organism = synthetic construct
SEQUENCE: 57
gggaaataag agagaaaaga agagtaagaa gaaatataag accccggcgc cgccaccatg  60
gagctgctga tcctgaaggc caacgccatc accaccatcc tgaccgccgt gaccttctgc  120
ttcgccagcg gccagaacat taccgaggag ttctaccagt ccacctgcag cgccgtgagc  180
aagggctacc tgagcgccct gcgcaccggg tggtacacca gcgtgatcac catcgagctg  240
tccaacatca aggagaacaa gtgcaacggc acagacgcca aggtgaagct gatcaagcag  300
gagctggaca agtacaagaa cgccgtgacc gagctccagc tgctgatgca gtccaccccg  360
gccaccggca gtggaagtgc tatctgcagc ggggtggccg tgtgcaaggt gctgcacctg  420
gagggcgagg tgaacaagat caagagcgcc ctgctgagca ccaacaaggc cgtggtgagc  480
ctgagcaacg gggtgtccgt gctgacattc aaggtgctgg acctgaagaa ctacatcgac  540
aagcagctgc tgcccatcct caacaagcag agctgctcca tctccaatat cgaaaccgtg  600
atcgagtttc agcagaagaa caaccggctg ctggagatca cccgggagtt ctccgtgaac  660
gccggggtga ccaccccagt gagcacctac atgctgacca actccgagct gctgagcctg  720
atcaacgata tgccaatcac aaacgatcag aagaagctga tgagcaacaa cgtgcagatc  780
gtgcggcagc agtcctacag catcatgtgc atcatcaagg aggaggtgct ggcctacgtg  840
gtgcagctgc ccctgtacgg cgtgatcgac actccttgct ggaagctgca cacctcaccg  900
ctgtgcacca cgaacactaa ggagggcagc aacatctgcc tgacccggac cgaccgaggc  960
tggtactgcg acaacgccgg cagcgtctct ttctttccgc aggccgagac gtgcaaggtg  1020
cagtccaacc gggtgttctg cgacaccatg aactcccgga ccctgccctc cgaggtgaac  1080
ctgtgcaacg tggacatttt caaccccaag tacgactgca agatcatgac cagtaagacc  1140
gacgtgtcca gctccgtaat caccagcctg ggcgccatcg tgtcctgtta cggcaagacc  1200
aagtgtaccg cctccaacaa gaaccgaggt atcatcaaga ccttctccaa cgggtgcgac  1260
tacgtgtcca acaagggcgt ggacaccgtg agcgtgggaa ataccctcta ctgcgtgaac  1320
aagcaggagg ggaagtccct gtacgtgaag ggtgagccca tcatcaactt ttacgatccc  1380
ctggtgttcc ccagcgacga gttcgacgca tccattagcc aggtgaacga gaagatcaac  1440
cagagtctgg ccttcatccg caagtccgac gagctgctgc acaacgtgaa cgctggcaag  1500
tcaacaacca acatcatgat cacgaccatc attatcgtga tcatcgtgat cctgctgtcc  1560
ctgatcgcag tgggcctgct cctgtactgc aaggcccgca gcacacccgt gaccctcagc  1620
aaggatcagc tcagcggcat caacaacatc gccttcagca actgataata ggctggagcc  1680
tcggtggcct agcttcttgc cccttgggcc tccccccagc ccctcctccc cttcctgcac  1740
ccgtaccccc gtggtctttg aataaagtct gagtgggcgg c                     1781

SEQ ID NO: 58            moltype = RNA  length = 1605
FEATURE                  Location/Qualifiers
misc_feature             1..1605
                         note = Synthetic Polynucleotide
source                   1..1605
                         mol_type = other RNA
                         organism = synthetic construct
SEQUENCE: 58
atggagctgc tgatcctgaa ggccaacgcc atcaccacca tcctgaccgc cgtgaccttc  60
tgcttcgcca gcggccagaa cattaccgag gagttctacc agtccacctg cagcgccgtg  120
agcaagggct acctgagcgc cctgcgcacc gggtggtaca ccagcgtgat caccatcgag  180
ctgtccaaca tcaaggagaa caagtgcaac ggcacagacg ccaaggtgaa gctgatcaag  240
caggagctgg acaagtacaa gaacgccgtg accgagctcc agctgctgat gcagtccacc  300
ccggccaccg gcagtggaag tgctatctgc agcggggtgg ccgtgtgcaa ggtgctgcac  360
ctggagggcg aggtgaacaa gatcaagagc gccctgctga gcaccaacaa ggccgtggtg  420
agcctgagca acggggtgtc cgtgctgaca ttcaaggtgc tggacctgaa gaactacatc  480
gacaagcagc tgctgcccat cctcaacaag cagagctgct ccatctccaa tatcgaaacc  540
gtgatcgagt ttcagcagaa gaacaaccgg ctgctggaga tcacccggga gttctccgtg  600
aacgccgggg tgaccacccc agtgagcacc tacatgctga ccaactccga gctgctgagc  660
ctgatcaacg atatgccaat cacaaacgat cagaagaagc tgatgagcaa caacgtgcag  720
atcgtgcggc agcagtccta cagcatcatg tgcatcatca aggaggaggt gctggcctac  780
gtggtgcagc tgcccctgta cggcgtgatc gacactcctt gctggaagct gcacacctca  840
ccgctgtgca ccacgaacac taaggagggc agcaacatct gcctgacccg gaccgaccga  900
ggctggtact gcgacaacgc cggcagcgtc tctttctttc cgcaggccga gacgtgcaag  960
gtgcagtcca accgggtgtt ctgcgacacc atgaactccc ggaccctgcc ctccgaggtg  1020
aacctgtgca acgtggacat tttcaacccc aagtacgact gcaagatcat gaccagtaag  1080
accgacgtgt ccagctccgt aatcaccagc ctgggcgcca tcgtgtcctg ttacggcaag  1140
accaagtgta ccgcctccaa caagaaccga ggtatcatca agaccttctc caacgggtgc  1200
gactacgtgt ccaacaaggg cgtggacacc gtgagcgtgg gaaataccct ctactgcgtg  1260
aacaagcagg aggggaagtc cctgtacgtg aagggtgagc ccatcatcaa cttttacgat  1320
cccctggtgt tccccagcga cgagttcgac gcatccatta gccaggtgaa cgagaagatc  1380
aaccagagtc tggccttcat ccgcaagtcc gacgagctgc tgcacaacgt gaacgctggc  1440
aagtcaacaa ccaacatcat gatcacgacc atcattatcg tgatcatcgt gatcctgctg  1500
tccctgatcg cagtgggcct gctcctgtac tgcaaggccc gcagcacacc cgtgaccctc  1560
agcaaggatc agctcagcgg catcaacaac atcgccttca gcaac                 1605

SEQ ID NO: 59            moltype = RNA  length = 1597
FEATURE                  Location/Qualifiers
misc_feature             1..1597
                         note = Synthetic Polynucleotide
source                   1..1597
                         mol_type = other RNA
                         organism = synthetic construct
SEQUENCE: 59
gggaaataag agagaaaaga agagtaagaa gaaatataag agccaccatg gaactgctca  60
```

-continued

```
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatggg aggcggtagc ggtggcggat  360
ccggcggtgg aagcggctct gccattgctt ccggcgtggc tgtatgtaaa gttctccacc  420
tcgagggaga ggttaataag attaagtcgg ccctgctgag tactaacaaa gcagtggtgt  480
cgctgagtaa cggagtaagt gtgttaacat ttaaggtgct ggacctcaag aattatattg  540
acaaacagtt gcttcctatt ctaaacaaac agagctgttc aataagtaat attgaaactg  600
ttattgagtt tcagcagaag aacaacaggc ttcttgagat tacacgcgag ttcagtgtca  660
atgccggcgt tacaacaccc gtgtctacct acatgctgac gaattctgag cttctctctc  720
tcataaacga catgcccatt acgaatgacc aaaagaaact tatgtccaac aacgtgcaga  780
ttgtgcgaca gcaatcctat agcattatgt gtatcatcaa ggaagaggta ctcgcttatg  840
ttgtgcagct accactctat ggtgtgattg acaccccctg ttggaagctg cataccagtc  900
cactctgcac cactaacaca aaggaaggga gcaatatttg cctcactcga accgacaggg  960
ggtggtattg cgataatgcg ggctccgtgt ccttctttcc acaggctgaa acttgtaagg  1020
tacagtcaaa ccgcgtgttc tgtgatacta tgaattctct gactcttccc agcgaggtta  1080
atctctgcaa cgtcgacatt ttcaatccta aatatgactg caagatcatg accagcaaga  1140
ccgacgtctc cagctcagta atcactagcc taggggccat tgtaagctgc tatggcaaaa  1200
ccaagtgtac tgcctctaat aagaacagag gcataattaa aacctttca aatggctgtg  1260
actatgtgtc gaataagggc gtcgacacgg tctcagtagg gaataccctc tactacgtta  1320
acaaacagga aggcaaatcc ctttatgtaa agggcgagcc catcataaat ttctacgacc  1380
cactttccgc catcggtggc tatatcccag aagccccaag agacggacaa gcgtacgtcc  1440
ggaaagatgg tgagtgggtc ctcctctcta cctttcttg ataataggct ggagcctcgg  1500
tggccatgct tcttgcccct tgggcctccc cccagcccct cctccccttc ctgcacccgt  1560
acccccgtgg tctttgaata aagtctgagt gggcggc                           1597

SEQ ID NO: 60          moltype = RNA  length = 1431
FEATURE                Location/Qualifiers
misc_feature           1..1431
                       note = Synthetic Polynucleotide
source                 1..1431
                       mol_type = other RNA
                       organism = synthetic construct
SEQUENCE: 60
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gggaggcggt  300
agcggtggcg gatccggcgg tggaagcggc tctgccattg cttccggcgt ggctgtatgt  360
aaagttctcc acctcgaggg agaggttaat aagattaagt cggccctgct gagtactaac  420
aaagcagtgg tgtcgctgag taacggagta agtgtgttaa catttaaggt gctggacctc  480
aagaattata ttgacaaaca gttgcttcct attctaaaca aacagagctg ttcaataagt  540
aatattgaaa ctgttattga gtttcagcag aagaacaaca ggcttcttga gattacacgc  600
gagttcagtg tcaatgccgg cgttacaaca cccgtgtcta cctacatgct gacgaattct  660
gagcttctct ctctcataaa cgacatgccc attacgaatg accaaaagaa acttatgtcc  720
aacaacgtgc agattgtgcg acagcaatcc tatagcatta tgtgtatcat caaggaagag  780
gtactcgctt atgttgtgca gctaccactc tatggtgtga ttgacacccc ctgttggaag  840
ctgcatacca gtccactctg caccactaac acaaaggaag ggagcaatat ttgcctcact  900
cgaaccgaca gggggtggta ttgcgataat gcgggctccg tgtccttctt tccacaggct  960
gaaacttgta aggtacagtc aaaccgcgtg ttctgtgata ctatgaattc tctgactctt  1020
cccagcgagg ttaatctctg caacgtcgac attttcaatc ctaaatatga ctgcaagatc  1080
atgaccagca agaccgacgt ctccagctca gtaatcacta gcctaggggc cattgtaagc  1140
tgctatggca aaaccaagtg tactgcctct aataagaaca gaggcataat taaaaccttt  1200
tcaaatggct gtgactatgt gtcgaataag ggcgtcgaca cggtctcagt agggaatacc  1260
ctctactacg ttaacaaaca ggaaggcaaa tccctttatg taaagggcga gcccatcata  1320
aatttctacg acccactttc cgccatcggt ggctatatcc cagaagcccc aagagacgga  1380
caagcgtacg tccggaaaga tggtgagtgg gtcctcctct ctacctttct t           1431

SEQ ID NO: 61          moltype = AA  length = 477
FEATURE                Location/Qualifiers
REGION                 1..477
                       note = Synthetic Polypeptide
source                 1..477
                       mol_type = protein
                       organism = synthetic construct
SEQUENCE: 61
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMGGG SGGGSGGGSG SAIASGVAVC  120
KVLHLEGEVN KIKSALLSTN KAVVSLSNGV SVLTFKVLDL KNYIDKQLLP ILNKQSCSIS  180
NIETVIEFQQ KNNRLLEITR EFSVNAGVTT PVSTYMLTNS ELLSLINDMP ITNDQKKLMS  240
NNVQIVRQQS YSIMCIIKEE VLAYVVQLPL YGVIDTPCWK LHTSPLCTTN TKEGSNICLT  300
RTDRGWYCDN AGSVSFFPQA ETCKVQSNRV FCDTMNSLTL PSEVNLCNVD IFNPKYDCKI  360
MTSKTDVSSS VITSLGAIVS CYGKTKCTAS NKNRGIIKTF SNGCDYVSNK GVDTVSVGNT  420
LYYVNKQEGK SLYVKGEPII NFYDPLSAIG GYIPEAPRDG QAYVRKDGEW VLLSTFL     477

SEQ ID NO: 62          moltype = RNA  length = 1702
FEATURE                Location/Qualifiers
```

```
misc_feature           1..1702
                       note = Synthetic Polynucleotide
source                 1..1702
                       mol_type = other RNA
                       organism = synthetic construct
SEQUENCE: 62
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatgca gagtacacct gccaccaata  360
acagagctag gagggagttg cctaggttta tgaactacac tctcaacaac gcgaagaaaa  420
ccaatgtgac gctatccaag aaacggaaga ggaggttcct ggggtttctt ttaggggtgg  480
gctctgccat tgcttccggc gtggctgtat gtaaagttct ccacctcgag ggagaggtta  540
ataagattaa gtcggccctg ctgagtacta acaaagcagt ggtgtcgctg agtaacggag  600
taagtgtgtt aacatttaag gtgctggacc tcaagaatta tattgacaaa cagttgcttc  660
ctattctaaa caaacagagc tgttcaataa gtaatattga aactgttatt gagtttcagc  720
agaagaacaa caggcttctt gagattacac gcgagttcag tgtcaatgcc ggcgttacaa  780
cacccgtgtc tacctacatg ctgacgaatt ctgagcttct ctctctcata aacgacatgc  840
ccattacgaa tgaccaaaag aaacttatgt ccaacaacgt gcagattgtg cgacagcaat  900
cctatagcat tatgtgtatc atcaaggaag aggtactcgc ttatgttgtg cagctaccac  960
tctatggtgt gattgacacc ccctgttgga agctgcatac cagtccactc tgcaccacta  1020
acacaaagga agggagcaat atttgcctca ctcgaaccga caggggggtgg tattgcgata  1080
atgcgggctc cgtgtccttc tttccacagg ctgaaacttg taaggtacag tcaaaccgcg  1140
tgttctgtga tactatgaat tctctgactc ttcccagcga ggttaatctc tgcaacgtcg  1200
acattttcaa tcctaaatat gactgcaaga tcatgaccag caagaccgac gtctccagct  1260
cagtaatcac tagcctaggg gccattgtaa gctgctatgg caaaaccaag tgtactgcct  1320
ctaataagaa cagaggcata attaaaacct tttcaaatgg ctgtgactat gtgtcgaata  1380
agggcgtcga cacggtctca gtagggaata ccctctacta cgttaacaaa caggaaggca  1440
aatcccttta tgtaaagggc gagcccatca taaatttcta cgacccactt tccgccatcg  1500
gtggctatat cccagaagcc ccaagagacg gacaagcgta cgtccggaaa gatggtgagt  1560
gggtcctcct ctctaccttt ctttgataat aggctggagc ctcggtggcc atgcttcttg  1620
ccccttgggc ctccccccag cccctcctcc ccttcctgca cccgtacccc cgtggtcttt  1680
gaataaagtc tgagtgggcg gc                                          1702

SEQ ID NO: 63          moltype = RNA  length = 1536
FEATURE                Location/Qualifiers
misc_feature           1..1536
                       note = Synthetic Polynucleotide
source                 1..1536
                       mol_type = other RNA
                       organism = synthetic construct
SEQUENCE: 63
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gcagagtaca  300
cctgccacca ataacagagc taggagggag ttgcctaggt ttatgaacta cactctcaac  360
aacgcgaaga aaaccaatgt gacgctatcc aagaaacgga agaggaggtt cctggggttt  420
cttttagggg tgggctctgc cattgcttcc ggcgtggctg tatgtaaagt tctccacctc  480
gagggagagg ttaataagat taagtcggcc ctgctgagta ctaacaaagc agtggtgtcg  540
ctgagtaacg gagtaagtgt gttaacattt aaggtgctgg acctcaagaa ttatattgac  600
aaacagttgc ttcctattct aaacaaacag agctgttcaa taagtaatat tgaaactgtt  660
attgagtttc agcagaagaa caacaggctt cttgagatta cacgcgagtt cagtgtcaat  720
gccggcgtta caacacccgt gtctacctac atgctgacga attctgagct tctctctctc  780
ataaacgaca tgcccattac gaatgaccaa aagaaactta tgtccaacaa cgtgcagatt  840
gtgcgacagc aatcctatag cattatgtgt atcatcaagg aagaggtact cgcttatgtt  900
gtgcagctac cactctatgg tgtgattgac accccctgtt ggaagctgca taccagtcca  960
ctctgcacca ctaacacaaa ggaagggagc aatatttgcc tcactcgaac cgacaggggg  1020
tggtattgcg ataatgcggg ctccgtgtcc ttctttccac aggctgaaac ttgtaaggta  1080
cagtcaaacc gcgtgttctg tgatactatg aattctctga ctcttcccag cgaggttaat  1140
ctctgcaacg tcgacatttt caatcctaaa tatgactgca agatcatgac cagcaagacc  1200
gacgtctcca gctcagtaat cactagccta ggggccattg taagctgcta tggcaaaacc  1260
aagtgtactg cctctaataa gaacagaggc ataattaaaa ccttttcaaa tggctgtgac  1320
tatgtgtcga ataagggcgt cgacacggtc tcagtaggga ataccctcta ctacgttaac  1380
aaacaggaag gcaaatccct ttatgtaaag ggcgagccca tcataaattt ctacgaccca  1440
ctttccgcca tcggtggcta tatcccagaa gccccaagag acggacaagc gtacgtccgg  1500
aaagatggtg agtgggtcct cctctctacc tttctt                           1536

SEQ ID NO: 64          moltype = AA  length = 512
FEATURE                Location/Qualifiers
REGION                 1..512
                       note = Synthetic Polypeptide
source                 1..512
                       mol_type = protein
                       organism = synthetic construct
SEQUENCE: 64
```

-continued

```
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LSAIGGYIPE APRDGQAYVR KDGEWVLLST FL                              512

SEQ ID NO: 65          moltype = RNA  length = 1798
FEATURE                Location/Qualifiers
misc_feature           1..1798
                       note = Synthetic Polynucleotide
source                 1..1798
                       mol_type = other RNA
                       organism = synthetic construct
SEQUENCE: 65
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatgca gagtacacct gccaccaata  360
acagagctag gagggagttg cctaggttta tgaactacac tctcaacaac gcgaagaaaa  420
ccaatgtgac gctatccaag aaacggaaga ggaggttcct ggggtttctt ttaggggtgg  480
gctctgccat tgcttccggc gtggctgtat gtaaagttct ccacctcgag ggagaggtta  540
ataagattaa gtcggccctg ctgagtacta acaaagcagt ggtgtcgctg agtaacggag  600
taagtgtgtt aacatttaag gtgctggacc tcaagaatta tattgacaaa cagttgcttc  660
ctattctaaa caaacagagc tgttcaataa gtaatattga aactgttatt gagtttcagc  720
agaagaacaa caggcttctt gagattacac gcgagttcag tgtcaatgcc ggcgttacaa  780
cacccgtgtc tacctacatg ctgacgaatt ctgagcttct ctctctcata aacgacatgc  840
ccattacgaa tgaccaaaag aaacttatgt ccaacaacgt gcagattgtg cgacagcaat  900
cctatagcat tatgtgtatc atcaaggaag aggtactcgc ttatgttgtg cagctaccac  960
tctatggtgt gattgacacc ccctgttgga agctgcatac cagtccactc tgcaccacta  1020
acacaaagga agggagcaat atttgcctca ctcgaaccga caggggggtgg tattgcgata  1080
atgcgggctc cgtgtccttc tttccacagg ctgaaacttg taaggtacag tcaaaccgcg  1140
tgttctgtga tactatgaat tctctgactc ttcccagcga ggttaatctc tgcaacgtcg  1200
acattttcaa tcctaaatat gactgcaaga tcatgaccag caagaccgac gtctccagct  1260
cagtaatcac tagcctaggg gccattgtaa gctgctatgg caaaaccaag tgtactgcct  1320
ctaataagaa cagaggcata attaaaacct tttcaaatgg ctgtgactat gtgtcgaata  1380
agggcgtcga cacggtctca gtagggaata ccctctacta cgttaacaaa caggaaggca  1440
aatcccttta tgtaaagggc gagcccatca taaatttcta cgacccactt gtgttcccca  1500
gttgcgaatt ctgcgcatca atctcccagg tgaacgaaaa gatcaatcaa tcccttgctt  1560
ttatacgaaa gtcagatgaa ctcctgtccg ccatcggtgg ctatatccca gaagccccaa  1620
gagacggaca agcgtacgtc cggaaagatg gtgagtgggt cctcctctct acctttcttt  1680
gataataggc tggagcctcg gtggccatgc ttcttgcccc ttgggcctcc ccccagcccc  1740
tcctcccctt cctgcacccg tacccccgtg gtctttgaat aaagtctgag tgggcggc   1798

SEQ ID NO: 66          moltype = RNA  length = 1632
FEATURE                Location/Qualifiers
misc_feature           1..1632
                       note = Synthetic Polynucleotide
source                 1..1632
                       mol_type = other RNA
                       organism = synthetic construct
SEQUENCE: 66
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gcagagtaca  300
cctgccacca ataacagagc taggagggag ttgcctaggt ttatgaacta cactctcaac  360
aacgcgaaga aaaccaatgt gacgctatcc aagaaacgga agaggaggtt cctggggttt  420
cttttagggg tgggctctgc cattgcttcc ggcgtggctg tatgtaaagt tctccacctc  480
gagggagagg ttaataagat taagtcggcc ctgctgagta ctaacaaagc agtggtgtcg  540
ctgagtaacg gagtaagtgt gttaacattt aaggtgctgg acctcaagaa ttatattgac  600
aaacagttgc ttcctattct aaacaaacag agctgttcaa taagtaatat tgaaactgtt  660
attgagtttc agcagaagaa caacaggctt cttgagatta cacgcgagtt cagtgtcaat  720
gccggcgtta caacacccgt gtctacctac atgctgacga attctgagct tctctctctc  780
ataaacgaca tgcccattac gaatgaccaa aagaaactta tgtccaacaa cgtgcagatt  840
gtgcgacagc aatcctatag cattatgtgt atcatcaagg aagaggtact cgcttatgtt  900
gtgcagctac cactctatgg tgtgattgac accccctgtt ggaagctgca taccagtcca  960
ctctgcacca ctaacacaaa ggaagggagc aatatttgcc tcactcgaac cgacaggggg  1020
tggtattgcg ataatgcggg ctccgtgtcc ttctttccac aggctgaaac ttgtaaggta  1080
cagtcaaacc gcgtgttctg tgatactatg aattctctga ctcttcccag cgaggttaat  1140
ctctgcaacg tcgacatttt caatcctaaa tatgactgca agatcatgac cagcaagacc  1200
gacgtctcca gctcagtaat cactagccta ggggccattg taagctgcta tggcaaaacc  1260
aagtgtactg cctctaataa gaacagaggc ataattaaaa ccttttcaaa tggctgtgac  1320
```

```
tatgtgtcga ataagggcgt cgacacggtc tcagtaggga ataccctcta ctacgttaac  1380
aaacaggaag gcaaatccct ttatgtaaag ggcgagccca tcataaattt ctacgaccca  1440
cttgtgttcc ccagttgcga attctgcgca tcaatctccc aggtgaacga aaagatcaat  1500
caatcccttg cttttatacg aaagtcagat gaactcctgt ccgccatcgg tggctatatc  1560
ccagaagccc caagagacgg acaagcgtac gtccggaaag atggtgagtg ggtcctcctc  1620
tctacctttc tt                                                       1632

SEQ ID NO: 67          moltype = AA  length = 544
FEATURE                Location/Qualifiers
REGION                 1..544
                       note = Synthetic Polypeptide
source                 1..544
                       mol_type = protein
                       organism = synthetic construct
SEQUENCE: 67
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSCEFCA SISQVNEKIN QSLAFIRKSD ELLSAIGGYI PEAPRDGQAY VRKDGEWVLL  540
STFL                                                                544

SEQ ID NO: 68          moltype = RNA  length = 1693
FEATURE                Location/Qualifiers
misc_feature           1..1693
                       note = Synthetic Polynucleotide
source                 1..1693
                       mol_type = other RNA
                       organism = synthetic construct
SEQUENCE: 68
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatggg aggcggtagc ggtggcggat  360
ccggcggtgg aagcggctct gccattgctt ccggcgtggc tgtatgtaaa gttctccacc  420
tcgagggaga ggttaataag attaagtcgg ccctgctgag tactaacaaa gcagtggtgt  480
cgctgagtaa cggagtaagt gtgttaacat ttaaggtgct ggacctcaag aattatattg  540
acaaacagtt gcttcctatt ctaaacaaac agagctgttc aataagtaat attgaaactg  600
ttattgagtt tcagcagaag aacaacaggc ttcttgagat tacacgcgag ttcagtgtca  660
atgccggcgt tacaacaccc gtgtctacct acatgctgac gaattctgag cttctctctc  720
tcataaacga catgcccatt acgaatgacc aaaagaaact tatgtccaac aacgtgcaga  780
ttgtgcgaca gcaatcctat agcattatgt gtatcatcaa ggaagaggta ctcgcttatg  840
ttgtgcagct accactctat ggtgtgattg acacccccctg ttggaagctg cataccagtc  900
cactctgcac cactaacaca aaggaaggga gcaatatttg cctcactcga accgacaggg  960
ggtggtattg cgataatgcg ggctccgtgt ccttctttcc acaggctgaa acttgtaagg  1020
tacagtcaaa ccgcgtgttc tgtgatacta tgaattctct gactcttccc agcgaggtta  1080
atctctgcaa cgtcgacatt ttcaatccta aatatgactg caagatcatg accagcaaga  1140
ccgacgtctc cagctcagta atcactagcc taggggccat tgtaagctgc tatggcaaaa  1200
ccaagtgtac tgcctctaat aagaacagag gcataattaa aaccttttca aatggctgtg  1260
actatgtgtc gaataagggc gtcgacacgg tctcagtagg gaataccctc tactacgtta  1320
acaaacagga aggcaaatcc ctttatgtaa agggcgagcc catcataaat ttctacgacc  1380
cacttgtgtt ccccagttgc gaattctgcg catcaatctc ccaggtgaac gaaaagatca  1440
atcaatccct tgcttttata cgaaagtcag atgaactcct gtccgccatc ggtggctata  1500
tcccagaagc cccaagagac ggacaagcgt acgtccggaa agatggtgag tgggtcctcc  1560
tctctacctt tctttgataa taggctggag cctcggtggc catgcttctt gccccttggg  1620
cctccccccca gcccctcctc cccttcctgc acccgtaccc ccgtggtctt tgaataaagt  1680
ctgagtgggc ggc                                                      1693

SEQ ID NO: 69          moltype = RNA  length = 1527
FEATURE                Location/Qualifiers
misc_feature           1..1527
                       note = Synthetic Polynucleotide
source                 1..1527
                       mol_type = other RNA
                       organism = synthetic construct
SEQUENCE: 69
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gggaggcggt  300
agcggtggcg gatccggcgg tggaagcggc tctgccattg cttccggcgt ggctgtatgt  360
aaagttctcc acctcgaggg agaggttaat aagattaagt cggccctgct gagtactaac  420
```

```
aaagcagtgg tgtcgctgag taacggagta agtgtgttaa catttaaggt gctggacctc  480
aagaattata ttgacaaaca gttgcttcct attctaaaca aacagagctg ttcaataagt  540
aatattgaaa ctgttattga gtttcagcag aagaacaaca ggcttcttga gattacacgc  600
gagttcagtg tcaatgccgg cgttacaaca cccgtgtcta cctacatgct gacgaattct  660
gagcttctct ctctcataaa cgacatgccc attacgaatg accaaaagaa acttatgtcc  720
aacaacgtgc agattgtgcg acagcaatcc tatagcatta tgtgtatcat caaggaagag  780
gtactcgctt atgttgtgca gctaccactc tatggtgtga ttgacacccc ctgttggaag  840
ctgcatacca gtccactctg caccactaac acaaaggaag ggagcaatat ttgcctcact  900
cgaaccgaca gggggtggta ttgcgataat gcgggctccg tgtccttctt tccacaggct  960
gaaacttgta aggtacagtc aaaccgcgtg ttctgtgata ctatgaattc tctgactctt  1020
cccagcgagg ttaatctctg caacgtcgac attttcaatc ctaaatatga ctgcaagatc  1080
atgaccagca agaccgacgt ctccagctca gtaatcacta gcctaggggc cattgtaagc  1140
tgctatggca aaaccaagtg tactgcctct aataagaaca gaggcataat taaaaccttt  1200
tcaaatggct gtgactatgt gtcgaataag ggcgtcgaca cggtctcagt agggaatacc  1260
ctctactacg ttaacaaaca ggaaggcaaa tccctttatg taaagggcga gcccatcata  1320
aatttctacg acccacttgt gttccccagt tgcgaattct gcgcatcaat ctcccaggtg  1380
aacgaaaaga tcaatcaatc ccttgctttt atacgaaagt cagatgaact cctgtccgcc  1440
atcggtggct atatcccaga agccccaaga gacggacaag cgtacgtccg gaaagatggt  1500
gagtgggtcc tcctctctac ctttctt                                     1527

SEQ ID NO: 70          moltype = AA  length = 509
FEATURE                Location/Qualifiers
REGION                 1..509
                       note = Synthetic Polypeptide
source                 1..509
                       mol_type = protein
                       organism = synthetic construct
SEQUENCE: 70
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMGGG SGGGSGGGSG SAIASGVAVC  120
KVLHLEGEVN KIKSALLSTN KAVVSLSNGV SVLTFKVLDL KNYIDKQLLP ILNKQSCSIS  180
NIETVIEFQQ KNNRLLEITR EFSVNAGVTT PVSTYMLTNS ELLSLINDMP ITNDQKKLMS  240
NNVQIVRQQS YSIMCIIKEE VLAYVVQLPL YGVIDTPCWK LHTSPLCTTN TKEGSNICLT  300
RTDRGWYCDN AGSVSFFPQA ETCKVQSNRV FCDTMNSLTL PSEVNLCNVD IFNPKYDCKI  360
MTSKTDVSSS VITSLGAIVS CYGKTKCTAS NKNRGIIKTF SNGCDYVSNK GVDTVSVGNT  420
LYYVNKQEGK SLYVKGEPII NFYDPLVFPS CEFCASISQV NEKINQSLAF IRKSDELLSA  480
IGGYIPEAPR DGQAYVRKDG EWVLLSTFL                                   509

SEQ ID NO: 71          moltype = RNA  length = 1888
FEATURE                Location/Qualifiers
misc_feature           1..1888
                       note = Synthetic Polynucleotide
source                 1..1888
                       mol_type = other RNA
                       organism = synthetic construct
SEQUENCE: 71
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatgca gagtacacct gccaccaata  360
acagagctag gagggagttg cctaggttta tgaactacac tctcaacaac gcgaagaaaa  420
ccaatgtgac gctatccaag aaacggaaga ggaggttcct ggggttcttt ttaggggtgg  480
gctctgccat tgcttccggc gtggctgtat gtaaagttct ccacctcgag ggagaggtta  540
ataagattaa gtcggccctg ctgagtacta acaaagcagt ggtgtcgctg agtaacggag  600
taagtgtgtt aacatttaag gtgctggacc tcaagaatta tattgacaaa cagttgcttc  660
ctattctaaa caaacagagc tgttcaataa gtaatattga aactgttatt gagtttcagc  720
agaagaacaa caggcttctt gagattacac gcgagttcag tgtcaatgcc ggcgttacaa  780
cacccgtgtc tacctacatg ctgacgaatt ctgagcttct ctctctcata aacgacatgc  840
ccattacgaa tgaccaaaag aaacttatgt ccaacaacgt gcagattgtg cgacagcaat  900
cctatagcat tatgtgtatc atcaaggaag aggtactcgc ttatgttgtg cagctaccac  960
tctatggtgt gattgacacc ccctgttgga agctgcatac cagtccactc tgcaccacta  1020
acacaaagga agggagcaat atttgcctca ctcgaaccga cagggggtgg tattgcgata  1080
atgcgggctc cgtgtccttc tttccacagg ctgaaacttg taaggtacag tcaaaccgcg  1140
tgttctgtga tactatgaat tctctgactc ttcccagcga ggttaatctc tgcaacgtcg  1200
acattttcaa tcctaaatat gactgcaaga tcatgaccag caagaccgac gtctccagct  1260
cagtaatcac tagcctaggg gccattgtaa gctgctatgg caaaaccaag tgtactgcct  1320
ctaataagaa cagaggcata attaaaacct tttcaaatgg ctgtgactat gtgtcgaata  1380
agggcgtcga cacggtctca gtagggaata ccctctacta cgttaacaaa caggaaggca  1440
aatcccttta tgtaaagggc gagcccatca taaatttcta cgacccactt gtgttcccca  1500
gttgcgaatt ctgcgcatca atctcccagg tgaacgaaaa gatcaatcaa tcccttgctt  1560
ttatacgaaa gtcagatgaa ctcctgcata acgtgaatgc tgggaaatct acaaccaaca  1620
tcatgatcac taccatcatt attgtgatta tcgtaattct gctatccttg attgctgtcg  1680
ggctgcttct gtactgtaag gccagatcga cgcctgtgac cctttcaaaa gaccaactta  1740
gcggtatcaa taatattgcc tttagcaatt gataataggc tggagcctcg gtggccatgc  1800
ttcttgcccc ttgggcctcc ccccagcccc tcctcccctt cctgcacccg tacccccgtg  1860
gtctttgaat aaagtctgag tgggcggc                                    1888
```

```
SEQ ID NO: 72          moltype = RNA  length = 1722
FEATURE                Location/Qualifiers
misc_feature           1..1722
                       note = Synthetic Polynucleotide
source                 1..1722
                       mol_type = other RNA
                       organism = synthetic construct
SEQUENCE: 72
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gcagagtaca  300
cctgccacca ataacagagc taggagggag ttgcctaggt ttatgaacta cactctcaac  360
aacgcgaaga aaaccaatgt gacgctatcc aagaaacgga agaggaggtt cctggggttt  420
cttttagggg tgggctctgc cattgcttcc ggcgtggctg tatgtaaagt tctccacctc  480
gagggagagg ttaataagat taagtcggcc ctgctgagta ctaacaaagc agtggtgtcg  540
ctgagtaacg gagtaagtgt gttaacattt aaggtgctgg acctcaagaa ttatattgac  600
aaacagttgc ttcctattct aaacaaacag agctgttcaa taagtaatat tgaaactgtt  660
attgagtttc agcagaagaa caacaggctt cttgagatta cacgcgagtt cagtgtcaat  720
gccggcgtta caacacccgt gtctacctac atgctgacga attctgagct tctctctctc  780
ataaacgaca tgcccattac gaatgaccaa aagaaactta tgtccaacaa cgtgcagatt  840
gtgcgacagc aatcctatag cattatgtgt atcatcaagg aagaggtact cgcttatgtt  900
gtgcagctac cactctatgg tgtgattgac accccctgtt ggaagctgca taccagtcca  960
ctctgcacca ctaacacaaa ggaagggagc aatatttgcc tcactcgaac cgacaggggg  1020
tggtattgcg ataatgcggg ctccgtgtcc ttctttccac aggctgaaac ttgtaaggta  1080
cagtcaaacc gcgtgttctg tgatactatg aattctctga ctcttcccag cgaggttaat  1140
ctctgcaacg tcgacatttt caatcctaaa tatgactgca agatcatgac cagcaagacc  1200
gacgtctcca gctcagtaat cactagccta ggggccattg taagctgcta tggcaaaacc  1260
aagtgtactg cctctaataa gaacagaggc ataattaaaa ccttttcaaa tggctgtgac  1320
tatgtgtcga ataagggcgt cgacacggtc tcagtaggga ataccctcta ctacgttaac  1380
aaacaggaag gcaaatccct ttatgtaaag ggcgagccca tcataaattt ctacgaccca  1440
cttgtgttcc ccagttgcga attctgcgca tcaatctccc aggtgaacga aaagatcaat  1500
caatcccttg cttttatacg aaagtcagat gaactcctgc ataacgtgaa tgctgggaaa  1560
tctacaacca acatcatgat cactaccatc attattgtga ttatcgtaat tctgctatcc  1620
ttgattgctg tcgggctgct tctgtactgt aaggccagat cgacgcctgt gaccctttca  1680
aaagaccaac ttagcggtat caataatatt gcctttagca at                    1722

SEQ ID NO: 73          moltype = AA  length = 574
FEATURE                Location/Qualifiers
REGION                 1..574
                       note = Synthetic Polypeptide
source                 1..574
                       mol_type = protein
                       organism = synthetic construct
SEQUENCE: 73
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSCEFCA SISQVNEKIN QSLAFIRKSD ELLHNVNAGK STTNIMITTI IVIIVILLS  540
LIAVGLLLYC KARSTPVTLS KDQLSGINNI AFSN                             574

SEQ ID NO: 74          moltype = RNA  length = 1783
FEATURE                Location/Qualifiers
misc_feature           1..1783
                       note = Synthetic Polynucleotide
source                 1..1783
                       mol_type = other RNA
                       organism = synthetic construct
SEQUENCE: 74
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatggg aggcggtagc ggtggcggat  360
ccggcggtgg aagcggctct gccattgctt ccggcgtggc tgtatgtaaa gttctccacc  420
tcgagggaga ggttaataag attaagtcgg ccctgctgag tactaacaaa gcagtggtgt  480
cgctgagtaa cggagtaagt gtgttaacat ttaaggtgct ggacctcaag aattatattg  540
acaaacagtt gcttcctatt ctaaacaaac agagctgttc aataagtaat attgaaactg  600
ttattgagtt tcagcagaag aacaacaggc ttcttgagat tacacgcgag ttcagtgtca  660
atgccggcgt tacaacaccc gtgtctacct acatgctgac gaattctgag cttctctctc  720
tcataaacga catgcccatt acgaatgacc aaaagaaact tatgtccaac aacgtgcaga  780
ttgtgcgaca gcaatcctat agcattatgt gtatcatcaa ggaagaggta ctcgcttatg  840
```

-continued

```
ttgtgcagct accactctat ggtgtgattg acaccccctg ttggaagctg cataccagtc  900
cactctgcac cactaacaca aaggaaggga gcaatatttg cctcactcga accgacaggg  960
ggtggtattg cgataatgcg ggctccgtgt ccttctttcc acaggctgaa acttgtaagg  1020
tacagtcaaa ccgcgtgttc tgtgatacta tgaattctct gactcttccc agcgaggtta  1080
atctctgcaa cgtcgacatt ttcaatccta aatatgactg caagatcatg accagcaaga  1140
ccgacgtctc cagctcagta atcactagcc taggggccat tgtaagctgc tatggcaaaa  1200
ccaagtgtac tgcctctaat aagaacagag gcataattaa aacctttca aatggctgtg  1260
actatgtgtc gaataagggc gtcgacacgg tctcagtagg gaataccctc tactacgtta  1320
acaaacagga aggcaaatcc ctttatgtaa agggcgagcc catcataaat ttctacgacc  1380
cacttgtgtt ccccagttgc gaattctgcg catcaatctc ccaggtgaac gaaaagatca  1440
atcaatccct tgcttttata cgaaagtcag atgaactcct gcataacgtg aatgctggga  1500
aatctacaac caacatcatg atcactacca tcattattgt gattatcgta attctgctat  1560
ccttgattgc tgtcgggctg cttctgtact gtaaggccag atcgacgcct gtgacccttt  1620
caaaagacca acttagcggt atcaataata ttgcctttag caattgataa taggctggag  1680
cctcggtggc catgcttctt gccccttggg cctcccccca gcccctcctc cccttcctgc  1740
acccgtaccc ccgtggtctt tgaataaagt ctgagtgggc ggc                   1783
```

```
SEQ ID NO: 75          moltype = RNA  length = 1617
FEATURE                Location/Qualifiers
misc_feature           1..1617
                       note = Synthetic Polynucleotide
source                 1..1617
                       mol_type = other RNA
                       organism = synthetic construct
SEQUENCE: 75
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gggaggcggt  300
agcggtggcg gatccggcgg tggaagcggc tctgccattg cttccggcgt ggctgtatgt  360
aaagttctcc acctcgaggg agaggttaat aagattaagt cggccctgct gagtactaac  420
aaagcagtgg tgtcgctgag taacggagta agtgtgttaa catttaaggt gctggacctc  480
aagaattata ttgacaaaca gttgcttcct attctaaaca aacagagctg ttcaataagt  540
aatattgaaa ctgttattga gtttcagcag aagaacaaca ggcttcttga gattacacgc  600
gagttcagtg tcaatgccgg cgttacaaca cccgtgtcta cctacatgct gacgaattct  660
gagcttctct ctctcataaa cgacatgccc attacgaatg accaaaagaa acttatgtcc  720
aacaacgtgc agattgtgcg acagcaatcc tatagcatta tgtgtatcat caaggaagag  780
gtactcgctt atgttgtgca gctaccactc tatggtgtga ttgacacccc ctgttggaag  840
ctgcatacca gtccactctg caccactaac acaaaggaag ggagcaatat ttgcctcact  900
cgaaccgaca gggggtggta ttgcgataat gcgggctccg tgtccttctt tccacaggct  960
gaaacttgta aggtacagtc aaaccgcgtg ttctgtgata ctatgaattc tctgactctt  1020
cccagcgagg ttaatctctg caacgtcgac attttcaatc ctaaatatga ctgcaagatc  1080
atgaccagca agaccgacgt ctccagctca gtaatcacta gcctaggggc cattgtaagc  1140
tgctatggca aaaccaagtg tactgcctct aataagaaca gaggcataat taaaaccttt  1200
tcaaatggct gtgactatgt gtcgaataag ggcgtcgaca cggtctcagt agggaatacc  1260
ctctactacg ttaacaaaca ggaaggcaaa tccctttatg taaagggcga gcccatcata  1320
aatttctacg acccacttgt gttccccagt tgcgaattct gcgcatcaat ctcccaggtg  1380
aacgaaaaga tcaatcaatc ccttgctttt atacgaaagt cagatgaact cctgcataac  1440
gtgaatgctg ggaaatctac aaccaacatc atgatcacta ccatcattat tgtgattatc  1500
gtaattctgc tatccttgat tgctgtcggg ctgcttctgt actgtaaggc cagatcgacg  1560
cctgtgaccc tttcaaaaga ccaacttagc ggtatcaata atattgcctt tagcaat     1617
```

```
SEQ ID NO: 76          moltype = AA  length = 539
FEATURE                Location/Qualifiers
REGION                 1..539
                       note = Synthetic Polypeptide
source                 1..539
                       mol_type = protein
                       organism = synthetic construct
SEQUENCE: 76
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMGGG SGGGSGGGSG SAIASGVAVC  120
KVLHLEGEVN KIKSALLSTN KAVVSLSNGV SVLTFKVLDL KNYIDKQLLP ILNKQSCSIS  180
NIETVIEFQQ KNNRLLEITR EFSVNAGVTT PVSTYMLTNS ELLSLINDMP ITNDQKKLMS  240
NNVQIVRQQS YSIMCIIKEE VLAYVVQLPL YGVIDTPCWK LHTSPLCTTN TKEGSNICLT  300
RTDRGWYCDN AGSVSFFPQA ETCKVQSNRV FCDTMNSLTL PSEVNLCNVD IFNPKYDCKI  360
MTSKTDVSSS VITSLGAIVS CYGKTKCTAS NKNRGIIKTF SNGCDYVSNK GVDTVSVGNT  420
LYYVNKQEGK SLYVKGEPII NFYDPLVFPS CEFCASISQV NEKINQSLAF IRKSDELLHN  480
VNAGKSTTNI MITTIIIVII VILLSLIAVG LLLYCKARST PVTLSKDQLS GINNIAFSN   539
```

```
SEQ ID NO: 77          moltype = RNA  length = 57
FEATURE                Location/Qualifiers
misc_feature           1..57
                       note = Synthetic Polynucleotide
source                 1..57
                       mol_type = other RNA
                       organism = synthetic construct
SEQUENCE: 77
```

```
gggaaataag agagaaaaga agagtaagaa gaaatataag accccggcgc cgccacc     57

SEQ ID NO: 78          moltype = RNA  length = 119
FEATURE                Location/Qualifiers
misc_feature           1..119
                       note = Synthetic Polynucleotide
source                 1..119
                       mol_type = other RNA
                       organism = synthetic construct
SEQUENCE: 78
tgataatagg ctggagcctc ggtggcctag cttcttgccc cttgggcctc cccccagccc  60
ctcctcccct tcctgcaccc gtacccccgt ggtctttgaa taaagtctga gtgggcggc   119

SEQ ID NO: 79          moltype = AA  length = 30
FEATURE                Location/Qualifiers
REGION                 1..30
                       note = Synthetic Polypeptide
source                 1..30
                       mol_type = protein
                       organism = synthetic construct
SEQUENCE: 79
MDSKGSSQKG SRLLLLLVVS NLLLPQGVVG                                    30

SEQ ID NO: 80          moltype = AA  length = 18
FEATURE                Location/Qualifiers
REGION                 1..18
                       note = Synthetic Polypeptide
source                 1..18
                       mol_type = protein
                       organism = synthetic construct
SEQUENCE: 80
MDWTWILFLV AAATRVHS                                                 18

SEQ ID NO: 81          moltype = AA  length = 20
FEATURE                Location/Qualifiers
REGION                 1..20
                       note = Synthetic Polypeptide
source                 1..20
                       mol_type = protein
                       organism = synthetic construct
SEQUENCE: 81
METPAQLLFL LLLWLPDTTG                                               20

SEQ ID NO: 82          moltype = AA  length = 24
FEATURE                Location/Qualifiers
REGION                 1..24
                       note = Synthetic Polypeptide
source                 1..24
                       mol_type = protein
                       organism = synthetic construct
SEQUENCE: 82
MLGSNSGQRV VFTILLLLVA PAYS                                          24

SEQ ID NO: 83          moltype = AA  length = 17
FEATURE                Location/Qualifiers
REGION                 1..17
                       note = Synthetic Polypeptide
source                 1..17
                       mol_type = protein
                       organism = synthetic construct
SEQUENCE: 83
MKCLLYLAFL FIGVNCA                                                  17

SEQ ID NO: 84          moltype = AA  length = 15
FEATURE                Location/Qualifiers
REGION                 1..15
                       note = Synthetic Polypeptide
source                 1..15
                       mol_type = protein
                       organism = synthetic construct
SEQUENCE: 84
MWLVSLAIVT ACAGA                                                    15

SEQ ID NO: 85          moltype =   length =
SEQUENCE: 85
000

SEQ ID NO: 86          moltype = RNA  length = 11
FEATURE                Location/Qualifiers
```

```
misc_feature           1..11
                       note = Synthetic Polynucleotide
source                 1..11
                       mol_type = other RNA
                       organism = synthetic construct
SEQUENCE: 86
gggatcctac c                                                    11

SEQ ID NO: 87          moltype =   length =
SEQUENCE: 87
000

SEQ ID NO: 88          moltype = RNA  length = 1722
FEATURE                Location/Qualifiers
misc_feature           1..1722
                       note = Synthetic Polynucleotide
source                 1..1722
                       mol_type = other RNA
                       organism = synthetic construct
SEQUENCE: 88
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa aaacgctgtg accgagctgc agttattgat gcagagtaca  300
cctgccacca ataacagagc taggagggag ttgcctaggt ttatgaacta cactctcaac  360
aacgcgaaaa aaaccaatgt gacgctatcc aagaaacgga agaggaggtt cctggggttt  420
cttttagggg tgggctctgc cattgcttcc ggcgtggctg tatgtaaagt tctccacctc  480
gagggagagg ttaataagat taagtcggcc ctgctgagta ctaacaaagc agtggtgtcg  540
ctgagtaacg gagtaagtgt gttaacattt aaggtgctgg acctcaagaa ttatattgac  600
aaacagttgc ttcctattct aaacaaacag agctgttcaa taagtaatat tgaaactgtt  660
attgagtttc agcagaagaa caacaggctt cttgagatta cacgcgagtt cagtgtcaat  720
gccggcgtta caacacccgt gtctacctac atgctgacga attctgagct tctctctctc  780
ataaacgaca tgcccattac gaatgaccaa aaaaaactta tgtccaacaa cgtgcagatt  840
gtgcgacagc aatcctatag cattatgtgt atcatcaagg aagaggtact cgcttatgtt  900
gtgcagctac cactctatgg tgtgattgac accccctgtt ggaagctgca taccagtcca  960
ctctgcacca ctaacacaaa ggaagggagc aatatttgcc tcactcgaac cgacaggggg  1020
tggtattgcg ataatgcggg ctccgtgtcc ttctttccac aggctgaaac ttgtaaggta  1080
cagtcaaacc gcgtgttctg tgatactatg aattctctga ctcttcccag cgaggttaat  1140
ctctgcaacg tcgacatttt caatcctaaa tatgactgca agatcatgac cagcaagacc  1200
gacgtctcca gctcagtaat cactagccta ggggccattg taagctgcta tggcaaaacc  1260
aagtgtactg cctctaataa gaacagaggc ataattaaaa ccttttcaaa tggctgtgac  1320
tatgtgtcga ataagggcgt cgacacggtc tcagtaggga ataccctcta ctacgttaac  1380
aaacaggaag gcaaatccct ttatgtaaag ggcgagccca tcataaattt ctacgaccca  1440
cttgtgttcc ccagtgatga attcgatgca tcaatctccc aggtgaacga aaagatcaat  1500
caatcccttg cttttatacg aaagtcagat gaactcctgc ataacgtgaa tgctgggaaa  1560
tctacaacca acatcatgat cactaccatc attattgtga ttatcgtaat tctgctatcc  1620
ttgattgctg tcgggctgct tctgtactgt aaggccagat cgacgcctgt gaccctttca  1680
aaagaccaac ttagcggtat caataatatt gcctttagca at                  1722

SEQ ID NO: 89          moltype = AA  length = 574
FEATURE                Location/Qualifiers
REGION                 1..574
                       note = Synthetic Polypeptide
source                 1..574
                       mol_type = protein
                       organism = synthetic construct
SEQUENCE: 89
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                           574

SEQ ID NO: 90          moltype = RNA  length = 1888
FEATURE                Location/Qualifiers
misc_feature           1..1888
                       note = Synthetic Polynucleotide
source                 1..1888
                       mol_type = other RNA
                       organism = synthetic construct
SEQUENCE: 90
gggaaataag agagaaaaga agagtaagaa gaaatataag agccaccatg gaactgctca  60
ttttgaaggc aaacgctatc acgacaatac tcactgcagt gaccttctgt tttgcctcag  120
```

-continued

```
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataaaaa cgctgtgacc gagctgcagt tattgatgca gagtacacct gccaccaata  360
acagagctag gagggagttg cctaggttta tgaactacac tctcaacaac gcgaaaaaaa  420
ccaatgtgac gctatccaag aaacggaaga ggaggttcct ggggtttctt ttaggggtgg  480
gctctgccat tgcttccggc gtggctgtat gtaaagttct ccacctcgag ggagaggtta  540
ataagattaa gtcggccctg ctgagtacta acaaagcagt ggtgtcgctg agtaacggag  600
taagtgtgtt aacatttaag gtgctggacc tcaagaatta tattgacaaa cagttgcttc  660
ctattctaaa caaacagagc tgttcaataa gtaatattga aactgttatt gagtttcagc  720
agaagaacaa caggcttctt gagattacac gcgagttcag tgtcaatgcc ggcgttacaa  780
cacccgtgtc tacctacatg ctgacgaatt ctgagcttct ctctctcata aacgacatgc  840
ccattacgaa tgaccaaaaa aaacttatgt ccaacaacgt gcagattgtg cgacagcaat  900
cctatagcat tatgtgtatc atcaaggaag aggtactcgc ttatgttgtg cagctaccac  960
tctatggtgt gattgacacc ccctgttgga agctgcatac cagtccactc tgcaccacta  1020
acacaaagga agggagcaat atttgcctca ctcgaaccga caggggggtgg tattgcgata  1080
atgcgggctc cgtgtccttc tttccacagg ctgaaacttg taaggtacag tcaaaccgcg  1140
tgttctgtga tactatgaat tctctgactc ttcccagcga ggttaatctc tgcaacgtcg  1200
acattttcaa tcctaaatat gactgcaaga tcatgaccag caagaccgac gtctccagct  1260
cagtaatcac tagcctaggg gccattgtaa gctgctatgg caaaaccaag tgtactgcct  1320
ctaataagaa cagaggcata attaaaacct tttcaaatgg ctgtgactat gtgtcgaata  1380
agggcgtcga cacggtctca gtagggaata ccctctacta cgttaacaaa caggaaggca  1440
aatcccttta tgtaaagggc gagcccatca taaatttcta cgacccactt gtgttcccca  1500
gtgatgaatt cgatgcatca atctcccagg tgaacgaaaa gatcaatcaa tcccttgctt  1560
ttatacgaaa gtcagatgaa ctcctgcata acgtgaatgc tgggaaatct acaaccaaca  1620
tcatgatcac taccatcatt attgtgatta tcgtaattct gctatccttg attgctgtcg  1680
ggctgcttct gtactgtaag gccagatcga cgcctgtgac cctttcaaaa gaccaactta  1740
gcggtatcaa taatattgcc tttagcaatt gataataggc tggagcctcg gtggccatgc  1800
ttcttgcccc ttgggcctcc ccccagcccc tcctcccctt cctgcacccg tacccccgtg  1860
gtctttgaat aaagtctgag tgggcggc                                    1888
```

```
SEQ ID NO: 91          moltype = RNA  length = 1722
FEATURE                Location/Qualifiers
misc_feature           1..1722
                       note = Synthetic Polynucleotide
source                 1..1722
                       mol_type = other RNA
                       organism = synthetic construct
SEQUENCE: 91
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgagtgc gctccgcaca ggatggtaca cctccgtgat caccatcgag  180
ctcagcaata ttaaagagaa caagtgcaat ggtaccgacg ctaaagtcaa acttatcaag  240
caggaactcg acaaatataa gaacgctgtg accgagctgc agttattgat gcagagtaca  300
cctgccacca ataacagagc taggagggag ttgcctaggt ttatgaacta cactctcaac  360
aacgcgaaga aaaccaatgt gacgctatcc aagaaacgga agaggaggtt cctggggttt  420
cttttagggg tgggctctgc cattgcttcc ggcgtggctg tatgtaaagt tctccacctc  480
gagggagagg ttaataagat taagtcggcc ctgctgagta ctaacaaagc agtggtgtcg  540
ctgagtaacg gagtaagtgt gttaacattt aaggtgctgg acctcaagaa ttatattgac  600
aaacagttgc ttcctattct aaacaaacag agctgttcaa taagtaatat tgaaactgtt  660
attgagtttc agcagaagaa caacaggctt cttgagatta cacgcgagtt cagtgtcaat  720
gccggcgtta caacacccgt gtctacctac atgctgacga attctgagct tctctctctc  780
ataaacgaca tgcccattac gaatgaccaa aagaaactta tgtccaacaa cgtgcagatt  840
gtgcgacagc aatcctatag cattatgtgt atcatcaagg aagaggtact cgcttatgtt  900
gtgcagctac cactctatgg tgtgattgac acccccctgtt ggaagctgca taccagtcca  960
ctctgcacca ctaacacaaa ggaagggagc aatatttgcc tcactcgaac cgacaggggg  1020
tggtattgcg ataatgcggg ctccgtgtcc ttctttccac aggctgaaac ttgtaaggta  1080
cagtcaaacc gcgtgttctg tgatactatg aattctctga ctcttcccag cgaggttaat  1140
ctctgcaacg tcgacatttt caatcctaaa tatgactgca agatcatgac cagcaagacc  1200
gacgtctcca gctcagtaat cactagccta ggggccattg taagctgcta tggcaaaacc  1260
aagtgtactg cctctaataa gaacagaggc ataattaaaa ccttttcaaa tggctgtgac  1320
tatgtgtcga ataagggcgt cgacacggtc tcagtaggga ataccctcta ctacgttaac  1380
aaacaggaag gcaaatccct ttatgtaaag ggcgagccca tcataaattt ctacgaccca  1440
cttgtgttcc ccagtgatga attcgatgca tcaatctccc aggtgaacga aaagatcaat  1500
caatcccttg cttttatacg aaagtcagat gaactcctgc ataacgtgaa tgctgggaaa  1560
tctacaacca acatcatgat cactaccatc attattgtga ttatcgtaat tctgctatcc  1620
ttgattgctg tcgggctgct tctgtactgt aaggccagat cgacgcctgt gaccctttca  1680
aaagaccaac ttagcggtat caataatatt gcctttagca at                    1722
```

```
SEQ ID NO: 92          moltype = RNA  length = 1888
FEATURE                Location/Qualifiers
misc_feature           1..1888
                       note = Synthetic Polynucleotide
source                 1..1888
                       mol_type = other RNA
                       organism = synthetic construct
SEQUENCE: 92
gggaaataag agagaaaaga agagtaagaa gaaatataag agccaccatg gaactgctca  60
ttttgaaggc aaacgctatc acgacaatac tcactgcagt gaccttctgt tttgcctcag  120
```

```
gccagaacat aaccgaggag ttttatcaat ctacatgcag cgctgtatct aaaggctacc  180
tgagtgcgct ccgcacagga tggtacacct ccgtgatcac catcgagctc agcaatatta  240
aagagaacaa gtgcaatggt accgacgcta aagtcaaact tatcaagcag gaactcgaca  300
aatataagaa cgctgtgacc gagctgcagt tattgatgca gagtacacct gccaccaata  360
acagagctag gagggagttg cctaggttta tgaactacac tctcaacaac gcgaagaaaa  420
ccaatgtgac gctatccaag aaacggaaga ggaggttcct ggggtttctt ttaggggtgg  480
gctctgccat tgcttccggc gtggctgtat gtaaagttct ccacctcgag ggagaggtta  540
ataagattaa gtcggccctg ctgagtacta acaaagcagt ggtgtcgctg agtaacggag  600
taagtgtgtt aacatttaag gtgctggacc tcaagaatta tattgacaaa cagttgcttc  660
ctattctaaa caaacagagc tgttcaataa gtaatattga aactgttatt gagtttcagc  720
agaagaacaa caggcttctt gagattacac gcgagttcag tgtcaatgcc ggcgttacaa  780
cacccgtgtc tacctacatg ctgacgaatt ctgagcttct ctctctcata aacgacatgc  840
ccattacgaa tgaccaaaag aaacttatgt ccaacaacgt gcagattgtg cgacagcaat  900
cctatagcat tatgtgtatc atcaaggaag aggtactcgc ttatgttgtg cagctaccac  960
tctatggtgt gattgacacc ccctgttgga agctgcatac cagtccactc tgcaccacta  1020
acacaaagga agggagcaat atttgcctca ctcgaaccga caggggggtgg tattgcgata  1080
atgcgggctc cgtgtccttc tttccacagg ctgaaacttg taaggtacag tcaaaccgcg  1140
tgttctgtga tactatgaat tctctgactc ttcccagcga ggttaatctc tgcaacgtcg  1200
acattttcaa tcctaaatat gactgcaaga tcatgaccag caagaccgac gtctccagct  1260
cagtaatcac tagcctaggg gccattgtaa gctgctatgg caaaaccaag tgtactgcct  1320
ctaataagaa cagaggcata attaaaacct tttcaaatgg ctgtgactat gtgtcgaata  1380
agggcgtcga cacggtctca gtagggaata ccctctacta cgttaacaaa caggaaggca  1440
aatcccttta tgtaaagggc gagcccatca taaatttcta cgacccactt gtgttcccca  1500
gtgatgaatt cgatgcatca atctcccagg tgaacgaaaa gatcaatcaa tcccttgctt  1560
ttatacgaaa gtcagatgaa ctcctgcata acgtgaatgc tgggaaatct acaaccaaca  1620
tcatgatcac taccatcatt attgtgatta tcgtaattct gctatccttg attgctgtcg  1680
ggctgcttct gtactgtaag gccagatcga cgcctgtgac cctttcaaaa gaccaactta  1740
gcggtatcaa taatattgcc tttagcaatt gataataggc tggagcctcg gtggccatgc  1800
ttcttgcccc ttgggcctcc ccccagcccc tcctcccctt cctgcacccg tacccccgtg  1860
gtctttgaat aaagtctgag tgggcggc                                   1888

SEQ ID NO: 93          moltype = DNA  length = 25
FEATURE                Location/Qualifiers
misc_feature           1..25
                       note = Synthetic Polynucleotide
source                 1..25
                       mol_type = other DNA
                       organism = synthetic construct
SEQUENCE: 93
ctcaatttcc tcacttctcc agtgt                                      25

SEQ ID NO: 94          moltype = DNA  length = 24
FEATURE                Location/Qualifiers
misc_feature           1..24
                       note = Synthetic Polynucleotide
source                 1..24
                       mol_type = other DNA
                       organism = synthetic construct
SEQUENCE: 94
cttgattcct cggtgtacct ctgt                                       24

SEQ ID NO: 95          moltype = DNA  length = 25
FEATURE                Location/Qualifiers
misc_feature           1..25
                       note = Synthetic Polynucleotide
source                 1..25
                       mol_type = other DNA
                       organism = synthetic construct
SEQUENCE: 95
tcccattatg cctaggccag cagca                                      25

SEQ ID NO: 96          moltype = RNA  length = 1515
FEATURE                Location/Qualifiers
misc_feature           1..1515
                       note = Synthetic Polynucleotide
source                 1..1515
                       mol_type = other RNA
                       organism = synthetic construct
SEQUENCE: 96
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgggcgc gctccgcaca ggatggtaca cctccgtgat caccatcgag  180
ctcagcaata ttaaagagat caagtgcaat ggtaccgacg ctaaagtcaa acttatcaag  240
caggaactcg acaaatataa gaacgctgtg accgacctgc agttattgat gcagagtaca  300
cctgccaccg ggtcgggctc tgccatttgc tccggcgtgg ctgtatgtaa agttctccac  360
ctcgagggag aggttaataa gattaagtcg gccctgctga gtactaacaa agcagtggtg  420
tcgctgagta acggagtaag tgtgttaaca tttaaggtgc tggacctcaa gaattatatt  480
gacaaacagt tgcttcctat tctaaacaaa cagagctgtt caatacccaa tattgaaact  540
gttattgagt ttcagcagaa gaacaacagg cttcttgaga ttacacgcga gttcagtgtc  600
```

```
aatgccggcg ttacaacacc cgtgtctacc tacatgctga cgaattctga gcttctctct  660
ctcataaacg acatgcccat tacgaatgac caaaagaaac ttatgtccaa caacgtgcag  720
attgtgcgac agcaatccta tagcattatg tgtatcatca aggaagaggt actcgcttat  780
gttgtgcagc taccactcta tggtgtgatt gacacccccct gttggaagct gcataccagt  840
ccactctgca ccactaacac aaaggaaggg agcaatattt gcctcactcg aaccgacagg  900
gggtggtatt gcgataatgc gggctccgtg tccttctttc cacaggctga aacttgtaag  960
gtacagtcaa accgcgtgtt ctgtgatact atgaattctc gtactcttcc cagcgaggtt  1020
aatctctgca acgtcgacat tttcaatcct aaatatgact gcaagatcat gaccagcaag  1080
accgacgtct ccagctcagt aatcactagc ctaggggcca ttgtaagctg ctatggcaaa  1140
accaagtgta ctgcctctaa taagaacaga ggcataatta aaacctttc aaatggctgt  1200
gactatgtgt cgaataaggg cgtcgacacg gtctcagtag ggaataccct ctactgcgtt  1260
aacaaacagg aaggccagtc cctttatgta aagggcgagc ccatcataaa tttctacgac  1320
ccacttgtgt tccccagtga tgaattcgat gcatcaatct cccaggtgaa cgaaaagatc  1380
aatcaatccc ttgcttttat acgaaagtca gatgaactcc tgtccgccat cggtggctat  1440
atcccagaag ccccaagaga cggacaagcg tacgtccgga aagatggtga gtgggtcctc  1500
ctctctacct ttctt                                                   1515
```

```
SEQ ID NO: 97          moltype = RNA  length = 1518
FEATURE                Location/Qualifiers
misc_feature           1..1518
                       note = Synthetic Polynucleotide
source                 1..1518
                       mol_type = other RNA
                       organism = synthetic construct
SEQUENCE: 97
atggaactgc tcattttgaa ggcaaacgct atcacgacaa tactcactgc agtgaccttc  60
tgttttgcct caggccagaa cataaccgag gagttttatc aatctacatg cagcgctgta  120
tctaaaggct acctgggcgc gctccgcaca ggatggtaca cctccgtgat caccatcgag  180
ctcagcaata ttaaagagat caagtgcaat ggtaccgacg ctaaagtcaa acttatcaag  240
caggaactcg acaaatataa gaacgctgtg accgacctgc agttattgat gcagagtaca  300
cctgccaccg ggtcgggctc tgccattgct tccggcgtgg ctgtatgtaa agttctccac  360
ctcgagggag aggttaataa gattaagtcg gccctgctga gtactaacaa agcagtggtg  420
tcgctgagtg gctgcggagt aagtgtgtta acatttaagg tgctggacct caagaattat  480
attgacaaac agttgcttcc tattctaaac aaacagagct gttcaatacc caatattgaa  540
actgttattg agtttcagca gaagaacaac aggcttcttg agattacacg cgagttcagt  600
gtcaatgccg gcgttacaac acccgtgtct acctacatgc tgacgaattc tgagcttctc  660
tctctcataa acgacatgcc cattacgaat gaccaaaaga aacttatgtc caacaacgtg  720
cagattgtgc gacagcaatc ctatagcatt atgtgtatca tcaaggaaga ggtactcgct  780
tatgttgtgc agctaccact ctatggtgtg attgacaccc cctgttggaa gctgcatacc  840
agtccactct gcaccactaa cacaaaggaa gggagcaata tttgcctcac tcgaaccgac  900
agggggtggt attgcgataa tgcgggctcc gtgtccttct ttccacaggc tgaaacttgt  960
aaggtacagt caaaccgcgt gttctgtgat actatgaatt ctcgtactct tcccagcgag  1020
gttaatctct gcaacgtcga cattttcaat cctaaatatg actgcaagat catgaccagc  1080
aagaccgacg tctccagctc agtaatcact agcctagggg ccattgtaag ctgctatggc  1140
aaaaccaagt gtactgcctc taataagtgc agaggcataa ttaaaacctt ttcaaatggc  1200
tgtgactatg tgtcgaataa gggcgtcgac acggtctcag tagggaatac cctctactac  1260
gttaacaaac aggaaggcca gtccctttat gtaaagggcg agcccatcat aaatttctac  1320
gacccacttg tgttccccag tgatgaattc gatgcatcaa tctcccaggt gaacgaaaag  1380
atcaatcaat cccttgcttt tatacgaaag tcagatgaac tcctgtccgc catcggtggc  1440
tatatcccag aagccccaag agacggacaa gcgtacgtcc ggaaagatgg tgagtgggtc  1500
ctcctctcta cctttctt                                                1518
```

```
SEQ ID NO: 98          moltype = RNA  length = 1681
FEATURE                Location/Qualifiers
misc_feature           1..1681
                       note = Synthetic Polynucleotide
source                 1..1681
                       mol_type = other RNA
                       organism = synthetic construct
SEQUENCE: 98
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgggcgcgct ccgcacagga tggtacacct ccgtgatcac catcgagctc agcaatatta  240
aagagatcaa gtgcaatggt accgacgcta aagtcaaact tatcaagcag gaactcgaca  300
aatataagaa cgctgtgacc gacctgcagt tattgatgca gagtacacct gccaccgggt  360
cgggctctgc catttgctcc ggcgtggctg tatgtaaagt tctccacctc gagggagagg  420
ttaataagat taagtcggcc ctgctgagta ctaacaaagc agtggtgtcg ctgagtaacg  480
gagtaagtgt gttaacattt aaggtgctgg acctcaagaa ttatattgac aaacagttgc  540
ttcctattct aaacaaacag agctgttcaa tacccaatat tgaaactgtt attgagtttc  600
agcagaagaa caacaggctt cttgagatta cacgcgagtt cagtgtcaat gccggcgtta  660
caacacccgt gtctacctac atgctgacga attctgagct tctctctctc ataaacgaca  720
tgcccattac gaatgaccaa aagaaactta tgtccaacaa cgtgcagatt gtgcgacagc  780
aatcctatag cattatgtgt atcatcaagg aagaggtact cgcttatgtt gtgcagctac  840
cactctatgg tgtgattgac accccctgtt ggaagctgca taccagtcca ctctgcacca  900
ctaacacaaa ggaagggagc aatatttgcc tcactcgaac cgacaggggg tggtattgcg  960
ataatgcggg ctccgtgtcc ttctttccac aggctgaaac ttgtaaggta cagtcaaacc  1020
gcgtgttctg tgatactatg aattctcgta ctcttcccag cgaggttaat ctctgcaacg  1080
tcgacatttt caatcctaaa tatgactgca agatcatgac cagcaagacc gacgtctcca  1140
```

-continued

```
gctcagtaat cactagccta ggggccattg taagctgcta tggcaaaacc aagtgtactg  1200
cctctaataa gaacagaggc ataattaaaa ccttttcaaa tggctgtgac tatgtgtcga  1260
ataagggcgt cgacacggtc tcagtaggga ataccctcta ctgcgttaac aaacaggaag  1320
gccagtccct ttatgtaaag ggcgagccca tcataaattt ctacgaccca cttgtgttcc  1380
ccagtgatga attcgatgca tcaatctccc aggtgaacga aaagatcaat caatcccttg  1440
cttttatacg aaagtcagat gaactcctgt ccgccatcgg tggctatatc ccagaagccc  1500
caagagacgg acaagcgtac gtccggaaag atggtgagtg ggtcctcctc tctacctttc  1560
tttgataata ggctggagcc tcggtggcca tgcttcttgc cccttgggcc tccccccagc  1620
ccctcctccc cttcctgcac ccgtaccccc gtggtctttg aataaagtct gagtgggcgg  1680
c                                                                  1681

SEQ ID NO: 99           moltype = RNA  length = 1684
FEATURE                 Location/Qualifiers
misc_feature            1..1684
                        note = Synthetic Polynucleotide
source                  1..1684
                        mol_type = other RNA
                        organism = synthetic construct
SEQUENCE: 99
gggaaataag agagaaaaga agagtaagaa gaaatataag agccaccatg gaactgctca  60
ttttgaaggc aaacgctatc acgacaatac tcactgcagt gaccttctgt tttgcctcag  120
gccagaacat aaccgaggag ttttatcaat ctacatgcag cgctgtatct aaaggctacc  180
tgggcgcgct ccgcacagga tggtacacct ccgtgatcac catcgagctc agcaatatta  240
aagagatcaa gtgcaatggt accgacgcta aagtcaaact tatcaagcag gaactcgaca  300
aatataagaa cgctgtgacc gacctgcagt tattgatgca gagtacacct gccaccgggt  360
cgggctctgc cattgcttcc ggcgtggctg tatgtaaagt tctccacctc gagggagagg  420
ttaataagat taagtcggcc ctgctgagta ctaacaaagc agtggtgtcg ctgagtggct  480
gcggagtaag tgtgttaaca tttaaggtgc tggacctcaa gaattatatt gacaaacagt  540
tgcttcctat tctaaacaaa cagagctgtt caatacccaa tattgaaact gttattgagt  600
ttcagcagaa gaacaacagg cttcttgaga ttacacgcga gttcagtgtc aatgccggcg  660
ttacaacacc cgtgtctacc tacatgctga cgaattctga gcttctctct ctcataaacg  720
acatgcccat tacgaatgac caaaagaaac ttatgtccaa caacgtgcag attgtgcgac  780
agcaatccta tagcattatg tgtatcatca aggaagaggt actcgcttat gttgtgcagc  840
taccactcta tggtgtgatt gacacccccct gttggaagct gcataccagt ccactctgca  900
ccactaacac aaaggaaggg agcaatattt gcctcactcg aaccgacagg gggtggtatt  960
gcgataatgc gggctccgtg tccttctttc cacaggctga aacttgtaag gtacagtcaa  1020
accgcgtgtt ctgtgatact atgaattctc gtactcttcc cagcgaggtt aatctctgca  1080
acgtcgacat tttcaatcct aaatatgact gcaagatcat gaccagcaag accgacgtct  1140
ccagctcagt aatcactagc ctaggggcca ttgtaagctg ctatggcaaa accaagtgta  1200
ctgcctctaa taagtgcaga ggcataatta aaaccttttc aaatggctgt gactatgtgt  1260
cgaataaggg cgtcgacacg gtctcagtag ggaataccct ctactacgtt aacaaacagg  1320
aaggccagtc cctttatgta aagggcgagc ccatcataaa tttctacgac ccacttgtgt  1380
tccccagtga tgaattcgat gcatcaatct cccaggtgaa cgaaaagatc aatcaatccc  1440
ttgcttttat acgaaagtca gatgaactcc tgtccgccat cggtggctat atcccagaag  1500
ccccaagaga cggacaagcg tacgtccgga aagatggtga gtgggtcctc ctctctacct  1560
ttctttgata ataggctgga gcctcggtgg ccatgcttct tgccccttgg gcctcccccc  1620
agcccctcct ccccttcctg cacccgtacc cccgtggtct ttgaataaag tctgagtggg  1680
cggc                                                               1684

SEQ ID NO: 100          moltype = AA  length = 25
FEATURE                 Location/Qualifiers
REGION                  1..25
                        note = Synthetic Polypeptide
source                  1..25
                        mol_type = protein
                        organism = synthetic construct
SEQUENCE: 100
MELLILKANA ITTILTAVTF CFASG                                        25
```

RSV RNA VACCINES

RELATED APPLICATIONS

This application is a continuation of U.S. application Ser. No. 16/965,589, filed Jul. 28, 2020, which is a national stage filing under 35 U.S.C. § 371 of international application number PCT/US2019/015412, filed Jan. 28, 2019, which was published under PCT Article 21 (2) in English and claims the benefit under 35 U.S.C. § 119 (e) of U.S. provisional application No. 62/623,240, filed Jan. 29, 2018, each of which is incorporated by reference herein in its entirety.

REFERENCE TO AN ELECTRONIC SEQUENCE LISTING

The contents of the electronic sequence listing (M137870101US02-SEQ-JXV.xml; Size: 240,818 bytes; and Date of Creation: Jan. 18, 2024) is herein incorporated by reference in its entirety.

BACKGROUND

The human respiratory syncytial virus (RSV) is a negative-sense, single-stranded RNA virus of the genus *Pneumovirinae* and of the family Paramyxoviridae. Symptoms in adults typically resemble a sinus infection or the common cold, although the infection may be asymptomatic. In older adults (e.g., >60 years), RSV infection may progress to bronchiolitis or pneumonia. Symptoms in children are often more severe. It is estimated that in the United States, most children are infected with RSV by the age of three. The RSV virion includes of an internal nucleocapsid comprised of the viral RNA bound to nucleoprotein (N), phosphoprotein (P), and large polymerase protein (L). The nucleocapsid is surrounded by matrix protein (M) and is encapsulated by a lipid bilayer into which the viral fusion (F) and attachment (G) proteins as well as the small hydrophobic protein (SH) are incorporated. The viral genome also encodes two non-structural proteins (NS1 and NS2), which inhibit type I interferon activity as well as the M-2 protein. Currently, there is no vaccine to prevent primary infection or disease.

SUMMARY

Provided herein, in some embodiments, are highly immunogenic respiratory syncytial virus (RSV) ribonucleic acid (RNA) (e.g., mRNA) compositions (e.g, vaccines) that elicit potent neutralizing antibodies responses at a dose that is at least 5-fold lower than a control, wherein the control is, for example, a RNA vaccine encoding a membrane-bound DS-CAV1-stabilized prefusion F protein of RSV (e.g., SEQ ID NO: 90 or SEQ ID NO: 92). The envelope of RSV contains three surface glycoproteins: F, G, and SH. The G and F proteins are protective antigens and targets of neutralizing antibodies. The F protein, however, is more conserved across RSV strains and types (A and B). RSV F is a type I viral fusion protein that structurally rearranges from a metastable prefusion form to a highly stable postfusion form. Although targets for neutralizing monoclonal antibodies exist on the postfusion conformation of F protein, the neutralizing Ab response primarily targets the F protein prefusion conformation in people naturally infected with RSV (Magro M et al., Proc Natl Acad Sci USA; 109(8): 3089-94, 2012; Ngwuta J O et al., Sci Transl Med 2015; 7(309):309ra162). Thus, the present disclosure focuses, in some aspects, on RNA vaccines encoding RSV F protein (e.g., F protein trimer) stabilized in its prefusion conformation. These RNA vaccines encode antigens that elicit an even greater immune response and that are even more stable in the prefusion form, relative to previously described recombinant RSV F trimers, which includes RSV F trimers containing the "DS-CAV1" substitutions (155C, 290C, 190F, and 207L).

In some aspects, the RSV vaccines of the present disclosure include a RNA comprising an open reading frame (ORF) encoding a RSV antigen, wherein intramuscular (IM) administration of a therapeutically effective amount of the vaccine to a subject induces in the subject a neutralizing antibody titer.

Some aspects of the present disclosure provide respiratory syncytial virus (RSV) vaccines comprising a ribonucleic acid (RNA) that comprises an open reading frame (ORF) encoding an RSV antigen, wherein the ORF comprises (or consists of, or consists essentially of) a sequence that is at least 95% (e.g., at least 96%, at least 97%, at least 98%, at least 99%) or 95%-99% identical to a sequence identified by any one of SEQ ID NOS: 3, 7, 10, 13, 16, 19, 22, 24, 26, 28, 30, 32, 34, 37, 40, 43, 46, 49, 52, 54, 56, 58, 60, 63, 66, 69, 75, 96, or 97. In some aspects, the vaccine is formulated in a lipid nanoparticle. In some embodiments, the ORF comprises a sequence that is at least 98% identical to a sequence identified by any one of SEQ ID NOS: 3, 7, 10, 13, 16, 19, 22, 24, 26, 28, 30, 32, 34, 37, 40, 43, 46, 49, 52, 54, 56, 58, 60, 63, 66, 69, 75, 96, or 97. In some embodiments, the RNA comprises an ORF encoding an RSV antigen, wherein the ORF comprises a sequence identified by (is 100% identical to) any one of SEQ ID NOS: 3, 7, 10, 13, 16, 19, 22, 24, 26, 28, 30, 32, 34, 37, 40, 43, 46, 49, 52, 54, 56, 58, 60, 63, 66, 69, 72, 75, 96 or 97.

In some embodiments, the ORF comprises (or consists of, or consists essentially of) a sequence that is identified by (is 100% identical to) SEQ ID NO: 22. In some embodiments, the ORF comprises a sequence that is identified by (is 100% identical to) SEQ ID NO: 75. In some embodiments, the ORF comprises (or consists of, or consists essentially of) a sequence that is identified by (is 100% identical to) SEQ ID NO: 3. In some embodiments, the ORF comprises (or consists of, or consists essentially of) a sequence that is identified by (is 100% identical to) SEQ ID NO: 52. In some embodiments, the ORF comprises a sequence that is identified by (is 100% identical to) SEQ ID NO: 54. In some embodiments, the ORF comprises a sequence that is identified by (is 100% identical to) SEQ ID NO: 56. In some embodiments, the ORF comprises a sequence that is identified by (is 100% identical to) SEQ ID NO: 58.

Other aspects of the present disclosure provide a RSV vaccine comprising (or consisting of, or consisting essentially of) a RNA that comprises an ORF encoding an RSV antigen, wherein the ORF encodes a sequence identified by any one of SEQ ID NOS: 5, 8, 11, 14, 17, 20, 22, 35, 38, 41, 44, 47, 50, 61, 65, 67, 70, 73, 76. In some aspects, said RSV vaccine is formulated in a lipid nanoparticle.

In some embodiments, the RNA comprises (or consists of, or consists essentially of) an ORF encoding a single chain recombinant RSV F peptide comprising a deletion of wild type RSV F amino acid positions 98-146 and a linker of eight to fourteen amino acids between wildtype RSV F amino acid positions 97 and 147, wherein the recombinant F peptide comprises the following amino acid modifications to stabilize the recombinant RSV F peptide when oligermized to form a trimer in a perfusion conformations: (i) 190F and 207L amino acid substitutions. (ii) 155C and 290C amino acid substitutions, and (iii) one (or more) of (a) 486C and 490C amino acid substitutions; (b) 180C and 186C amino acid substitutions; (c) 486C and 489C amino acid substitutions; (d) 512C and 513C amino acid substitutions; and (e) an 505C amino acid substitution. The amino acid substitutions that introduce additional cysteine amino acid residues may result in either intra-peptide or inter-peptide disulfide bonds, specifically between the recited substitution pairs (e.g., a non-native intra peptide disulfide bond between 155C and 290C or between 180C and 186C; a non-native inter-peptide disulfide bond between 486C and 490C, between 486C and 489C or between 512C and 513C).

In some embodiments, intramuscular (IM) administration of a therapeutically effective amount of the vaccine to a subject induces in the subject a neutralizing antibody titer to (or against) the RSV F.

In some embodiments, the neutralizing antibody titer is at least 5-fold to at least 100-fold (e.g., at least 5-fold, at least 10-fold, at least 15-fold, at least 20-fold, at least 25-fold, or at least 50-fold) higher relative to control. In some embodiments the control is a RNA vaccine encoding a membrane-bound DS-CAV1-stabilized prefusion F protein of RSV. In some embodiments, the control RNA vaccine encoding a membrane-bound DS-CAV1-stabilized prefusion F protein of RSV comprises (or consists of, or consists essentially of) a sequence identified by SEQ ID NO: 90 or SEQ ID NO: 92. In some embodiments, the control is a live attenuated RSV vaccine, an inactivated RSV vaccine, or a protein subunit RSV vaccine.

In some embodiments, the at least 5-fold to at least 100-fold (e.g., at least 5-fold, at least 10-fold, at least 15-fold, at least 20-fold, at least 25-fold, or at least 50-fold) higher neutralizing antibody titer is induced in the subject following administration of a dose of the vaccine that is at least 5-fold (e.g., at least 6-fold, at least 7-fold, at least 8-fold, at least 9-fold, at least 10-fold) lower relative to the control.

In some embodiments, IM administration of a therapeutically effective amount of the vaccine to a subject induces in the subject at least 10-fold, at least 15-fold, at least 20-fold, or at least 25-fold higher prefusion RSV F-specific neutralizing antibody titers relative to the control.

In some embodiments. IM administration of a therapeutically effective amount of the vaccine to a subject confers prophylactic protection at a 5-fold (e.g., at least 6-fold, at least 7-fold, at least 8-fold, at least 9-fold, at least 10-fold) lower dose relative to the control.

In some embodiments, the RSV F neutralizing antibody titer is induced in the subject following fewer than three (e.g., one or two) doses of the vaccine.

In some embodiments, a single dose is of 5 μg-25 μg (e.g., 5 μg, 10 μg, 15 μg, 20 μg, or 25 μg).

In some embodiments, a 5 μg booster dose of the vaccine induces in African green monkeys a $NT_{50}$ neutralizing antibody titer of about $10^3$. In some embodiments, a 5 μg booster dose of the vaccine induces in African green monkeys a $NT_{50}$ neutralizing antibody titer of at least $10^3$. In some embodiments, a 5 μg booster dose of the vaccine induces in African green monkeys a $NT_{50}$ neutralizing antibody titer of about $10^4$. In some embodiments, a 5 μg booster dose of the vaccine induces in African green monkeys a $NT_{50}$ neutralizing antibody titer of at least $10^4$. In some embodiments, the $NT_{50}$ neutralizing antibody titer (e.g., of about $10^4$ or about $10^4$) is induced 2 weeks post vaccine administration. Methods of assessing neutralizing antibody titers are known and described, for example, by Zhang L, et al. Design and characterization of a fusion glycoprotein vaccine for Respiratory Syncytial Virus with improved stability. *Vaccine* 2018; 36: 8119-8130; and Shambaugh C, et al. Development of a high-throughput respiratory syncytial virus fluorescent focus-based microneutralization assay. *Clin Vaccine Immnunol* 2017; 24: e00225-17, each of which is incorporated by reference herein in its entirety.

In some embodiments, the RSV vaccine comprises (a) a ribonucleic acid (RNA) comprising an open reading frame (ORF) encoding two RSV antigens, or (b) two RNAs, each comprising an ORF encoding an RSV antigen.

In some embodiments, the lipid nanoparticle comprises a molar ratio of 20-60% ionizable cationic lipid, 5-25% non-cationic lipid, 25-55% sterol, and 0.5-15% PEG-modified lipid.

In some embodiments, the RSV antigen is fused to a scaffold moiety. In some embodiments, the scaffold moiety is selected from the group consisting of: ferritin, encapsulin, lumazine synthase, hepatitis B surface antigen, and hepatitis B core antigen.

In some embodiments, the RNA comprises messenger RNA (mRNA).

In some embodiments, the RNA further comprises a 5' UTR. In some embodiments, the 5'UTR comprises a sequence identified by SEQ ID NO: 2 or SEQ ID NO: 77. In some embodiments, the RNA further comprises a 3' UTR. In some embodiments, the 3'UTR comprises a sequence identified by SEQ ID NO: 4 or SEQ ID NO: 78.

In some embodiments, the RNA is unmodified. In some embodiments, the RNA comprise at least one modified nucleotide. In some embodiments, at least 80% of the uracil in the ORF comprise a 1-methyl-pseudouridine modification.

Some aspects of the present disclosure provide methods comprising administering to a subject the RSV RNA vaccine as provided herein in a therapeutically effective amount to induce in the subject a neutralizing antibody titer against the RSV antigen delivered to the subject. In some embodiments, provided are methods comprising administering to a subject the RSV RNA vaccine as provided herein in a therapeutically effective amount to induct in the subject a RSV F neutralizing antibody titer.

In some embodiments, the vaccine is administered intramuscularly.

Also provided herein, in some aspects, are methods comprising intramuscularly administering to a subject a respiratory syncytial virus (RSV) vaccine, comprising a ribonucleic acid (RNA) that comprises a sequence that is at least 95% identical to a sequence identified by SEQ ID NO: 21 formulated in a lipid nanoparticle, wherein an at least 5-fold neutralizing antibody titer is induced in the subject following administration of a dose of the vaccine that is at least 5-fold lower relative to a control, wherein the control is a RNA vaccine encoding a membrane-bound DS-CAV1-stabilized prefusion F protein of RSV, optionally wherein the control comprises a sequence identified by SEQ ID NO: 90 or SEQ ID NO: 92. In some embodiments, the RNA of the RSV vaccine comprise a sequence identified by SEQ ID NO: 22.

Provided herein in other aspects are methods comprising intramuscularly administering to a subject a respiratory syncytial virus (RSV) vaccine, comprising a ribonucleic acid (RNA) that comprises a sequence that is at least 95% identical to a sequence identified by SEQ ID NO: 75 formulated in a lipid nanoparticle, wherein an at least 5-fold neutralizing antibody titer is induced in the subject following administration of a dose of the vaccine that is at least 5-fold lower relative to a control, wherein the control is a RNA vaccine encoding a membrane-bound DS-CAV1-stabilized prefusion F protein of RSV. In some embodiments, the RNA of the RSV vaccine comprises a sequence identified by SEQ ID NO: 75. In some embodiments, the control RNA RSV vaccine encodes a membrane-bound DS-CAV1-stabilized prefusion F protein of RSV and the sequence of the control comprises a sequence identified by SEQ TD NO: 90 or SEQ ID NO: 92.

In some aspects, the present disclosure provides an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 22. In some embodiments, the ORF shares at least 96% identity with SEQ ID NO: 22. In other embodiments, the ORF shares at least 97% identity with SEQ ID NO: 22. In some embodiments, the ORF shares at least 98% identity with SEQ ID NO: 22. In some embodiments, the ORF shares at least 99% identity SEQ ID NO: 22. In some embodiments, the ORF comprises the sequence of SEQ ID NO: 22.

In some aspects, the present disclosure provides an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 3. In some embodiments, the ORF shares at least 96% identity with SEQ ID NO: 3. In other embodiments, the ORF shares at least 97% identity with SEQ ID NO: 3. In some embodiments, the ORF shares at least 98% identity with SEQ ID NO: 3. In some embodiments, the ORF shares at least 99% identity SEQ ID NO: 22. In some embodiments, the ORF comprises the sequence of SEQ ID NO: 3.

In some aspects, the present disclosure provides an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 52. In some embodiments, the ORF shares at least 96% identity with SEQ ID NO: 52. In other embodiments, the ORF shares at least 97% identity with SEQ ID NO: 52. In some embodiments, the ORF shares at least 98% identity with SEQ ID NO: 52. In some embodiments, the ORF shares at least 99% identity SEQ ID NO: 52. In some embodiments, the ORF comprises the sequence of SEQ ID NO: 52.

In some aspects, the present disclosure provides an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 54. In some embodiments, the ORF shares at least 96% identity with SEQ ID NO: 54. In other embodiments, the ORF shares at least 97% identity with SEQ ID NO: 54. In some embodiments, the ORF shares at least 98% identity with SEQ ID NO: 54. In some embodiments, the ORF shares at least 99% identity SEQ ID NO: 54. In some embodiments, the ORF comprises the sequence of SEQ ID NO: 54.

In some aspects, the present disclosure provides an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 56. In some embodiments, the ORF shares at least 96% identity with SEQ ID NO: 56. In other embodiments, the ORF shares at least 97% identity with SEQ ID NO: 56. In some embodiments, the ORF shares at least 98% identity with SEQ ID NO: 56. In some embodiments, the ORF shares at least 99% identity SEQ ID NO: 56. In some embodiments, the ORF comprises the sequence of SEQ ID NO: 56.

In some aspects, the present disclosure provides an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 58. In some embodiments, the ORF shares at least 96% identity with SEQ ID NO: 58. In other embodiments, the ORF shares at least 97% identity with SEQ ID NO: 58. In some embodiments, the ORF shares at least 98% identity with SEQ ID NO: 58. In some embodiments, the ORF shares at least 99% identity SEQ ID NO: 58. In some embodiments, the ORF comprises the sequence of SEQ ID NO: 58.

In some aspects, the present disclosure provides an immunogenic composition (e.g., vaccine) comprising a RNA (e.g., mRNA) that comprises an ORF encoding an RSV antigen, wherein the RSV antigen comprises (or consists of, or consists essentially of) SEQ ID NO: 5 (with or without a signal sequence MELLILKANAITTILTAVTFCFASG (SEQ ID NO: 100)).

In some embodiments, the immunogenic composition is formulated in a lipid nanoparticle. In some embodiments, the lipid nanoparticle comprises a molar ratio of 20-60% ionizable cationic lipid, 5-25% non-cationic lipid, 25-55% sterol, and 0.5-15% PEG-modified lipid. In some embodiments, the lipid nanoparticle comprises (13Z,16Z)—N,N-dimethyl-2-nonylhenicosa-12,15-dien-1-amine, cholesterol. DSPC, and PEG-2000 DMG. In some embodiments, the lipid nanoparticle comprises 55-65 mole % (13Z,16Z)—N,N-dimethyl-2-nonylhenicosa-12,15-dien-1-amine, 25-35 mole % cholesterol, 5-15 mole % DSPC, and 1-5 mole % PEG-2000 DMG. In some embodiments, the lipid nanoparticle comprises 58 mole % (13Z,16Z)—N,N-dimethyl-2-nonylhenicosa-12,15-dien-1-amine, 30 mole % cholesterol, 10 mole % DSPC, and 2 mole % PEG-2000 DMG.

Thus, in some aspects, immunogenic compositions of the present disclosure comprise a RNA (e.g., mRNA) that comprises an ORF that comprises (or consists of, or consists essentially of) a sequence that shares at least 95% identity with a sequence of SEQ ID NO: 22, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, immunogenic compositions of the present disclosure comprise a RNA (e.g., mRNA) that comprises an ORF that comprises (or consists of, or consists essentially of) a sequence that shares at least 95% identity with a sequence of SEQ ID NO: 3, wherein the RNA is formulated in a lipid nanoparticle that comprises (13Z,16Z)—N,N-dimethyl-2-nonylhenicosa-12,15-dien-1-amine, cholesterol. DSPC, and PEG-2000 DMG.

In some aspects, immunogenic compositions of the present disclosure comprise a RNA (e.g., mRNA) that comprises an ORF that comprises (or consists of, or consists essentially of) a sequence that shares at least 95% identity with a sequence of SEQ ID NO: 52, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, immunogenic compositions of the present disclosure comprise a RNA (e.g., mRNA) that comprises an ORF that comprises (or consists of, or consists essentially of) a sequence that shares at least 95% identity with a sequence of SEQ ID NO: 54, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, immunogenic compositions of the present disclosure comprise a RNA (e.g., mRNA) that comprises an ORF that comprises (or consists of, or consists essentially of) a sequence that shares at least 95% identity with a sequence of SEQ ID NO: 56, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, immunogenic compositions of the present disclosure comprise a RNA (e.g., mRNA) that comprises an ORF that comprises (or consists of, or consists essentially of) a sequence that shares at least 95% identity with a sequence of SEQ ID NO: 58, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some embodiments of the immunogenic compositions of the present disclosure, the RNA further comprises a 5' cap. In some embodiments, the 5' cap comprises 7mG(5')ppp(5')NlmpNp.

In some embodiments of the immunogenic compositions of the present disclosure, the RNA further comprises a 5' UTR and/or 3' UTR. In some embodiments, the RNA further comprises a 5' UTR comprising a sequence of SEQ ID NO: 2. In some embodiments, the RNA further comprises a 3' UTR comprising a sequence of SEQ ID NO: 4. In some embodiments, the RNA further comprises a 5' UTR comprising a sequence of SEQ ID NO: 2 and a 3' UTR comprising a sequence of SEQ ID NO: 4.

In some embodiments, the RNA further comprises a polyA tail. In some embodiments, the polyA tail has a length of 100 nucleotides. In some embodiments, the polyA tail has at least 50 nucleotides. In some embodiments, the polyA tail has at least 60 nucleotides. In some embodiments, the polyA tail has at least 70 nucleotides. In some embodiments, the polyA tail has at least 80 nucleotides. In some embodiments, the polyA tail has at least 90 nucleotides. In some embodiments, the polyA tail has at least 100 nucleotides. In some embodiments, the polyA tail has 100 nucleotides.

In some embodiments of the immunogenic compositions of the present disclosure, the RNA is chemically modified. In some embodiments, at least 80%, at least 90%, 80%-100%, 90%-100%, or 100% of the uracil residues of the RNA comprise a chemical modification. In some embodiments, the chemical modification is 1-methylpseudouridine.

In some aspects, an immunogenic composition comprises a RNA (e.g., mRNA) that comprises an ORF that comprises (or consists of, or consists essentially of) a sequence that shares at least 95% identity with a sequence of SEQ ID NO: 22, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

Thus, in some aspects, an immunogenic composition comprises a RNA (e.g., mRNA) that comprises an ORF that comprises (or consists of, or consists essentially of) a sequence that shares at least 95% identity with a sequence of SEQ ID NO: 22, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, an immunogenic composition comprises a RNA (e.g., mRNA) that comprises an ORF that comprises (or consists of, or consists essentially of) a sequence that shares at least 95% identity with a sequence of SEQ ID NO: 3, wherein the RNA further comprise a 5' cap, a 5' UTR, a 3' UTR and a polyA tail. In some embodiments. RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

Thus, in some aspects, an immunogenic composition comprises a RNA (e.g., mRNA) that comprises an ORF that comprises (or consists of, or consists essentially of) a sequence that shares at least 95% identity with a sequence of SEQ ID NO: 3, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol. DSPC, and PEG-2000 DMG.

In some aspects, an immunogenic composition comprises a RNA (e.g., mRNA) that comprises an ORF that comprises (or consists of, or consists essentially of) a sequence that shares at least 95% identity with a sequence of SEQ ID NO: 52, wherein the RNA further comprise a 5' cap, a 5' UTR, a 3' UTR and a polyA tail. In some embodiments. RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

Thus, in some aspects, an immunogenic composition comprises a RNA (e.g., mRNA) that comprises an ORF that comprises (or consists of, or consists essentially of) a sequence that shares at least 95% identity with a sequence of SEQ ID NO: 52, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol. DSPC, and PEG-2000 DMG.

In some aspects, an immunogenic composition comprises a RNA (e.g., mRNA) that comprises an ORF that comprises (or consists of, or consists essentially of) a sequence that shares at least 95% identity with a sequence of SEQ ID NO: 54, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol. DSPC, and PEG-2000 DMG.

Thus, in some aspects, an immunogenic composition comprises a RNA (e.g., mRNA) that comprises an ORF that comprises (or consists of, or consists essentially of) a sequence that shares at least 95% identity with a sequence of SEQ ID NO: 54, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, an immunogenic composition comprises a RNA (e.g., mRNA) that comprises an ORF that comprises (or consists of, or consists essentially of) a sequence that shares at least 95% identity with a sequence of SEQ ID NO: 56, wherein the RNA further comprise a 5' cap, a 5' UTR, a 3' UTR and a polyA tail. In some embodiments. RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

Thus, in some aspects, an immunogenic composition comprises a RNA (e.g., mRNA) that comprises an ORF that comprises (or consists of, or consists essentially of) a sequence that shares at least 95% identity with a sequence of SEQ ID NO: 56, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, an immunogenic composition comprises a RNA (e.g., mRNA) that comprises an ORF that comprises (or consists of, or consists essentially of) a sequence that shares at least 95% identity with a sequence of SEQ ID NO: 58, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

Thus, in some aspects, an immunogenic composition comprises a RNA (e.g., mRNA) that comprises an ORF that comprises (or consists of, or consists essentially of) a sequence that shares at least 95% identity with a sequence of SEQ ID NO: 58, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the present disclosure provides an immunogenic composition (e.g., vaccine) comprising a RNA (e.g., mRNA) that comprises (or consists of, or consists essentially of) a sequence that shares at least 95% identity with SEQ ID NO: 21. In some embodiments, the RNA comprises a sequence that shares at least 96% identity with SEQ ID NO: 21. In some embodiments, the RNA comprises a sequence that shares at least 97% identity with SEQ ID NO: 21. In other embodiments, the RNA comprises a sequence that shares at least 98% identity with SEQ ID NO: 21. In some embodiments, the RNA comprises a sequence that shares at least 99% identity with SEQ ID NO: 21. In some embodiments, the RNA comprises the sequence of SEQ ID NO: 21. In some embodiments, the RNA consists of the sequence of SEQ ID NO: 21. In some embodiments, the RNA consists essentially of the sequence of SEQ ID NO: 21.

In some aspects, the present disclosure provides an immunogenic composition (e.g., vaccine) comprising a RNA (e.g., mRNA) that comprises (or consists of, or consists essentially of) a sequence that shares at least 95% identity with SEQ ID NO: 1. In some embodiments, the RNA comprises a sequence that shares at least 96% identity with SEQ ID NO: 1. In some embodiments, the RNA comprises a sequence that shares at least 97% identity with SEQ ID NO: 1. In other embodiments, the RNA comprises a sequence that shares at least 98% identity with SEQ ID NO: 1. In some embodiments, the RNA comprises a sequence that shares at least 99% identity with SEQ ID NO: 1. In some embodiments, the RNA comprises the sequence of SEQ ID NO: 1. In some embodiments, the RNA consists of the sequence of SEQ ID NO: 1. In some embodiments, the RNA consists essentially of the sequence of SEQ ID NO: 1.

In some aspects, the present disclosure provides an immunogenic composition (e.g., vaccine) comprising a RNA (e.g., mRNA) that comprises (or consists of, or consists essentially of) a sequence that shares at least 95% identity with SEQ ID NO: 51. In some embodiments, the RNA comprises a sequence that shares at least 96% identity with SEQ ID NO: 51. In some embodiments, the RNA comprises a sequence that shares at least 97% identity with SEQ ID NO: 51. In other embodiments, the RNA comprises a sequence that shares at least 98% identity with SEQ ID NO: 51. In some embodiments, the RNA comprises a sequence that shares at least 99% identity with SEQ ID NO: 51. In some embodiments, the RNA comprises the sequence of SEQ ID NO: 51. In some embodiments, the RNA consists of the sequence of SEQ ID NO: 51. In some embodiments, the RNA consists essentially of the sequence of SEQ ID NO: 51.

In some aspects, the present disclosure provides an immunogenic composition (e.g., vaccine) comprising a RNA (e.g., mRNA) that comprises (or consists of, or consists essentially of) a sequence that shares at least 95% identity with SEQ ID NO: 53. In some embodiments, the RNA comprises a sequence that shares at least 96% identity with SEQ ID NO: 53. In some embodiments, the RNA comprises a sequence that shares at least 97% identity with SEQ ID NO: 53. In other embodiments, the RNA comprises a sequence that shares at least 98% identity with SEQ ID NO: 53. In some embodiments, the RNA comprises a sequence that shares at least 99% identity with SEQ ID NO: 53. In some embodiments, the RNA comprises the sequence of SEQ ID NO: 53. In some embodiments, the RNA consists of the sequence of SEQ ID NO: 53. In some embodiments, the RNA consists essentially of the sequence of SEQ ID NO: 53.

In some aspects, the present disclosure provides an immunogenic composition (e.g., vaccine) comprising a RNA (e.g., mRNA) that comprises (or consists of, or consists essentially of) a sequence that shares at least 95% identity with SEQ ID NO: 55. In some embodiments, the RNA comprises a sequence that shares at least 96% identity with SEQ ID NO: 55. In some embodiments, the RNA comprises a sequence that shares at least 97% identity with SEQ ID NO:

55. In other embodiments, the RNA comprises a sequence that shares at least 98% identity with SEQ ID NO: 55. In some embodiments, the RNA comprises a sequence that shares at least 99% identity with SEQ ID NO: 55. In some embodiments, the RNA comprises the sequence of SEQ ID NO: 55. In some embodiments, the RNA consists of the sequence of SEQ ID NO: 55. In some embodiments, the RNA consists essentially of the sequence of SEQ ID NO: 55.

In some aspects, the present disclosure provides an immunogenic composition (e.g., vaccine) comprising a RNA (e.g., mRNA) that comprises (or consists of, or consists essentially of) a sequence that shares at least 95% identity with SEQ ID NO: 57. In some embodiments, the RNA comprises a sequence that shares at least 96% identity with SEQ ID NO: 57. In some embodiments, the RNA comprises a sequence that shares at least 97% identity with SEQ ID NO: 57. In other embodiments, the RNA comprises a sequence that shares at least 98% identity with SEQ ID NO: 57. In some embodiments, the RNA comprises a sequence that shares at least 99% identity with SEQ ID NO: 57. In some embodiments, the RNA comprises the sequence of SEQ ID NO: 57. In some embodiments, the RNA consists of the sequence of SEQ ID NO: 57. In some embodiments, the RNA consists essentially of the sequence of SEQ ID NO: 57.

In some aspects, the present disclosure provides an immunogenic composition (e.g., vaccine) comprising a mRNA that comprises (or consists of, or consists essentially of) the sequence of SEQ ID NO: 21 formulated in a lipid nanoparticle comprising 58 mole % (13Z,16Z)—N,N-dimethyl-2-nonylhenicosa-12,15-dien-1-amine, 30 mole % cholesterol, 10 mole % DSPC, and 2 mole % PEG-2000 DMG, wherein the mRNA further comprises a 5' 7mG(5')ppp(5')NlmpNp cap, and wherein at least 80% of the uracil of the mRNA are 1-methylpseudouridine.

Also provided herein are methods of inducing in a subject an immune response to RSV, the methods comprising administering to the subject any of the immunogenic compositions (e.g., vaccines) described above.

Thus, in some aspects, the present disclosure provides methods that comprise delivering to a subject (e.g., via intramuscular administration) an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 22. In some embodiments, the ORF shares at least 96% identity with SEQ ID NO: 22. In other embodiments, the ORF shares at least 97% identity with SEQ ID NO: 22. In some embodiments, the ORF shares at least 98% identity with SEQ ID NO: 22. In some embodiments, the ORF shares at least 99% identity SEQ ID NO: 22. In some embodiments, the ORF comprises the sequence of SEQ ID NO: 22.

In some aspects, the present disclosure provides methods that comprise delivering to a subject (e.g., via intramuscular administration) an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 3. In some embodiments, the ORF shares at least 96% identity with SEQ ID NO: 3. In other embodiments, the ORF shares at least 97% identity with SEQ ID NO: 3. In some embodiments, the ORF shares at least 98% identity with SEQ ID NO: 3. In some embodiments, the ORF shares at least 99% identity SEQ ID NO: 3. In some embodiments, the ORF comprises the sequence of SEQ ID NO: 3.

In some aspects, the present disclosure provides methods that comprise delivering to a subject (e.g., via intramuscular administration) an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 52. In some embodiments, the ORF shares at least 96% identity with SEQ ID NO: 52. In other embodiments, the ORF shares at least 97% identity with SEQ ID NO: 52. In some embodiments, the ORF shares at least 98% identity with SEQ ID NO: 52. In some embodiments, the ORF shares at least 99% identity SEQ ID NO: 52. In some embodiments, the ORF comprises the sequence of SEQ ID NO: 52.

In some aspects, the present disclosure provides methods that comprise delivering to a subject (e.g., via intramuscular administration) an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 54. In some embodiments, the ORF shares at least 96% identity with SEQ ID NO: 54. In other embodiments, the ORF shares at least 97% identity with SEQ ID NO: 54. In some embodiments, the ORF shares at least 98% identity with SEQ ID NO: 54. In some embodiments, the ORF shares at least 99% identity SEQ ID NO: 54. In some embodiments, the ORF comprises the sequence of SEQ ID NO: 54.

In some aspects, the present disclosure provides methods that comprise delivering to a subject (e.g., via intramuscular administration) an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 56. In some embodiments, the ORF shares at least 96% identity with SEQ ID NO: 56. In other embodiments, the ORF shares at least 97% identity with SEQ ID NO: 56. In some embodiments, the ORF shares at least 98% identity with SEQ ID NO: 56. In some embodiments, the ORF shares at least 99% identity SEQ ID NO: 56. In some embodiments, the ORF comprises the sequence of SEQ ID NO: 56.

In some aspects, the present disclosure provides methods that comprise delivering to a subject (e.g., via intramuscular administration) an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 58. In some embodiments, the ORF shares at least 96% identity with SEQ ID NO: 58. In other embodiments, the ORF shares at least 97% identity with SEQ ID NO: 58. In some embodiments, the ORF shares at least 98% identity with SEQ ID NO: 58. In some embodiments, the ORF shares at least 99% identity SEQ ID NO: 58. In some embodiments, the ORF comprises the sequence of SEQ ID NO: 58.

In some aspects, the present disclosure provides methods that comprise delivering to a subject (e.g., via intramuscular administration) an immunogenic composition (e.g., vaccine) comprising a RNA (e.g., mRNA) that comprises an ORF encoding an RSV antigen, wherein the RSV antigen comprises (or consists of, or consists essentially of) SEQ ID NO: 5 (with or without a signal sequence MELLILKANAITTILTAVTFCFASG (SEQ ID NO: 100). In some embodiments, the immunogenic composition used in the methods is formulated in a lipid nanoparticle. In some embodiments, the lipid nanoparticle comprises a molar ratio of 20-60% ionizable cationic lipid, 5-25% non-cationic lipid, 25-55% sterol, and 0.5-15% PEG-modified lipid. In some embodiments, the lipid nanoparticle comprises (13Z,16Z)—N,N-dimethyl-2-nonylhenicosa-12,15-dien-1-amine, cholesterol. DSPC, and PEG-2000 DMG. In some embodiments, the lipid nanoparticle comprises 55-65 mole % (13Z,16Z)—N,N-dimethyl-2-nonylhenicosa-12,15-dien-1-amine, 25-35 mole % cholesterol, 5-15 mole % DSPC, and 1-5 mole % PEG-2000 DMG. In some embodiments, the lipid nanoparticle comprises 58 mole % (13Z,16Z)—N,N-dimethyl-2-nonylhenicosa-12,15-dien-1-amine, 30 mole % cholesterol, 10 mole % DSPC, and 2 mole % PEG-2000 DMG.

Thus, in some aspects, the methods comprise delivering to a subject (e.g., via intramuscular administration) an immunogenic composition that comprises a RNA (e.g., mRNA) that comprises an ORF that comprises (or consists of, or consists essentially of) a sequence that shares at least 95% identity with a sequence of SEQ ID NO: 22, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG. In some embodiments, the RNA further comprises a 5' cap. In some embodiments, the 5' cap comprises 7mG(5')ppp(5')NlmpNp. In some embodiments, the RNA of the immunogenic composition used in the methods provided herein further comprises a 5' UTR and/or 3' UTR. In some embodiments, the RNA further comprises a 5' UTR comprising a sequence of SEQ ID NO: 2. In some embodiments, the RNA further comprises a 3' UTR comprising a sequence of SEQ ID NO: 4. In some embodiments, the RNA further comprises a 5' UTR comprising a sequence of SEQ ID NO: 2 and a 3' UTR comprising a sequence of SEQ ID NO: 4.

In some aspects, the methods comprise delivering to a subject (e.g., via intramuscular administration) an immunogenic composition that comprises a RNA (e.g., mRNA) that comprises an ORF that comprises (or consists of, or consists essentially of) a sequence that shares at least 95% identity with a sequence of SEQ ID NO: 3, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, the methods comprise delivering to a subject (e.g., via intramuscular administration) an immunogenic composition that comprises a RNA (e.g., mRNA) that comprises an ORF that comprises (or consists of, or consists essentially of) a sequence that shares at least 95% identity with a sequence of SEQ ID NO: 52, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, the methods comprise delivering to a subject (e.g., via intramuscular administration) an immunogenic composition that comprises a RNA (e.g., mRNA) that comprises an ORF that comprises (or consists of, or consists essentially of) a sequence that shares at least 95% identity with a sequence of SEQ ID NO: 54, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, the methods comprise delivering to a subject (e.g., via intramuscular administration) an immunogenic composition that comprises a RNA (e.g., mRNA) that comprises an ORF that comprises (or consists of, or consists essentially of) a sequence that shares at least 95% identity with a sequence of SEQ ID NO: 56, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, the methods comprise delivering to a subject (e.g., via intramuscular administration) an immunogenic composition that comprises a RNA (e.g., mRNA) that comprises an ORF that comprises (or consists of, or consists essentially of) a sequence that shares at least 95% identity with a sequence of SEQ ID NO: 58, wherein the RNA is formulated in a lipid nanoparticle that comprises (13Z,16Z)—N,N-dimethyl-2-nonylhenicosa-12,15-dien-1-amine, cholesterol. DSPC, and PEG-2000 DMG. In some embodiments, the RNA of the immunogenic composition used in the methods provided herein further comprises a polyA tail. In some embodiments, the polyA tail has a length of 100 nucleotides. In some embodiments, the polyA tail has at least 50 nucleotides. In some embodiments, the polyA tail has at least 60 nucleotides. In some embodiments, the polyA tail has at least 70 nucleotides. In some embodiments, the polyA tail has at least 80 nucleotides. In some embodiments, the polyA tail has at least 90 nucleotides. In some embodiments, the polyA tail has at least 100 nucleotides. In some embodiments, the polyA tail has 100 nucleotides.

In some embodiments, the RNA of the immunogenic composition used in the methods provided herein is chemically modified. In some embodiments, at least 80%, at least 90%, 80%-100%, 90%-100%, or 100% of the uracil residues of the RNA comprise a chemical modification. In some embodiments, the chemical modification is 1-methylpseudouridine.

In some aspects, the RNA (e.g., mRNA) of the immunogenic composition used in the methods provided herein comprises an ORF that comprises (or consists of, or consists essentially of) a sequence that shares at least 95% identity with a sequence of SEQ ID NO: 22, wherein the RNA further comprise a 5' cap, a 5' UTR, a 3' UTR and a polyA tail. In some embodiments. RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the RNA (e.g., mRNA) of the immunogenic composition used in the methods provided herein comprises an ORF that comprises (or consists of, or consists essentially of) a sequence that shares at least 95% identity with a sequence of SEQ ID NO: 3, wherein the RNA further comprise a 5' cap, a 5' UTR, a 3' UTR and a polyA tail. In some embodiments. RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the RNA (e.g., mRNA) of the immunogenic composition used in the methods provided herein comprises an ORF that comprises (or consists of, or consists essentially of) a sequence that shares at least 95% identity with a sequence of SEQ ID NO: 52, wherein the RNA further comprise a 5' cap, a 5' UTR, a 3' UTR and a polyA tail. In some embodiments. RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the RNA (e.g., mRNA) of the immunogenic composition used in the methods provided herein comprises an ORF that comprises (or consists of, or consists essentially of) a sequence that shares at least 95% identity with a sequence of SEQ ID NO: 54, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol. DSPC, and PEG-2000 DMG.

In some aspects, the RNA (e.g., mRNA) of the immunogenic composition used in the methods provided herein comprises an ORF that comprises (or consists of, or consists essentially of) a sequence that shares at least 95% identity with a sequence of SEQ ID NO: 56, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the RNA (e.g., mRNA) of the immunogenic composition used in the methods provided herein comprises an ORF that comprises (or consists of, or consists essentially of) a sequence that shares at least 95% identity with a sequence of SEQ ID NO: 58, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the methods of the present disclosure provide delivering to a subject (e.g., via intramuscular injection) an immunogenic composition comprising a RNA (e.g., mRNA) that comprises an ORF that comprises (or consists of, or consists essentially of) a sequence that shares at least 95% identity with a sequence of SEQ ID NO: 22, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the methods of the present disclosure provide delivering to a subject (e.g., via intramuscular injection) an immunogenic composition comprising a RNA (e.g., mRNA) that comprises an ORF that comprises (or consists of, or consists essentially of) a sequence that shares at least 95% identity with a sequence of SEQ ID NO: 3, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol. DSPC, and PEG-2000 DMG.

In some aspects, the methods of the present disclosure provide delivering to a subject (e.g., via intramuscular injection) an immunogenic composition comprising a RNA (e.g., mRNA) that comprises an ORF that comprises (or consists of, or consists essentially of) a sequence that shares at least 95% identity with a sequence of SEQ ID NO: 52, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the methods of the present disclosure provide delivering to a subject (e.g., via intramuscular injection) an immunogenic composition comprising a RNA (e.g., mRNA) that comprises an ORF that comprises (or consists of, or consists essentially of) a sequence that shares at least 95% identity with a sequence of SEQ ID NO: 54, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the methods of the present disclosure provide delivering to a subject (e.g., via intramuscular injection) an immunogenic composition comprising a RNA (e.g., mRNA) that comprises an ORF that comprises (or consists of, or consists essentially of) a sequence that shares at least 95% identity with a sequence of SEQ ID NO: 56, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the methods of the present disclosure provide delivering to a subject (e.g., via intramuscular injection) an immunogenic composition comprising a RNA (e.g., mRNA) that comprises an ORF that comprises (or consists of, or consists essentially of) a sequence that shares at least 95% identity with a sequence of SEQ ID NO: 58, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the present disclosure provides methods comprising delivering to a subject (e.g., via intramuscular injection) an immunogenic composition (e.g., vaccine) comprising a RNA (e.g., mRNA) that comprises (or consists of, or consists essentially of) a sequence that shares at least 95% identity with SEQ ID NO: 21. In some embodiments, the RNA comprises a sequence that shares at least 96% identity with SEQ ID NO: 21. In some embodiments, the RNA comprises a sequence that shares at least 97% identity with SEQ ID NO: 21. In other embodiments, the RNA comprises a sequence that shares at least 98% identity with SEQ ID NO: 21. In some embodiments, the RNA comprises a sequence that shares at least 99% identity with SEQ ID NO: 21. In some embodiments, the RNA comprises the sequence of SEQ ID NO: 21. In some embodiments, the RNA consists of the sequence of SEQ ID NO: 21. In some embodiments, the RNA consists essentially of the sequence of SEQ ID NO: 21.

In some aspects, the present disclosure provides methods comprising delivering to a subject (e.g., via intramuscular injection) an immunogenic composition (e.g., vaccine) comprising a RNA (e.g., mRNA) that comprises (or consists of, or consists essentially of) a sequence that shares at least 95% identity with SEQ ID NO: 1. In some embodiments, the RNA comprises a sequence that shares at least 96% identity with SEQ ID NO: 1. In some embodiments, the RNA comprises a sequence that shares at least 97% identity with SEQ ID NO: 1. In other embodiments, the RNA comprises a sequence that shares at least 98% identity with SEQ ID NO: 1. In some embodiments, the RNA comprises a sequence that shares at least 99% identity with SEQ ID NO: 1. In some embodiments, the RNA comprises the sequence of SEQ ID NO: 1. In some embodiments, the RNA consists of the sequence of SEQ ID NO: 1. In some embodiments, the RNA consists essentially of the sequence of SEQ ID NO: 1.

In some aspects, the present disclosure provides methods comprising delivering to a subject (e.g., via intramuscular injection) an immunogenic composition (e.g., vaccine) comprising a RNA (e.g., mRNA) that comprises (or consists of, or consists essentially of) a sequence that shares at least 95% identity with SEQ ID NO: 51. In some embodiments, the RNA comprises a sequence that shares at least 96% identity with SEQ ID NO: 51. In some embodiments, the RNA comprises a sequence that shares at least 97% identity with SEQ ID NO: 51. In other embodiments, the RNA comprises a sequence that shares at least 98% identity with SEQ ID NO: 51. In some embodiments, the RNA comprises a sequence that shares at least 99% identity with SEQ ID NO: 51. In some embodiments, the RNA comprises the sequence of SEQ ID NO: 51. In some embodiments, the RNA consists of the sequence of SEQ ID NO: 51. In some embodiments, the RNA consists essentially of the sequence of SEQ ID NO: 51.

In some aspects, the present disclosure provides methods comprising delivering to a subject (e.g., via intramuscular injection) an immunogenic composition (e.g., vaccine) comprising a RNA (e.g., mRNA) that comprises (or consists of, or consists essentially of) a sequence that shares at least 95% identity with SEQ ID NO: 53. In some embodiments, the RNA comprises a sequence that shares at least 96% identity with SEQ ID NO: 53. In some embodiments, the RNA comprises a sequence that shares at least 97% identity with SEQ ID NO: 53. In other embodiments, the RNA comprises a sequence that shares at least 98% identity with SEQ ID NO: 53. In some embodiments, the RNA comprises a sequence that shares at least 99% identity with SEQ ID NO: 53. In some embodiments, the RNA comprises the sequence of SEQ ID NO: 53. In some embodiments, the RNA consists of the sequence of SEQ ID NO: 53. In some embodiments, the RNA consists essentially of the sequence of SEQ ID NO: 53.

In some aspects, the present disclosure provides methods comprising delivering to a subject (e.g., via intramuscular injection) an immunogenic composition (e.g., vaccine) comprising a RNA (e.g., mRNA) that comprises (or consists of, or consists essentially of) a sequence that shares at least 95% identity with SEQ ID NO: 55. In some embodiments, the RNA comprises a sequence that shares at least 96% identity with SEQ ID NO: 55. In some embodiments, the RNA comprises a sequence that shares at least 97% identity with SEQ ID NO: 55. In other embodiments, the RNA comprises a sequence that shares at least 98% identity with SEQ ID NO: 55. In some embodiments, the RNA comprises a sequence that shares at least 99% identity with SEQ ID NO: 55. In some embodiments, the RNA comprises the sequence of SEQ ID NO: 55. In some embodiments, the RNA consists of the sequence of SEQ ID NO: 55. In some embodiments, the RNA consists essentially of the sequence of SEQ ID NO: 55.

In some aspects, the present disclosure provides methods comprising delivering to a subject (e.g., via intramuscular injection) an immunogenic composition (e.g., vaccine) comprising a RNA (e.g., mRNA) that comprises (or consists of, or consists essentially of) a sequence that shares at least 95% identity with SEQ ID NO: 57. In some embodiments, the RNA comprises a sequence that shares at least 96% identity with SEQ ID NO: 57. In some embodiments, the RNA comprises a sequence that shares at least 97% identity with SEQ ID NO: 57. In other embodiments, the RNA comprises a sequence that shares at least 98% identity with SEQ ID NO: 57. In some embodiments, the RNA comprises a sequence that shares at least 99% identity with SEQ ID NO: 57. In some embodiments, the RNA comprises the sequence of SEQ ID NO: 57. In some embodiments, the RNA consists of the sequence of SEQ ID NO: 57. In some embodiments, the RNA consists essentially of the sequence of SEQ ID NO: 57.

In some aspects, the present disclosure provides methods that comprise delivering to a subject (e.g., via intramuscular injection) an immunogenic composition (e.g., vaccine) comprising a mRNA that comprises (or consists of, or consists essentially of) the sequence of SEQ ID NO: 21 formulated in a lipid nanoparticle comprising 58 mole % (13Z,16Z)—N,N-dimethyl-2-nonylhenicosa-12,15-dien-1-amine, 30 mole % cholesterol, 10 mole % DSPC, and 2 mole % PEG-2000 DMG, wherein the mRNA further comprises a 5' 7mG(5')ppp(5')NlmpNp cap, and wherein at least 80% of the uracil of the mRNA arc 1-methylpseudouridine.

In some aspects, the present disclosure provides methods that comprise delivering to a subject (e.g., via intramuscular injection) an immunogenic composition (e.g., vaccine) comprising a mRNA that comprises (or consists of, or consists essentially of) the sequence of SEQ ID NO: 1 formulated in a lipid nanoparticle comprising 58 mole % (13Z,16Z)—N,N-dimethyl-2-nonylhenicosa-12,15-dien-1-amine, 30 mole % cholesterol, 10 mole % DSPC, and 2 mole % PEG-2000 DMG, wherein the mRNA further comprises a 5' 7mG(5')ppp(5')NlmpNp cap, and wherein at least 80% of the uracil of the mRNA are 1-methylpseudouridine.

In some aspects, the present disclosure provides methods that comprise delivering to a subject (e.g., via intramuscular injection) an immunogenic composition (e.g., vaccine) comprising a mRNA that comprises (or consists of, or consists essentially of) the sequence of SEQ ID NO: 51 formulated in a lipid nanoparticle comprising 58 mole % (13Z,16Z)—N,N-dimethyl-2-nonylhenicosa-12,15-dien-1-amine, 30 mole % cholesterol, 10 mole % DSPC, and 2 mole % PEG-2000 DMG, wherein the mRNA further comprises a 5' 7mG(5')ppp(5')NlmpNp cap, and wherein at least 80% of the uracil of the mRNA are 1-methylpseudouridine.

In some aspects, the present disclosure provides methods that comprise delivering to a subject (e.g., via intramuscular injection) an immunogenic composition (e.g., vaccine) comprising a mRNA that comprises (or consists of, or consists essentially of) the sequence of SEQ ID NO: 53 formulated in a lipid nanoparticle comprising 58 mole % (13Z,16Z)—N,N-dimethyl-2-nonylhenicosa-12,15-dien-1-amine, 30 mole % cholesterol, 10 mole % DSPC, and 2 mole % PEG-2000 DMG, wherein the mRNA further comprises a 5' 7mG(5')ppp(5')NlmpNp cap, and wherein at least 80% of the uracil of the mRNA are 1-methylpseudouridine.

In some aspects, the present disclosure provides methods that comprise delivering to a subject (e.g., via intramuscular injection) an immunogenic composition (e.g., vaccine) comprising a mRNA that comprises (or consists of, or consists essentially of) the sequence of SEQ ID NO: 55 formulated in a lipid nanoparticle comprising 58 mole % (13Z,16Z)—N,N-dimethyl-2-nonylhenicosa-12,15-dien-1-amine, 30 mole % cholesterol, 10 mole % DSPC, and 2 mole % PEG-2000 DMG, wherein the mRNA further comprises a 5' 7mG(5')ppp(5')NlmpNp cap, and wherein at least 80% of the uracil of the mRNA are 1-methylpseudouridine.

In some aspects, the present disclosure provides methods that comprise delivering to a subject (e.g., via intramuscular injection) an immunogenic composition (e.g., vaccine) comprising a mRNA that comprises (or consists of, or consists essentially of) the sequence of SEQ ID NO: 57 formulated in a lipid nanoparticle comprising 58 mole % (13Z,16Z)—N,N-dimethyl-2-nonylhenicosa-12,15-dien-1-amine, 30 mole % cholesterol, 10 mole % DSPC, and 2 mole % PEG-2000 DMG, wherein the mRNA further comprises a 5' 7mG(5')ppp(5')NlmpNp cap, and wherein at least 80% of the uracil of the mRNA are 1-methylpseudouridine.

BRIEF DESCRIPTION OF THE DRAWINGS

FIG. 6A: High dose immunization. FIG. 6B: Low dose immunization. FIG. 6C: Area under the curve.

DETAILED DESCRIPTION

Figure 1:
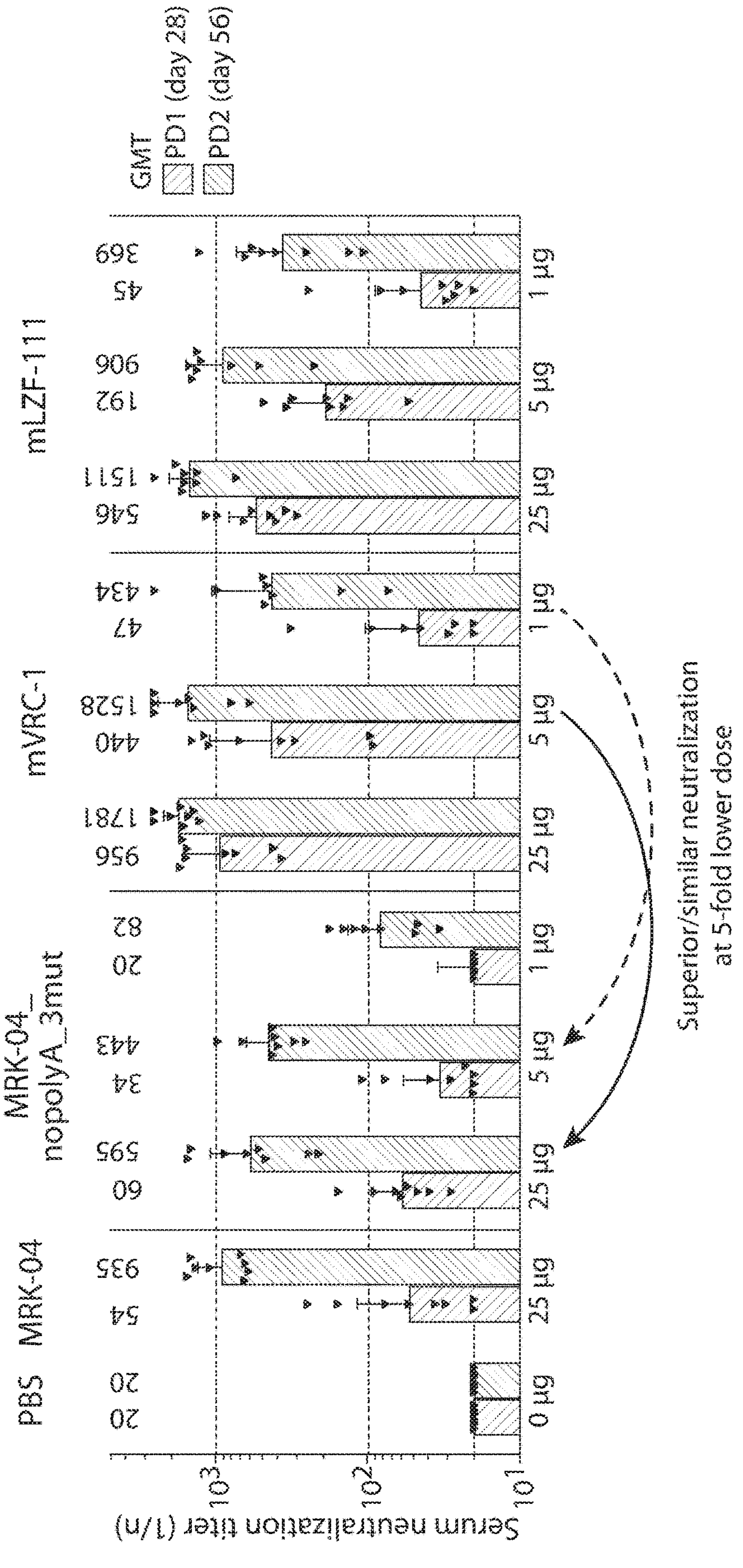
FIG. 1 shows a graph of serum neutralizing antibody titers (NTs individual and GMT with 95% confidence intervals) to RSV A induced in cotton rats by mRNA vaccines and control formulations.

Embodiments of the present disclosure provide highly immunogenic RNA (e.g., mRNA) compositions (e.g., vaccines) that include a (at least one) polynucleotide encoding a respiratory syncytial virus (RSV) antigen and elicit potent neutralizing antibodies. RSV is a negative-sense, single-stranded RNA virus of the genus Pneumovirinae. The virus is present in at least two antigenic subgroups, known as Group A and Group B, primarily resulting from differences in the surface G glycoproteins. Two RSV surface glycoproteins—G and F—mediate attachment with and attachment to cells of the respiratory epithelium. F surface glycoproteins mediate coalescence of neighboring cells. This results in the formation of syncytial cells. RSV is the most common cause of bronchiolitis. Most infected adults develop mild cold-like symptoms such as congestion, low-grade fever, and wheezing. Infants and small children may suffer more severe symptoms such as bronchiolitis and pneumonia. The disease may be transmitted among humans via contact with respiratory secretions.

RSV F protein is a type I fusion glycoprotein that is well conserved between clinical isolates, including between the RSV-A and RSV-B antigenic subgroups. The F protein transitions between prefusion and more stable postfusion states, thereby facilitating entry into target cells. RSV F glycoprotein is initially synthesized as an F0 precursor protein. RSV F0 folds into a trimer, which is activated by furin cleavage into the mature prefusion protein comprising F1 and F2 subunits (Bolt, et al., Virus Res., 68:25, 2000). RSV F protein stabilized in the prefusion conformation produce a greater neutralizing immune response in animal models than that observed with RSV F protein stabilized in the post fusion conformation (McLellan et al., Science, 342: 592-598, 2013). As such, stabilized prefusion RSV F proteins are good candidates for inclusion in an RSV vaccine. Soluble RSV cctodomains stabilized in the prefusion conformation have previously been generated, including the DS-CAV1 substitutions. "DS-CAV1" and "DS-CAV1 substitutions." each as used herein, refers to genetic modifications to the RSV F protein, which contains the "DS" substitutions 155C and 290C so as to introduce a non-native disulfide bond between cysteines introduced by the substitutions (such as S155C and S290C substitutions) and the "CAV1" substitutions, which include 190F and 207L cavity filling amino acid substitutions (such as S190F and V207L), mVRC-1 (e.g., SEQ ID NO: 21), used in some of the immunogenic compositions of the present disclosure, as compared to DS-CAV1, includes an additional stabilizing disulfide bond (resulting from the introduction of the amino acid substitutions A149C and Y458C) and is engineered so that the $F_2$ and $F_1$ subunits are genetically linked, with the fusion peptide and p27 region deleted. See, WO 2014/160463A1 and WO 2017/172890A1, the contents of each of which are hereby incorporated by reference.

It has been previously shown that the prefusion stabilized RSV F construct, DS-CAV1, undergoes conformational changes and forms intermediate structures upon long-term storage at 4° C. (Flynn J A et al., PLoS ONE 2016; 11(10): e0164789). Long term stability at 4° C., or higher is a desirable attribute for a RSV F subunit vaccine antigen. Described herein are additional structure-based modifications to further improve the stability of the RSV F trimer in the prefusion conformation. Such constructs have increased stability at 4° C., as compared to DS-CAV1 while retaining immunogenicity.

"RSV Fusion Protein" or "RSV F protein", each as used herein, refers to an RSV envelope glycoprotein that facilitates fusion of viral and cellular membranes. In nature, the RSV F protein is synthesized into a single polypeptide precursor designated $F_0$, which includes a signal peptide that directs localization to the endoplasmic reticulum, where the signal peptide is cleaved. The remaining $F_0$ residues oligomerize to form a trimer and are proteolytically processed by a protease at two conserved furin cleavage sequences to generate two disulfide linked fragments. F1 and F2. In nature, three $F_2$-$F_1$ peptides oligomerize into a trimer to form the mature F protein, which adopts a prefusion conformation that is metastable and can undergo a conformation change to a postfusion conformation.

The genome of RSV encodes at least three surface glycoproteins, including F, G, and SH, four nucleocapsid proteins, including L. P. N, and M2, and one matrix protein, M.

Glycoprotein F directs viral penetration by fusion between the virion and the host membrane. Glycoprotein G is a type II transmembrane glycoprotein and is the major attachment protein. SH is a short integral membrane protein. Matrix protein M is found in the inner layer of the lipid bilayer and assists virion formation. Nucleocapsid proteins L. P. N, and MP2 modulate replication and transcription of the RSV genome. It is thought that glycoprotein G tethers and stabilizes the virus particle at the surface of bronchial epithelial cells, while glycoprotein F interacts with cellular glycosaminoglycans to mediate fusion and delivery of the RSV virion contents into the host cell (Krzyzaniak M A et al. PLoS Pathog 2013:9(4)).

The present disclosure is not limited by a particular strain of RSV. The strain of RSV used in a vaccine may be any strain of RSV.

The RSV RNA vaccines described herein are superior to current vaccines in several ways. For example, the lipid nanoparticle (LNP) delivery system used herein increases the efficacy of RNA vaccines in comparison to other formulations, including a protamine-based approach described in the literature. The use of this LNP delivery system enables the effective delivery of chemically-modified RNA vaccines or unmodified RNA vaccines, without requiring additional adjuvant to produce a therapeutic result (e.g., production neutralizing antibody titer). In some embodiments, the RSV RNA vaccines disclosed herein are superior to conventional vaccines by a factor of at least 10 fold, 20, fold, 40, fold, 50 fold, 100 fold, 500 fold, or 1.000 fold when administered intramuscularly (IM) or intradermally (ID). These results can be achieved even when significantly lower doses of the RNA (e.g., mRNA) are administered in comparison with RNA doses used in other classes of lipid based formulations.

Although attempts have been made to produce functional RNA vaccines, including mRNA vaccines and self-replicating RNA vaccines, the therapeutic efficacy of these RNA vaccines have not yet been fully established. Quite surprisingly, the inventors have discovered, according to aspects of the present disclosure, a class of formulations for delivering mRNA vaccines in vivo that results in significantly enhanced, and in many respects synergistic, immune responses including enhanced antigen generation and functional antibody production with neutralization capability. These results can be achieved even when significantly lower doses of the mRNA are administered in comparison with mRNA doses used in other classes of lipid based formulations. The formulations of the present disclosure have demonstrated significant unexpected in vivo immune responses sufficient to establish the efficacy of functional mRNA vaccines as prophylactic and therapeutic agents. Additionally, self-replicating RNA vaccines rely on viral replication pathways to deliver enough RNA to a cell to produce an immunogenic response. The formulations of the present disclosure do not require viral replication to produce enough protein to result in a strong immune response. Thus, the mRNA of the present disclosure are not self-replicating RNA and do not include components necessary for viral replication.

It should also be understood that the immunogenic compositions, e.g, vaccines, of the present disclosure are not naturally-occurring. That is, the immunogenic compositions, e.g, vaccines, provided herein do not occur in nature.

Exemplary Respiratory Syncytial Virus (RSV) Antigens

Antigens are proteins capable of inducing an immune response (e.g., causing an immune system to produce antibodies against the antigens). Herein, use of the term antigen encompasses immunogenic proteins and immunogenic fragments (an immunogenic fragment that induces (or is capable of inducing) an immune response to RSV), unless otherwise stated. It should be understood that the term "protein" encompasses peptides and the term "antigen" encompasses antigenic fragments.

A number of different antigens are associated with RSV. RSV vaccines, as provided herein, comprise at least one (one or more) ribonucleic acid (RNA, e.g., mRNA) comprising an open reading frame encoding at least one RSV antigen. Non-limiting examples of RSV antigens are provided below.

Exemplary RSV antigens are provided in the Sequence Listing elsewhere herein. For example, the antigens may be encoded by (thus the RNA may comprise or consist of) any one of sequences set forth in SEQ ID NOS: 3, 7, 10, 13, 16, 19, 22, 24, 26, 28, 30, 32, 34, 37, 40, 43, 46, 49, 52, 54, 56, 58, 60, 63, 66, 69, 72, or 75. In some embodiments, the aforementioned sequences may further comprise a 5' cap (e.g., 7mG(5')ppp(5')NlmpNp), a polyA tail, or a 5' cap and a polyA tail).

It should be understood that the RSV vaccines of the present disclosure may comprise any of the RNA open reading frames (ORFs), or encode any of the protein ORFs, described herein, with or without a signal sequence. It should also be understood that the RSV vaccines of the present disclosure may include any 5' untranslated region (UTR) and/or any 3' UTR. Exemplary UTR sequences are provided in the Sequence Listing (e.g., SEQ ID NOS: 2, 4, 77, and 78); however, other UTR sequences (e.g., of the prior art) may be used or exchanged for any of the UTR sequences described herein. UTRs may also be omitted from the vaccine constructs provided herein.

At least two antigenic subgroups (A and B) of RSV are known to exist. This antigenic dimorphism is due primarily to difference in the surface G glycoproteins. Two surface glycoproteins. G and F, are present in the envelope and mediate attachment and fusion with cells of the respiratory epithelium. The F proteins also mediate coalescence of neighboring cells to form the characteristic syncytial cells for which the virus receives its name. The epidemiologic and biologic significance of the two antigenic variants of RSV is uncertain. Nonetheless, there is some evidence to suggest that Group A infections tend to be more severe.

The RSV genome is ~15,000 nucleotides in length and is composed of a single strand of RNA with negative polarity. It has 10 genes encoding 11 proteins—there are 2 open reading frames of M2. The genome is transcribed sequentially from NS1 to L with reduction in expression levels along its length.

SH protein, G protein and F protein form the viral coat. The G protein is a surface protein that is heavily glycosylated and functions as the attachment protein. The F protein is another important surface protein that mediates fusion, allowing entry of the virus into the cell cytoplasm and also allowing the formation of syncytia. The F protein is homologous in both subtypes of RSV; antibodies directed at the F protein are neutralizing. In contrast, the G protein differs considerably between the two RSV subtypes. In some embodiments, a RSV vaccine comprises a RNA (e.g., mRNA) polynucleotide comprising an ORF encoding RSV F protein and a RNA (e.g., mRNA) polynucleotide comprising an ORF encoding RSV SH protein. In some embodiments, a RSV vaccine comprises a RNA (e.g., mRNA) polynucleotide comprising an ORF encoding RSV F protein and a RNA (e.g., mRNA) polynucleotide comprising an ORF encoding RSV G protein.

NS1 and NS2 inhibit type I interferon activity. In some embodiments, a RSV vaccine comprises a RNA (e.g., mRNA) polynucleotide comprising an ORF encoding RSV F protein and a RNA (e.g., mRNA) polynucleotide comprising an ORF encoding RSV NS1 and/or RSV NS2.

N encodes nucleocapsid protein that associates with the genomic RNA forming the nucleocapsid. In some embodiments, a RSV vaccine comprises a RNA (e.g., mRNA) polynucleotide comprising an ORF encoding RSV F protein and a RNA (e.g., mRNA) polynucleotide comprising an ORF encoding RSV nucleocapsid protein.

M encodes the Matrix protein required for viral assembly. In some embodiments, a RSV vaccine comprises a RNA (e.g., mRNA) polynucleotide comprising an ORF encoding RSV F protein and a RNA (e.g., mRNA) polynucleotide comprising an ORF encoding RSV Matrix protein.

Nucleolin at the cell surface is the receptor for the RSV fusion protein. Interference with the nucleolin-RSV fusion protein interaction has been shown to be therapeutic against RSV infection in cell cultures and animal models. In some embodiments, a RSV vaccine comprises a RNA (e.g., mRNA) polynucleotide comprising an ORF encoding RSV F protein and a RNA (e.g., mRNA) polynucleotide comprising an ORF encoding RSV nucleolin.

M2 is the second matrix protein also required for transcription and encodes M2-1 (elongation factor) and M2-2 (transcription regulation). M2 contains CD8 epitopes. In some embodiments, a RSV vaccine comprises a RNA (e.g., mRNA) polynucleotide comprising an ORF encoding RSV F protein and a RNA (e.g., mRNA) polynucleotide comprising an ORF encoding RSV second matrix protein.

L encodes the RNA polymerase. In some embodiments, a RSV vaccine comprises a RNA (e.g., mRNA) polynucleotide comprising an ORF encoding RSV F protein and a RNA (e.g., mRNA) polynucleotide comprising an ORF encoding RSV RNA polymerase (L).

The phosphoprotein P is a cofactor for the L protein. In some embodiments, a RSV vaccine comprises a RNA (e.g., mRNA) polynucleotide comprising an ORF encoding RSV F protein and a RNA (e.g., mRNA) polynucleotide comprising an ORF encoding RSV phosphoprotein P.

Some embodiments of the present disclosure provide RSV vaccines that include at least one RNA (e.g., mRNA) polynucleotide comprising an open reading frame encoding RSV glycoprotein F.

Some embodiments of the present invention disclose RSV vaccines that include at least one RNA (e.g, mRNA) polynucleotide comprising an open reading frame encoding a polypeptide in the post-fusion form. Some embodiments of the present invention disclose RSV vaccines that include at least one RNA (e.g, mRNA) polynucleotide comprising an open reading frame encoding a polypeptide in the pre-fusion form. In some embodiments, the polypeptides comprise glycoproteins in a prefusion conformation, for example, but not limited to, prefusion glycoprotein F or DS-CAV1. Without wishing to be bound by theory, certain polypeptides, when in a prefusion conformation, may contain more epitopes for neutralizing antibodies relative to the postfusion conformation of the same proteins. For example, prefusion glycoprotein F has a unique antigen site ("antigenic site 0") at its membrane distal apex. Antigenic site 0 may, but not necessarily, comprise residues 62-69 and 196-209 of a RSV F protein sequence. In some instances, such as, but not limited to, prefusion glycoprotein F, prefusion polypeptides may exhibit many fold greater immune responses than those achieved with post-fusion polypeptides. Prefusion RSV glycoproteins and their methods of use are described in WO 2014/160463 and in WO 2017/172890, each of which is incorporated by reference herein in its entirety.

In some embodiments. RSV vaccines include at least one RNA (e.g., mRNA) polynucleotide comprising an open reading frame encoding glycoprotein F obtained from RSV strain A2 (RSV A2). Other RSV strains are encompassed by the present disclosure, including subtype A strains and subtype B strains.

Nucleic Acids

The RSV vaccines of the present disclosure comprise at least one (one or more) ribonucleic acid (RNA) comprising an open reading frame encoding at least one RSV antigen. In some embodiments, the RNA is a messenger RNA (mRNA) comprising an open reading frame encoding at least one RSV antigen. In some embodiments, the RNA (e.g., mRNA) further comprises a (at least one) 5' UTR, 3' UTR, a polyA tail and/or a 5' cap.

Nucleic acids comprise a polymer of nucleotides (nucleotide monomers), also referred to as polynucleotides. Nucleic acids may be or may include, for example, deoxyribonucleic acids (DNAs), ribonucleic acids (RNAs), threose nucleic acids (TNAs), glycol nucleic acids (GNAs), peptide nucleic acids (PNAs), locked nucleic acids (LNAs, including LNA having a μ-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) and/or chimeras and/or combinations thereof.

Messenger RNA (mRNA) is any ribonucleic acid that encodes a (at least one) protein (a naturally-occurring, non-naturally-occurring, or modified polymer of amino acids) and can be translated to produce the encoded protein in vitro, in vivo, in situ or ex vivo. The skilled artisan will appreciate that, except where otherwise noted, nucleic acid sequences set forth in the instant application may recite "T"s in a representative DNA sequence but where the sequence represents RNA (e.g., mRNA), the "T"s would be substituted for "U"s. Thus, any of the DNAs disclosed and identified by a particular sequence identification number herein also disclose the corresponding RNA (e.g., mRNA) sequence complementary to the DNA, where each "T" of the DNA sequence is substituted with "U." Likewise, any of the RNAs disclosed and identified by a particular sequence identification number herein also disclose the corresponding DNA sequence complementary to the RNA, where each "U" of the RNA sequence is substituted with "T."

An open reading frame (ORF) is a continuous stretch of DNA or RNA beginning with a start codon (e.g., methionine (ATG or AUG)) and ending with a stop codon (e.g., TAA, TAG or TGA, or UAA, UAG or UGA). An ORF typically encodes a protein. It will be understood that the sequences disclosed herein may further comprise additional elements, e.g., 5' and 3' UTRs, but that those elements, unlike the ORF, need not necessarily be present in a vaccine of the present disclosure.

Variants

In some embodiments, an RNA of the present disclosure encodes an RSV antigen variant. Antigen or other polypeptide variants refers to molecules that differ in their amino acid sequence from a wild-type, native or reference sequence. The antigen/polypeptide variants may possess substitutions, deletions, and/or insertions at certain positions within the amino acid sequence, as compared to a native or reference sequence. Ordinarily, variants possess at least 50% identity to a wild-type, native or reference sequence. In some embodiments, variants share at least 80%, or at least 90% identity with a wild-type, native or reference sequence.

Variant antigens/polypeptides encoded by nucleic acids of the disclosure may contain amino acid changes that confer any of a number of desirable properties, e.g., that enhance their immunogenicity, enhance their expression, and/or improve their stability or PK/PD properties in a subject. Variant antigens/polypeptides can be made using routine mutagenesis techniques and assayed as appropriate to determine whether they possess the desired property. Assays to determine expression levels and immunogenicity are well known in the art and exemplary such assays are set forth in the Examples section. Similarly, PK/PD properties of a protein variant can be measured using art recognized techniques, e.g., by determining expression of antigens in a vaccinated subject over time and/or by looking at the durability of the induced immune response. The stability of protein(s) encoded by a variant nucleic acid may be measured by assaying thermal stability or stability upon urea denaturation or may be measured using in silico prediction. Methods for such experiments and in silico determinations are known in the art.

In some embodiments, an RSV vaccine comprises an mRNA ORF comprising a nucleotide sequence identified by any one of the sequences provided herein (see e.g., Sequence Listing), or comprising a nucleotide sequence at least 85%, at least 90%, at least 95%, at least 96%, at least 97%, at least 98%, or at least 99% identical to a nucleotide sequence identified by any one of the sequence provided herein.

The term "identity" refers to a relationship between the sequences of two or more polypeptides (e.g, antigens) or polynucleotides (nucleic acids), as determined by comparing the sequences. Identity also refers to the degree of sequence relatedness between or among sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related antigens or nucleic acids can be readily calculated by known methods. "Percent (%) identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide (e.g., antigen) have at least 85%, 86%, 87%, 88%, 89%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al(1997). "Gapped BLAST and PSI-BLAST: a new generation of protein database search programs". *Nucleic Acids Res.* 25:3389-3402). Another popular local alignment technique is based on the Smith-Waterman algorithm (Smith. T. F. & Waterman, M. S. (1981) "Identification of common molecular subsequences." *J. Mol. Biol.* 147:195-197). A general global alignment technique based on dynamic programming is the Needleman-Wunsch algorithm (Needleman. S. B. & Wunsch, C. D. (1970) "A general method applicable to the search for similarities in the amino acid sequences of two proteins." *J. Mol. Biol.* 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm.

As such, polynucleotides encoding peptides or polypeptides containing substitutions, insertions and/or additions, deletions and covalent modifications with respect to reference sequences, in particular the polypeptide (e.g., antigen) sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support. In some embodiments, sequences for (or encoding) signal sequences, termination sequences, transmembrane domains, linkers, multimerization domains (such as, e.g., foldon regions) and the like may be substituted with alterative sequences that achieve the same or a similar function. In some embodiments, cavities in the core of proteins can be filled to improve stability, e.g., by introducing larger amino acids. In other embodiments, buried hydrogen bond networks may be replaced with hydrophobic resides to improve stability. In yet other embodiments, glycosylation sites may be removed and replaced with appropriate residues. Such sequences are readily identifiable to one of skill in the art. It should also be understood that some of the sequences provided herein contain sequence tags or terminal peptide sequences (e.g., at the N-terminal or C-terminal ends) that may be deleted, for example, prior to use in the preparation of an RNA (e.g., mRNA) vaccine.

As recognized by those skilled in the art, protein fragments, functional protein domains, and homologous proteins are also considered to be within the scope of RSV antigens of interest. For example, provided herein is any protein fragment (meaning a polypeptide sequence at least one amino acid residue shorter than a reference antigen sequence but otherwise identical) of a reference protein, provided that the fragment is immunogenic and confers a protective immune response to the RSV pathogen. In addition to variants that are identical to the reference protein but are truncated, in some embodiments, an antigen includes 2, 3, 4, 5, 6, 7, 8, 9, 10, or more mutations, as shown in any of the sequences provided or referenced herein. Antigens/antigenic polypeptides can range in length from about 4, 6, or 8 amino acids to full length proteins.

Stabilizing Elements

Naturally-occurring eukaryotic mRNA molecules can contain stabilizing elements, including, but not limited to untranslated regions (UTR) at their 5'-end (5' UTR) and/or at their 3'-end (3' UTR), in addition to other structural features, such as a 5'-cap structure or a 3'-poly(A) tail. Both the 5' UTR and the 3' UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing.

In some embodiments, a vaccine includes at least one RNA polynucleotide comprising an open reading frame encoding at least one antigenic polypeptide comprising at least one modification, at least one 5' terminal cap, and is formulated within a lipid nanoparticle. 5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp (5') G [the ARCA cap]; G(5')ppp(5')A; G(5')ppp(5')G; m7G (5')ppp(5')A; m7G(5')ppp(5')G (New England BioLabs, Ipswich, MA). 5'-capping of modified RNA may be completed post-transcriptionally using a Vaccinia Virus Capping Enzyme to generate the "Cap 0" structure: m7G(5')ppp(5')G (New England BioLabs, Ipswich, MA). Cap 1 structure may be generated using both Vaccinia Virus Capping Enzyme and a 2'-O methyl-transferase to generate: m7G(5')ppp(5') G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes may be derived from a recombinant source.

The 3'-poly(A) tail is typically a stretch of adenine nucleotides added to the 3'-end of the transcribed mRNA. It can, in some instances, comprise up to about 400 adenine nucleotides. In some embodiments, the length of the 3'-poly (A) tail may be an essential element with respect to the stability of the individual mRNA.

In some embodiments, RSV RNA vaccines may include one or more stabilizing elements. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stein-loop.

In some embodiments. RSV RNA vaccines include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g, alpha-Globin, Galactokinase and Xanthine: guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. The synergistic effect of the combination of poly(A) and at least one histone stem-loop does not depend on the order of the elements or the length of the poly(A) sequence.

In some embodiments, RSV RNA vaccines do not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. In some embodiments, the nucleic acid does not include an intron.

In some embodiments. RSV RNA vaccines may or may not contain an enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In some embodiments. RSV RNA vaccines may have one or more AU-rich sequences removed. These sequences, sometimes referred to as AURES are destabilizing sequences found in the 3'UTR. The AURES may be removed from the RNA vaccines. Alternatively the AURES may remain in the RNA vaccine.

Signal Peptides

In some embodiments, an RSV vaccine comprises a RNA comprising an ORF that encodes a signal peptide fused to the RSV antigen. Signal peptides, comprising the N-terminal 15-60 amino acids of proteins, arm typically needed for the translocation across the membrane on the secretory pathway and, thus, universally control the entry of most proteins both in eukaryotes and prokaryotes to the secretory pathway. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by a ER-resident signal peptidase of the host cell, or they remain uncleaved and function as a membrane anchor. A signal peptide may also facilitate the targeting of the protein to the cell membrane.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide has a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

Signal peptides from heterologous genes (which regulate expression of genes other than RSV antigens in nature) are known in the art and can be tested for desired properties and then incorporated into a nucleic acid of the disclosure. In some embodiments, the signal peptide is a bovine prolactin signal peptide. For example, the bovine prolactin signal peptide may comprise sequence MDSKGSSQKGSRLLLLLVVSNLLLPQGVVG (SEQ ID NO: 79). Other signal peptide sequences may also be used. For example, the signal peptide may comprise one of the following sequences: MDWTWILFLVAAATRVHS (SEQ ID NO: 80); METPAQLLFLLLLWLPDTTG (SEQ ID NO:81); MLGSNSGQRVVFTILLLLVAPAYS (SEQ ID NO: 82); MKCLLYLAFLFIGVNCA (SEQ ID NO: 83); MWLVSLAIVTACAGA (SEQ ID NO: 84); or MELLILKANAITTILTAVTFCFASG (SEQ ID NO:100).

Fusion Proteins

In some embodiments, an RSV RNA vaccine of the present disclosure includes an RNA encoding an antigenic fusion protein. Thus, the encoded antigen or antigens may include two or more proteins (e.g., protein and/or protein fragment) joined together. Alternatively, the protein to which a protein antigen is fused does not promote a strong immune response to itself, but rather to the RSV antigen. Antigenic fusion proteins, in some embodiments, retain the functional property from each original protein.

Scaffold Moieties

The RNA (e.g., mRNA) vaccines as provided herein, in some embodiments, encode fusion proteins which comprise RSV antigens linked to scaffold moieties. In some embodiments, such scaffold moieties impart desired properties to an antigen encoded by a nucleic acid of the disclosure. For example scaffold proteins may improve the immunogenicity of an antigen, e.g., by altering the structure of the antigen, altering the uptake and processing of the antigen, and/or causing the antigen to bind to a binding partner.

In some embodiments, the scaffold moiety is protein that can self-assemble into protein nanoparticles that are highly symmetric, stable, and structurally organized, with diameters of 10-150 nm, a highly suitable size range for optimal interactions with various cells of the immune system. In some embodiments, viral proteins or virus-like particles can be used to form stable nanoparticle structures. Examples of such viral proteins are known in the art. For example, in some embodiments, the scaffold moiety is a hepatitis B surface antigen (HBsAg). HBsAg forms spherical particles with an average diameter of ~22 nm and which lacked nucleic acid and hence are non-infectious (Lopez-Sagaseta, J, et al. *Computational and Structural Biotechnology Journal* 14 (2016) 58-68). In some embodiments, the scaffold moiety is a hepatitis B core antigen (HBcAg) self-assembles into particles of 24-31 nm diameter, which resembled the viral cores obtained from HBV-infected human liver. HBcAg produced in self-assembles into two classes of differently sized nanoparticles of 300 Å and 360 Å diameter, corresponding to 180 or 240 protomers. In some embodiments an RSV antigen is fused to HBsAG or HBcAG to facilitate self-assembly of nanoparticles displaying the RSV antigen.

In another embodiment, bacterial protein platforms may be used. Non-limiting examples of these self-assembling proteins include ferritin, lumazine and encapsulin.

Ferritin is a protein whose main function is intracellular iron storage. Ferritin is made of 24 subunits, each composed of a four-alpha-helix bundle, that self-assemble in a quaternary structure with octahedral symmetry (Cho K. J. et al. *J Mol Biol.* 2009; 390:83-98). Several high-resolution structures of ferritin have been determined, confirming that *Helicobacter pylori* ferritin is made of 24 identical protomers, whereas in animals, there are ferritin light and heavy chains that can assemble alone or combine with different ratios into particles of 24 subunits (Granier T, et al. *J Biol Inorg Chem.* 2003; 8:105-111; Lawson D. M. et al. *Nature.* 1991; 349:541-544). Ferritin self-assembles into nanoparticles with robust thermal and chemical stability. Thus, the ferritin nanoparticle is well-suited to carry and expose antigens.

Lumazine synthase (LS) is also well-suited as a nanoparticle platform for antigen display. LS, which is responsible for the penultimate catalytic step in the biosynthesis of riboflavin, is an enzyme present in a broad variety of organisms, including archaea, bacteria, fungi, plants, and eubacteria (Weber S. E. Flavins and Flavoproteins. Methods and Protocols. Series: Methods in Molecular Biology. 2014). The LS monomer is 150 amino acids long, and consists of beta-sheets along with tandem alpha-helices flanking its sides. A number of different quaternary structures have been reported for LS, illustrating its morphological versatility: from homopentamers up to symmetrical assemblies of 12 pentamers forming capsids of 150 Å diameter. Even LS cages of more than 100 subunits have been described (Zhang X, et al. *J Mol Biol.* 2006:362:753-770).

Encapsulin, a novel protein cage nanoparticle isolated from thermophile *Thermotoga maritima*, may also be used as a platform to present antigens on the surface of self-assembling nanoparticles. Encapsulin is assembled from 60 copies of identical 31 kDa monomers having a thin and icosahedral T=1 symmetric cage structure with interior and exterior diameters of 20 and 24 nm, respectively (Sutter M, et al. *Nat Struct Mol Biol.* 2008, 15: 939-947). Although the exact function of encapsulin in *T. maritima* is not clearly understood yet, its crystal structure has been recently solved and its function was postulated as a cellular compartment that encapsulates proteins such as DyP (Dye decolorizing peroxidase) and Flp (Ferritin like protein), which are involved in oxidative stress responses (Rahmanpour R. et al. *FEBS J.* 2013, 280: 2097-2104).

Linkers and Cleavable Peptides

In some embodiments, the mRNAs of the disclosure encode more than one polypeptide, referred to herein as fusion proteins. In some embodiments, the mRNA further encodes a linker located between at least one or each domain of the fusion protein. The linker can be, for example, a cleavable linker or protease-sensitive linker. In some embodiments, the linker is selected from the group consisting of F2A linker, P2A linker. T2A linker. E2A linker, and combinations thereof. This family of self-cleaving peptide linkers, referred to as 2A peptides, has been described in the art (see for example, Kim, J. H, et al. (2011) *PLoS ONE* 6:e18556). In some embodiments, the linker is an F2A linker. In some embodiments, the linker is a GGGS linker. In some embodiments, the fusion protein contains three domains with intervening linkers, having the structure: domain-linker-domain-linker-domain.

Cleavable linkers known in the art may be used in connection with the disclosure. Exemplary such linkers include: F2A linkers, T2A linkers, P2A linkers, E2A linkers (See, e.g., WO2017127750). The skilled artisan will appreciate that other art-recognized linkers may be suitable for use in the constructs of the disclosure (e.g., encoded by the nucleic acids of the disclosure). The skilled artisan will likewise appreciate that other polycistronic constructs (mRNA encoding more than one antigen/polypeptide separately within the same molecule) may be suitable for use as provided herein.

Sequence Optimization

In some embodiments, an ORF encoding an antigen of the disclosure is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences: remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence ORF (e.g., a naturally-occurring or wild-type mRNA sequence encoding an RSV antigen). In some embodiments, a codon optimized sequence shares less than 90% sequence identity to a naturally-occurring or wild-type sequence (e.g., a naturally-occurring or wild-type mRNA sequence encoding an RSV antigen). In some embodiments, a codon optimized sequence shares less than 85% sequence identity to a naturally-occurring or wild-type sequence (e.g., a naturally-occurring or wild-type mRNA sequence encoding an RSV antigen). In some embodiments, a codon optimized sequence shares less than 80% sequence identity to a naturally-occurring or wild-type sequence (e.g., a naturally-occurring or wild-type mRNA sequence encoding an RSV antigen). In some embodiments, a codon optimized sequence shares less than 75% sequence identity to a naturally-occurring or wild-type sequence (e.g., a naturally-occurring or wild-type mRNA sequence encoding an RSV antigen).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding an RSV antigen). In some embodiments, a codon optimized sequence shares between 65% and 75% or about 80% sequence identity to a naturally-occurring or wild-type sequence (e.g., a naturally-occurring or wild-type mRNA sequence encoding an RSV antigen).

In some embodiments, a codon-optimized sequence encodes an antigen that is as immunogenic as, or more immunogenic than (e.g., at least 10%, at least 20%, at least 30%, at least 40%, at least 50%, at least 100%, or at least 200% more), than an RSV antigen encoded by a non-codon-optimized sequence.

When transfected into mammalian host cells, the modified mRNAs have a stability of between 12-18 hours, or greater than 18 hours, e.g., 24, 36, 48, 60, 72, or greater than 72 hours and are capable of being expressed by the mammalian host cells.

In some embodiments, a codon optimized RNA may be one in which the levels of G/C are enhanced. The G/C-content of nucleic acid molecules (e.g., mRNA) may influence the stability of the RNA. RNA having an increased amount of guanine (G) and/or cytosine (C) residues may be functionally more stable than RNA containing a large amount of adenine (A) and thymine (T) or uracil (U) nucleotides. As an example, WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Chemically Umnodified Nucleotides

In some embodiments, at least one RNA (e.g., mRNA) of an RSV vaccines of the present disclosure is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g, dA, dG, dC, or dT).

Chemical Modifications

RSV RNA vaccines of the present disclosure comprise, in some embodiments, at least one nucleic acid (e.g., RNA) comprising an open reading frame encoding at least one RSV antigen, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or mom modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosin-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids comprising at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise 1-methyl-pseudouridine (m1ψ). 1-ethyl-pseudouridine (e1ψ). 5-methoxy-uridine (mo5U). 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine. 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a RNA nucleic acid of the disclosure comprises 1-methyl-pseudouridine (m1ψ) substitutions at one or more or all uridine positions of the nucleic acid.

In some embodiments, a RNA nucleic acid of the disclosure comprises 1-methyl-pseudouridine (m1ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises pseudouridine (ψ) substitutions at one or more or all uridine positions of the nucleic acid.

In some embodiments, a RNA nucleic acid of the disclosure comprises pseudouridine (ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises uridine at one or more or all uridine positions of the nucleic acid.

In some embodiments, nucleic acids (e.g., RNA nucleic acids, such as mRNA nucleic acids) are uniformly modified (e.g., fully modified, modified throughout the entire sequence) for a particular modification. For example, a nucleic acid can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A. G. U. C) may be uniformly modified in a nucleic acid of the disclosure, or in a predetermined sequence region thereof (e.g., in the mRNA including or excluding the polyA tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G. U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The nucleic acids may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

Untranslated Regions (UTRs)

The nucleic acids of the present disclosure may comprise one or more regions or parts which act or function as an untranslated region. Where nucleic acids are designed to encode at least one antigen of interest, the nucleic may comprise one or more of these untranslated regions (UTRs). Wild-type untranslated regions of a nucleic acid are transcribed but not translated. In mRNA, the 5' UTR starts at the transcription start site and continues to the start codon but does not include the start codon: whereas, the 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. A variety of 5'UTR and 3'UTR sequences are known and available in the art.

A 5' UTR is region of an mRNA that is directly upstream (5') from the start codon (the first codon of an mRNA transcript translated by a ribosome). A 5' UTR does not encode a protein (is non-coding). Natural 5'UTRs have features that play roles in translation initiation. They harbor signatures like Kozak sequences which are commonly known to be involved in the process by which the ribosome initiates translation of many genes. Kozak sequences have the consensus CCR(A/G)CCAUGG (SEQ ID NO: 85), where R is a purine (adenine or guanine) three bases upstream of the smart codon (AUG), which is followed by another 'G'.5'UTR also have been known to form secondary structures which are involved in elongation factor binding.

In some embodiments of the disclosure, a 5' UTR is a heterologous UTR, i.e., is a UTR found in nature associated with a different ORF. In another embodiment, a 5' UTR is a synthetic UTR, i.e., does not occur in nature. Synthetic UTRs include UTRs that have been mutated to improve their properties, e.g., which increase gene expression as well as those which are completely synthetic. Exemplary 5' UTRs include *Xenopus* or human derived α-globin or b-globin (U.S. Pat. Nos. 8,278,063; 9,012,219), human cytochrome b-245 a polypeptide, and hydroxysteroid (17b) dehydrogenase, and Tobacco etch virus (U.S. Pat. Nos. 8,278,063, 9,012,219). CMV immediate-early 1 (IE1) gene (US20140206753, WO2013/185069), the sequence GGGAUCCUACC (SEQ ID NO: 86) (WO2014144196) may also be used. In another embodiment, 5' UTR of a TOP gene is a 5' UTR of a TOP gene lacking the 5' TOP motif (the oligopyrimidine tract) (e.g., WO/2015101414. WO2015101415. WO/2015/062738, WO2015024667, WO2015024667; 5' UTR element derived from ribosomal protein Large 32 (132) gene (WO/2015101414. WO2015101415. WO/2015/062738), 5' UTR element derived from the 5'UTR of an hydroxysteroid (17-β) dehydrogenase 4 gene (HSD17B4) (WO2015024667), or a 5 UTR element derived from the 5' UTR of ATP5A1 (WO2015024667) can be used. In some embodiments, an internal ribosome entry site (IRES) is used instead of a 5' UTR.

In some embodiments, a 5' UTR of the present disclosure comprises a sequence selected from SEQ ID NO: 2 and SEQ ID NO: 77.

A 3' UTR is region of an mRNA that is directly downstream (3') from the stop codon (the codon of an mRNA transcript that signals a termination of translation). A 3' UTR does not encode a protein (is non-coding). Natural or wild type 3' UTRs are known to have stretches of adenosines and uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) (SEQ ID NO: 87) nonamers. Molecules containing this type of AREs include GM-CSF and TNF-α. Class 111 ARES are less well defined. These U rich regions do not contain an AUUUA motif, c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of nucleic acids (e.g., RNA) of the disclosure. When engineering specific nucleic acids, one or more copies of an ARE can be introduced to make nucleic acids of the disclosure less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using nucleic acids of the disclosure and protein production can be assayed at various time points post-transfection. For example, cells can be transfected with different ARE-engineering molecules and by using an ELISA kit to the relevant protein and assaying protein produced at 6 hour, 12 hour, 24 hour, 48 hour, and 7 days post-transfection.

Figure 4:
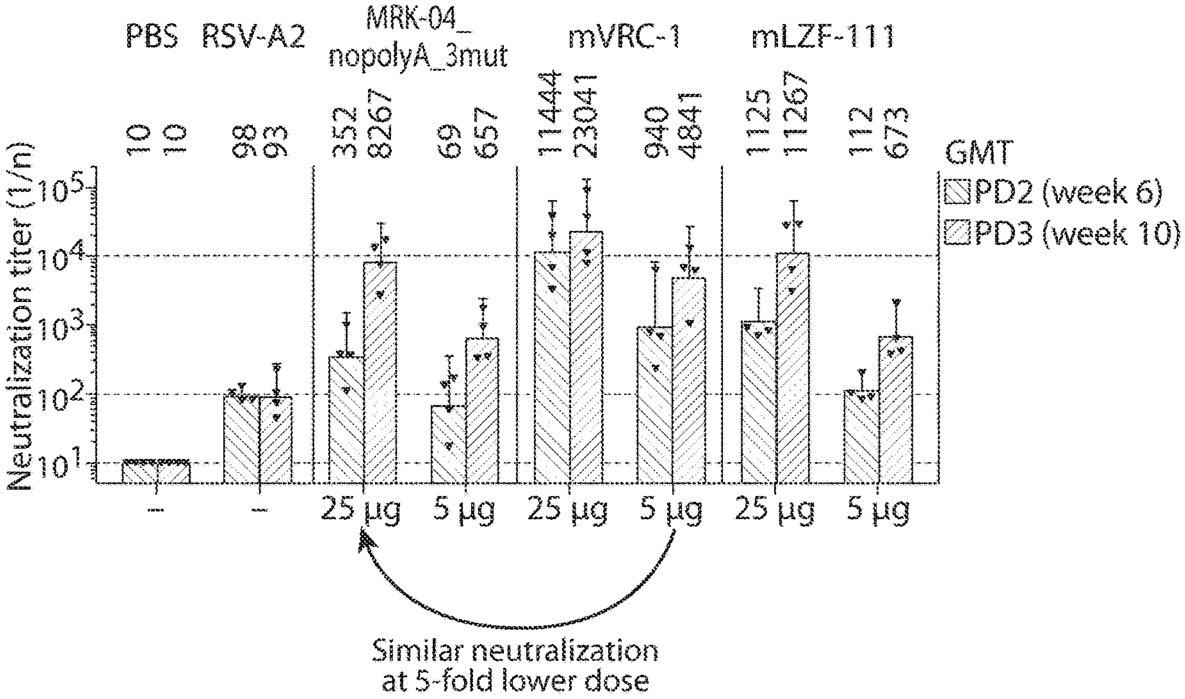
FIG. 4 shows serum neutralizing antibody titers ($NT_{50}$ Individual and GMT with 95% confidence Iintervals) to RSV A induced in African green monkeys by mRNA vaccines and control Formulations.

3' UTRs may be heterologous or synthetic. With respect to 3' UTRs, globin UTRs, including *Xenopus* β-globin UTRs and human β-globin UTRs are known in the art (8278063, 9012219. US20110086907). A modified β-globin construct with enhanced stability in some cell types by cloning two sequential human β-globin 3'UTRs head to tail has been developed and is well known in the art (US2012/0195936. WO2014/071963). In addition a2-globin, a1-globin. UTRs and mutants thereof are also known in the art (WO2015101415, WO2015024667). Other 3' UTRs described in the mRNA constructs in the non-patent literature include CYBA (Ferizi et al., 2015) and albumin (Thess et al., 2015). Other exemplary 3' UTRs include that of bovine or human growth hormone (wild type or modified) (WO2013/185069, US20140206753, WO2014/152774), rabbit β globin and hepatitis B virus (HBV), α-globin 3' UTR and Viral VEEV 3' UTR sequences are also known in the art. In some embodiments, the sequence UUUGAAUU (WO2014/144196) is used. In some embodiments, 3' UTRs of human and mouse ribosomal protein arm used. Other examples include rps9 3'UTR (WO2015101414). FIG. 4 (WO2015/101415), and human albumin 7 (WO2015/101415).

In some embodiments, a 3' UTR of the present disclosure comprises a sequence selected from SEQ ID NO: 4 and SEQ ID NO: 78.

Those of ordinary skill in the art will understand that 5'UTRs that are heterologous or synthetic may be used with any desired 3' UTR sequence. For example, a heterologous 5'UTR may be used with a synthetic 3'UTR with a heterologous 3" UTR.

Non-UTR sequences may also be used as regions or subregions within a nucleic acid. For example, introns or portions of introns sequences may be incorporated into regions of nucleic acid of the disclosure. Incorporation of intronic sequences may increase protein production as well as nucleic acid levels.

Combinations of features may be included in flanking regions and may be contained within other features. For example, the ORF may be flanked by a 5' UTR which may contain a strong Kozak translational initiation signal and/or a 3' UTR which may include an oligo(dT) sequence for templated addition of a poly-A tail. 5' UTR may comprise a first polynucleotide fragment and a second polynucleotide fragment from the same and/or different genes such as the 5' UTRs described in US Patent Application Publication No. 20100293625 and PCT/US2014/069155, herein incorporated by reference in its entirety.

It should be understood that any UTR from any gene may be incorporated into the regions of a nucleic acid. Furthermore, multiple wild-type UTRs of any known gene may be utilized. It is also within the scope of the present disclosure to provide artificial UTRs which are not variants of wild type regions. These UTRs or portions thereof may be placed in the same orientation as in the transcript from which they were selected or may be altered in orientation or location. Hence a 5' or 3' UTR may be inverted, shortened, lengthened, made with one or more other 5' UTRs or 3' UTRs. As used herein, the term "altered" as it relates to a UTR sequence, means that the UTR has been changed in some way in relation to a reference sequence. For example, a 3' UTR or 5' UTR may be altered relative to a wild-type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' UTR or 3' UTR may be used. As used herein, a "double" UTR is one in which two copies of the same UTR are encoded either in series or substantially in series. For example, a double beta-globin 3' UTR may be used as described in US Patent publication 20100129877, the contents of which are incorporated herein by reference in its entirety.

It is also within the scope of the present disclosure to have patterned UTRs. As used herein "patterned UTRs" are those UTRs which reflect a repeating or alternating pattern, such as ABABAB or AABBAABBAAIBB or ABCAIBCABC or variants thereof repeated once, twice, or more than 3 times. In these patterns, each letter, A, B, or C represent a different UTR at the nucleotide level.

In some embodiments, flanking regions are selected from a family of transcripts whose proteins share a common function, structure, feature or property. For example, polypeptides of interest may belong to a family of proteins which are expressed in a particular cell, tissue or at some time during development. The UTRs from any of these genes may be swapped for any other UTR of the same or different family of proteins to create a new polynucleotide. As used herein, a "family of proteins" is used in the broadest sense to refer to a group of two or more polypeptides of interest which share at least one function, structure, feature, localization, origin, or expression pattern.

The untranslated region may also include translation enhancer elements (TEE). As a non-limiting example, the TEE may include those described in US Application No. 20090226470, herein incorporated by reference in its entirety, and those known in the art.

In Vitro Transcription of RNA cDNA encoding the polynucleotides described herein may be transcribed using an in vitro transcription (IVT) system. In vitro transcription of RNA is known in the art and is described in International Publication WO/2014/152027, which is incorporated by reference herein in its entirety.

In some embodiments, the RNA transcript is generated using a non-amplified, linearized DNA template in an in vitro transcription reaction to generate the RNA transcript. In some embodiments, the template DNA is isolated DNA. In some embodiments, the template DNA is cDNA. In some embodiments, the cDNA is formed by reverse transcription of a RNA polynucleotide, for example, but not limited to RSV RNA, e.g. RSV mRNA. In some embodiments, cells, e.g., bacterial cells, e.g., *E, coli*, e.g., DH-1 cells are transfected with the plasmid DNA template. In some embodiments, the transfected cells are cultured to replicate the plasmid DNA which is then isolated and purified. In some embodiments, the DNA template includes a RNA polymerase promoter, e.g., a T7 promoter located 5' to and operably linked to the gene of interest.

In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide. When RNA transcripts are being generated, the 5' UTR may comprise a promoter sequence. Such promoter sequences are known in the art. It should be understood that such promoter sequences will not be present in a vaccine of the disclosure.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, a nucleic acid includes 200 to 3.000 nucleotides. For example, a nucleic acid may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

An in vitro transcription system typically comprises a transcription buffer, nucleotide triphosphates (NTPs), an RNase inhibitor and a polymerase.

The NTPs may be manufactured in house, may be selected from a supplier, or may be synthesized as described herein. The NTPs may be selected from, but are not limited to, those described herein including natural and unnatural (modified) NTPs.

Any number of RNA polymerases or variants may be used in the method of the present disclosure. The polymerase may be selected from, but is not limited to, a phage RNA polymerase, e.g., a T7 RNA polymerase, a T3 RNA polymerase, a SP6 RNA polymerase, and/or mutant polymerases such as, but not limited to, polymerases able to incorporate modified nucleic acids and/or modified nucleotides, including chemically modified nucleic acids and/or nucleotides. Some embodiments exclude the use of DNase.

In some embodiments, the RNA transcript is capped via enzymatic capping. In some embodiments, the RNA comprises 5' terminal cap, for example, 7mG(5')ppp(5')NlmpNp.

Chemical Synthesis

Solid-phase chemical synthesis. Nucleic acids the present disclosure may be manufactured in whole or in part using solid phase techniques. Solid-phase chemical synthesis of nucleic acids is an automated method wherein molecules are immobilized on a solid support and synthesized step by step in a reactant solution. Solid-phase synthesis is useful in site-specific introduction of chemical modifications in the nucleic acid sequences.

Liquid Phase Chemical Synthesis. The synthesis of nucleic acids of the present disclosure by the sequential addition of monomer building blocks may be carried out in a liquid phase.

Combination of Synthetic Methods. The synthetic methods discussed above each has its own advantages and limitations. Attempts have been conducted to combine these methods to overcome the limitations. Such combinations of methods are within the scope of the present disclosure. The use of solid-phase or liquid-phase chemical synthesis in combination with enzymatic ligation provides an efficient way to generate long chain nucleic acids that cannot be obtained by chemical synthesis alone.

Ligation of Nucleic Acid Regions or Subregions

Assembling nucleic acids by a ligase may also be used. DNA or RNA ligases promote intermolecular ligation of the 5' and 3' ends of polynucleotide chains through the formation of a phosphodiester bond. Nucleic acids such as chimeric polynucleotides and/or circular nucleic acids may be prepared by ligation of one or more regions or subregions. DNA fragments can be joined by a ligase catalyzed reaction to create recombinant DNA with different functions. Two oligodeoxynucleotides, one with a 5' phosphoryl group and another with a free 3' hydroxyl group, serve as substrates for a DNA ligase.

Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, MA), poly-T beads, LNA™ oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis. UV absorbance, or analytical HPLC.

In some embodiments, the nucleic acids may be sequenced by methods including, but not limited to reverse-transcriptase-PCR.

Quantification

In some embodiments, the nucleic acids of the present invention may be quantified in exosomes or when derived from one or more bodily fluid. Bodily fluids include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using construct specific probes, cytometry, qRT-PCR, real-time PCR. PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Nis). A non-limiting example of a UV/Nis spectrometer is a NANODROP® spectrometer (ThermoFisher, Waltham, MA). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Pharmaceutical Formulations

Provided herein are compositions (e.g., pharmaceutical compositions), methods, kits and reagents for prevention or treatment of RSV in humans and other mammals, for example, RSV RNA (e.g., mRNA) vaccines can be used as therapeutic or prophylactic agents. They may be used in medicine to prevent and/or treat infectious disease.

In some embodiments, an RSV vaccine containing RNA polynucleotides as described herein can be administered to a subject (e.g., a mammalian subject, such as a human subject), and the RNA polynucleotides are translated in vivo to produce an antigenic polypeptide (antigen).

An "effective amount" of an RSV vaccine is based, at least in part, on the target tissue, target cell type, means of administration, physical characteristics of the RNA (e.g., length, nucleotide composition, and/or extent of modified nucleosides), other components of the vaccine, and other determinants, such as age, body weight, height, sex and general health of the subject. Typically, an effective amount of an RSV vaccine provides an induced or boosted immune response as a function of antigen production in the cells of the subject. In some embodiments, an effective amount of the RSV RNA vaccine containing RNA polynucleotides comprising at least one chemical modifications are more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation and/or expression from the polynucleotide, decreased nucleic acid degradation (as demonstrated, for example, by increased duration of protein translation from a modified polynucleotide), or altered antigen specific immune response of the host cell.

The term "pharmaceutical composition" refers to the combination of an active agent with a carrier, inert or active, making the composition especially suitable for diagnostic or therapeutic use in vivo or ex vivo. A "pharmaceutically acceptable carrier." after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, RNA vaccines (including polynucleotides and their encoded polypeptides) in accordance with the present disclosure may be used for treatment or prevention of RSV. RSV RNA vaccines may be administered prophylactically or therapeutically as part of an active immunization scheme to healthy individuals or early in infection during the incubation phase or during active infection after onset of symptoms. In some embodiments, the amount of RNA vaccines of the present disclosure provided to a cell, a tissue or a subject may be an amount effective for immune prophylaxis.

RSV RNA (e.g., mRNA) vaccines may be administered with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments. RSV RNA vaccines may be administered intramuscularly, intranasally or intradermally, similarly to the administration of inactivated vaccines known in the art.

The RSV RNA vaccines may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers, better neutralizing immunity, produce more durable immune responses, and/or produce responses earlier than commercially available vaccines.

Provided herein are pharmaceutical compositions including RSV RNA vaccines and RNA vaccine compositions and/or complexes optionally in combination with one or more pharmaceutically acceptable excipients.

RSV RNA (e.g., mRNA) vaccines may be formulated or administered alone or in conjunction with one or more other components. For instance, RSV RNA vaccines (vaccine compositions) may comprise other components including, but not limited to, adjuvants.

In some embodiments, RSV RNA vaccines do not include an adjuvant (they are adjuvant free).

RSV RNA (e.g., mRNA) vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments. RSV RNA vaccines are administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigens.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments. RSV RNA vaccines are formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with RSV RNA vaccines (e.g., for transplantation into a subject), hyaluronidase, nanoparticle mimics and combinations thereof.

Lipid Nanoparticles (LNPs)

In some embodiments. RSV RNA (e.g., mRNA) vaccines of the disclosure are formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the disclosure can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entirety.

Vaccines of the present disclosure are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 3040%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid. 5-25% non-cationic lipid, 25-55% sterol, and 0.5-15% PEG-modified lipid.

In some embodiments, an ionizable cationic lipid of the disclosure comprises a compound of Formula (I):

(I)

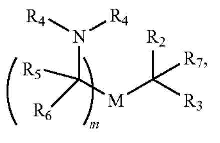

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q. —$(CH_2)_n$CHQR, —CHQR, —CQ$(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —C(O)$N(R)_2$, —N(R)C(O)R, —N(R)S$(O)_2$R, —N(R)C(O)$N(R)_2$, —N(R)C(S)$N(R)_2$, —N(R)$R_8$, —$O(CH_2)_n$OR, —N(R)C(=$NR_9$)$N(R)_2$, —N(R)C(=$CHR_9$)$N(R)_2$, —OC(O)$N(R)_2$, —N(R)C(O)OR, —N(OR)C(O)R, —N(OR)S$(O)_2$R, —N(OR)C(O)OR, —N(OR)C(O)$N(R)_2$, —N(OR)C(S)$N(R)_2$, —N(OR)C(=$NR_9$)$N(R)_2$, —N(OR)C(=$CHR_9$)$N(R)_2$, —C(=$NR_9$)$N(R)_2$, —C(=$NR_9$)R, —C(O)N(R)OR, and —C(R)$N(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_3$, carbocycle and heterocycle;

$R_9$ is selected from the group consisting of H, CN, $NO_2$, $C_{1-6}$ alkyl, —OR, —S$(O)_2$R, —S$(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_n$Q, —$(CH_2)_n$CHQR, —CHQR, or —CQ$(R)_2$, then (i) Q is not —$N(R)_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q. —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —C(O)$N(R)_2$, —N(R)C(O)R, —N(R)S$(O)_2$R, —N(R)C(O)$N(R)_2$, —N(R)C(S)$N(R)_2$, —CRN$(R)_2$C(O)OR, —N(R)$R_8$, —$O(CH_2)_n$OR, —N(R)C(=$NR_9$)$N(R)_2$, —N(R)C(=$CHR_9$)$N(R)_2$, —OC(O)$N(R)_2$, —N(R)C(O)OR, —N(OR)C(O)R, —N(OR)S$(O)_2$R, —N(OR)C(O)OR, —N(OR)C(O)$N(R)_2$, —N(OR)C(S)$N(R)_2$, —N(OR)C(=$NR_9$)$N(R)_2$, —N(OR)C(=$CHR_9$)$N(R)_2$. —C(=$NR_9$)$N(R)_2$, —C(=$NR_9$)R, —C(O)N(R)OR, and a 5- to 14-membered heterocycloalkyl comprising one or more heteroatoms selected from N, O, and S which is substituted with one or more substituents selected from oxo (=O). OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S$(O)_2$R, —S$(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-12}$ alkyl, $C_{2-12}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heterocycle comprising one or more heteroatoms selected from N, O, and S, —OR, —$O(CH_2)_nN(R)_2$, —C(O)OR, —OC(O)R, —$CX_3$, —$CX_2H$, —$CXH_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5; and when Q is a 5- to 14-membered heterocycle and (i) R$_4$ is —(CH$_2$)$_n$Q in which n is 1 or 2, or (ii) R$_4$ is —(CH$_2$)$_n$CHQR in which n is 1, or (iii) R$_4$ is —CHQR, and —CQ(R)$_2$, then Q is either a 5- to 14-membered heteroaryl or 8- to 14-membered heterocycloalkyl;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$, carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and 1; and m is selected from 5, 6, 7, 8, 9, 10, 11, 12, and 13, or salts or isomers thereof.

In some embodiments, another subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of H, C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$CHQR, —CHQR, —CQ(R)$_2$, and unsubstituted C$_{1-6}$ alkyl, where Q is selected from a C$_{3-6}$ carbocycle, a 5- to 14-membered heteroaryl comprising one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13.

or salts or isomers thereof.

In some embodiments, another subset of compounds of Formula (I) includes those in which R$_1$ is selected from the group consisting of C$_{5-3}$ alkyl, C$_{5-20}$ alkenyl, —R*YR", —YR", and —R"M'R';

R$_2$ and R$_3$ are independently selected from the group consisting of H, C$_{2-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is —(CH$_2$)$_n$Q or —(CH$_2$)$_n$CHQR, where Q is —N(R)$_2$, and n is selected from 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{1-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13.

or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —CQ$(R)_2$, where Q is —N$(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-4}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

or salts or isomers thereof.

In some embodiments, a subset of compounds of Formula (T) includes those of Formula (IA):

(IA)

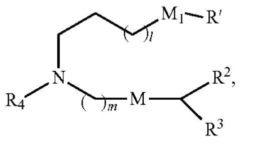

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)N$(R)_2$, —NHC(O)N$(R)_2$, —N(R)C(O)R, —N(R)$S(O)_2$R, —N(R)$R_8$, —NHC(=$NR_9$)N$(R)_2$, —NHC(=$CHR_9$)N$(R)_2$, —OC(O)N$(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

(II)

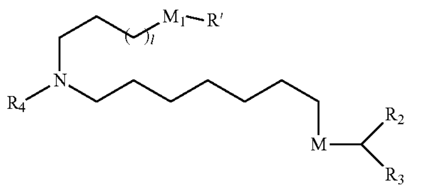

or a salt or isomer thereof, wherein 1 is selected from 1, 2, 3, 4, and 5; $M_1$ is a bond or M'; $R_4$ is unsubstituted $C_{1-3}$ alkyl, or —$(CH_2)_n$Q, in which n is 2, 3, or 4, and Q is OH, —NHC(S)N$(R)_2$, —NHC(O)N$(R)_2$, —N(R)C(O)R, —N(R)$S(O)_2$R, —N(R)$R_8$, —NHC(=$NR_9$)N$(R)_2$, —NHC(=$CHR_9$)N$(R)_2$, —OC(O)N$(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-4}$ alkyl, and $C_{2-14}$ alkenyl.

In some embodiments, a subset of compounds of Formula (I) includes those of Formula (IIa), (IIb), (IIc), or (IIe):

(IIa)

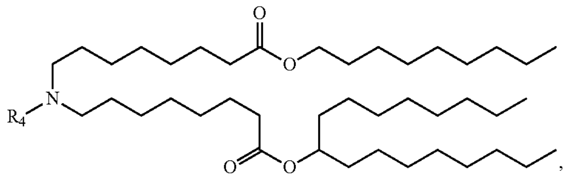

, (IIb)

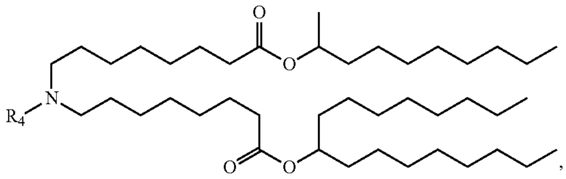

, (IIc)

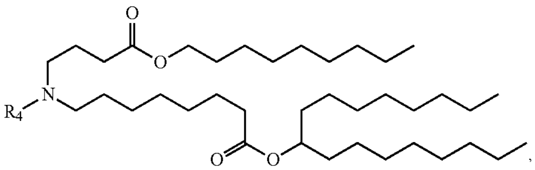

, or (IIe)

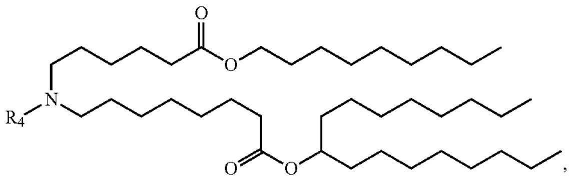

, or a salt isomer thereof, wherein $R_4$ is as described herein.

In some embodiments, a subset of compounds of Formula (I) includes those of Formula (IId):

(IId)

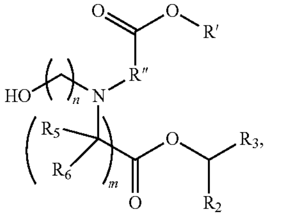

or a salt or isomer thereof, wherein n is 2, 3, or 4; and m, R', R", and $R_2$ through $R_6$, are as described herein. For example, each of $R_2$ and $R_3$ may be independently selected from the group consisting of $C_{5-14}$ alkyl and $C_{5-14}$ alkenyl.

In some embodiments, an ionizable cationic lipid of the disclosure comprises a compound having structure:

(Compound 1)

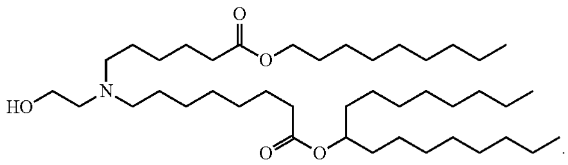

In some embodiments, an ionizable cationic lipid of the disclosure comprises a compound having structure:

(Compound 2)

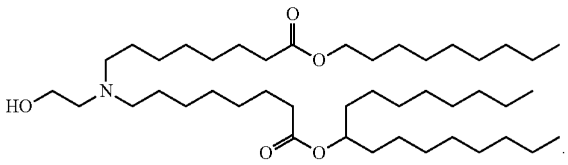

In some embodiments, an ionizable cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino) butanoyl)oxy)heptadecanedioate (L319). (13Z,16Z)—N,N-dimethyl-3-nonyldocosa-13,16-dien-1-amine, (12Z,5Z)—N,N-dimethyl-2-nonylhenicosa-12,15-dien-1-amine, and N,N-dimethyl-1-[(1S,2R)-2-octylcyclopropyl]heptadecan-8-amine. In one embodiment, the lipid is (13Z,16Z)—N,N-dimethyl-3-nonyldocosa-13,16-dien-1-amine or N,N-dimethyl-1-[(1S,2R)-2-octylcyclopropyl]heptadecan-8-amine, each of which are described in PCT/US2011/052328, the entire contents of which are hereby incorporated by reference. In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cerophosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC). 1-oleoyl-2 cholesterylhemisuccinoyl-sn-glycero-3-phosphocholine (OChemsPC). 1-hexadecyl-sn-glycero-3-phosphocholine (C16 Lyso PC). 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In some embodiments, a PEG modified lipid of the disclosure comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG. PEG-c-DOMG (also referred to as PEG-DOMG), PEG-DSG and/or PEG-DPG.

In some embodiments, a sterol of the disclosure comprises cholesterol, fecosterol, sitosterol, ergosterol, campesterol, stigmasterol, brassicasterol, tomatidine, ursolic acid, alpha-tocopherol, and mixtures thereof.

In some embodiments, a LNP of the disclosure comprises an ionizable cationic lipid of Compound 1, wherein the non-cationic lipid is DSPC, the structural lipid that is cholesterol, and the PEG lipid is PEG-DMG.

In some embodiments, a LNP of the disclosure comprises an ionizable cationic lipid selected from the group consisting of (2S)-1-({6-[(3β))-cholest-5-en-3-yloxy]hexyl)oxy)-N,N-dimethyl-3-[(9 Z)-octadec-9-en-1-yloxy]propan-2-amine; (13Z,16Z)—N,N-dimethyl-3-nonyldocosa-13,16-dien-1-amine; and N,N-dimethyl-1-[(1S,2R)-2-octylcyclopropyl] heptadecan-8-amine; or a pharmaceutically acceptable salt thereof, or a stereoisomer of any of the foregoing.

In some embodiments, the LNP comprises 30-75 mole % ionizable cationic lipid and 0.1-20 mole % PEG-lipid.

In some embodiments, the LNP further comprises one or more non-cationic lipids selected from a phospholipid, a phospholipid derivative, a fatty acid, a sterol, or a combination thereof. In some embodiments, the sterol is cholesterol, stigmasterol or stigmastanol.

In some embodiments, the phospholipid is selected from phosphatidylserine. 1,2-Distearoyl-sn-glycero-3-phosphocholine (DSPC), 1,2-dipalmitoleoyl-sn-glycero-3-phosphocholine, 1,2-dimyristoyl-sn-glycero-3-phosphocholine (DMPC), dilauroylphosphatidylcholine (DLPC), 1,2-dieicosenoyl-sn-glycero-3-phosphocholine, and 1,2-dioleoyl-sn-glycero-3-phosphocholine (DOPC).

In some embodiments, the PEG-lipid is 1,2-Dimyristoyl-sn-glycerol methoxypolyethylene glycol (PEG-DMG). PEG-disteryl glycerol (PEG-DSG), PEG-dipalmetoleyl. PEG-dioleyl, PEG-distearyl, PEG-diacylglycamide (PEG-DAG). PEG-dipalmitoyl phosphatidylethanolamine (PEG-DPPE), or PEG-1,2-dimyristyloxlpropyl-3-amine (PEG-c-DMA). In some embodiments, the PEG-lipid is PEG coupled to dimyristoylglycerol (PEG-DMG), e.g., as described in Abrams et al., 2010. Molecular Therapy 18(1): 171, and U.S. Patent Application Publication Nos. US 2006/0240554 and US 2008/0020058, including for example, 2KPEG/PEG200-DMG.

In some embodiments, the LNP comprises 20-99.8 mole % ionizable cationic lipids, 0.1-65 mole % non-cationic lipids, and 0.1-20 mole % PEG-lipid.

In some embodiments, the non-cationic lipids comprise a mixture of cholesterol and DSPC.

In some embodiments, the LNP comprises 34-59 mole % ionizable cationic lipids selected from the group consisting of (2S)-1-({6-[(3β)-cholest-5-en-3-yloxy]hexyl)oxy)-N,N-dimethyl-3-[(9 Z)-octadec-9-en-1-yloxy]propan-2-amine; (13Z,16Z)—N,N-dimethyl-3-nonyldocosa-13,16-dien-1-amine; and N,N-dimethyl-1-[(1S,2R)-2-octylcyclopropyl] heptadecan-8-amine, 30-48 mole % cholesterol, 10-24% DSPC and 1-2 mole % PEG-DMG.

In some embodiments, the LNP comprises 58 mole % cationic lipid, 30 mole % cholesterol, 10 mole % DSPC, and 2 mole % PEG-2000 DMG.

In some embodiments, a LNP of the disclosure comprises an N:P ratio of from about 2:1 to about 30:1.

In some embodiments, a LNP of the disclosure comprises an N:P ratio of about 6:1.

In some embodiments, a LNP of the disclosure comprises an N:P ratio of about 3:1.

In some embodiments, a LNP of the disclosure comprises a wt/wt ratio of the ionizable cationic lipid component to the RNA of from about 10:1 to about 100:1.

In some embodiments, a LNP of the disclosure comprises a wt/wt ratio of the ionizable cationic lipid component to the RNA of about 20:1.

In some embodiments, a LNP of the disclosure comprises a wt/wt ratio of the ionizable cationic lipid component to the RNA of about 10:1.

In some embodiments, a LNP of the disclosure has a mean diameter from about 50 nm to about 150 nm.

In some embodiments, a LNP of the disclosure has a mean diameter from about 70 nm to about 120 nm.

Multivalent Vaccines

The RSV vaccines, as provided herein, may include an RNA (e.g, mRNA) or multiple RNAs encoding two or more antigens of the same or different RSV species. In some embodiments, an RSV vaccine includes an RNA or multiple RNAs encoding two or more antigens selected from glycoprotein G (G), glycoprotein F (F), matrix protein (M), small hydrophobic protein (SH), nonstructural protein 1 (NS1), and nonstructural protein 2 (NS2). In some embodiments, the RNA (at least one RNA) of an RSV vaccine may encode 1, 2, 3, 4, 5, 6, 7, 8, 9, 10, 11, 12, or more antigens.

In some embodiments, an RSV vaccine includes an RNA or multiple RNAs encoding two or more antigens selected from glycoprotein G and glycoprotein F. In some embodiments, an RSV vaccine includes an RNA or multiple RNAs encoding two or more antigens selected from glycoprotein G and matrix protein. In some embodiments, an RSV vaccine includes an RNA or multiple RNAs encoding two or more antigens selected from glycoprotein F and matrix protein.

In some embodiments, two or more different RNA (e.g., mRNA) encoding antigens may be formulated in the same lipid nanoparticle. In other embodiments, two or more different RNA encoding antigens may be formulated in separate lipid nanoparticles (each RNA formulated in a single lipid nanoparticle). The lipid nanoparticles may then be combined and administered as a single vaccine composition (e.g., comprising multiple RNA encoding multiple antigens) or may be administered separately.

Combination Vaccines

The RSV vaccines, as provided herein, may include an RNA or multiple RNAs encoding two or more antigens of the same or different RSV strains. Also provided herein are combination vaccines that include RNA encoding one or more RSV antigen(s) and one or more antigen(s) of a different organisms (e.g., bacterial and/or viral organism). Thus, the vaccines of the present disclosure may be combination vaccines that target one or more antigens of the same strain/species, or one or more antigens of different strains/species, e.g., antigens which induce immunity to organisms which are found in the same geographic areas where the risk of RSV infection is high or organisms to which an individual is likely to be exposed to when exposed to RSV.

Dosing/Administration

Provided herein are compositions (e.g., pharmaceutical compositions), methods, kits and reagents for prevention and/or treatment of RSV in humans and other mammals. RSV RNA vaccines can be used as therapeutic or prophylactic agents. In some aspects, the RNA vaccines of the disclosure are used to provide prophylactic protection from RSV. In some aspects, the RNA vaccines of the disclosure are used to treat an RSV infection. In some embodiments, the RSV vaccines of the present disclosure are used in the priming of immune effector cells, for example, to activate peripheral blood mononuclear cells (PBMCs) ex vivo, which are then infused (re-infused) into a subject.

A subject may be any mammal, including non-human primate and human subjects. Typically, a subject is a human subject.

In some embodiments, the RSV vaccines are administered to a subject (e.g., a mammalian subject, such as a human subject) in an effective amount to induce an antigen-specific immune response. The RNA encoding the RSV antigen is expressed and translated in vivo to produce the antigen, which then stimulates an immune response in the subject.

Prophylactic protection from RSV can be achieved following administration of an RSV RNA vaccine of the present disclosure. Vaccines can be administered once, twice, three times, four times or more but it is likely sufficient to administer the vaccine once (optionally followed by a single booster). It is possible, although less desirable, to administer the vaccine to an infected individual to achieve a therapeutic response. Dosing may need to be adjusted accordingly.

A method of eliciting an immune response in a subject against RSV is provided in aspects of the present disclosure. The method involves administering to the subject an RSV RNA vaccine comprising at least one RNA (e.g., mRNA) comprising an open reading frame encoding at least one RSV antigen, thereby inducing in the subject an immune response specific to RSV antigen, wherein anti-antigen antibody titer in the subject is increased following vaccination relative to anti-antigen antibody titer in a subject vaccinated with a prophylactically effective dose of a traditional vaccine against the RSV. An "anti-antigen antibody" is a serum antibody the binds specifically to the antigen.

A prophylactically effective dose is an effective dose that prevents infection with the virus at a clinically acceptable level. In some embodiments, the effective dose is a dose listed in a package insert for the vaccine. A traditional vaccine, as used herein, refers to a vaccine other than the mRNA vaccines of the present disclosure. For instance, a traditional vaccine includes, but is not limited, to live microorganism vaccines, killed microorganism vaccines, subunit vaccines, protein antigen vaccines, DNA vaccines, virus like particle (VLP) vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments, the anti-antigen antibody titer in the subject is increased 1 log to 10 log following vaccination relative to anti-antigen antibody titer in a subject vaccinated with a prophylactically effective dose of a traditional vaccine against the RSV or an unvaccinated subject. In some embodiments, the anti-antigen antibody titer in the subject is increased 1 log, 2 log, 3 log, 4 log, 5 log, or 10 log following vaccination relative to anti-antigen antibody titer in a subject vaccinated with a prophylactically effective dose of a traditional vaccine against the RSV or an unvaccinated subject.

A method of eliciting an immune response in a subject against an RSV is provided in other aspects of the disclosure. The method involves administering to the subject an RSV RNA vaccine comprising at least one RNA polynucleotide comprising an open reading frame encoding at least one RSV antigen, thereby inducing in the subject an immune response specific to RSV antigen, wherein the immune response in the subject is equivalent to an immune response in a subject vaccinated with a traditional vaccine against the RSV at 2 times to 100 times the dosage level relative to the RNA vaccine.

In some embodiments, the immune response in the subject is equivalent to an immune response in a subject vaccinated with a traditional vaccine at twice the dosage level relative to the RSV RNA vaccine. In some embodiments, the immune response in the subject is equivalent to an immune response in a subject vaccinated with a traditional vaccine at three times the dosage level relative to the RSV RNA vaccine. In some embodiments, the immune response in the subject is equivalent to an immune response in a subject vaccinated with a traditional vaccine at 4 times, 5 times, 10 times, 50 times, or 100 times the dosage level relative to the RSV RNA vaccine. In some embodiments, the immune response in the subject is equivalent to an immune response in a subject vaccinated with a traditional vaccine at 10 times to 1000 times the dosage level relative to the RSV RNA vaccine. In some embodiments, the immune response in the subject is equivalent to an immune response in a subject vaccinated with a traditional vaccine at 100 times to 1000 times the dosage level relative to the RSV RNA vaccine.

In other embodiments, the immune response is assessed by determining antibody titer in the subject. In other embodiments, the ability of serum or antibody from an immunized subject is tested for its ability to neutralize viral uptake or reduce RSV transformation of human B lymphocytes. In other embodiments, the ability to promote a robust T cell response(s) is measured using art recognized techniques.

Other aspects the disclosure provide methods of eliciting an immune response in a subject against an RSV by administering to the subject an RSV RNA vaccine comprising at least one RNA polynucleotide comprising an open reading frame encoding at least one RSV antigen, thereby inducing in the subject an immune response specific to RSV antigen, wherein the immune response in the subject is induced 2 days to 10 weeks earlier relative to an immune response induced in a subject vaccinated with a prophylactically effective dose of a traditional vaccine against the RSV. In some embodiments, the immune response in the subject is induced in a subject vaccinated with a prophylactically effective dose of a traditional vaccine at 2 times to 100 times the dosage level relative to the RNA vaccine.

In some embodiments, the immune response in the subject is induced 2 days, 3 days, 1 week, 2 weeks, 3 weeks, 5 weeks, or 10 weeks earlier relative to an immune response induced in a subject vaccinated with a prophylactically effective dose of a traditional vaccine.

Also provided herein are methods of eliciting an immune response in a subject against an RSV by administering to the subject an RSV RNA vaccine comprising an open reading frame encoding a first antigen, wherein the RNA polynucleotide does not include a stabilization element, and wherein an adjuvant is not co-formulated or co-administered with the vaccine.

RSV RNA (e.g., mRNA) vaccines may be administered by any route which results in a therapeutically effective outcome. These include, but are not limited, to intradermal, intramuscular, intranasal, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. RSV RNA (e.g., mRNA) vaccines compositions are typically formulated in dosage unit form for ease of administration and uniformity of dosage. It will be understood, however, that the total daily usage of RSV RNA (e.g., mRNA) vaccines compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The effective amount of an RSV vaccine, as provided herein, may be as low as 20 μg, administered for example as a single dose or as two 10 μg doses. In some embodiments, the effective amount is a total dose of 20 μg-200 μg. For example, the effective amount may be a total dose of 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 110 μg, 120 μg, 130 μg, 140 μg, 150 μg, 160 μg, 170 μg, 180 μg, 190 μg or 200 μg. In some embodiments, the effective amount is a total dose of 25 μg-200 μg. In some embodiments, the effective amount is a total dose of 50 μg-200 μg.

In some embodiments. RSV RNA (e.g., mRNA) vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc, to obtain the desired therapeutic, diagnostic, prophylactic, or imaging effect (see e.g., the range of unit doses described in International Publication No. WO2013/078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments. RSV RNA (e.g., mRNA) vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, RSV RNA (e.g., mRNA) vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments. RSV RNA (e.g., mRNA) vaccine compositions may be administered twice (e.g., Day 0 and Day 7, Day 0 and Day 14, Day 0 and Day 21, Day 0 and Day 28. Day 0 and Day 60, Day 0 and Day 90. Day 0 and Day 120. Day 0 and Day 150, Day 0 and Day 180, Day 0 and 3 months later, Day 0 and 6 months later. Day 0 and 9 months later, Day 0 and 12 months later. Day 0 and 18 months later. Day 0 and 2 years later. Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, an RSV RNA (e.g., mRNA) vaccine composition may be administered three or four times.

In some embodiments, RSV RNA (e.g., mRNA) vaccine compositions may be administered twice (e.g., Day 0 and Day 7. Day 0 and Day 14. Day 0 and Day 21, Day 0 and Day 28. Day 0 and Day 60, Day 0 and Day 90, Day 0 and Day 120. Day 0 and Day 150, Day 0 and Day 180, Day 0 and 3 months later, Day 0 and 6 months later. Day 0 and 9 months later, Day 0 and 12 months later. Day 0 and 18 months later. Day 0 and 2 years later. Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments, the RSV RNA (e.g., mRNA) vaccine for use in a method of vaccinating a subject is administered the subject a single dosage of between 10 μg/kg and 400 μg/kg of the nucleic acid vaccine in an effective amount to vaccinate the subject. In some embodiments, the RNA vaccine for use in a method of vaccinating a subject is administered the subject a single dosage of between 10 μg and 400 μg of the nucleic acid vaccine in an effective amount to vaccinate the subject. In some embodiments, an RSV RNA (e.g., mRNA) vaccine for use in a method of vaccinating a subject is administered to the subject as a single dosage of 25-1000 μg (e.g., a single dosage of mRNA encoding an RSV antigen). In some embodiments, an RSV RNA vaccine is administered to the subject as a single dosage of 25, 50, 100, 150, 200, 250, 300, 350, 400, 450, 500, 550, 600, 650, 700, 750, 800, 850, 900, 950 or 1000 μg. For example, an RSV RNA vaccine may be administered to a subject as a single dose of 25-100, 25-500, 50-100, 50-500, 50-1000, 100-500, 100-1000, 250-500, 250-1000, or 500-1000 μg. In some embodiments, an RSV RNA (e.g., mRNA) vaccine for use in a method of vaccinating a subject is administered to the subject as two dosages, the combination of which equals 25-1000 μg of the RSV RNA (e.g., mRNA) vaccine.

An RSV RNA (e.g., mRNA) vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

Vaccine Efficacy

Some aspects of the present disclosure provide formulations of the RSV RNA (e.g., mRNA) vaccine, wherein the RSV RNA vaccine is formulated in an effective amount to produce an antigen specific immune response in a subject (e.g., production of antibodies specific to an anti-RSV antigen). "An effective amount" is a dose of an RSV RNA (e.g., mRNA) vaccine effective to produce an antigen-specific immune response. Also provided herein are methods of inducing an antigen-specific immune response in a subject.

As used herein, an immune response to a composition (e.g., mRNA formulated with or without LNP) of the present disclosure is the development in a subject of a humoral and/or a cellular immune response to a (one or more) RSV protein(s) present in the composition. For purposes of the present disclosure, a "humoral" immune response refers to an immune response mediated by antibody molecules, including, e.g., secretory (IgA) or IgG molecules, while a "cellular" immune response is one mediated by T-lymphocytes (e.g., CD4+ helper and/or CD8+ T cells (e.g., CTLs) and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the destruction of intracellular microbes or the lysis of cells infected with such microbes. Another aspect of cellular immunity involves and antigen-specific response by helper T-cells. Helper T-cells act to help stimulate the function, and focus the activity nonspecific effector cells against cells displaying peptide antigens in association with MHC molecules on their surface. A cellular immune response also leads to the production of cytokines, chemokines, and other such molecules produced by activated T-cells and/or other white blood cells including those derived from CD4+ and CD8+ T-cells.

In some embodiments, the antigen-specific immune response is characterized by measuring an anti-RSV antigen antibody titer produced in a subject administered an RSV RNA (e.g., mRNA) vaccine as provided herein. An antibody titer is a measurement of the amount of antibodies within a subject, for example, antibodies that are specific to a particular antigen (e.g., an anti-RSV antigen) or epitope of an antigen. Antibody titer is typically expressed as the inverse of the greatest dilution that provides a positive result. Enzyme-linked inmmunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the RSV RNA (e.g., mRNA) vaccine.

In some embodiments, an anti-RSV antigen antibody titer produced in a subject is increased by at least 1 log relative to a control. For example, anti-RSV antigen antibody titer produced in a subject may be increased by at least 1.5, at least 2, at least 2.5, or at least 3 log relative to a control. In some embodiments, the anti-RSV antigen antibody titer produced in the subject is increased by 1, 1.5, 2, 2.5 or 3 log relative to a control. In some embodiments, the anti-RSV antigen antibody titer produced in the subject is increased by 1-3 log relative to a control. For example, the anti-RSV antigen antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-RSV antigen antibody titer produced in a subject is increased at least 2 times relative to a control. For example, the anti-RSV antigen antibody titer produced in a subject may be increased at least 3 times, at least 4 times, at least 5 times, at least 6 times, at least 7 times, at least 8 times, at least 9 times, or at least 10 times relative to a control. In some embodiments, the anti-RSV antigen antibody titer produced in the subject is increased 2, 3, 4, 5, 6, 7, 8, 9, or 10 times relative to a control. In some embodiments, the anti-RSV antigen antibody titer produced in a subject is increased 2-10 times relative to a control. For example, the anti-RSV antigen antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-RSV antigen antibody titer produced in a subject who has not been administered an RSV RNA (e.g., mRNA) vaccine. In some embodiments, a control is an anti-RSV antigen antibody titer produced in a subject administered a recombinant or purified RSV protein vaccine. Recombinant protein vaccines typically include protein antigens that either have been produced in a heterologous expression system (e.g., bacteria or yeast) or purified from large amounts of the pathogenic organism.

In some embodiments, the ability of an RSV vaccine to be effective is measured in a murine model. For example, the RSV vaccines may be administered to a murine model and the murine model assayed for induction of neutralizing antibody titers. Viral challenge studies may also be used to assess the efficacy of a vaccine of the present disclosure. For example, the RSV vaccines may be administered to a murine model, the murine model challenged with RSV, and the murine model assayed for survival and/or immune response (e.g., neutralizing antibody response).

In some embodiments, the ability of an RSV vaccine to be effective is measured in a non-human primate (e.g., African green monkey) model. For example, the RSV vaccines may be administered to a non-human primate model and the murine model assayed for induction of neutralizing antibody titers. Viral challenge studies may also be used to assess the efficacy of a vaccine of the present disclosure. For example, the RSV vaccines may be administered to a non-human primate model, the non-human primate model challenged with RSV, and the non-human primate model assayed for survival and/or immune response (e.g., neutralizing antibody response).

In some embodiments, an effective amount of an RSV RNA (e.g., mRNA) vaccine is a dose that is reduced compared to the standard of care dose of a recombinant RSV protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified RSV protein vaccine, or a live attenuated or inactivated RSV vaccine, or an RSV VLP vaccine, that a physician/clinician or other medical professional would administer to a subject to treat or prevent RSV, or an RSV-related condition, while following the standard of care guideline for treating or preventing RSV, or an RSV-related condition.

In some embodiments, the anti-RSV antigen antibody titer produced in a subject administered an effective amount of an RSV RNA vaccine is equivalent to an anti-RSV antigen antibody titer produced in a control subject administered a standard of care dose of a recombinant or purified RSV protein vaccine, or a live attenuated or inactivated RSV vaccine, or an RSV VLP vaccine.

In some embodiments, an effective amount of an RSV RNA (e.g., mRNA) vaccine is a dose equivalent to an at least 2-fold reduction in a standard of care dose of a recombinant or purified RSV protein vaccine. For example, an effective amount of an RSV RNA vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified RSV protein vaccine. In some embodiments, an effective amount of an RSV RNA vaccine is a dose equivalent to an at least 100-fold, at least 500-fold, or at least 1000-fold reduction in a standard of care dose of a recombinant or purified RSV protein vaccine. In some embodiments, an effective amount of an RSV RNA vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified RSV protein vaccine. In some embodiments, the anti-RSV antigen antibody titer produced in a subject administered an effective amount of an RSV RNA vaccine is equivalent to an anti-RSV antigen antibody titer produced in a control subject administered the standard of care dose of a recombinant or protein RSV protein vaccine, or a live attenuated or inactivated RSV vaccine, or an RSV VLP vaccine. In some embodiments, an effective amount of an RSV RNA (e.g., mRNA) vaccine is a dose equivalent to a 2-fold to 1000-fold (e.g., 2-fold to 100-fold, 10-fold to 1000-fold) reduction in the standard of care dose of a recombinant or purified RSV protein vaccine, wherein the anti-RSV antigen antibody titer produced in the subject is equivalent to an anti-RSV antigen antibody titer produced in a control subject administered the standard of care dose of a recombinant or purified RSV protein vaccine, or a live attenuated or inactivated RSV vaccine, or an RSV VLP vaccine.

In some embodiments, the effective amount of an RSV RNA (e.g., mRNA) vaccine is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 3 to 0-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 60-, 4 to 500-, 4 to 400-, 4 to 300-, 4 to 200-, 4 to 100-, 4 to 90-, 4 to 80-, 4 to 70-, 4 to 60-, 4 to 50, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, 30 to 200-, 30 to 100-, 30 to 90-, 30 to 80-, 30 to 70-, 30 to 60-, 30 to 50-, 30 to 40-, 40 to 1000-, 40 to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 30, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900 to 1000-fold reduction in the standard of care dose of a recombinant RSV protein vaccine. In some embodiments, such as the foregoing, the anti-RSV antigen antibody titer produced in the subject is equivalent to an anti-RSV antigen antibody titer produced in a control subject administered the standard of care dose of a recombinant or purified RSV protein vaccine, or a live attenuated or inactivated RSV vaccine, or an RSV VLP vaccine. In some embodiments, the effective amount is a dose equivalent to (or equivalent to an at least) 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 1280-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 460-, 470-, 480-, 490-, 500-, 510-, 520-, 530-, 540-, 550-, 560-, 5760-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820-, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant RSV protein vaccine. In some embodiments, such as the foregoing, an anti-RSV antigen antibody titer produced in the subject is equivalent to an anti-RSV antigen antibody titer produced in a control subject administered the standard of care dose of a recombinant or purified RSV protein vaccine, or a live attenuated or inactivated RSV vaccine, or an RSV VLP vaccine.

In some embodiments, the effective amount of an RSV RNA (e.g., mRNA) vaccine is a total dose of 50-1000 μg. In some embodiments, the effective amount of an RSV RNA (e.g., mRNA) vaccine is a total dose of 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-900, 600-700, 700-1000, 700-900, 700-800, 800-1000, 800-900, or 900-1000 μg. In some embodiments, the effective amount of an RSV RNA (e.g., mRNA) vaccine is a total dose of 50, 100, 150, 200, 250, 300, 350, 400, 450, 500, 550, 600, 650, 700, 750, 800, 850, 900, 950 or 1000 sg. In some embodiments, the effective amount is a dose of 25-500 μg administered to the subject a total of two times. In some embodiments, the effective amount of an RSV RNA (e.g., mRNA) vaccine is a dose of 25-500, 25-400, 25-300, 25-200, 25-100, 25-50, 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, 250-300, 300-500, 300-400, 350-500, 350-400, 400-500 or 450-500 μg administered to the subject a total of two times. In some embodiments, the effective amount of an RSV RNA (e.g., mRNA) vaccine is a total dose of 25, 50, 100, 150, 200, 250, 300, 350, 400, 450, or 500 μg administered to the subject a total of two times.

Vaccine efficacy may be assessed using standard analyses (see, e.g., Weinberg et al., J Infect Dis. 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy} = (ARU - ARV)/ARU \times 100;$$

and $$\text{Efficacy} = (1 - RR) \times 100.$$

Likewise, vaccine effectiveness may be assessed using standard analyses (see, e.g., Weinberg et al., J Infect Dis. 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

$$\text{Effectiveness} = (1 - OR) \times 100.$$

In some embodiments, efficacy of the RSV vaccine is at least 60% relative to unvaccinated control subjects. For example, efficacy of the RSV vaccine may be at least 65%, at least 70%, at least 75%, at least 80%, at least 85%, at least 95%, at least 98%, or 100% relative to unvaccinated control subjects.

Sterilizing Immunity. Sterilizing immunity refers to a unique immune status that prevents effective pathogen infection into the host. In some embodiments, the effective amount of an RSV vaccine of the present disclosure is sufficient to provide sterilizing immunity in the subject for at least 1 year. For example, the effective amount of an RSV vaccine of the present disclosure is sufficient to provide sterilizing immunity in the subject for at least 2 years, at least 3 years, at least 4 years, or at least 5 years. In some embodiments, the effective amount of an RSV vaccine of the present disclosure is sufficient to provide sterilizing immunity in the subject at an at least 5-fold lower dose relative to control. For example, the effective amount may be sufficient to provide sterilizing immunity in the subject at an at least 10-fold lower, 15-fold, or 20-fold lower dose relative to a control.

Detectable Antigen. In some embodiments, the effective amount of an RSV vaccine of the present disclosure is sufficient to produce detectable levels of RSV antigen as measured in serum of the subject at 1-72 hours post administration.

Titer. An antibody liter is a measurement of the amount of antibodies within a subject, for example, antibodies that are specific to a particular antigen (e.g., an anti-RSV antigen). Antibody titer is typically expressed as the inverse of the greatest dilution that provides a positive result. Enzyme-linked immunosorbent assay (ELISA) is a common assay for determining antibody titers, for example.

In some embodiments, the effective amount of an RSV vaccine of the present disclosure is sufficient to produce a 1.000-10,000 neutralizing antibody titer produced by neutralizing antibody against the RSV antigen as measured in serum of the subject at 1-72 hours post administration. In some embodiments, the effective amount is sufficient to produce a 1.000-5,000 neutralizing antibody titer produced by neutralizing antibody against the RSV antigen as measured in serum of the subject at 1-72 hours post administration. In some embodiments, the effective amount is sufficient to produce a 5,000-10,000 neutralizing antibody titer produced by neutralizing antibody against the RSV antigen as measured in serum of the subject at 1-72 hours post administration.

In some embodiments, the neutralizing antibody titer is at least 100 $NT_{50}$. For example, the neutralizing antibody titer may be at least 200, 300, 400, 500, 600, 700, 800, 900 or 1000 $NT_{50}$. In some embodiments, the neutralizing antibody titer is at least 10,000 $NT_{50}$.

In some embodiments, the neutralizing antibody titer is at least 100 neutralizing units per milliliter (NU/mL). For example, the neutralizing antibody titer may be at least 200, 300, 400, 500, 600, 700, 800, 900 or 1000 NU/mL. In some embodiments, the neutralizing antibody titer is at least 10,000 NU/mL.

In some embodiments, an anti-RSV antigen antibody titer produced in the subject is increased by at least 1 log relative to a control. For example, an anti-RSV antigen antibody titer produced in the subject may be increased by at least 2, 3, 4, 5, 6, 7, 8, 9 or 10 log relative to a control.

In some embodiments, an anti-RSV antigen antibody titer produced in the subject is increased at least 2 times relative to a control. For example, an anti-RSV antigen antibody titer produced in the subject is increased by at least 3, 4, 5, 6, 7, 8, 9 or 10 times relative to a control.

In some embodiments, a geometric mean, which is the nth root of the product of n numbers, is generally used to describe proportional growth. Geometric mean, in some embodiments, is used to characterize antibody titer produced in a subject.

A control may be, for example, an unvaccinated subject, or a subject administered a live attenuated RSV vaccine, an inactivated RSV vaccine, or a protein subunit RSV vaccine.

EXAMPLES

Example 1: Cotton Rat Immunogenicity and Efficacy

In this example, assays were carried out to test the immunogenicity and efficacy of mRNA/LNP vaccines in the cotton rat RSV challenge model. More specifically, female *Signiodon hispidus* cotton rats were used and immunizations began at 6-7 weeks of age. The mRNA vaccines used were generated and formulated in lipid nanoparticles (e.g the LNP comprises 58 mole % (13Z,16Z)—N,N-dimethyl-2-nonylhenicosa-12,15-dien-1-amine, 30 mole % cholesterol, 10 mole % DSPC, and 2 mole % PEG-2000 DMG). The mRNA vaccines evaluated in this study included:

MRK-04 membrane-bound DS-Cav1 (stabilized prefusion F protein) (SEQ ID NO: 90)

MRK-04_nopolyA_3mut membrane-bound DS-Cav1 (stabilized prefusion F protein) (SEQ ID NO: 92)

mVRC-1 (v2) membrane-bound single chain sc9 mDS-Cav1, A149C. Y458C (stabilized prefusion F protein) (SEQ ID NO: 21)

mLZF-111 membrane-bound single chain mDS-Cav1, D486C, D489C (stabilized prefusion F protein) (SEQ ID NO: 74)

Groups of 8 cotton rats were immunized intramuscularly with 100 μL of vaccine, delivered with 50 μL injections into each quadriceps. The groups were vaccinated with the following vaccines:

TABLE 1

Vaccine Formulations Tested for Cotton Rats

| Group | Vaccine | SEQ ID NO: | Conc (μg/ml) | Dose (μg) |
|---|---|---|---|---|
| 1 | None | n/a | NA | NA |
| 2 | MRK-04, I.M. | 90 | 250 | 25 |
| 3 | MRK-04_nopolyA_3mut, I.M. | 92 | 250 | 25 |
| 4 | MRK-04_nopolyA_3mut, I.M. | 92 | 50 | 5 |
| 5 | MRK-04_nopolyA_3mut, I.M.. | 92 | 10 | 1 |
| 6 | mVRC-1 (v2), L.M. | 21 | 250 | 25 |
| 7 | mVRC-1 (v2), I.M. | 21 | 50 | 5 |
| 8 | mVRC-1 (v2), I.M. | 21 | 10 | 1 |
| 9 | mLZF-111, I.M. | 74 | 250 | 25 |
| 10 | mLZF-111, I.M. | 74 | 50 | 5 |
| 11 | mLZF-111, I.M. | 74 | 10 | 1 |

The animals were immunized on day 0 and day 28 of the experiment. On days 28 and 56, blood was drawn from each animal and used for serological assays. On day 56, the cotton rats were challenged intranasally with $1\times10^{5.5}$ PFU RSV A2. Four days post inoculation animals were sacrificed by $CO_2$ inhalation and lung (left lobes) and nasal turbinates were removed and homogenized in 10 volumes of Hanks Balanced Salt Solution (Lonza) containing SPG on wet ice. The samples were clarified by centrifugation at 2000 rpm for 10 minutes, aliquoted, flash frozen, and immediately stored frozen at −70° C.

A. RSV Neutralization Assay:

Cotton rat sera from each animal was evaluated for neutralization of RSV-A (Long strain) using the following procedures:

1. All sera samples were heat inactivated by placing in dry bath incubator set at 56° C., for 30 minutes. Samples and control sera were then diluted 1:3 in virus diluent (2% FBS in EMEM) and duplicate samples were added to an assay plate and serially diluted.

2. RSV-Long stock virus was removed from the freezer and quickly thawed in 37° C., water bath. Viruses were diluted to 2000 pfu/mL in virus diluent.

3. 50 μL of diluted virus was added to each well of the 96-well plate, with the exception of one column of cells, which used as a "no-virus" control 4. HEp-2 cells were trypsinized, washed, resuspended at $1.5\times10^5$ cells/ml in virus diluent, and 100 mL of the suspended cells were added to each well of the 96-well plate. The plates were then incubated for 72 hours at 37° C., 5% $CO_2$.

5. Following the 72 hour incubation, the cells were washed with PBS, and fixed using 80% acetone dissolved in PBS for 10-20 minutes at 16-24° C. The fixative was removed and the plates were allowed to air-dry.

6. Plates were then washed thoroughly with PBS+0.05% Tween™ (polysorbate). The detections monoclonal antibodies, 143-F3-1B8 and 34C9 were diluted to 2.5 μg/mL in assay diluent (1% BSA-PBS-0.1% Tween), and 50 μL of the diluted antibodies were added to each well of the 96-well plate. The plates were then incubated in a humid chamber at 16-24° C., for 60-75 minutes on rocker.

7. Following the incubation, the plates were thoroughly washed.

8. Biotinylated horse anti-mouse IgG was diluted 1:200 in assay diluent and added to each well of the 96-well plate. Plates were incubated as above and washed.

9. A cocktail of IRDyc 800CW Streptavidin (1:1000 final dilution), Sapphire 700 (1:1000 dilution) and 5 mM DRAQ5 solution (1:10,000 dilution) was prepared in assay diluent and 50 mL of the cocktail was added to each well of the 96-well plate. Plates were incubated as above in the dark, washed, and allowed to air dry.

10. Plates were then read using an Aerius Imager. Serum neutralizing titers were then calculated using a 4 parameter curve fit in Graphpad Prism.

The titers determined post dose 1 (day 28) and post dose 2 (day 56) are shown in FIG. 1. It was found that the neutralizing titers were elicited in a dose dependent manner for all mRNA vaccines. All mRNA vaccines resulted in increased titers after a second dose regardless of the dose evaluated. Both mVRC-1 (v2) and mLVF 111 induced higher titers then MRK-04 and MRK-04_nopolyA_3mut demonstrating superior or similar serum neutralizing titers at a 5-fold lower dose.

B. Competition alphaLISA:

The immune response to specific epitopes on RSV F-protein for neutralizing antibodies was characterized. The antigenic site II is the binding site for palivizumab, a monoclonal antibody developed for the prevention of lower respiratory infection with RSV in at risk infants and toddlers. Antigenic site Ø is a binding site for more potent neutralizing antibodies that are elicited by natural infection with RSV. Additionally, we have generated an antibody (4D7) that targets site I, an epitope not presented in the prefusion conformation. Therefore, in contrast to D25, elicitation of 4D7-competing antibodies would suggest the in vivo generation of postF-like proteins. A competition alphaLISA was developed to characterize the antigenic site Ø, antigenic site I and antigenic site II response to the various mRNA-based vaccines.

To measure competing antibody titers, 10 μl of samples serially diluted in HiBlock buffer (PerkinElmer) are placed in a 384 well alphaLiSA plate. Diluted samples are mixed with 5 μl of AlphaLISA acceptor beads (100 μg/ml) that has been previously conjugated to a prefusion-stabilized RSV F protein (DS-Cav1) or a postfusion RSV F protein (RSV F wt). After 30 min incubation at room temperature, 10 μl of biotinylated D25, palimizumab, or 4D7 antibody diluted in Hiblock buffer is added to every well. After additional 30 min incubation, 25 μl of streptavidin-donor beads (20 μg/ml) in HiBlock buffer is added to each well and incubated for 30 min in the dark. Plate is then read on an EnVision_Alpha Reader (615 nm detection).

Figure 2:
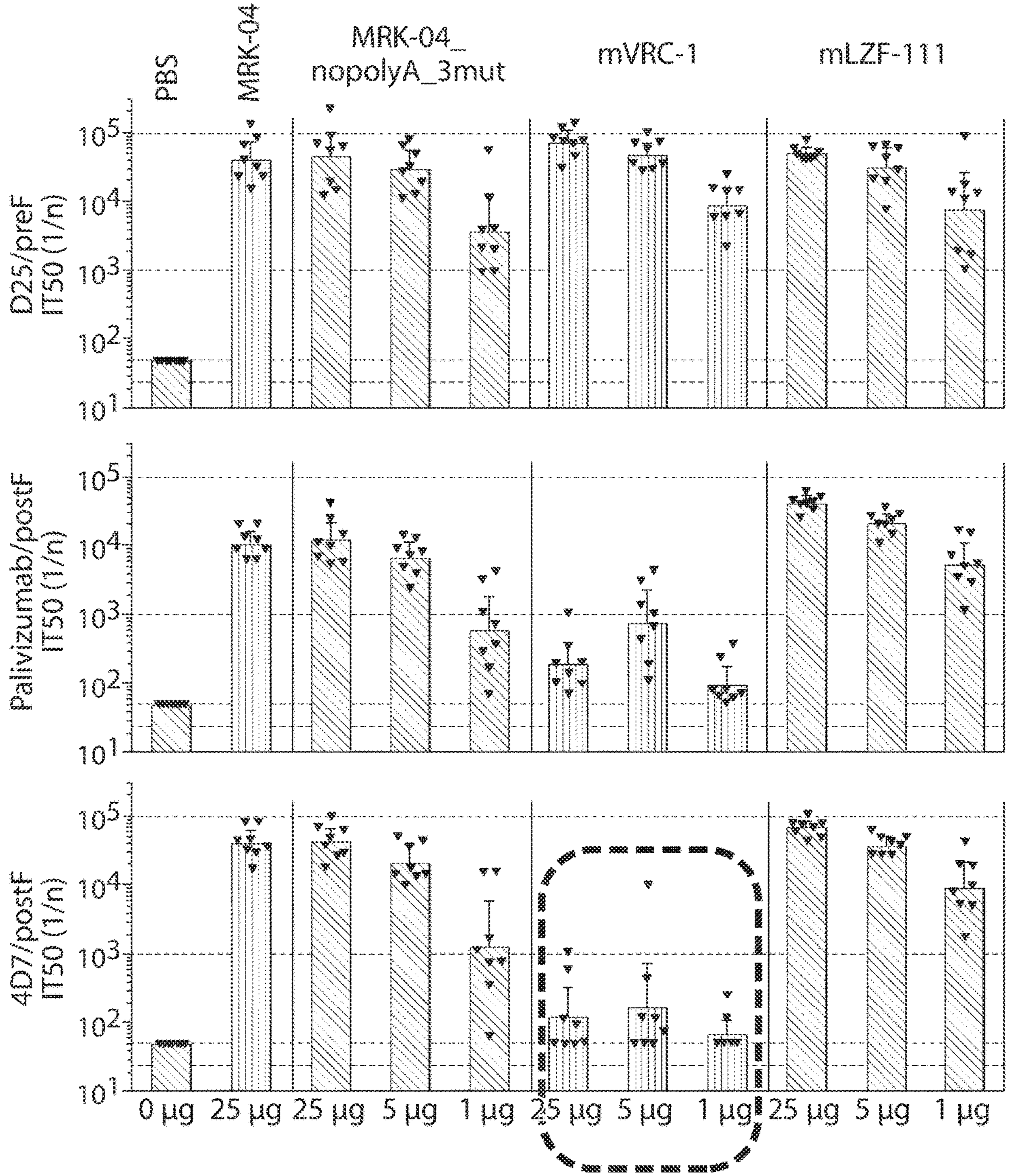
FIG. 2 shows a graph of serum antibody competition ELISA Titers ($IT_{50}$ Individual and GMT with 95% confidence intervals) against D25 (site Ø), palivizumab (site II), and 4D7 (site 1) measured at Day 56 (4 weeks PD2).

The palivizumab, D25 and 4D7 competing antibody titers measured on Day 56 (4 weeks PD2) are presented in FIG. 2. The competition data revealed that mVRC-1 (v2) induced lower levels of 4D7-postfusion F competing antibodies, while D25-prefusion titers and palivizumab titers are not affected. This different competition profile correlates with mVRC-1 (v2) mRNA expressing a more prefusion stabilized protein then MRK-04_nopolyA_3mut and mLZF-111.

C. Cotton Rat Challenge Results

Procedures for measuring RSV titers in the cotton rat Lung and nose homogenates are described below. Lung and nose homogenates were clarified by centrifugation and diluted 1:10 and 1:100 in EMEM. Confluent HEp-2 monolayers were infected in duplicates with 50 μl per well starting with undiluted (neat) samples followed by diluted homogenates in 24-well plates. After one hour incubation at 37° C., in a 5% $CO_2$ incubator, wells were overlaid with 0.75% methylcellulose medium and plates restored into the 37° C., incubator. After 4 days of incubation the overlay was removed and the cells were fixed with 0.1% crystal violet stain for one hour, then rinsed, and air-dried. Plaques were counted and virus titers were expressed as plaque forming units per gram of tissue.

Figure 3:
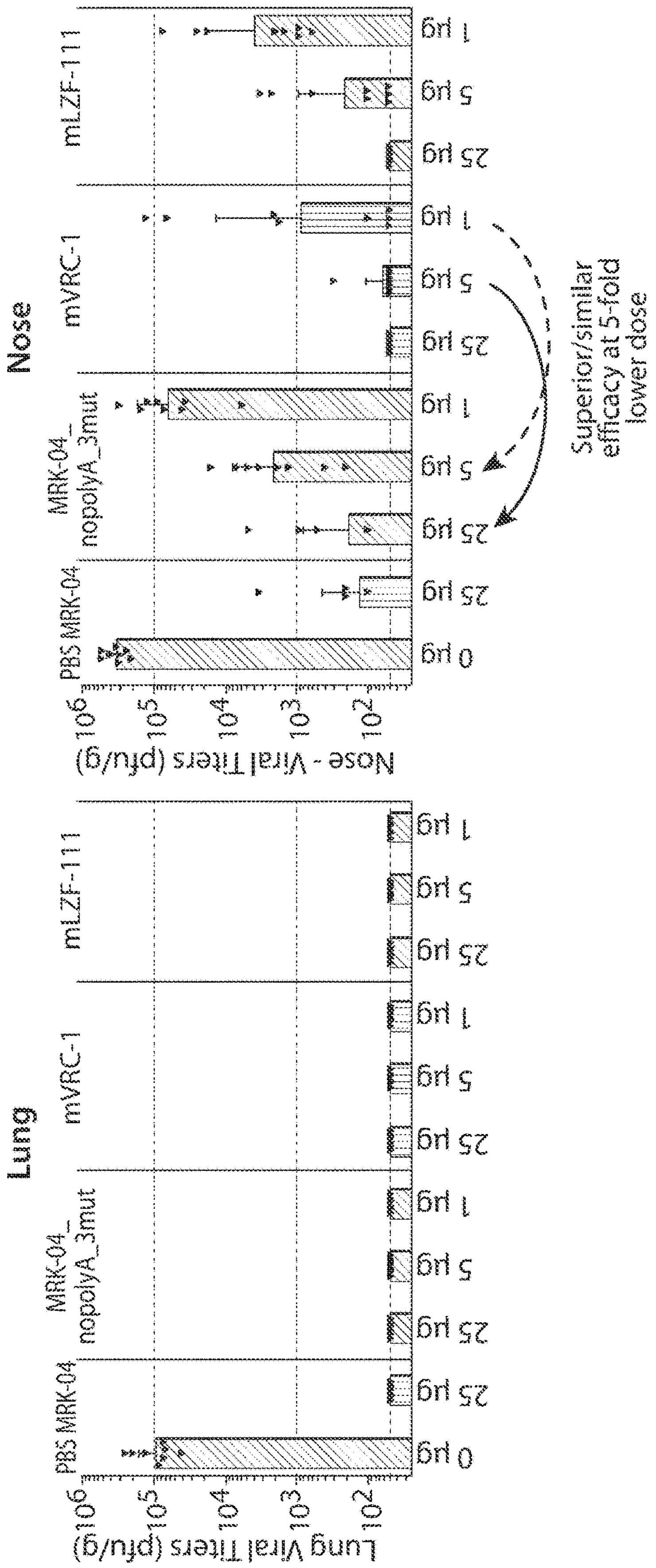
FIG. 3 shows graphs of RSV content in lung and nose after challenge of cotton rats with RSV A.

To assess vaccine-mediated protection, viral titers were measured in lung and nose 5 days after challenge. All mRNA vaccines achieved total protection in the lung, but mVRC-1 (v2) and mLZF-111 showed improved protection in the nose, demonstrating superior or similar efficacy to MRK-04 and MRK-04_nopolyA_3mut, at a 5-fold lower dose (FIG. 3).

Example 2: African Green Monkey Immunogenicity and Efficacy

In this example, assays were carried out to test the immunogenicity and efficacy of mRNA/LNP vaccines in the African Green Monkey RSV challenge model.

More specifically, male and female adult African Green Monkeys with body weights ranging from 1.6 to 2.65 kg, which were confirmed to be RSV-negative by neutralizing antibody titer, were used. The mRNA vaccines used were generated and formulated in lipid nanoparticles (e.g the LNP comprises 58 mole % (13Z,16Z)—N,N-dimethyl-2-nonylhenicosa-12,15-dien-1-amine, 30 mole % cholesterol, 10 mole % DSPC, and 2 mole % PEG-2000 DMG). The mRNA vaccines evaluated in this study included:

MRK-04_nopolyA_3mut membrane-bound DS-Cav1 (stabilized prefusion F protein) (SEQ ID NO: 92)

mVRC-1 (v2) membrane-bound single chain sc9 mDS-Cav1, A149C, Y458C (stabilized prefusion F protein) (SEQ ID NO: 21)

mLZF-111 membrane-bound single chain mDS-Cav1, D486C, D489C (stabilized prefusion F protein) (SEQ ID NO: 74)

Groups of 4 African Green Monkeys were immunized intramuscularly with 500 μL of vaccine into one deltoid. The groups were vaccinated with the following vaccines as out in

TABLE 2

Vaccine Formulations Tested for Immunogenicity in African Green Monkeys

| Group | Vaccine | Conc (μg/ml) | Dose (μg) |
|---|---|---|---|
| 1 | MRK-04_nopolyA_3mut, I.M. | 50 | 25 |
| 2 | MRK-04_nopolyA_3mut, I.M. | 10 | 5 |
| 3 | mVRC-1 (v2) | 50 | 25 |
| 4 | mVRC-1 (v2) | 10 | 5 |
| 5 | mLZF-111 | 50 | 25 |
| 6 | mLZF-111 | 10 | 5 |
| 7 | RSV A2 5.5log10pfu, I.N. | NA | NA |
| 8 | None | NA | NA |

The animals were immunized on day 0, day 28, and day 56 of the experiment. On days 0, 14, 28, 42, 56, and 70, blood was drawn from each animal and used for serological assays. On day 70, the African Green Monkeys were challenged intranasally with $1\times10^{5.5}$ PFU RSV A2. Nasopharyngeal swabs were collected on days 1-14 post challenge, and lung lavage samples were collected on days 3, 5, 7, 9, 12 and 14 post challenge to test for viral replication.

A. RSV Neutralization Assay:

Monkey sera from each animal were evaluated for neutralization of RSV-A (Long strain) as described above. The $NT_{50}$ titers determined post dose 1 and post dose 2 are shown in FIG. 4. Titers were seen to increase after each dose all groups receiving mRNA vaccines. The GMTs obtained with mRNA vaccines at week 10 (2 weeks post-dose 3) were 1 to 2 orders of magnitude higher than in the animals that received RSV A2 depending on the dose and mRNA being tested. Serum samples from mVRC-1 (v2) immunized animals exhibited the highest neutralization titers, demonstrating a five-fold higher potency relative to MRK-04_nopolyA_3mut.

B. Competition ELISA

Competition ELISA titers were determined for palivizumab, D25 and 4D7 to characterize the antigenic site Ø, antigenic site I and antigenic site II response to the various mRNA-based vaccines as described above.

Figure 5:
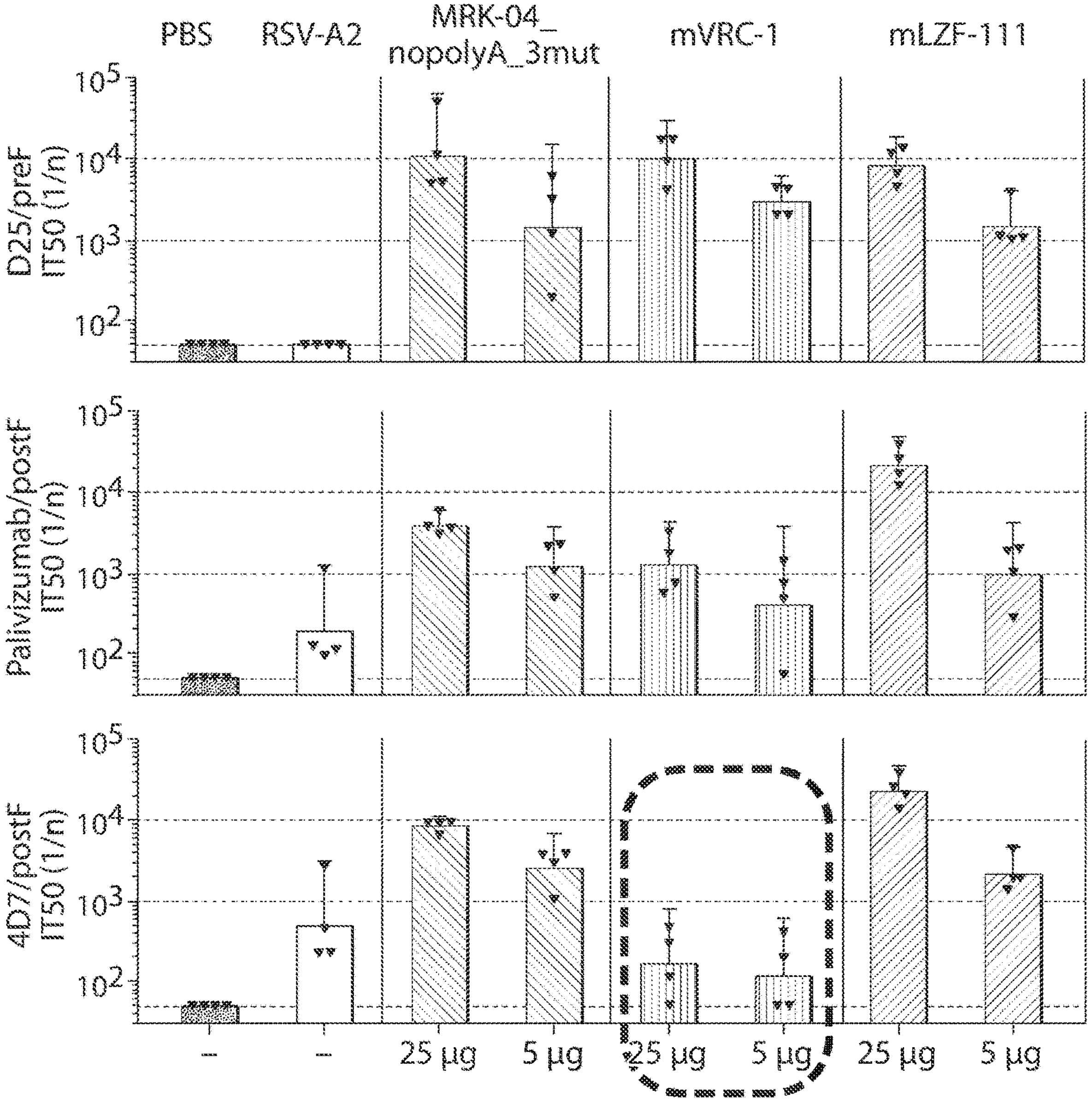
FIG. 5 shows serum antibody competition ELISA titers ($IT_{50}$, Individual and GMT with 95% confidence intervals) against D25 (site Ø), palivizumab (site II), and 4D7 (site I) measured at week 10 (2 weeks PD3).

The palivizumab, D25 and 4D7 competing antibody titers measured at week 10 (2 weeks PD3) are presented in FIG. 5. The competition data revealed that mVRC-1 (v2) induced lower levels of 4D7-postfusion F competing antibodies, while D25-prefusion titers and palivizumab titers are not affected. This different competition profile correlates with mVRC-1 (v2) mRNA expressing a more prefusion stabilized protein then MRK-04_nopolyA_3mut and mLZF-111.

C. African Green Monkey Challenge Results

As mentioned above, in order to evaluate vaccine efficacy African Green Monkeys were challenged intranasally with $1\times10^{5.5}$ PFU RSV A2 on day 70 post vaccination and nasopharyngeal swabs and lung lavage samples were collected post challenge to test for the presence of virus.

Figure 6A:
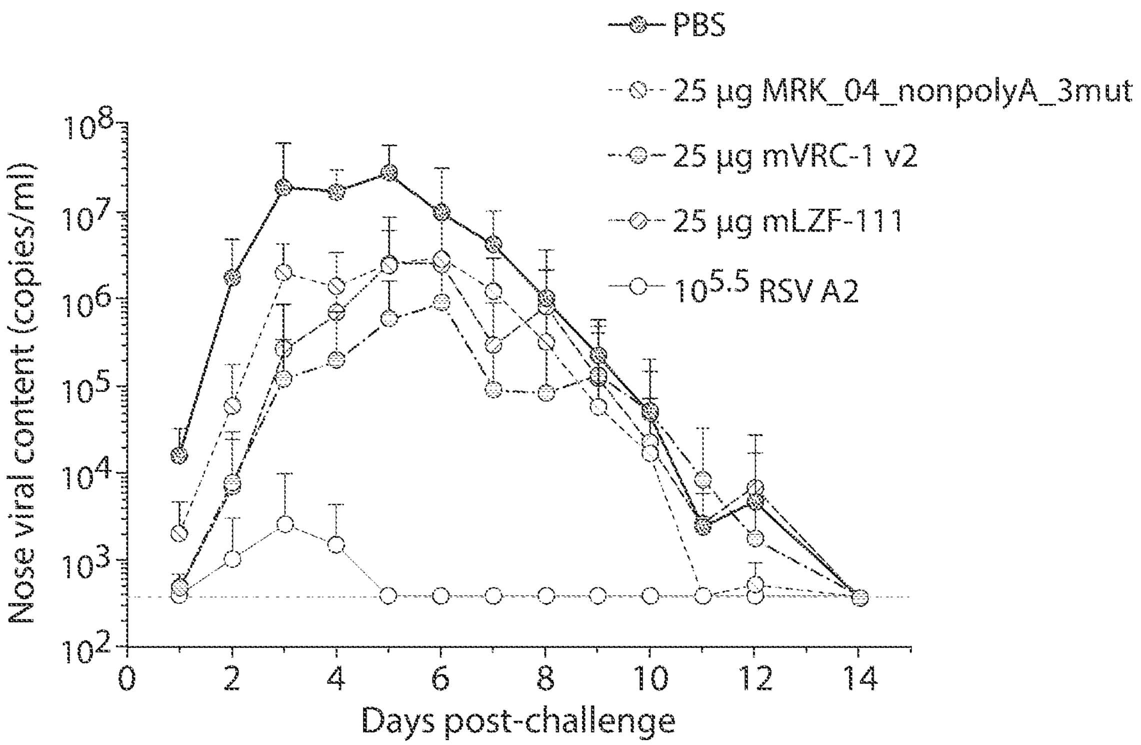
FIGS. 6A-6C shows RSV content in bronchoalveolar (BAL) fluid after challenge of AGMs
Figure 6B:
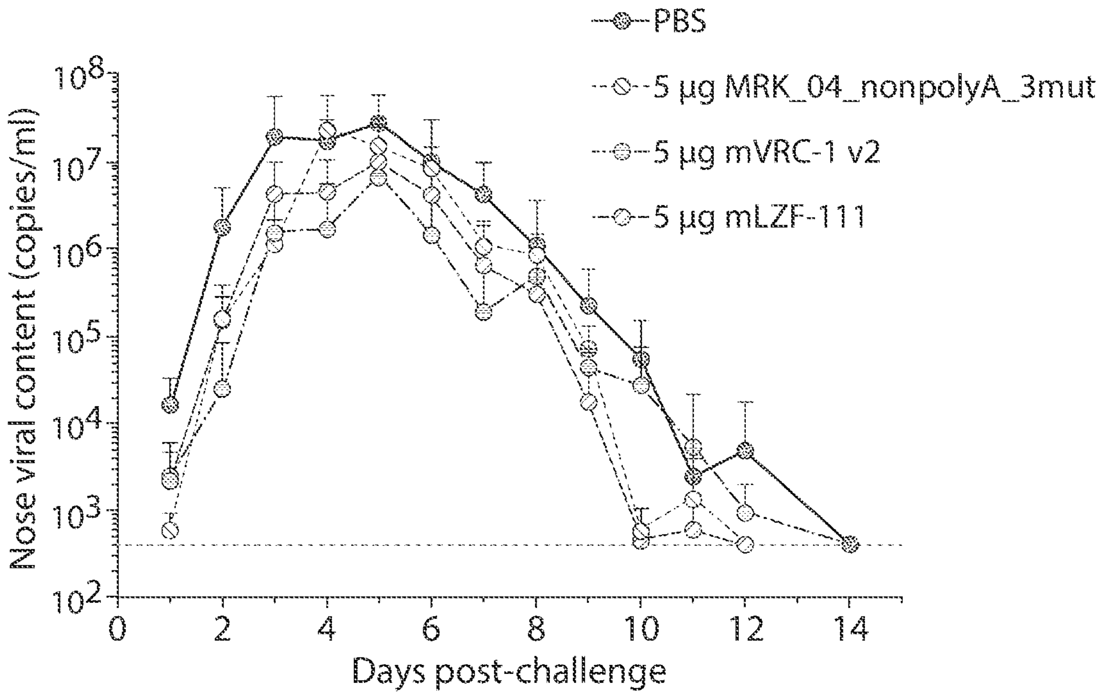
Figure 6C:
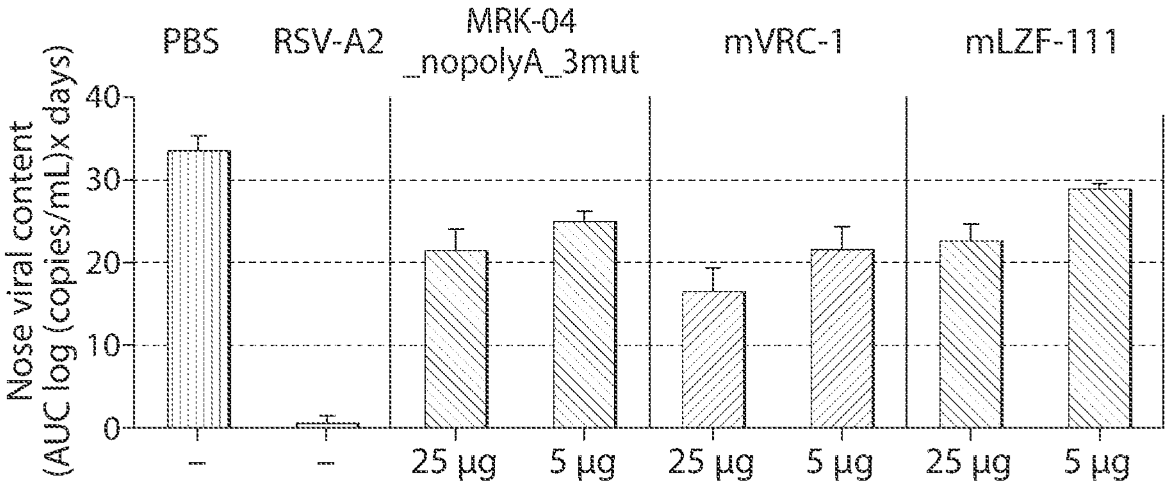

In order to measure RSV titers in the African Green Monkey lung lavage samples a viral plaque assay procedure for measuring viral titers was followed as outlined below. Briefly, samples were diluted and added in duplicate to 24-well plates containing confluent HEp-2 cell monolayers. The plates were incubated at 37° C., for one hour. Following the one hour incubation, sample inoculum was aspirated and 1 ml of overlay containing 0.75% methylcellulose was added. The plates were incubated at 37° C., for 5 days. Following the 5 day incubation, the cells were fixed and stained with crystal violet/glutaraldehyde solution. Plaques were counted and titers were expressed as pfu/ml. Analysis of viral content in bronchoalveolar lavage (BAL) fluid (FIGS. 6A-6C) revealed that only mVRC-1 (v2) (25 μg) conferred total protection in the lung, and it afforded the best protection at a lower dose (5 μg).

In order to measure RSV titers in the African Green Monkey nasopharyngeal swabs an RSV RT-qPCR assay to detect RSV A was carried out as follows:

1) Equipment and Materials:

A. Equipment

1. Stratagene Mx3005P Real Time PCR system and MxPro Software
2. Jouan GR422 centrifuge or equivalent
3. Jouan Plate carriers or equivalent B. Reagents 1. Quantitect® Probe Rt-PCR kit (1000) catalog #204445
2. Water. Molecular Biology Grade DNAase-free and Protease free. 5 Prime, catalog #2900136
3. TE buffer, 10 mM Tris 1 mM EDTA ph 8.0. Fisher Bioreagents, catalog #BP2473-100
4. Viral primers: RSV A Forward and Reverse primers. Sigma custom, HPLC purified. Primer stocks are reconstituted to 100 uM in Molecular grade water and stored at −20° C.
5. RSV dual labeled probe. Sigma custom, HPLC purified. Probe stocks are reconstituted to 100 uM in TE buffer and stored at −20° C., protected from light.
6. RSV A standard were generated in-house and stored at −20° C. Standards for the assay were generated by designing primer pairs to the N gene of RSV A. The product length for the RSV A standard is 885 bp. QIAGEN OneStep RT-PCR was used to generate this standard.

TABLE 3

| Primer Sequences | |
|---|---|
| Primers | Sequences |
| RSV A FN gene | 5' CTC AAT TTC CTC ACT TCT CCA GTG T (SEQ ID NO: 93) |
| RSV A R N gene | 5' CTT GAT TCC TCG GTG TAC CTC TGT (SEQ ID NO: 94) |
| RSV A FAM N gene | 5'FAM-TCC CAT TAT GCC TAG GCC AGC AGC A (BHQ1) (SEQ ID NO: 95) |

7. Promega, Maxwell® 16 Viral Total Nucleic Acid Purification Kit (Product #AS1150

C. Supplies
1. Stratagene Optical cap 8× strip, catalog #401425
2. Stratagene Mx3000P 96 well plates, skirted, catalog #401334
3. ART filtered pipet tips 2) RT-PCR Reactions and set up A. Preparation of Complete Master Mix
1. Prepare complete Master Mix following the set up below for a final reaction volume of 50 μL. The following table is volume per well. Final primer concentration is 300 nM and final probe concentration is 200 nM.

TABLE 4

| Reagents | |
|---|---|
| Reagent | μL |
| 2X Master Mix | 25 |
| RSV A F 100 uM | 0.2 |
| RSV A R 100 uM | 0.2 |
| RSV A FAM 100 uM | 0.1 |
| RT enzyme mix | 0.5 |
| Water | 19 |

2. Add 45 μL of complete master mix to each well. Cover plate with plate cover and wrap in aluminum foil to protect from light.

B. Preparation of Standard curve
1. Remove standard from −20° C.
2. Dilute standards to final concentrations of 1e6 copy/5 μL to 1copy/5 μL using 10-fold dilutions.

C. Sample Preparation
1. Nasopharyngeal swab and lung lavage samples are prepared for the RT-PCR reaction using the Maxwell® 16 Viral Total Nucleic Acid Purification Kit (Promega, product #AS1150)
2. 200 μL of sample is extracted following the manufactures protocol and eluted into 50 μL to be used in PCR reactions.

D. Additions of Samples
1. Add 5 μL of extracted samples to appropriate wells. After addition of samples, carefully cap sample wells before adding standard curves.
2. Add 5 μL of diluted standard to appropriate wells and cap.
3. Add 5 μL of molecular grade water to No Template Control (NTC) wells.
4. Wrap plates in aluminum foil and transfer plates to centrifuge.
5. Spin plates for 2 mins at 100 rpm to pull down any samples or master mix that may be on the sides of well.
6. Wrap plates in aluminum foil and transfer to Stratagene instrument.

E. Thermo cycler. Stratagene MX 3005P
1. Place plates in Stratagene Mx3005P and set thermal profile conditions to:

TABLE 5

| PCR Conditions | | |
|---|---|---|
| Step | Time | Temperature |
| Reverse Transcription | 30 min | 50 |
| PCR intial activation step | 15 min | 95 |
| 2-step cycling: | | |
| Denaturation | 16 sec | 94 |
| Combined annealing/extension | 60 sec | 62 |
| Number of cycles | 40 | |

2. Analyze results using the Stratagene Mx3005p software

Figure 7:
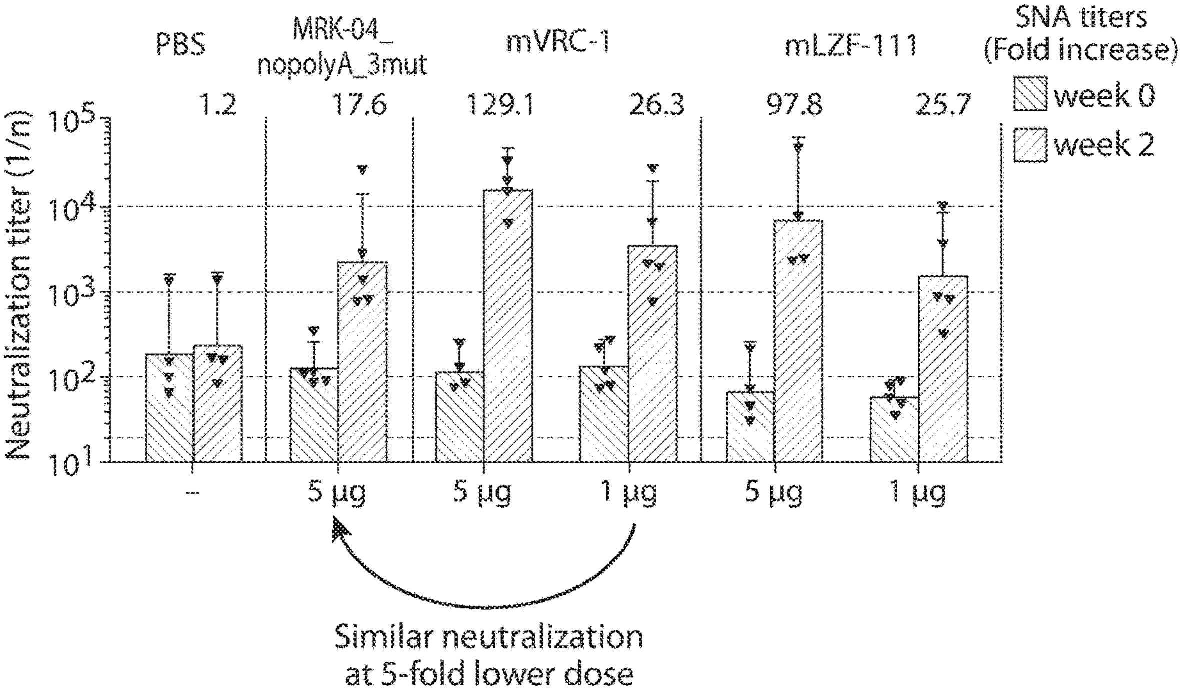
FIG. 7 shows serum neutralizing antibody titers ($NT_{50}$, Individual and GMT with 95% confidence intervals) to RSV A induced in RSV experienced African green monkeys by mRNA vaccines and control formulations.

The mean RNA copy number detected in the nose samples are presented in FIG. 7. The protective effect of all mRNA-based vaccines was less apparent in the nose, but again mVRC-1 (v2) demonstrated a 5-fold higher efficacy over MRK-04_nopolyA_3mut, mLZF-111 demonstrated decreased protection efficacy in lung and nose of AGMs relative to MRK-04_nopolyA_3mut.

Example 3: Immunogenicity in RSV-Experienced African Green Monkeys

The immunogenicity of mRNA vaccines formulated in LNP was tested in RSV-experienced African Green Monkeys.

Healthy adult, African Green Monkeys of either sex (n=4 or 5/group), with body weights ranging from 2.85 to 4.65 kg, that were confirmed to be RSV seropositive by ELISA and neutralizing antibody titers, were selected for the study. The pool of animals selected for this study had been experimentally infected with RSV in previous vaccine studies and were distributed across study groups based on their pre study RSV neutralization titers so that all groups would have similar group GMTs at study start. RSV experienced animals provide a model of immune memory recall response to vaccination that may reflect the responses that can be anticipated in seropositive human adults, with the caveat that the antibody response in AGMs following RSV exposure is more biased towards postfusion F protein epitopes than the human immune repertoire.

A single vaccine dose was administered to each animal at week 0 by the intramuscular (IM) route. A control group receiving only PBS was also included in the study design. Vaccines were administered as described in Table 6. After vaccination, the animals were observed daily for any changes at the inoculation site or other changes in activity or feeding habits that might indicate an adverse reaction to the vaccine but none were noted. Serum samples were collected for assessment of RSV neutralizing antibody titers, as well as palivizumab (site II), D25 (site Ø) and 4D7 (site I) competing antibody titers. PBMC samples were collected to assess cell mediated immune responses.

TABLE 6

| Vaccine Formulations Tested for Immunogenicity in RSV Seropositive African Green Monkeys | | | |
|---|---|---|---|
| Group | Vaccine | Conc (μg/ml) | Dose (μg) |
| 1 | MRK-04_nopolyA_3mut, I.M. | 10 | 5 |
| 2 | mVRC-1 (v2), I.M. | 10 | 5 |
| 3 | mVRC-1 (v2), I.M | 2 | 1 |
| 4 | mLZF-111 | 10 | 5 |
| 5 | mLZF-111 | 2 | 1 |
| 6 | None (PBS) | NA | NA |

Individual animal $NT_{50}$ titers were measured in serum samples collected at baseline and 2 weeks post vaccination using methods described above and the results are shown in FIG. 8. All vaccines were found to be highly immunogenic as demonstrated by the increase in levels of serum antibodies binding RSV F proteins (both prefusion and postfusion RSV F, data not shown) and increases in serum neutralizing antibody levels, mVRC-1 (v2) induced the highest boost in neutralizing titers (>100 fold at the highest dose), and exhibited similar potency at a 5-fold lower dose relative to MRK-04_nopolyA_3mut. Similarly, mLZF-111 also demonstrated increased potency relative to MRK-04_nopolyA_3mut. No increase in titers was observed in the PBS control group. As this study is still ongoing the durability of these immune responses will continue to be evaluated over the next several months.

Figure 8:
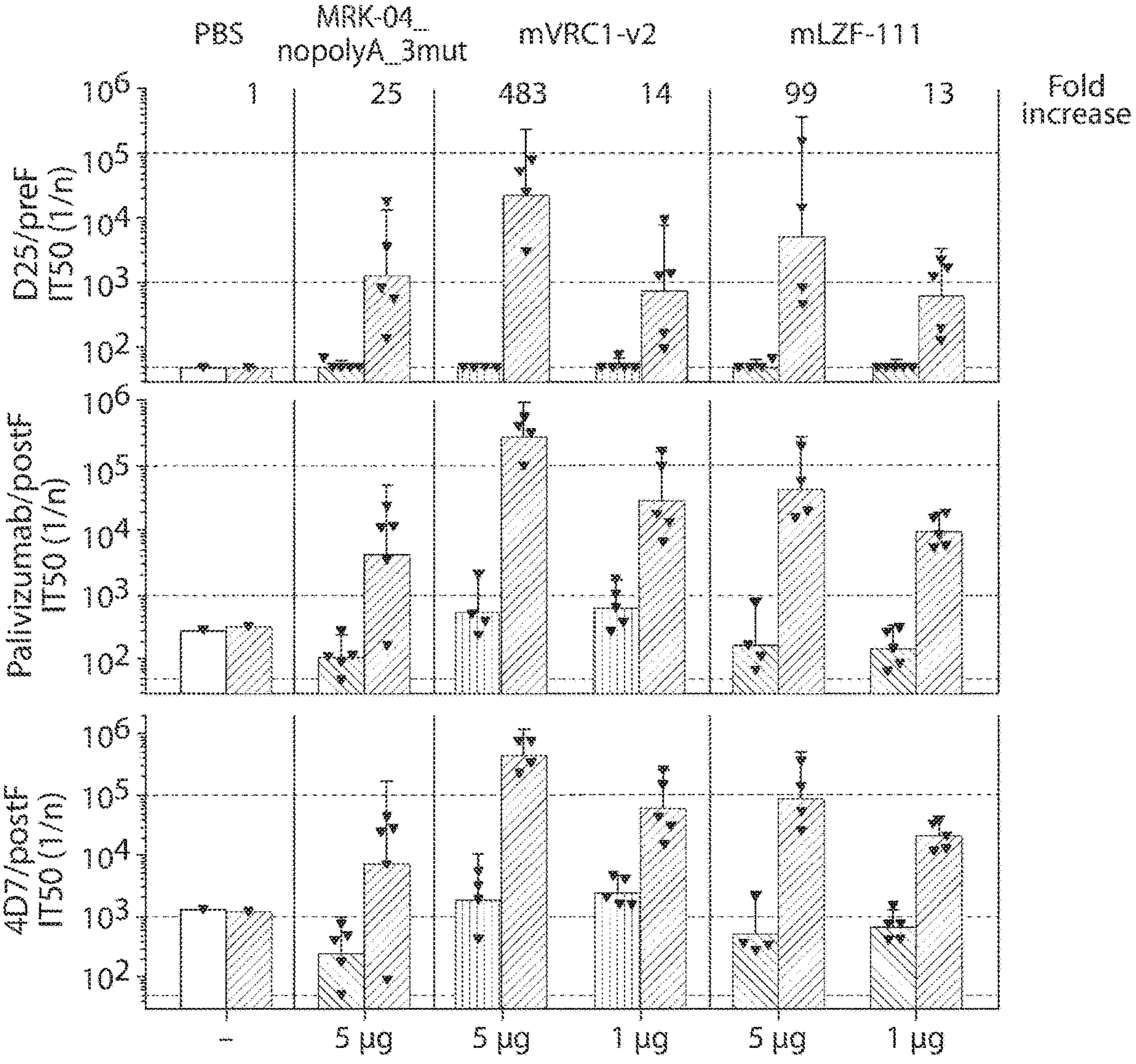
FIG. 8 shows serum antibody competition ELISA titers ($IT_{50}$ Individual and GMT with 95% confidence intervals) against D25 (site Ø), palivizumab (site II), and 4D7 (site I) measured at week 2 (2 weeks PD).

To evaluate the quality of the boosted responses in the vaccinated animals, palivizumab (site II), D25 (site Ø) and 4D7 (site I) competing antibody titers were determined in serum collected at 2 weeks post vaccination (FIG. 8). As described above, antigenic site II is a neutralization epitope found on both the prefusion and the postfusion conformation of the F protein, site Ø is a prefusion specific neutralization epitope and 4D7 is a postfusion specific neutralization epitope. Due to the baseline immune bias to the postfusion conformation. RSV-experienced AGMs do not have detectable D25-competing antibody titers prior to immunization. However, all three mRNA antigens induced high competing antibodies titers, demonstrating that AGMs do mount an antigenic site Ø immune response after RSV infection that can be boosted by immunization. The boost in D25 competing antibody titers following mVRC-1 (v2) immunization were the highest (>450 fold), and demonstrating again similar potency at a 5-fold lower dose than the MRK-04_nopolyA_3mut. In contrast to naïve animals (cotton rats and AGMs) we observed a high boost of 4D7/post-F specific antibodies in RSV-experienced AGMs in the mVRC-1 (v2) group, demonstrating that the baseline antibody pool can determine the outcome of the epitope-specific antibody profile after immunization. Since the B cell memory pool from natural RSV infection in humans is thought to be strongly biased towards the prefusion conformation, we speculate mVRC-1 (v2) immunization in humans will boost preferentially antibodies against these epitopes, known to have more potent neutralizing activity, leading to increased efficacy over MRK-04_nopolyA_3mut.

SEQUENCE LISTING

It should be understood that any of the mRNA sequences described herein may include a 5' UTR and/or a 3' UTR. The UTR sequences may be selected from the following sequences, or other known UTR sequences may be used. It should also be understood that any of the mRNA constructs described herein may further comprise a polyA tail and/or cap (e.g., 7mG(5')ppp(5')NlmpNp). Further, while many of the mRNAs and encoded antigen sequences described herein include a signal peptide and/or a peptide tag (e.g., C-terminal His tag), it should be understood that the indicated signal peptide and/or peptide tag may be substituted for a different signal peptide and/or peptide tag, or the signal peptide and/or peptide tag may be omitted.

5' UTR:
(SEQ ID NO: 2)
GGGAAAUAAGAGAGAAAAGAAGAGUAAGAAGAAAUAUAAGAGCCACC

5' UTR:
(SEQ ID NO: 77)
GGGAAAUAAGAGAGAAAAGAAGAGUAAGAAGAAAUAUAAGACCCCGGCG
CCGCCACC

3' UTR:
(SEQ ID NO: 4)
UGAUAAUAGGCUGGAGCCUCGGUGGCCAUGCUUCUUGCCCCUUGGGCCU
CCCCCCAGCCCCUCCUCCCCUUCCUGCACCCGUACCCCCGUGGUCUUUG
AAUAAAGUCUGAGUGGGGGC

3' UTR:
(SEQ ID NO: 78)
UGAUAAUAGGCUGGAGCCUCGGUGGCCUAGCUUCUUGCCCCUUGGGCCU
CCCCCCAGCCCCUCCUCCCCUUCCUGCACCCGUACCCCCGUGGUCUUUG
AAUAAAGUCUGAGUGGGCGGC

TABLE 7

| mVRC-1 | | |
|---|---|---|
| SEQ ID NO: 1 consists of from 5' end to 3' end: 5' UTR SEQ ID NO: 2, mRNA ORF SEQ ID NO: 3, and 3' UTR SEQ ID NO: 4. | | 1 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAAAACGCUGUGACC<br>GAGCUGCAGUUAUUGAUGCAGAGUACACCUGCCACCGGG<br>UCGGGCUCUGCCAUUUGCUCCGGCGUGGCUGUAUGUAAA<br>GUUCUCCACCUCGAGGGAGAGGUUAAUAAGAUUAAGUCG | 3 |

TABLE 7-continued

| | | |
|---|---|---|
| | GCCCUGCUGAGUACUAACAAAGCAGUGGUGUCGCUGAGU<br>AACGGAGUAAGUGUGUUAACAUUUAAGGUGCUGGACCUC<br>AAGAAUUAUAUUGACAAACAGUUGCUUCCUAUUCUAAAC<br>AAACAGAGCUGUUCAAUAAGUAAUAUUGAAACUGUUAUU<br>GAGUUUCAGCAGAAGAACAACAGGCUUCUUGAGAUUACA<br>CGCGAGUUCAGUGUCAAUGCCGGCGUUACAACACCCGUG<br>UCUACCUACAUGCUGACGAAUUCUGAGCUUCUCUCUCUC<br>AUAAACGACAUGCCCAUUACGAAUGACCAAAAAAAACUU<br>AUGUCCAACAACGUGCAGAUUGUGCGACAGCAAUCCUAU<br>AGCAUUAUGUGUAUCAUCAAGGAAGAGGUACUCGCUUAU<br>GUUGUGCAGCUACCACUCUAUGGUGUGAUUGACACCCCC<br>UGUUGGAAGCUGCAUACCAGUCCACUCUGCACCACUAAC<br>ACAAAGGAAGGGAGCAAUAUUUGCCUCACUCGAACCGAC<br>AGGGGGUGGUAUUGCGAUAAUGCGGGCUCCGUGUCCUUC<br>UUUCCACAGGCUGAAACUUGUAAGGUACAGUCAAACCGC<br>GUGUUCUGUGAUACUAUGAAUUCUCGUACUCUUCCCAGC<br>GAGGUUAAUCUCUGCAACGUCGACAUUUUCAAUCCUAAA<br>UAUGACUGCAAGAUCAUGACCAGCAAGACCGACGUCUCC<br>AGCUCAGUAAUCACUAGCCUAGGGGCCAUUGUAAGCUGC<br>UAUGGCAAAACCAAGUGUACUGCCUCUAAUAAGAACAGA<br>GGCAUAAUUAAAACCUUUUCAAAUGGCUGUGACUAUGUG<br>UCGAAUAAGGGCGUCGACACGGUCUCAGUAGGGAAUACC<br>CUCUACUGCGUUAACAAACAGGAAGCCAAAUCCCUUUAU<br>GUAAAGGGCGAGCCCAUCAUAAAUUUCUACGACCCACUU<br>GUGUUCCCCAGUGAUGAAUUCGAUGCAUCAAUCUCCCAG<br>GUGAACGAAAAGAUCAAUCAAUCCCUUGCUUUUAUACGA<br>AAGUCAGAUGAACUCCUGCAUAACGUGAAUGCUGGGAAA<br>UCUACAACCAACAUCAUGAUCACUACCAUCAUUAUUGUG<br>AUUAUCGUAAUUCUGCUAUCCUUGAUUGCUGUCGGGCUG<br>CUUCUGUACUGUAAGGCCAGAUCGACGCCUGUGACCCUU<br>UCAAAAGACCAACUUAGCGGUAUCAAUAAUAUUGCCUUU<br>AGCAAU | |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGGC | 4 |
| Corresponding amino acid sequence | MELLILKANAITTILTAVTECEASGQNITEEFYQSTCSAVSKGY<br>LSALRTGWYTSVITIELSNIKENKCNGTDAKVKLIKQELDKYK<br>NAVTELQLLMQSTPATGSGSAICSGVAVCKVLHLEGEVNKIK<br>SALLSTNKAVVSLSNGVSVLTFKVLDLKNYIDKQLLPILNKQS<br>CSISNIETVIEFQQKNNRLLEITREFSVNAGVTTPVSTYMLINSE<br>LLSLINDMPITNDQKKLMSNNVQIVRQQSYSIMCHIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLQN<br>VDIFNPKYDCKIMTSKTDVSSSVITSLGAIVSCYGKTKCTASNK<br>NRGIIKTFSNGCDYVSNKGVDTVSVGNTLYCVNKQEGKSLYV<br>KGEPINFYDPLVFPSDEFDASISQVNEKINQSLAFIRKSDELLH<br>NVNAGKSTTNIMITTIIIVIVILLSLIAVGLLLYCKARSTPVTLS<br>KDQLSGINNIAFSN | 5 |
| PolyA tail | 100 nt | |

mVRC-2

| | | |
|---|---|---|
| SEQ ID NO: 6 consists of from 5' end to 3' end: 5' UTR SEQ ID NO: 2, mRNA ORF SEQ ID NO: 7, and 3' UTR SEQ ID NO: 4. | | 6 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCCACGCUAAAGUCAAACUU<br>AUCAAGCAGGAACUCGACAAAUAUAAAAACGCUGUGACC<br>GAGCUGCAGUUAUUGAUGCAGAGUACACCUGCCACCGGG<br>UCGGGCUCUGCCAUUGCUUCCGGCGUGGCUGUAUGUAAA<br>GUUCUCCACCUCGAGGGAGAGCUUAAUAAGAUUAAGUCG<br>GCCCUGCUGAGUACUAACAAAGCAGUGGUGUCGCUGAGU<br>GGCUGCGGAGUAAGUGUGUUAACAUUUAAGGUGCUGGAC<br>CUCAAGAAUUAUAUUGACAAACAGUUGCUUCCUAUUCUA<br>AACAAACAGAGCUGUUCAAUAAGUAAUAUUGAAACUGUU<br>AUUGAGUUUCAGCAGAAGAACAACAGGCUUCUUGAGAUU<br>ACACGCGAGUUCAGUGUCAAUGCCGGCGUUACAACACCC<br>GUGUCUACCUACAUGCUGACGAAUUCUGAGCUUCUCUCU<br>CUCAUAAACGACAUGCCCAUUACGAAUGACCAAAAAAAA<br>CUUAUGUCCAACAACGUGCAGAUUGUGCGACAGCAAUCC<br>UAUAGCAUUAUGUGUAUCAUCAAGGAAGAGGUACUCGCU<br>UAUGUUGUGCAGCUACCACUCUAUGGUGUGAUUGACACC<br>CCCUGUUGGAAGCUGCAUACCAGUCCACUCUGCACCACUA | 7 |

TABLE 7-continued

| | | |
|---|---|---|
| | ACACAAAGGAAGGGAGCAAUAUUUGCCUCACUCGAACCG<br>ACAGGGGGUGGUAUUGCGAUAAUGCGGGCUCCGUGUCCU<br>UCUUUCCACAGGCUGAAACUUGUAAGGUACAGUCAAACC<br>GCGUGUUCUGUGAUACUAUGAAUUCUCGUACUCUUCCCA<br>GCGAGGUUAAUCUCUGCAACGUCGACAUUUUCAAUCCUA<br>AAUAUGACUGCAAGAUCAUGACCAGCAAGACCGACGUCU<br>CCAGCUCAGUAAUCACUAGCCUAGGGGCCAUUGUAAGCU<br>GCUAUGGCAAAACCAAGUGUACUGCCUCUAAUAAGUGCA<br>GAGGCAUAAUUAAAACCUUUUCAAAUGGCUGUGACUAUG<br>UGUCGAAUAAGGGCGUCCACACGGUCUCAGUAGGGAAUA<br>CCCUCUACUACGUUAACAAACAGGAAGGCAAAUCCCUUU<br>AUGUAAAGGGCGAGCCCAUCAUAAAUUUCUACGACCCAC<br>UUGUGUUCCCCAGUGAUGAAUUCGAUGCAUCAAUCUCCC<br>AGGUGAACGAAAAGAUCAAUCAAUCCCUUGCUUUUAUAC<br>GAAAGUCAGAUGAACUCCUGCAUAACGUGAAUGCUGGGA<br>AAUCUACAACCAACAUCAUGAUCACUACCAUCAUUAUUG<br>UGAUUAUCGUAAUUCUGCUAUCCUUGAUUGCUGUCGGGC<br>UGCUUCUGUACUGUAAGGCCAGAUCGACGCCUGUGACCC<br>UUUCAAAAGACCAACUUAGCGGUAUCAAUAAUAUUGCCU<br>UUAGCAAU | |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MELLILKANAITTILTAVTECFASGQNITEEFYQSTCSAVSKGY<br>LSALRTGWYTSVITIELSNIKENKCNGTDAKVKLIKQELDKYK<br>NAVTELQLLMQSTPATGSGSAIASGVAVCKVLHLEGEVNKIK<br>SALLSTNKAVVSLSGCGVSVLTFKVLDLKNYIDKQLLPILNKQ<br>SCSISNIETVIEFQQKNNRLLEITREFSVNAGVTTPVSTYMLINS<br>ELLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>CRGIIKTESNGCDYVSNKGVDTVSVGNTLYYVNKQEGKSLYV<br>KGEPINFYDPLVFPSDEFDASISQVNEKINQSLAFIRKSDELLH<br>NVNAGKSTTNIMITTIVIVILLSLIAVGLLLYCKARSTPVTLS<br>KDQLSGINNIAFSN | 8 |
| PolyA tail | 100 nt | |

mVRC-3

| | | |
|---|---|---|
| SEQ ID NO: 9 consists of from 5' end to 3' end: 5' UTR SEQ ID NO: 2, mRNA ORF SEQ ID NO: 10, and 3' UTR SEQ ID NO: 4. | | 9 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGC<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAAAACGCUGUGACC<br>GAGCUGCAGUUAUUGAUGCAGAGUACACCUGCCACCAAU<br>AACGGGUCGGGCUCUGCCAUUGCUUCCGGCGUGGCUGUA<br>UGUAAAGUUCUCCACCUCGAGGGAGAGGUUAAUAAGAUU<br>AAGUCGGCCCUGCUGAGUACUAACAAAGCAGUGGUGUCG<br>CUGAGUAACGGAGUAAGUGUGUUAACAUUUAAGGUGCUG<br>GACCUCAAGAAUUAUAUUGACAAACAGUUGCUUCCUAUU<br>CUAAACAAACAGAGCUGUUCAAUAAGUAAUAUUGAAACU<br>GUUAUUGAGUUUCAGCAGAAGAACAACAGGCUUCUUGAG<br>AUUACACGCGAGUUCAGUGUCAAUGCCGGCGUUACAACA<br>CCCGUGUCUACCUACAUGCUGACGAAUUCUGAGCUUCUC<br>UCUCUCAUAAACGACAUGCCCAUUACGAAUGACCAAAAA<br>AAACUUAUGUCCAACAACGUGCAGAUUGUGCGACAGCAA<br>UCCUAUAGCAUUAUGUGUAUCAUCAAGGAAGAGGUACUC<br>GCUUAUGUUGUGCAGCUACCACUCUAUGGUGUGAUUGAC<br>ACCCCCUGUUGGAAGCUGCAUACCAGUCCACUCUGCACCA<br>CUAACACAAAGGAAGGGAGCAAUAUUUGCCUCACUCGAA<br>CCGACAGGGGGUGGUAUUGCGAUAAUGCGGGCUCCGUGU<br>CCUUCUUUCCACAGGCUGAAACUUGUAAGGUACAGUCAA<br>ACCGCGUGUUCUGUGAUACUAUGAAUUCUCGUACUCUUC<br>CCAGCGAGGUUAAUCUCUGCAACGUCGACAUUUUCAAUC<br>CUAAAUAUGACUGCAAGAUCAUGACCAGCAAGACCGACG<br>UCUCCAGCUCAGUAAUCACUAGCCUAGGGGCCAUUGUAA<br>GCUGCUAUGGCAAAACCAAGUGUACUGCCUCUAAUAAGA<br>ACAGAGGCAUAAUUAAAACCUUUUCAAAUGGCUGUGACU<br>AUGUGUCGAAUAAGGGCGUCGACACGGUCUCAGUAGGGA<br>AUACCCUCUACUACGUUAACAAACAGGAAGGCAAAUCCC | 10 |

TABLE 7-continued

| | | |
|---|---|---|
| | UUUAUGUAAAGGGCGAGCCCAUCAUAAAUUUCUACGACC | |
| | CACUUGUGUUCCCCAGUGAUGAAUUCGAUGCAUCAAUCU | |
| | CCCAGGUGAACGAAAAGAUCAAUCAAUCCCUUGCUUUUA | |
| | UACGAAAGUCAGAUGAACUCCUGCAUAACGUGAAUGCUG | |
| | GGAAAUCUACAACCAACAUCAUGAUCACUACCAUCAUUA | |
| | UUGUGAUUAUCGUAAUUCUGCUAUCCUUGAUUGCUGUCG | |
| | GGCUGCUUCUGUACUGUAAGGCCAGAUCGACGCCUGUGA | |
| | CCCUUUCAAAAGACCAACUUAGCGGUAUCAAUAAUAUUG | |
| | CCUUUAGCAAU | |
| 3' UTR | UGAUAAUAGGCUGGAGCCUCGGUGGCCAUGCUUCUUGCC | 4 |
| | CCUUGGGCCUCCCCCCAGCCCCUCCUCCCCUUCCUGCACC | |
| | CGUACCCCCGUGGUCUUUGAAUAAAGUCUGAGUGGGCGGC | |
| Corresponding amino acid sequence | MELLILKANAITTILTAVTECEASGQNITEEFYQSTCSAVSKGY | 11 |
| | LSALRTGWYTSVITIELSNIKENKCNGTDAKVKLIKQELDKYK | |
| | NAVTELQLLMQSTPATNNGSGSAIASGVAVCKVLHLEGEVNK | |
| | IKSALLSTNKAVVSLSNGVSVLTFKVLDLKNYIDKQLLPILNK | |
| | QSCSISNIETVIETQQKNNRLLEITREFSVNAGVTTPVSTYMLT | |
| | NSELLSLINDMPITNDQKKLMSNNVQIVRQQSYSIMCIIKEEVL | |
| | AYVVQLPLYGVIDTPCWKLHTSPLCTTNTKEGSNICLTRTDRG | |
| | WYCDNAGSVSFFPQAETCKVQSNRVFCDTMNSRTLPSEVNLC | |
| | NVDIFNPKYDCKIMTSKTDVSSSVITSLGAIVSCYGKTKCTASN | |
| | KNRGHIKTFSNGCDYVSNKGVDTVSVGNTLYYVNKQEGKSLY | |
| | VKGEPIINFYDPLVFPSDEFDASISQVNEKINQSLAFIRKSDELL | |
| | HNVNAGKSTTNIMITTIIIVIIVILLSLIAVGLLLYCKARSTPVTL | |
| | SKDQLSGINNIAPSN | |
| PolyA tail | 100 nt | |

VRC-1

| | | |
|---|---|---|
| SEQ ID NO: 12 consists of from 5' end to 3' end: 5' UTR SEQ ID NO: 2, mRNA ORF SEQ ID NO: 13, and 3' UTR SEQ ID NO: 4. | | 12 |
| Chemistry | 1-metbylpseudouridine | |
| Cap | 7mG(5')ppp(5')NimpNp | |
| 5' UTR | GGGAAAUAAGAGAGAAAAGAAGAGUAAGAAGAAAUAUA | 2 |
| | AGAGCCACC | |
| ORF of mRNA Construct (excluding the stop codon) | AUGGAACUGCUCAUUUUGAAGGCAAACGCUAUCACGACA | 13 |
| | AUACUCACUGCAGUGACCUUCUGUUUUGCCUCAGGCCAG | |
| | AACAUAACCGAGGAGUUUUAUCAAUCUACAUGCAGCCCU | |
| | GUAUCUAAAGGCUACCUGAGUGCGCUCCGCACAGGAUGG | |
| | UACACCUCCGUGAUCACCAUCGAGCUCAGCAAUAUUAAA | |
| | GAGAACAAGUGCAAUGGUACCGACGCUAAAGUCAAACUU | |
| | AUCAAGCAGGAACUCGACAAAUAUAAAAACGCUGUGACC | |
| | GAGCUGCAGUUAUUGAUGCAGAGUACACCUGCCACCGGG | |
| | UCGGGCUCUGCCAUUUGCUCCGGCGUGGCUGUAUGUAAA | |
| | GUUCUCCACCUCGAGGGAGAGGUUAAUAAGAUUAAGUCG | |
| | GCCCUGCUGAGUACUAACAAAGCAGUGGUGUCGCUGAGU | |
| | AACGGAGUAAGUGUGUUAACAUUUAAGGUGCUGGACCUC | |
| | AAGAAUUAUAUUGACAAACAGUUGCUUCCUAUUCUAAAC | |
| | AAACAGAGCUGUUCAAUAAGUAAUAUUGAAACUGUUAUU | |
| | GAGUUUCAGCAGAAGAACAACAGGCUUCUUGAGAUUACA | |
| | CGCGAGUUCAGUGUCAAUGCCGGCGUUACAACACCCGUG | |
| | UCUACCUACAUGCUGACGAAUUCUGAGCUUCUCUCUCUC | |
| | AUAAACGACAUGCCCAUUACGAAUGACCAAAAAAAACUU | |
| | AUGUCCAACAACCUGCAGAUUGUGCGACAGCAAUCCUAU | |
| | AGCAUUAUGUGUAUCAUCAAGGAAGAGGUACUCGCUUAU | |
| | GUUGUGCAGCUACCACUCUAUGGUGUGAUUGACACCCCC | |
| | UGUUGGAAGCUGCAUACCAGUCCACUCUGCACCACUAAC | |
| | ACAAAGGAAGGGAGCAAUAUUUGCCUCACUCGAACCGAC | |
| | AGGGGGUGGUAUUGCGAUAAUGCGGGCUCCGUGUCCUUC | |
| | UUUCCACAGGCUGAAACUUGUAAGGUACAGUCAAACCGC | |
| | GUGUUCUGUGAUACUAUGAAUUCUCGUACUCUUCCCAGC | |
| | GAGGUUAAUCUCUGCAACGUCGACAUUUUCAAUCCUAAA | |
| | UAUGACUGCAAGAUCAUGACCAGCAAGACCGACGUCUCC | |
| | AGCUCAGUAAUCACUAGCCUAGGGGCCAUUGUAAGCUGC | |
| | UAUGGCAAAACCAAGUGUACUCCCUCUAAUAAGAACAGA | |
| | GGCAUAAUUAAAACCUUUUCAAAUGGCUGUGACUAUGUG | |
| | UCGAAUAAGGGCGUCGACACGGUCUCAGUAGGGAAUACC | |
| | CUCUACUGCGUUAACAAACAGGAAGGCAAAUCCCUUUAU | |
| | GUAAAGGCCGAGCCCAUCAUAAAUUUCUACGACCCACUU | |
| | GUGUUCCCCAGUGAUGAAUUCGAUGCAUCAAUCUCCCAG | |
| | GUGAACGAAAAGAUCAAUCAAUCCCUUGCUUUUAUACGA | |
| | AAGUCAGAUGAACUCCUGUCCGCCAUCGGUGGCUAUAUC | |
| | CCAGAAGCCCCAAGAGACGGACAAGCGUACGUCCGGAAA | |
| | GAUGGUGAGUGGGUCCUCCUCUCUACCUUUCUU | |
| 3' UTR | UGAUAAUAGGCUGGAGCCUCGGUGGCCAUGCUUCUUGCC | 4 |
| | CCUUGGGCCUCCCCCCAGCCCCUCCUCCCCUUCCUGCACC | |
| | CGUACCCCCGUGGUCUUUGAAUAAAGUCUGAGUGGGGG | |
| | C | |

TABLE 7-continued

| | | |
|---|---|---|
| Corresponding amino acid sequence | MELLILKANAITTILTAVTECFASGQNITEEFYQSTCSAVSKGY<br>LSALRTGWYTSVITIELSNIKENKCNGTDAKVKLIKQELDKYK<br>NAVTELQLLMQSTPATGSGSAICSGVAVCKVLHLEGEVNKIK<br>SALLSTNKAVVSLSNGVSVLTFKVLDLKNYIDKQLLPILNKQS<br>CSISNIETVIEFQQKNNRLLEITREFSVNAGVTTPVSTYMLINSE<br>LLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>NRGIIKTESNGCDYVSNKGVDTVSVGNTLYCVNKQEGKSLYV<br>KGEPIINFYDPLVFPSDEFDASISQVNEKINQSLAFIRKSDELLS<br>AIGGYIPEAPRDGQAYVRKDGEWVLLSTFL | 14 |
| PolyA tail | 100 nt | |

VRC-2

| | | |
|---|---|---|
| SEQ ID NO: 15 consists of from 5' end to 3' end: 5' UTR SEQ ID NO: 2, mRNA ORF SEQ ID NO: 16, and 3' UTR SEQ ID NO: 4. | | 15 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAAAACGCUGUGACC<br>GAGCUGCAGUUAUUGAUGCAGAGUACACCUGCCACCGGG<br>UCGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>GGCUGCGGAGUAAGUGUGUUAACAUUUAAGGUGCUGGAC<br>CUCAAGAAUUAUAUUGACAAACAGUUGCUUCCUAUUCUA<br>AACAAACAGAGCUGUUCAAUAAGUAAUAUUGAAACUGUU<br>AUUGAGUUUCAGCAGAAGAACAACAGGCUUCUUGAGAUU<br>ACACGCGAGUUCAGUGUCAAUGCCGGCGUUACAACACCC<br>GUGUCUACCUACAUGCUGACGAAUUCUGAGCUUCUCUCU<br>CUCAUAAACGACAUGCCCAUUACGAAUGACCAAAAAAAA<br>CUUAUGUCCAACAACGUGCAGAUUGUGCGACAGCAAUCC<br>UAUAGCAUUAUGUGUAUCAUCAAGGAAGAGGUACUCGCU<br>UAUGUUGUGCAGCUACCACUCUAUGGUGUGAUUGACACC<br>CCCUGUUGGAAGCUGCAUACCAGUCCACUCUGCACCACUA<br>ACACAAAGGAAGGGAGCAAUAUUUGCCUCACUCGAACCG<br>ACAGGGGGUGGUAUUGCGAUAAUGCGGGCUCCGUGUCCU<br>UCUUUCCACAGGCUGAAACUUGUAAGGUACAGUCAAACC<br>GCGUGUUCUGUGAUACUAUGAAUUCUCGUACUCUUCCCA<br>GCGAGGUUAAUCUCUGCAACGUCGACAUUUUCAAUCCUA<br>AAUAUGACUGCAAGAUCAUGACCAGCAAGACCGACGUCU<br>CCAGCUCAGUAAUCACUAGCCUAGGGGCCAUUGUAAGCU<br>GCUAUGGCAAAACCAAGUGUACUGCCUCUAAUAAGUGCA<br>GAGGCAUAAUUAAAACCUUUUCAAAUGGCUGUGACUAUG<br>UGUCGAAUAAGGGCGUCGACACGGUCUCAGUAGGGAAUA<br>CCCUCUACUACGUUAACAAACAGGAAGGCAAAUCCCUUU<br>AUGUAAAGGGCGAGCCCAUCAUAAAUUUCUACGACCCAC<br>UUGUGUUCCCCAGUGAUGAAUUCGAUGCAUCAAUCUCCC<br>AGGUGAACGAAAAGAUCAAUCAAUCCCUUGCUUUUAUAC<br>GAAAGUCAGAUGAACUCCUGUCCGCCAUCGGUGGCUAUA<br>UCCCAGAAGCCCCAAGAGACGGACAAGCGUACGUCCGGA<br>AAGAUGGUGAGUGGGUCCUCCUCUCUACCUUUCUU | 16 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGGGC | 4 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSTPATGSGSAIASGVAVCKVLHLEGEVNKIK<br>SALLSTNKAVVSLSGCGVSVLTFKVLDLKNYIDKQLLPILNKQ<br>SCSISNIETVIEFQQKNNRLLEITREFSVNAGVTTPVSTYMLTNS<br>ELLSLINDMPITNDQKKLMSNNVQIVRQQSYSIMCHIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>CRGIIKTFSNGCDYVSNKGVDTVSVGNTLYYVNKQEGKSLYV<br>KGEPIINFYDPLVFPSDEFDASISQVNEKINQSLAFIRKSDELLS<br>AIGGYIPEAPRDGQAYVRKDGEWVLLSTFL | 17 |
| PolyA tail | 100 nt | |

TABLE 7-continued

| | | |
|---|---|---|
| **VRC-3** | | |
| SEQ ID NO: 18 consists of from 5' end to 3' end: 5' UTR SEQ ID NO: 2, mRNA ORF SEQ ID NO: 19, and 3' UTR SEQ ID NO: 4. | | 18 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGC<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAAAACGCUGUGACC<br>GAGCUGCAGUUAUUGAUGCAGAGUACACCUGCCACCAAU<br>AACGGGUCGGGCUCUGCCAUUGCUUCCGGCGUGGCUGUA<br>UGUAAAGUUCUCCACCUCGAGGGAGAGGUUAAUAAGAUU<br>AAGUCGGCCCUGCUGAGUACUAACAAAGCAGUGGUGUCG<br>CUGAGUAACGGAGUAAGUGUGUUAACAUUUAAGGUGCUG<br>GACCUCAAGAAUUAUAUUGACAAACAGUUGCUUCCUAUU<br>CUAAACAAACAGAGCUGUUCAAUAAGUAAUAUUGAAACU<br>GUUAUUGAGUUUCAGCAGAAGAACAACAGGCUUCUUGAG<br>AUUACACGCGAGUUCAGUGUCAAUGCCGGCGUUACAACA<br>CCCGUGUCUACCUACAUGCUGACGAAUUCUGAGCUUCUC<br>UCUCUCAUAAACGACAUGCCCAUUACGAAUGACCAAAAA<br>AAACUUAUGUCCAACAACGUGCAGAUUGUGCGACAGCAA<br>UCCUAUAGCAUUAUGUGUAUCAUCAAGGAAGAGGUACUC<br>GCUUAUGUUGUGCAGCUACCACUCUAUGGUGUGAUUGAC<br>ACCCCCUGUUGGAAGCUGCAUACCAGUCCACUCUGCACCA<br>CUAACACAAAGGAAGGGAGCAAUAUUUGCCUCACUCGAA<br>CCGACAGGGGGUGGUAUUGCGAUAAUGCGGGCUCCGUGU<br>CCUUCUUUCCACAGGCUGAAACUUGUAAGGUACAGUCAA<br>ACCGCGUGUUCUGUGAUACUAUGAAUUCUCGUACUCUUC<br>CCAGCGAGGUUAAUCUCUGCAACGUCGACAUUUUCAAUC<br>CUAAAUAUGACUGCAAGAUCAUGACCAGCAAGACCGACG<br>UCUCCAGCUCAGUAAUCACUAGCCUAGGGGCCAUUGUAA<br>GCUGCUAUGGCAAAACCAAGUGUACUGCCUCUAAUAAGA<br>ACAGAGGCAUAAUUAAAACCUUUUCAAAUGGCUGUGACU<br>AUGUGUCGAAUAAGGGCGUCGACACGGUCUCAGUAGGGA<br>AUACCCUCUACUACGUUAACAAACAGGAAGGCAAAUCCC<br>UUUAUGUAAAGGGCGAGCCCAUCAUAAAUUUCUACGACC<br>CACUUGUGUUCCCCAGUGAUGAAUUCGAUGCAUCAAUCU<br>CCCAGGUGAACGAAAAGAUCAAUCAAUCCCUUGCUUUUA<br>UACGAAAGUCAGAUGAACUCCUGUCCGCCAUCGGUGGCU<br>AUAUCCCAGAAGCCCCAAGAGACGGACAAGCGUACGUCC<br>GGAAAGAUGGUGAGUGGGUCCUCCUCUCUACCUUUCUU | 19 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGGGC | 4 |
| Corresponding amino acid sequence | MELLILKANAITTILTAVTECFASGQNITEEFYQSTCSAVSKGY<br>LSALRTGWYTSVITIELSNIKENKCNGTDAKVKLIKQELDKYK<br>NAVTELQLLMQSTPATNNGSGSAIASGVAVCKVLHLEGEVNK<br>IKSALLSTNKAVVSLSNGVSVLTFKVLDLKNYIDKQLLPILNK<br>QSCSISNIETVIEFQQKNNRLLBITREFSVNAGVTTPVSTYMLT<br>NSELLSLINDMPITNDQKKLMSNNVQIVRQQSYSIMCIIKEEVL<br>AYVVQLPLYGVIDTPCWKLHTSPLCTTNTKEGSNICLTRTDRG<br>WYCDNAGSVSFFPQAETCKVQSNRVFCDTMNSRTLPSEVNLC<br>NVDIFNPKYDCKIMTSKTDVSSSVITSLGAIVSCYGKTKCTASN<br>KNRGIIKTESNGCDYVSNKGVDTVSVGNTLYYVNKQEGKSLY<br>VKGEPIINFYDPLVFPSDEFDASISQVNEKINQSLAFIRKSDELL<br>SAIGGYIPEAPRDGQAYVRKDGEWVLLSTFL | 20 |
| PolyA tail | 100 nt | |
| **mVRC-1 (v2)** | | |
| SEQ ID NO: 21 consists of from 5' end to 3' end: 5' UTR SEQ ID NO: 2, mRNA ORF SEQ ID NO: 22, and 3' UTR SEQ ID NO: 4. | | 21 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCCCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC | 22 |

TABLE 7-continued

| | | |
|---|---|---|
| | GAGCUGCAGUUAUUGAUGCAGAGUACACCUGCCACCGGG<br>UCGGGCUCUGCCAUUUGCUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>AACGGAGUAAGUGUGUUAACAUUUAAGGUGCUGGACCUC<br>AAGAAUUAUAUUGACAAACAGUUGCUUCCUAUUCUAAAC<br>AAACAGAGCUGUUCAAUAAGUAAUAUUGAAACUGUUAUU<br>GAGUUUCAGCAGAAGAACAACAGGCUUCUUGAGAUUACA<br>CGCGAGUUCAGUGUCAAUGCCGGCGUUACAACACCCGUG<br>UCUACCUACAUGCUGACGAAUUCUGAGCUUCUCUCUCUC<br>AUAAACGACAUGCCCAUUACGAAUGACCAAAAGAAACUU<br>AUGUCCAACAACGUGCAGAUUGUGCGACAGCAAUCCUAU<br>AGCAUUAUGUGUAUCAUCAAGGAAGAGGUACUCGCUUAU<br>GUUGUGCAGCUACCACUCUAUGGUGUGAUUGACACCCCC<br>UGUUGGAAGCUGCAUACCAGUCCACUCUGCACCACUAAC<br>ACAAAGGAAGGGAGCAAUAUUUGCCUCACUCGAACCGAC<br>AGGGGGUGGUAUUGCGAUAAUGCGGGCUCCGUGUCCUUC<br>UUUCCACAGGCUGAAACUUGUAAGGUACAGUCAAACCGC<br>GUGUUCUGUGAUACUAUGAAUUCUCGUACUCUUCCCAGC<br>GAGGUUAAUCUCUGCAACGUCGACAUUUUCAAUCCUAAA<br>UAUGACUGCAAGAUCAUGACCAGCAAGACCGACGUCUCC<br>AGCUCAGUAAUCACUAGCCUAGGGGCCAUUGUAAGCUGC<br>UAUGGCAAAACCAAGUGUACUGCCUCUAAUAAGAACAGA<br>GGCAUAAUUAAAACCUUUUCAAAUGGCUGUGACUAUGUG<br>UCGAAUAAGGGCGUCGACACGGUCUCAGUAGGGAAUACC<br>CUCUACUGCGUUAACAAACAGGAAGCCAAAUCCCUUUAU<br>GUAAAGGGCGAGCCCAUCAUAAAUUUCUACGACCCACUU<br>GUGUUCCCCAGUGAUGAAUUCGAUGCAUCAAUCUCCCAG<br>GUGAACGAAAAGAUCAAUCAAUCCCUUGCUUUUAUACGA<br>AAGUCAGAUGAACUCCUGCAUAACGUGAAUGCUGGGAAA<br>UCUACAACCAACAUCAUGAUCACUACCAUCAUUAUUGUG<br>AUUAUCGUAAUUCUGCUAUCCUUGAUUGCUGUCGGGCUG<br>CUUCUGUACUGUAAGGCCAGAUCGACGCCUGUGACCCUU<br>UCAAAAGACCAACUUAGCGGUAUCAAUAAUAUUGCCUUU<br>AGCAAU | |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGGGG<br>C | 4 |
| Corresponding amino acid sequence | MELLILKANAITTILTAVTECFASGQNITEEFYQSTCSAVSKGY<br>LSALRTGWYTSVITIELSNIKENKCNGTDAKVKLIKQELDKYK<br>NAVTELQLLMQSTPATGSGSAICSGVAVCKVLHLEGEVNKIK<br>SALLSTNKAVVSLSNGVSVLTFKVLDLKNYIDKQLLPILNKQS<br>CSISNIETVIEFQQKNNRLLEITREFSVNAGVTTPVSTYMLINSE<br>LLSLINDMPITNDQKKLMSNNVQIVRQQSYSIMCHIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>NRGIIKTESNGCDYVSNKGVDTVSVGNTLYCVNKQECKSLYV<br>KGEPIINFYDPLVFPSDEFDASISQVNEKINQSLAFIRKSDELLH<br>NVNAGKSTTNIMITTIVQVILLSLIAVGLLLYCKARSTPVTLS<br>KDQLSGINNIAFSN | 5 |
| PolyA tail | 100 nt | |

mVRC-2 (v2)

| | | |
|---|---|---|
| SEQ ID NO: 23 consists of from 5' end to 3' end: 5' UTR SEQ ID NO: 2, mRNA ORF SEQ ID NO: 24, and 3' UTR SEQ ID NO: 4. | | 23 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA | 2 |
| ORF of mRNA Construct (excluding the stop codon) | AGAGCCACC<br>AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC<br>GAGCUGCAGUUAUUGAUGCAGAGUACACCUGCCACCGCG<br>UCGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>GGCUGCGGAGUAAGUGUGUUAACAUUUAAGGUGCUGGAC<br>CUCAAGAAUUAUAUUGACAAACAGUUGCUUCCUAUUCUA<br>AACAAACAGAGCUGUUCAAUAAGUAAUAUUGAAACUGUU<br>AUUGAGUUUCAGCAGAAGAACAACAGGCUUCUUGAGAUU<br>ACACGCGAGUUCAGUGUCAAUGCCGGCGUUACAACACCC<br>GUGUCUACCUACAUGCUGACGAAUUCUGAGCUUCUCUCU<br>CUCAUAAACGACAUGCCCAUUACGAAUGACCAAAAGAAA | 24 |

TABLE 7-continued

| | | |
|---|---|---|
| | CUUAUGUCCAACAACGUGCAGAUUGUGCGACAGCAAUCC<br>UAUAGCAUUAUGUGUAUCAUCAAGGAAGAGGUACUCGCU<br>UAUGUUGUGCAGCUACCACUCUAUGGUGUGAUUGACACC<br>CCCUGUUGGAAGCUGCAUACCAGUCCACUCUGCACCACUA<br>ACACAAAGGAAGGGAGCAAUAUUUGCCUCACUCGAACCG<br>ACAGGGGGUGGUAUUGCGAUAAUGCGGGCUCCGUGUCCU<br>UCUUUCCACAGGCUGAAACUUGUAAGGUACAGUCAAACC<br>GCGUGUUCUGUGAUACUAUGAAUUCUCGUACUCUUCCCA<br>GCGAGGUUAAUCUCUGCAACGUCGACAUUUUCAAUCCUA<br>AAUAUGACUGCAAGAUCAUGACCAGCAAGACCGACGUCU<br>CCAGCUCAGUAAUCACUAGCCUAGGGGCCAUUGUAAGCU<br>GCUAUGGCAAAACCAAGUGUACUGCCUCUAAUAAGUGCA<br>GAGGCAUAAUUAAAACCUUUUCAAAUGGCUGUGACUAUG<br>UGUCGAAUAAGGGCGUCGACACGGUCUCAGUAGGGAAUA<br>CCCUCUACUACGUUAACAAACAGGAAGGCAAAUCCCUUU<br>AUGUAAAGGGCGAGCCCAUCAUAAAUUUCUACGACCCAC<br>UUGUGUUCCCCAGUGAUGAAUUCGAUGCAUCAAUCUCCC<br>AGGUGAACGAAAAGAUCAAUCAAUCCCUUGCUUUUAUAC<br>GAAAGUCAGAUGAACUCCUGCAUAACGUGAAUGCUGGGA<br>AAUCUACAACCAACAUCAUGAUCACUACCAUCAUUAUUG<br>UGAUUAUCGUAAUUCUGCUAUCCUUGAUUGCUGUCGGGC<br>UGCUUCUGUACUGUAAGGCCAGAUCGACGCCUGUGACCC<br>UUUCAAAAGACCAACUUAGCGGUAUCAAUAAUAUUGCCU<br>UUAGCAAU | |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSTPATGSGSAIASGVAVCKVLHLEGEVNKIK<br>SALLSTNKAVVSLSGCGVSVLTFKVLDLKNYIDKQLLPILNKQ<br>SCSISNIETVIEFQQKNNRLLETTREFSVNAGVTTPVSTYMLTNS<br>ELLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>CRGIIKTESNGCDYVSNKGVDTVSVGNTLYYVNKQEGKSLYV<br>KGEPIINFYDPLVFPSDEFDASISQVNEKINQSLAFIRKSDELLH<br>NVNAGKSTTNIMITTIIIVIIVILLSLIAVGLLLYCKARSTPVTLS<br>KDQLSGINNIAFSN | 8 |
| PolyA tail | 100 nt | |

mVRC-3 (v2)

| | | |
|---|---|---|
| SEQ ID NO: 25 consists of from 5' end to 3' end: 5' UTR SEQ ID NO: 2, mRNA ORF SEQ ID NO: 26, and 3' UTR SEQ ID NO: 4. | | 25 |
| Chemistry | 1-methylpseudouridine | |
| Cap | 7mG(5')ppp(5')NimpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC<br>GAGCUGCAGUUAUUGAUGCAGAGUACACCUGCCACCAAU<br>AACGGGUCGGGCUCUGCCAUUGCUUCCGGCGUGGCUGUA<br>UGUAAAGUUCUCCACCUCGAGGGAGAGGUUAAUAAGAUU<br>AAGUCGGCCCUGCUGAGUACUAACAAAGCAGUGGUGUCG<br>CUGAGUAACGGAGUAAGUGUGUUAACAUUUAAGGUGCUG<br>GACCUCAAGAAUUAUAUUGACAAACAGUUGCUUCCUAUU<br>CUAAACAAACAGAGCUGUUCAAUAAGUAAUAUUGAAACU<br>GUUAUUGAGUUUCAGCAGAAGAACAACAGGCUUCUUGAG<br>AUUACACGCGAGUUCAGUGUCAAUGCCGGCGUUACAACA<br>CCCGUGUCUACCUACAUGCUGACGAAUUCUGAGCUUCUC<br>UCUCUCAUAAACGACAUGCCCAUUACGAAUGACCAAAAG<br>AAACUUAUGUCCAACAACGUGCAGAUUGUGCGACAGCAA<br>UCCUAUAGCAUUAUGUGUAUCAUCAAGGAAGAGGUACUC<br>GCUUAUGUUGUGCAGCUACCACUCUAUGGUGUGAUUGAC<br>ACCCCCUGUUGGAAGCUGCAUACCAGUCCACUCUGCACCA<br>CUAACACAAAGGAAGGGAGCAAUAUUUGCCUCACUCGAA<br>CCGACAGGGGGUGGUAUUGCGAUAAUGCGGGCUCCGUGU<br>CCUUCUUUCCACAGGCUGAAACUUGUAAGGUACAGUCAA<br>ACCGCGUGUUCUGUGAUACUAUGAAUUCUCGUACUCUUC<br>CCAGCGAGGUUAAUCUCUGCAACGUCGACAUUUUCAAUC<br>CUAAAUAUGACUGCAAGAUCAUGACCAGCAAGACCGACG<br>UCUCCAGCUCAGUAAUCACUAGCCUAGGGGCCAUUGUAA | 26 |

TABLE 7-continued

| | | |
|---|---|---|
| | GCUGCUAUGGCAAAACCAAGUGUACUGCCUCUAAUAAGA<br>ACAGAGGCAUAAUUAAAACCUUUUCAAAUGGCUGUGACU<br>AUGUGUCGAAUAAGGGCGUCGACACGGUCUCAGUAGGGA<br>AUACCCUCUACUACGUUAACAAACAGGAAGGCAAAUCCC<br>UUUAUGUAAAGGGCGAGCCCAUCAUAAAUUUCUACGACC<br>CACUUGUGUUCCCCAGUGAUGAAUUCGAUGCAUCAAUCU<br>CCCAGGUGAACGAAAAGAUCAAUCAAUCCCUUGCUUUUA<br>UACGAAAGUCAGAUGAACUCCUGCAUAACGUGAAUGCUG<br>GGAAAUCUACAACCAACAUCAUGAUCACUACCAUCAUUA<br>UUGUGAUUAUCGUAAUUCUGCUAUCCUUGAUUGCUGUCG<br>GGCUGCUUCUGUACUGUAAGGCCAGAUCGACGCCUGUGA<br>CCCUUUCAAAAGACCAACUUAGCGGUAUCAAUAAUAUUG<br>CCUUUAGCAAU | |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGGG<br>C | 4 |
| Corresponding amino acid sequence | MELLILKANAITTILTAVTECEASGQNITEEFYQSTCSAVSKGY<br>LSALRTGWYTSVITIELSNIKENKCNGTDAKVKLIKQELDKYK<br>NAVTELQLLMQSTPATNNGSGSAIASGVAVCKVLHLEGEVNK<br>IKSALLSTNKAVVSLSNGVSVLTFKVLDLKNYIDKQLLPILNK<br>QSCSISNIETVIEFQQKNNRLLEITREFSVNAGVTTPVSTYMLT<br>NSELLSLINDMPITNDQKKLMSNNVQIVRQQSYSIMCIIKEEVL<br>AYVVQLPLYGVIDTPCWKLHTSPLCTTNTKEGSNICLTRTDRG<br>WYCDNAGSVSFFPQAETCKVQSNRVFCDTMNSRTLPSEVNLC<br>NVDIFNPKYDCKIMTSKTDVSSSVITSLGAIVSCYGKTKCTASN<br>KNRGIIKTFSNGCDYVSNKGVDTVSVGNTLYYVNKQEGKSLY<br>VKGEPIINFYDPLVFPSDEFDASISQVNEKINQSLAFIRKSDELL<br>HNVNAGKSTINIMITTHIVIIVILLSLIAVGLLLYCKARSTPVTL<br>SKDQLSGINNIAFSN | |
| PolyA tail | 100 nt | |

VRC-1 (v2)

| | | |
|---|---|---|
| SEQ ID NO: 27 consists of from 5' end to 3' end: 5' UTR SEQ ID NO: 2, mRNA ORF SEQ ID NO: 28, and 3' UTR SEQ ID NO: 4. | | 27 |
| 0000€ Chemistry | 1-methylpseudouridine | |
| Cap | 7mG(5')ppp(5*)NlmpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC<br>GAGCUGCAGUUAUUGAUGCAGAGUACACCUGCCACCGGG<br>UCGGGCUCUGCCAUUUGCUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>AACGGAGUAAGUGUGUUAACAUUUAAGGUGCUGGACCUC<br>AAGAAUUAUAUUGACAAACAGUUGCUUCCUAUUCUAAAC<br>AAACAGAGCUGUUCAAUAAGUAAUAUUGAAACUGUUAUU<br>GAGUUUCAGCAGAAGAACAACAGGCUUCUUGAGAUUACA<br>CGCGAGUUCAGUGUCAAUGCCGGCGUUACAACACCCGUG<br>UCUACCUACAUGCUGACGAAUUCUGAGCUUCUCUCUCUC<br>AUAAACGACAUGCCCAUUACGAAUGACCAAAAGAAACUU<br>AUGUCCAACAACGUGCAGAUUGUGCGACAGCAAUCCUAU<br>AGCAUUAUGUGUAUCAUCAAGGAAGAGGUACUCGCUUAU<br>GUUGUGCAGCUACCACUCUAUGGUGUGAUUGACACCCCC<br>UGUUGGAAGCUGCAUACCAGUCCACUCUGCACCACUAAC<br>ACAAAGGAAGGGAGCAAUAUUUGCCUCACUCGAACCGAC<br>AGGGGGUGGUAUUGCGAUAAUGCGGGCUCCGUGUCCUUC<br>UUUCCACAGGCUGAAACUUGUAAGGUACAGUCAAACCGC<br>GUGUUCUGUGAUACUAUGAAUUCUCGUACUCUUCCCAGC<br>GAGGUUAAUCUCUGCAACGUCGACAUUUUCAAUCCUAAA<br>UAUGACUGCAAGAUCAUGACCAGCAAGACCGACGUCUCC<br>AGCUCAGUAAUCACUAGCCUAGGGGCCAUUGUAAGCUGC<br>UAUGGCAAAACCAAGUGUACUGCCUCUAAUAAGAACAGA<br>GGCAUAAUUAAAACCUUUUCAAAUGGCUGUGACUAUGUG<br>UCGAAUAAGGGCGUCGACACGGUCUCAGUAGGGAAUACC<br>CUCUACUGCGUUAACAAACAGGAAGGCAAAUCCCUUUAU<br>GUAAAGGGCGAGCCCAUCAUAAAUUUCUACGACCCACUU<br>GUGUUCCCCAGUGAUGAAUUCGAUGCAUCAAUCUCCCAG<br>GUGAACGAAAAGAUCAAUCAAUCCCUUGCUUUUAUACGA<br>AAGUCAGAUGAACUCCUGUCCGCCAUCGGUGGCUAUAUC<br>CCAGAAGCCCCAAGAGACGGACAAGCGUACGUCCGGAAA<br>GAUGGUGAGUGGGUCCUCCUCUCUACCUUUCUU | 28 |

TABLE 7-continued

| | | |
|---|---|---|
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGGGC | 4 |
| Corresponding amino acid sequence | MELLILKANAITTILTAVTECFASGQNITEEFYQSTCSAVSKGY<br>LSALRTGWYTSVITIELSNIKENKCNGTDAKVKLIKQELDKYK<br>NAVTELQLLMQSTPATGSGSAICSGVAVCKVLHLEGEVNKIK<br>SALLSTNKAVVSLSNGVSVLTFKVLDLKNYIDKQLLPILNKQS<br>CSISNIETVIEFQQKNNRLLEITREFSVNAGVTTPVSTYMLINSE<br>LLSLINDMPITNDQKKLMSNNVQIVRQQSYSIMCHIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>NRGIIKTFSNGCDYVSNKGVDTVSVGNTLYCVNKQEGKSLYV<br>KGEPIINFYDPLVFPSDEFDASISQVNEKINQSLAFIRKSDELLS<br>AIGGYIPEAPRDGQAYVRKDGEWVLLSTFL | 14 |
| PolyA tail | 100 nt | |

VRC-2 (v2)

| | | |
|---|---|---|
| SEQ ID NO: 29 consists of from 5' end to 3' end: 5' UTR SEQ ID NO: 2, mRNA ORF SEQ ID NO: 30, and 3' UTR SEQ ID NO: 4. | | 29 |
| Chemistry | 1-methylpseudouridine | |
| Cap | 7mG(5')ppp(5')NimpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC<br>GAGCUGCAGUUAUUGAUGCAGAGUACACCUGCCACCGGG<br>UCGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>GGCUGCGGAGUAAGUGUGUUAACAUUUAAGGUGCUGGAC<br>CUCAAGAAUUAUAUUGACAAACAGUUGCUUCCUAUUCUA<br>AACAAACAGAGCUGUUCAAUAAGUAAUAUUGAAACUGUU<br>AUUGAGUUUCAGCAGAAGAACAACAGGCUUCUUGAGAUU<br>ACACGCGAGUUCAGUGUCAAUGCCGGCGUUACAACACCC<br>GUGUCUACCUACAUGCUGACGAAUUCUGAGCUUCUCUCU<br>CUCAUAAACGACAUGCCCAUUACGAAUGACCAAAAGAAA<br>CUUAUGUCCAACAACGUGCAGAUUGUGCGACAGCAAUCC<br>UAUAGCAUUAUGUGUAUCAUCAAGGAAGAGGUACUCGCU<br>UAUGUUGUGCAGCUACCACUCUAUGGUGUGAUUGACACC<br>CCCUGUUGGAAGCUGCAUACCAGUCCACUCUGCACCACUA<br>ACACAAAGGAAGGGAGCAAUAUUUGCCUCACUCGAACCG<br>ACAGGGGGUGGUAUUGCGAUAAUGCGGGCUCCGUGUCCU<br>UCUUUCCACAGGCUGAAACUUGUAAGGUACAGUCAAACC<br>GCGUGUUCUGUGAUACUAUGAAUUCUCGUACUCUUCCCA<br>GCGAGGUUAAUCUCUGCAACGUCGACAUUUUCAAUCCUA<br>AAUAUGACUGCAAGAUCAUGACCAGCAAGACCGACGUCU<br>CCAGCUCAGUAAUCACUAGCCUAGGGGCCAUUGUAAGCU<br>GCUAUGGCAAAACCAAGUGUACUGCCUCUAAUAAGUGCA<br>GAGGCAUAAUUAAAACCUUUUCAAAUGGCUGUGACUAUG<br>UGUCGAAUAAGGGCGUCGACACGGUCUCAGUAGGGAAUA<br>CCCUCUACUACGUUAACAAACAGGAAGGCAAAUCCCUUU<br>AUGUAAAGGGCGAGCCCAUCAUAAAUUUCUACGACCCAC<br>UUGUGUUCCCCAGUGAUGAAUUCGAUGCAUCAAUCUCCC<br>AGGUGAACGAAAAGAUCAAUCAAUCCCUUGCUUUUAUAC<br>GAAAGUCAGAUGAACUCCUGUCCGCCAUCGGUGGCUAUA<br>UCCCAGAAGCCCCAAGAGACGGACAAGCGUACGUCCGGA<br>AAGAUGGUGAGUGGGUCCUCCUCUCUACCUUUCUU | 30 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGGC | 4 |
| Corresponding amino acid sequence | MELLILKANAITTILTAVTICIASGQNITEEFYQSTCSAVSKGY<br>LSALRTGWYTSVITIELSNIKENKCNGTDAKVKLIKQELDKYK<br>NAVTELQLLMQSTPATGSGSALASGVAVCKVLHLEGEVNKIK<br>SALLSTNKAVVSLSGCGVSVLTFKVLDLKNYIDKQLLPILNKQ<br>SCSISNIETVIEFQQKNNRLLEITREFSVNAGVTTPVSTYMLINS<br>ELLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>CRGIIKTESNGCDYVSNKGVDTVSVGNTLYYVNKQEGKSLYV<br>KGEPINFYDPLVFPSDEFDASISQVNEKINQSLAFIRKSDELLS<br>AIGGYIPEAPRDGQAYVRKDGEWVLLSTFL | 17 |
| PolyA tail | 100 nt | |

TABLE 7-continued

| | | |
|---|---|---|
| | VRC-3 (v2) | |
| SEQ ID NO: 31 consists of from 5' end to 3' end: 5' UTR SEQ ID NO: 2, mRNA ORF SEQ ID NO: 32, and 3' UTR SEQ ID NO: 4. | | 31 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC<br>GAGCUGCAGUUAUUGAUGCAGAGUACACCUGCCACCAAU<br>AACGGGUCGGGCUCUGCCAUUGCUUCCGGCGUGGCUGUA<br>UGUAAAGUUCUCCACCUCGAGGGAGAGGUUAAUAAGAUU<br>AAGUCGGCCCUGCUGAGUACUAACAAAGCAGUGGUGUCG<br>CUGAGUAACGGAGUAAGUGUGUUAACAUUUAAGGUGCUG<br>GACCUCAAGAAUUAUAUUGACAAACAGUUGCUUCCUAUU<br>CUAAACAAACAGAGCUGUUCAAUAAGUAAUAUUGAAACU<br>GUUAUUGAGUUUCAGCAGAAGAACAACAGGCUUCUUGAG<br>AUUACACGCGAGUUCAGUGUCAAUGCCGGCGUUACAACA<br>CCCGUGUCUACCUACAUGCUGACGAAUUCUGAGCUUCUC<br>UCUCUCAUAAACGACAUGCCCAUUACGAAUGACCAAAAG<br>AAACUUAUGUCCAACAACGUGCAGAUUGUGCGACAGCAA<br>UCCUAUAGCAUUAUGUGUAUCAUCAAGGAAGAGGUACUC<br>GCUUAUGUUGUGCAGCUACCACUCUAUGGUGUGAUUGAC<br>ACCCCCUGUUGGAAGCUGCAUACCAGUCCACUCUGCACCA<br>CUAACACAAAGGAAGGGAGCAAUAUUUGCCUCACUCGAA<br>CCGACAGGGGGUGGUAUUGCGAUAAUGCGGGCUCCGUGU<br>CCUUCUUUCCACAGGCUGAAACUUGUAAGGUACAGUCAA<br>ACCGCGUGUUCUGUGAUACUAUGAAUUCUCGUACUCUUC<br>CCAGCGAGGUUAAUCUCUGCAACGUCGACAUUUUCAAUC<br>CUAAAUAUGACUGCAAGAUCAUGACCAGCAAGACCGACG<br>UCUCCAGCUCAGUAAUCACUAGCCUAGGGGCCAUUGUAA<br>GCUGCUAUGGCAAAACCAAGUGUACUGCCUCUAAUAAGA<br>ACAGAGGCAUAAUUAAAACCUUUUCAAAUGGCUGUGACU<br>AUGUGUCGAAUAAGGGCGUCGACACGGUCUCAGUAGGGA<br>AUACCCUCUACUACGUUAACAAACAGGAAGGCAAAUCCC<br>UUUAUGUAAAGGGCGAGCCCAUCAUAAAUUUCUACGACC<br>CACUUGUGUUCCCCAGUGAUGAAUUCGAUGCAUCAAUCU<br>CCCAGGUGAACGAAAAGAUCAAUCAAUCCCUUGCUUUUA<br>UACGAAAGUCAGAUGAACUCCUGUCCGCCAUCGGUGGCU<br>AUAUCCCAGAAGCCCCAAGAGACGGACAAGCGUACGUCC<br>GGAAAGAUGGUGAGUGGGUCCUCCUCUCUACCUUUCUU | 32 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGGC | 4 |
| Corresponding amino acid sequence | MELLILKANAITTILTAVTECFASGQNITEEFYQSTCSAVSKGY<br>LSALRTGWYTSVITIELSNIKENKCNGTDAKVKLIKQELDKYK<br>NAVTELQLLMQSTPATNNGSGSAIASGVAVCKVLHLEGEVNK<br>IKSALLSTNKAVVSLSNGVSVLTFKVLDLKNYIDKQLLPILNK<br>QSCSISNIETVIEFQQKNNRLLEITREPSVNAGVTTPVSTYMLT<br>NSELLSLINDMPITNDQKKLMSNNVQIVRQQSYSIMCIKEEVL<br>AYVVQLPLYGVIDTPCWKLHTSPLCTTNTKEGSNICLTRTDRG<br>WYCDNAGSVSFFPQAETCKVQSNRVFCDTMNSRTLPSEVNLC<br>NVDIFNPKYDCKIMTSKTDVSSSVITSLGAIVSCYGKTKCTASN<br>KNRGHIKTESNGCDYVSNKGVDTVSVQNTLYYVNKQEGKSLY<br>VKGEPIINFYDPLVFPSDEFDASISQVNEKINQSLAFIRKSDELL<br>SAIGGYIPEAPRDGQAYVRKDGEWVLLSTFL | 20 |
| Poly A tail | 100 nt | |
| | mVRC-4 | |
| SEQ ID NO: 33 consists of from 5' end to 3' end: 5' UTR SEQ ID NO: 2, mRNA ORF SEQ ID NO: 34, and 3' UTR SEQ ID NO: 4. | | 33 |
| Chemistry | 1-methylpsendouridine | |
| Cap | 7mG(5')ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGGGCGCGCUCCGCACAGGAUGG<br>UACACCUCCGUGAUCACCAUCGAGCUCAGCAAUAUUAAA<br>GAGAUUAAGUGCAAUGGUACCGACGCUAAAGUCAAACUU<br>AUCAAGCAGGAACUCGACAAAUAUAAGAACGCUGUGACC | 34 |

TABLE 7-continued

| | | |
|---|---|---|
| | GACCUGCAGUUAUUGAUGCAGAGUACACCUGCCACCGGG<br>UCGGGCUCUGCCAUUUGCUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>AACGGAGUAAGUGUGUUAACAUUUAAGGUGCUGGACCUC<br>AAGAAUUAUAUUGACAAACAGUUGCUUCCUAUUCUAAAC<br>AAACAGAGCUGUUCAAUACCCAAUAUUGAAACUGUUAUU<br>GAGUUUCAGCAGAAGAACAACAGGCUUCUUGAGAUUACA<br>CGCGAGUUCAGUGUCAAUGCCGGCGUUACAACACCCGUG<br>UCUACCUACAUGCUGACGAAUUCUGAGCUUCUCUCUCUC<br>AUJAAACGACAUGCCCAUUACGAAUGACCAAAAGAAACUU<br>AUGUCCAACAACGUGCAGAUUGUGCGACAGCAAUCCUAU<br>AGCAUUAUGUGUAUCAUCAAGGAAGAGGUACUCGCUUAU<br>GUUGUGCAGCUACCACUCUAUGGUGUGAUUGACACCCCC<br>UGUUGGAAGCUGCAUACCAGUCCACUCUGCACCACUAAC<br>ACAAAGGAAGGGAGCAAUAUUUGCCUCACUCGAACCGAC<br>AGGGGGUGGUAUUGCGAUAAUGCGGGCUCCGUGUCCUUC<br>UUUCCACAGGCUGAAACUUGUAAGGUACAGUCAAACCGC<br>GUGUUCUGUGAUACUAUGAAUUCUCGUACUCUUCCCAGC<br>GAGGUUAAUCUCUGCAACGUCGACAUUUUCAAUCCUAAA<br>UAUGACUGCAAGAUCAUGACCAGCAAGACCGACGUCUCC<br>AGCUCAGUAAUCACUAGCCUAGGGGCCAUUGUAAGCUGC<br>UAUGGCAAAACCAAGUGUACUGCCUCUAAUAAGAACAGA<br>GGCAUAAUUAAAACCUUUUCAAAUGGCUGUGACUAUGUG<br>UCGAAUAAGGGCGUCGACACGGUCUCAGUAGGGAAUACC<br>CUCUACUGCGUUAACAAACAGGAAGGCCAGUCCCUUUAU<br>GUAAAGGGCGAGCCCAUCAUAAAUUUCUACGACCCACUU<br>GUGUUCCCCAGUGAUGAAUUCGAUGCAUCAAUCUCCCAG<br>GUGAACGAAAAGAUCAAUCAAUCCCUUGCUUUUAUACGA<br>AAGUCAGAUGAACUCCUGCAUAACGUGAAUGCUGGGAAA<br>UCUACAACCAACAUCAUGAUCACUACCAUCAUUAUUGUG<br>AUUAUCGUAAUUCUGCUAUCCUUGAUUGCUGUCGGGCUG<br>CUUCUGUACUGUAAGGCCAGAUCGACGCCUGUGACCCUU<br>UCAAAAGACCAACUUAGCGGUAUCAAUAAUAUUGCCUUU<br>AGCAAU | |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGGC | 4 |
| Corresponding amino acid sequence | MELLILKANAITTILTAVTFCFASGQNITEEFYQSTCSAVSKGY<br>LGALRTGWYTSVITIELSNIKEIKCNGTDAKVKLIKQELDKYK<br>NAVTDLQLLMQSTPATGSGSAICSGVAVCKVLHLEGEVNKIK<br>SALLSTNKAVVSLSNGVSVLTFKVLDLKNYIDKQLLPILNKQS<br>CSIPNIETVIEFQQKNNRLLEITREFSVNAGVTTPVSTYMLINSE<br>LLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>NRGIIKTFSNGCDYVSNKGVDTVSVGNTLYCVNKQEGQSLYV<br>KGEPIINFYDPLVFPSDEFDASISQVNEKINQSLAFIRKSDELLH<br>NVNAGKSTTNIMITTIIIVIIVILLSLIAVGLLLYCKARSTPVTLS<br>KDQLSGINNIAFSN | 35 |
| PolyA tail | 100 nt | |

m VRC-5

| | | |
|---|---|---|
| SEQ ID NO: 36 consists of from 5' end to 3' end: 5' UTR SEQ ID NO: 2, mRNA ORF SEQ ID NO: 37, and 3' UTR SEQ ID NO: 4. | | 36 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGGGCGCGCUCCGCACAGGAUGG<br>UACACCUCCGUGAUCACCAUCGAGCUCAGCAAUAUUAAA<br>GAGAUUAAGUGCAAUGGUACCGACGCUAAAGUCAAACUU<br>AUCAAGCAGGAACUCGACAAAUAUAAGAACGCUGUGACC<br>GACCUGCAGUUAUUGAUGCAGAGUACACCUGCCACCGGG<br>UCGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>GGCUGCGGAGUAAGUGUGUUAACAUUUAAGGUGCUGGAC<br>CUCAAGAAUUAUAUUGACAAACAGUUGCUUCCUAUUCUA<br>AACAAACAGAGCUGUUCAAUACCCAAUAUUGAAACUGUU<br>AUUGAGUUUCAGCAGAAGAACAACAGGCUUCUUGAGAUU<br>ACACGCGAGUUCAGUGUCAAUGCCGGCGUUACAACACCC<br>GUGUCUACCUACAUGCUGACGAAUUCUGAGCUUCUCUCU<br>CUCAUAAACGACAUGCCCAUUACGAAUGACCAAAAGAAA<br>CUUAUGUCCAACAACGUGCAGAUUGUGCGACAGCAAUCC | 37 |

TABLE 7-continued

| | | |
|---|---|---|
| | UAUAGCAUUAUGUGUAUCAUCAAGGAAGAGGUACUCGCU | |
| | UAUGUUGUGCAGCUACCACUCUAUGGUGUGAUUGACACC | |
| | CCCUGUUGGAAGCUGCAUACCAGUCCACUCUGCACCACUA | |
| | ACACAAAGGAAGGGAGCAAUAUUUGCCUCACUCGAACCG | |
| | ACAGGGGGUGGUAUUGCGAUAAUGCGGGCUCCGUGUCCU | |
| | UCUUUCCACAGGCUGAAACUUGUAAGGUACAGUCAAACC | |
| | GCGUGUUCUGUGAUACUAUGAAUUCUCGUACUCUUCCCA | |
| | GCGAGGUUAAUCUCUGCAACGUCGACAUUUUCAAUCCUA | |
| | AAUAUGACUGCAAGAUCAUGACCAGCAAGACCGACGUCU | |
| | CCAGCUCAGUAAUCACUAGCCUAGGGGCCAUUGUAAGCU | |
| | GCUAUGGCAAAACCAAGUGUACUGCCUCUAAUAAGUGCA | |
| | GAGGCAUAAUUAAAACCUUUUCAAAUGGCUGUGACUAUG | |
| | UGUCGAAUAAGGGCGUCGACACGGUCUCAGUAGGGAAUA | |
| | CCCUCUACUACGUUAACAAACAGGAAGGCCAGUCCCUUU | |
| | AUGUAAAGGGCGAGCCCAUCAUAAAUUUCUACGACCCAC | |
| | UUGUGUUCCCCAGUGAUGAAUUCGAUGCAUCAAUCUCCC | |
| | AGGUGAACGAAAAGAUCAAUCAAUCCCUUGCUUUUAUAC | |
| | GAAAGUCAGAUGAACUCCUGCAUAACGUGAAUGCUGGGA | |
| | AAUCUACAACCAACAUCAUGAUCACUACCAUCAUUAUUG | |
| | UGAUUAUCGUAAUUCUGCUAUCCUUGAUUGCUGUCGGGC | |
| | UGCUUCUGUACUGUAAGGCCAGAUCGACGCCUGUGACCC | |
| | UUUCAAAAGACCAACUUAGCGGUAUCAAUAAUAUUGCCU | |
| | UUAGCAAU | |
| 3' UTR | UGAUAAUAGGCUGGAGCCUCGGUGGCCAUGCUUCUUGCC | 4 |
| | CCUUGGGCCUCCCCCCAGCCCCUCCUCCCCUUCCUGCACC | |
| | CGUACCCCCGUGGUCUUUGAAUAAAGUCUGAGUGGGCGGC | |
| Corresponding amino | MELLILKANAITTILTAVTCEASGQNITEEFYQSTCSAVSKGY | 38 |
| acid sequence | LGALRTGWYTSVITIELSNIKEIKCNGTDAKVKLIKQELDKYK. | |
| | NAVTDLQLLMQSTPATGSGSAIASGVAVCKVLHLEGEVNKIK | |
| | SALLSTNKAVVSLSGCGVSVLTFKVLDLKNYIDKQLLPILNKQ | |
| | SCSIPNIETVIEFQQKNNRLLEITREFSVNAGVTTPVSTYMLTNS | |
| | ELLSLINDMPITNDQKKLMSNNVQIVRQQSYSIMCHIKEEVLAY | |
| | VVQLPLYGVIDTPCWKLHTSPLCTTNTKEGSNICLTRTDRGW | |
| | YCDNAGSVSFFPQAETCKVQSNRVFCDTMNSRTLPSEVNLCN | |
| | VDIFNPKYDCKIMTSKTDVSSSVITSLGAIVSCYGKTKCTASNK | |
| | CRGIIKTESNGCDYVSNKGVDTVSVGNTLYYVNKQEGQSLYV | |
| | KGEPIINFYDPLVFPSDEFDASISQVNEKINQSLAFIRKSDELLH | |
| | NVNAGKSTTNIMITTIIIVIIVILLSLIAVGLLLYCKARSTPVTLS | |
| | KDQLSGINNIAFSN | |
| PolyA tail | 100 nt | |

mVRC-6

| | | |
|---|---|---|
| SEQ ID NO: 39 consists of from 5' end to 3' end: 5' UTR SEQ ID NO: 2, mRNA ORF SEQ ID NO: 40, and 3' UTR SEQ ID NO: 4. | | 39 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA | 2 |
| | AGAGCCACC | |
| ORF of mRNA | AUGGAACUGCUCAUUUUGAAGGCAAACGCUAUCACGACA | 40 |
| Construct | AUACUCACUGCAGUGACCUUCUGUUUUGCCUCAGGCCAG | |
| (excluding the stop | AACAUAACCGAGGAGUUUUAUCAAUCUACAUGCAGCGCU | |
| codon) | GUAUCUAAAGGCUACCUGAGUGCGCUCCGCACAGGAUGG | |
| | UACACCUCCGUGAUCACCAUCGAGCUCAGCAAUAUUAAA | |
| | GAGAACAAGUGCAAUGGUACCGACGCUAAAGUCAAACUU | |
| | AUCAAGCAGGAACUCGACAAAUAUAAGAACGCUGUGACC | |
| | GAGCUGCAGUUAUUGAUGCAGAGUACACCUGCCACCGGG | |
| | UCGGGCUCUGCCAUUGCUUCCGGCGUGGCUGUAUGUAAA | |
| | GUUCUCCACCUCGAGGGAGAGGUUAAUAAGAUUAAGUCG | |
| | GCCCUGCUGAGUACUAACAAAGCAGUGGUGUCGCUGAGU | |
| | AACGGAGUAAGUGUGUUAACAUUUAAGGUGCUGGACCUC | |
| | AAGAAUUAUAUUGACAAACAGUUGCUUCCUAUUCUAAAC | |
| | AAACAGAGCUGUUCAAUAAGUAAUAUUGAAACUGUUAUU | |
| | GAGUUUCAGCAGAAGAACAACAGGCUUCUUGAGAUUACA | |
| | CGCGAGUUCAGUGUCAAUGCCGGCGUUACAACACCCGUG | |
| | UCUACCUACAUGCUGACGAAUUCUGAGCUUCUCUCUCUC | |
| | AUAAACGACAUGCCCAUUACGAAUGACCAAAAGAAACUU | |
| | AUGUCCAACAACGUGCAGAUUGUGCGACAGCAAUCCUAU | |
| | AGCAUUAUGUGUAUCAUCAAGGAAGAGGUACUCGCUUAU | |
| | GUUGUGCAGCUACCACUCUAUGGUGUGAUUGACACCCCC | |
| | UGUUGGAAGCUGCAUACCAGUCCACUCUGCACCACUAAC | |
| | ACAAAGGAAGGGAGCAAUAUUUCCCUCACUCGAACCGAC | |
| | AGGGGGUGGUAUUGCGAUAAUGCGGGCUCCGUGUCCUUC | |
| | UUUCCACAGGCUGAAACUUGUAAGGUACAGUCAAACCGC | |
| | GUGUUCUGUGAUACUAUGAAUUCUCGUACUCUUCCCAGC | |
| | GAGGUUAAUCUCUGCAACGUCGACAUUUUCAAUCCUAAA | |
| | UAUGACUGCAAGAUCAUGACCAGCAAGACCGACGUCUCC | |
| | AGCUCAGUAAUCACUAGCCUAGGGGCCAUUGUAAGCUGC | |
| | UAUGGCAAAACCAAGUGUACUGCCUCUAAUAAGAACAGA | |
| | GGCAUAAUUAAAACCUUUUCAAAUGGCUGUGACUAUGUG | |

TABLE 7-continued

| | | |
|---|---|---|
| | UCGAAUAAGGGCGUCGACACGGUCUCAGUAGGGAAUACC<br>CUCUACUACGUUAACAAACAGGAAGGCAAAUCCCUUUAU<br>GUAAAGGGCGAGCCCAUCAUAAAUUUCUACGACCCACUU<br>GUGUUCCCCAGUGAUGAAUUCGAUGCAUCAAUCUCCCAG<br>GUGAACGAAAAGAUCAAUCAAUCCCUUGCUUUUAUACGA<br>AAGUCAGAUGAACUCCUGCAUAACGUGAAUGCUGGGAAA<br>UCUACAACCAACAUCAUGAUCACUACCAUCAUUAUUGUG<br>AUUAUCGUAAUUCUGCUAUCCUUGAUUGCUGUCGGGCUG<br>CUUCUGUACUGUAAGGCCAGAUCGACGCCUGUGACCCUU<br>UCAAAAGACCAACUUAGCGGUAUCAAUAAUAUUGCCUUU<br>AGCAAU | |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGGGGC | 4 |
| Corresponding amino acid sequence | MELLILKANAITTILTAVTICHASGQNITEEFYQSTCSAVSKGY<br>LSALRTGWYTSVITIELSNIKENKCNGTDAKVKLIKQELDKYK<br>NAVTELQLLMQSTPATGSGSAIASGVAVCKVLHLEGEVNKIK<br>SALLSTNKAVVSLSNGVSVLTFKVLDLKNYIDKQLLPILNKQS<br>CSISNIETVIEFQQKNNRLLEITREFSVNAGVTTPVSTYMLINSE<br>LLSLINDMPITNDQKKLMSNNVQIVRQQSYSIMCHIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>NRGHIKTESNGCDYVSNKGVDTVSVQNTLYYVNKQEGKSLYV<br>KGEPIINFYDPLVFPSDEFDASISQVNEKINQSLAFIRKSDELLH<br>NVNAGKSTTNIMITTIIIVIIVILLSLIAVGLLLYCKARSTPVTLS<br>KDQLSGINNIAFSN | 41 |
| PolyA tail | 100 nt | |

VRC-4

| | | |
|---|---|---|
| SEQ ID NO: 42 consists of from 5' end to 3' end: 5' UTR SEQ ID NO: 2, mRNA ORF SEQ ID NO: 43, and 3' UTR SEQ ID NO: 4. | | 42 |
| 6000<br>Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGGGCGCGCUCCGCACAGGAUGG<br>UACACCUCCGUGAUCACCAUCGAGCUCAGCAAUAUUAAA<br>GAGAUUAAGUGCAAUGGUACCGACGCUAAAGUCAAACUU<br>AUCAAGCAGGAACUCGACAAAUAUAAGAACGCUGUGACC<br>GACCUGCAGUUAUUGAUGCAGAGUACACCUGCCACCGGG<br>UCGGGCUCUGCCAUUUGCUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>AACGGAGUAAGUGUGUUAACAUUUAAGGUGCUGGACCUC<br>AAGAAUUAUAUUGACAAACAGUUGCUUCCUAUUCUAAAC<br>AAACAGAGCUGUUCAAUACCCAAUAUUGAAACUGUUAUU<br>GAGUUUCAGCAGAAGAACAACAGCCUUCUUGAGAUUACA<br>CGCGAGUUCAGUGUCAAUGCCGGCGUUACAACACCCGUG<br>UCUACCUACAUGCUGACGAAUUCUGAGCUUCUCUCUCUC<br>AUAAACGACAUGCCCAUUACGAAUGACCAAAAGAAACUU<br>AUGUCCAACAACGUGCAGAUUGUGCGACAGCAAUCCUAU<br>AGCAUUAUGUGUAUCAUCAAGGAAGAGGUACUCGCUUAU<br>GUUGUGCAGCUACCACUCUAUGGUGUGAUUGACACCCCC<br>UGUUGGAAGCUGCAUACCAGUCCACUCUGCACCACUAAC<br>ACAAAGGAAGGGAGCAAUAUUUGCCUCACUCGAACCGAC<br>AGGGGGUGGUAUUGCGAUAAUGCGGGCUCCGUGUCCUUC<br>UUUCCACAGGCUGAAACUUGUAAGGUACAGUCAAACCGC<br>GUGUUCUGUGAUACUAUGAAUUCUCGUACUCUUCCCAGC<br>GAGGUUAAUCUCUGCAACGUCGACAUUUUCAAUCCUAAA<br>UAUGACUGCAAGAUCAUGACCAGCAAGACCGACGUCUCC<br>AGCUCAGUAAUCACUAGCCUAGGGGCCAUUGUAAGCUGC<br>UAUGGCAAAACCAAGUGUACUGCCUCUAAUAAGAACAGA<br>GGCAUAAUUAAAACCUUUUCAAAUGGCUGUGACUAUGUG<br>UCGAAUAAGGGCGUCGACACGGUCUCAGUAGGGAAUACC<br>CUCUACUGCGUUAACAAACAGGAAGGCCAGUCCCUUUAU<br>GUAAAGGGCGAGCCCAUCAUAAAUUUCUACGACCCACUU<br>GUGUUCCCCAGUGAUGAAUUCGAUGCAUCAAUCUCCCAG<br>GUGAACGAAAAGAUCAAUCAAUCCCUUGCUUUUAUACGA<br>AAGUCAGAUGAACUCCUGUCCGCCAUCGGUGGCUAUAUC<br>CCAGAAGCCCCAAGAGACGGACAAGCGUACGUCCGGAAA<br>GAUGGUGAGUGGGUCCUCCUCUCUACCUUUCUU | 43 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGGC | 4 |

TABLE 7-continued

| | | |
|---|---|---|
| Corresponding amino acid sequence | MELLILKANAITTILTAVTECFASGQNITEEFYQSTCSAVSKGY<br>LGALRTGWYTSVITIELSNIKEIKCNGTDAKVKLIKQELDKYK<br>NAVTDLQLLMQSTPATGSGSAICSGVAVCKVLHLEGEVNKIK<br>SALLSTNKAVVSLSNGVSVLTFKVLDLKNYIDKQLLPILNKQS<br>CSIPNIETVIEFQQKNNRLLEITREFSVNAGVTTPVSTYMLINSE<br>LLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>NRGIIKTFSNGCDYVSNKGVDTVSVGNTLYCVNKQEGQSLYV<br>KGEPIINFYDPLVFPSDEFDASISQVNEKINQSLAFIRKSDELLS<br>AIGGYTPEAPRDGQAYVRKDGEWVLLSTFL | 44 |
| PolyA tail | 100 nt | |

VRC-5

| | | |
|---|---|---|
| SEQ ID NO: 45 consists of from 5' end to 3' end: 5' UTR SEQ ID NO: 2, mRNA ORF SEQ ID NO: 46, and 3' UTR SEQ ID NO: 4. | | 45 |
| Chemistry | 1-methylpseudouridine | |
| Cap | 7mG(5")ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGGGCGCGCUCCGCACAGGAUGG<br>UACACCUCCGUGAUCACCAUCGAGCUCAGCAAUAUUAAA<br>GAGAUUAAGUGCAAUGGUACCGACGCUAAAGUCAAACUU<br>AUCAAGCAGGAACUCGACAAAUAUAAGAACGCUGUGACC<br>GACCUGCAGUUAUUGAUGCAGAGUACACCUGCCACCGGG<br>UCGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>GGCUGCGGAGUAAGUGUGUUAACAUUUAAGGUGCUGGAC<br>CUCAAGAAUUAUAUUGACAAACAGUUGCUUCCUAUUCUA<br>AACAAACAGAGCUGUUCAAUACCCAAUAUUGAAACUGUU<br>AUUGAGUUUCAGCAGAAGAACAACAGGCUUCUUGAGAUU<br>ACACGCGAGUUCAGUGUCAAUGCCGGCGUUACAACACCC<br>GUGUCUACCUACAUGCUGACGAAUUCUGAGCUUCUCUCU<br>CUCAUAAACGACAUGCCCAUUACGAAUGACCAAAAGAAA<br>CUUAUGUCCAACAACGUGCAGAUUGUGCGACAGCAAUCC<br>UAUAGCAUUAUGUGUAUCAUCAAGGAAGAGGUACUCGCU<br>UAUGUUGUGCAGCUACCACUCUAUGGUGUGAUUGACACC<br>CCCUGUUGGAAGCUGCAUACCAGUCCACUCUGCACCACUA<br>ACACAAAGGAAGGGAGCAAUAUUUGCCUCACUCGAACCG<br>ACAGGGGGUGGUAUUGCGAUAAUGCGGGCUCCGUGUCCU<br>UCUUUCCACAGGCUGAAACUUGUAAGGUACAGUCAAACC<br>GCGUGUUCUGUGAUACUAUGAAUUCUCGUACUCUUCCCA<br>GCGAGGUUAAUCUCUGCAACGUCGACAUUUUCAAUCCUA<br>AAUAUGACUGCAAGAUCAUGACCAGCAAGACCGACGUCU<br>CCAGCUCAGUAAUCACUAGCCUAGGGGCCAUUGUAAGCU<br>GCUAUGGCAAAACCAAGUGUACUGCCUCUAAUAAGUGCA<br>GAGGCAUAAUUAAAACCUUUUCAAAUGGCUGUGACUAUG<br>UGUCGAAUAAGGGCGUCGACACGGUCUCAGUAGGGAAUA<br>CCCUCUACUACGUUAACAAACAGGAAGGCCAGUCCCUUU<br>AUGUAAAGGCCGAGCCCAUCAUAAAUUUCUACGACCCAC<br>UUGUGUUCCCCAGUGAUGAAUUCGAUGCAUCAAUCUCCC<br>AGGUGAACGAAAAGAUCAAUCAAUCCCUUGCUUUUAUAC<br>GAAAGUCAGAUGAACUCCUGUCCGCCAUCGGUGGCUAUA<br>UCCCAGAAGCCCCAAGAGACGGACAAGCGUACGUCCGGA<br>AAGAUGGUGAGUGGGUCCUCCUCUCUACCUUUCUU | 46 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MELLILKANAITTILTAVTECFASGQNITEEFYQSTCSAVSKGY<br>LGALRTGWYTSVITIELSNIKEIKCNGTDAKVKLIKQELDKYK<br>NAVTDLQLLMQSTPATGSGSAIASGVAVCKVLHLEGEVNKIK<br>SALLSTNKAVVSLSGCGVSVLTFKVLDLKNYIDKQLLPILNKQ<br>SCSIPNIETVIEFQQKNNRLLEITREFSVNAGVTTPVSTYMLINS<br>ELLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>CRGIIKTFSNGCDYVSNKGVDTVSVGNTLYYVNKQEGQSLYV<br>KGEPIINFYDPLVFPSDEFDASISQVNEKINQSLAFIRKSDELLS<br>AIGGYIPEAPRDGQAYVRKDGEWVLLSTFL | 47 |
| PolyA tail | 100 nt | |

TABLE 7-continued

VRC-6

SEQ ID NO: 48 consists of from 5' end to 3' end: 5' UTR SEQ ID NO: 2, mRNA ORF SEQ ID NO: 49, and UTR SEQ ID NO: 4.

| | | |
|---|---|---|
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC<br>GAGCUGCAGUUAUUGAUGCAGAGUACACCUGCCACCCGG<br>UCGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>AACGGAGUAAGUGUGUUAACAUUUAAGGUGCUGGACCUC<br>AAGAAUUAUAUUGACAAACAGUUGCUUCCUAUUCUAAAC<br>AAACAGAGCUGUUCAAUAAGUAAUAUUGAAACUGUUAUU<br>GAGUUUCAGCAGAAGAACAACAGGCUUCUUGAGAUUACA<br>CGCGAGUUCAGUGUCAAUGCCCGCGUUACAACACCCGUG<br>UCUACCUACAUGCUGACGAAUUCUGAGCUUCUCUCUCUC<br>AUAAACGACAUGCCCAUUACGAAUGACCAAAAGAAACUU<br>AUGUCCAACAACGUGCAGAUUGUGCGACAGCAAUCCUAU<br>AGCAUUAUGUGUAUCAUCAAGGAAGAGGUACUCGCUUAU<br>GUUGUGCAGCUACCACUCUAUGGUGUGAUUGACACCCCC<br>UGUUGGAAGCUGCAUACCAGUCCACUCUGCACCACUAAC<br>ACAAAGGAAGGGAGCAAUAUUUGCCUCACUCGAACCGAC<br>AGGGGGUGGUAUUGCGAUAAUGCGGGCUCCGUGUCCUUC<br>UUUCCACAGGCUGAAACUUGUAAGGUACAGUCAAACCGC<br>GUGUUCUGUGAUACUAUGAAUUCUCGUACUCUUCCCAGC<br>GAGGUUAAUCUCUGCAACGUCGACAUUUUCAAUCCUAAA<br>UAUGACUGCAAGAUCAUGACCAGCAAGACCGACGUCUCC<br>AGCUCAGUAAUCACUAGCCUAGGGGCCAUUGUAAGCUGC<br>UAUGGCAAAACCAAGUGUACUGCCUCUAAUAAGAACAGA<br>GGCAUAAUUAAAACCUUUUCAAAUGGCUGUGACUAUGUG<br>UCGAAUAAGGGCGUCGACACGGUCUCAGUAGGGAAUACC<br>CUCUACUACGUUAACAAACAGGAAGGCAAAUCCCUUUAU<br>GUAAAGGGCGAGCCCAUCAUAAAUUUCUACGACCCACUU<br>GUGUUCCCCAGUGAUGAAUUCGAUGCAUCAAUCUCCCAG<br>GUGAACGAAAAGAUCAAUCAAUCCCUUGCUUUUAUACGA<br>AAGUCAGAUGAACUCCUGUCCGCCAUCGGUGGCUAUAUC<br>CCAGAAGCCCCAAGAGACGGACAAGCGUACGUCCGGAAA<br>GAUGGUGAGUGGGUCCUCCUCUCUACCUUUCUU | 49 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGGGC | 4 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSTPATGSGSAIASGVAVCKVLHLEGEVNKIK<br>SALLSTNKAVVSLSNGVSVLTFKVLDLKNYIDKQLLPILNKQS<br>CSISNIETVIEFQQKNNRLLEITREFSVNAGVTTPVSTYMLINSE<br>LLSLINDMPITNDQKKLMSNNVQIVRQQSYSIMCHIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>NRGHKTESNGCDYVSNKGVDTVSVGNTLYYVNKQEGKSLYV<br>KGEPIINFYDPLVFPSDEFDASISQVNEKINQSLAFIRKSDELLS<br>AIGGYIPEAPRDGQAYVRKDGEWVLLSTFL | 50 |
| Polya tail | 100 nt | |

RSVF mRC1(v2) UTR v1.1

SEQ ID NO: 51 consists of from 5' end to 3' end: 5' UTR SEQ ID NO: 77, mRNA ORF SEQ ID NO: 52, and 3' UTR SEQ ID NO: 78. 51

| | | |
|---|---|---|
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGACCCCGGCGCCGCCACC | 77 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC | 52 |

TABLE 7-continued

| | | |
|---|---|---|
| | GAGCUGCAGUUAUUGAUGCAGAGUACACCUGCCACCCGG<br>UCGGGCUCUGCCAUUUGCUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>AACGGAGUAAGUGUGUUAACAUUUAAGGUGCUGGACCUC<br>AAGAAUUAUAUUGACAAACAGUUGCUUCCUAUUCUAAAC<br>AAACAGAGCUGUUCAAUAAGUAAUAUUGAAACUGUUAUU<br>GAGUUUCAGCAGAAGAACAACAGGCUUCUUGAGAUUACA<br>CGCGAGUUCAGUGUCAAUGCCGGCGUUACAACACCCGUG<br>UCUACCUACAUGCUGACGAAUUCUGAGCUUCUCUCUCUC<br>AUAAACGACAUGCCCAUUACGAAUGACCAAAAGAAACUU<br>AUGUCCAACAACGUGCAGAUUGUGCGACAGCAAUCCUAU<br>AGCAUUAUGUGUAUCAUCAAGGAAGAGGUACUCGCUUAU<br>GUUGUGCAGCUACCACUCUAUGGUGUGAUUGACACCCCC<br>UGUUGGAAGCUGCAUACCAGUCCACUCUGCACCACUAAC<br>ACAAAGGAAGGGAGCAAUAUUUGCCUCACUCGAACCGAC<br>AGGGGGUGGUAUUGCGAUAAUGCGGGCUCCGUGUCCUUC<br>UUUCCACAGGCUGAAACUUGUAAGGUACAGUCAAACCGC<br>GUGUUCUGUGAUACUAUGAAUUCUCGUACUCUUCCCAGC<br>GAGGUUAAUCUCUGCAACGUCGACAUUUUCAAUCCUAAA<br>UAUGACUGCAAGAUCAUGACCAGCAAGACCGACGUCUCC<br>AGCUCAGUAAUCACUAGCCUAGGGGCCAUUGUAAGCUGC<br>UAUGGCAAAACCAAGUGUACUGCCUCUAAUAAGAACAGA<br>GGCAUAAUUAAAACCUUUUCAAAUGGCUGUGACUAUGUG<br>UCGAAUAAGGGCGUCGACACGGUCUCAGUAGGGAAUACC<br>CUCUACUGCGUUAACAAACAGGAAGGCAAAUCCCUUUAU<br>GUAAAGGGCGAGCCCAUCAUAAAUUUCUACGACCCACUU<br>GUGUUCCCCAGUGAUGAAUUCGAUGCAUCAAUCUCCCAG<br>GUGAACGAAAAGAUCAAUCAAUCCCUUGCUUUUAUACGA<br>AAGUCAGAUGAACUCCUGCAUAACGUGAAUGCUGGGAAA<br>UCUACAACCAACAUCAUGAUCACUACCAUCAUUAUUGUG<br>AUUAUCGUAAUUCUGCUAUCCUUGAUUGCUGUCGGGCUG<br>CUUCUGUACUGUAAGGCCAGAUCGACGCCUGUGACCCUU<br>UCAAAAGACCAACUUAGCGGUAUCAAUAAUAUUGCCUUU<br>AGCAAU | |
| 3' UTR | UGAUAAUAGGCUGGAGCCUCGCUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGGGC | 78 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSTPATGSGSAICSGVAVCKVLHLEGEVNKIK<br>SALLSTNKAVVSLSNGVSVLTFKVLDLKNYIDKQLLPILNKQS<br>CSISNIETVIEFQQKNNRLLEITREFSVNAGVTTPVSTYMLINSE<br>LLSLINDMPITNDQKKLMSNNVQIVRQQSYSIMCHIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>NRGIIKTFSNGCDYVSNKGVDTVSVGNTLYCVNKQEGKSLYV<br>KGEPIINFYDPLVFPSDEFDASISQVNEKINQSLAFIRKSDELLH<br>NVNAGKSTTNIMITTIIIVIVILLSLIAVGLLLYCKARSTPVTLS<br>KDQLSGINNIAFSN | 5 |
| PolyA tail | 100 nt | |

MRK_RSVF mVRC1(v2)_SE_001

| | | |
|---|---|---|
| SEQ ID NO: 53 consists of from 5' end to 3' end: 5' UTR SEQ ID NO: 77, mRNA ORF SEQ ID NO: 54, and 3' UTR SEQ ID NO: 78. | | 53 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGACCCCOGCGCCGCCACC | 77 |
| ORF of mRNA Construct (excluding the stop codon) | AUGGAGCUGCUGAUCCUCAAGGCUAACGCCAUCACCACC<br>AUCCUGACCGCCGUGACCUUCUGCUUCGCCAGCGGGCAGA<br>ACAUCACCGAGGAGUUCUACCAGAGCACUUGCAGCGCCG<br>UGAGCAAGGGCUACCUGUCAGCCCUGCGGACCGGCUGGU<br>ACACCAGCGUGAUCACCAUCGAGCUGAGCAACAUCAAGG<br>AGAACAAGUGCAACGGCACCGACGCCAAGGUGAAGCUGA<br>UCAAGCAGGAGCUGGACAAGUACAAGAACGCCGUGACCG<br>AGCUGCAGCUGCUGAUGCAGUCCACGCCCGCUACCGGGUC<br>AGGCAGCGCCAUCUGCUCCGGCGUGGCCGUGUGCAAGGU<br>GCUGCACCUGGAGGGCGAGGUGAACAAGAUCAAGAGCGC<br>CCUGCUGAGCACCAACAAGGCCGUGGUGAGCCUGAGCAA<br>CGGCGUGAGCGUGCUGACCUUCAAGGUGCUGGACCUGAA<br>GAACUACAUCGACAAGCAGCUGCUGCCCAUCCUGAACAA<br>GCAGUCCUGCUCCAUCUCCAACAUCGAAACUGUGAUCGA<br>GUUCCAGCAGAAGAACAACCGCCUGCUGGAGAUCACCCG<br>CGAGUUCAGCGUGAACGCCGCCGUGACCACCCCAGUGAG<br>CACCUACAUGCUGACCAACAGCGAGCUGCUGAGCCUGAU<br>CAACGACAUGCCCAUCACCAACGACCAGAAGAAGCUGAU<br>GAGCAACAACGUGCAGAUCGUGCGCCAGCAGUCCUACUC | 54 |

TABLE 7-continued

| | | |
|---|---|---|
| | UAUCAUGUGCAUCAUCAAGGAGGAGGUGCUGGCCUACGU<br>GGUGCAGCUGCCCCUGUACGGCGUGAUCGACACACCCUGC<br>UGGAAGCUGCACACCUCCCCUCUGUGCACCACUAACACCA<br>AGGAGGGGAGCAACAUCUGCCUGACCCGGACCGACCGCG<br>GCUGGUACUGCGACAACGCCGGCAGCGUGAGCUUCUUCC<br>CUCAGGCCGAAACCUGCAAGGUGCAGAGCAACAGGGUGU<br>UCUGCGACACCAUGAACUCCCGGACCCUGCCCAGCGAGGU<br>GAACCUGUGCAACGUGGACAUCUUCAACCCCAAGUACGA<br>UUGCAAGAUCAUGACCUCCAAGACCGACGUGAGCAGCUC<br>CGUGAUCACCUCCCUGGGCGCCAUCGUGAGUUGCUACGG<br>CAAGACCAAGUGCACCGCCAGCAACAAGAACCGCGGCAUC<br>AUCAAGACCUUCAGCAACGGCUGCGACUACGUGUCCAAC<br>AAGGGCGUGGACACCGUGAGCGUGGGCAACACCCUGUAC<br>UGCGUGAACAAGCAGGAGGGCAAGAGCCUGUACGUGAAG<br>GGCGAGCCCAUCAUCAACUUCUACGAUCCGCUGGUGUUC<br>CCCUCCGACGAGUUCGACGCCUCCAUCAGCCAGGUGAACG<br>AGAAGAUCAACCAGAGCCUGGCCUUCAUCCGCAAGUCCG<br>ACGAGCUGCUGCACAACGUCAACGCCGGUAAGAGCACCA<br>CCAACAUCAUGAUCACCACAAUCAUCAUCGUGAUCAUUG<br>UGAUCUUGCUCUCCUUAAUCGCCGUGGGCCUGCUGCUGU<br>ACUGCAAGGCCCGGAGCACCCCAGUGACCCUGAGCAAAG<br>AUCAGCUGUCCGGCAUCAACAACAUCGCCUUCUCCAAC | |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGGC | 78 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSTPATGSGSAICSGVAVCKVLHLEGEVNKIK<br>SALLSTNKAVVSLSNGVSVLTFKVLDLKNYIDKQLLPILNKQS<br>CSISNIETVIERQQKNNRLLEITREFSVNAGVTTPVSTYMLINSE<br>LLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>NRGIIKTFSNGCDYVSNKGVDTVSVGNTLYCVNKQEGKSLYV<br>KGEPIINFYDPLVFPSDEFDASISQVNEKINQSLAFIRKSDELLH<br>NVNAGKSTTNIMITTIIIVIIVILLSLIAVGLLLYCKARSTPVTLS<br>KDQLSGINNIAFSN | 5 |
| PolyA tail | 100 nt | |

MRK_RSVF mVRC1(v2)_SE_002

| | | |
|---|---|---|
| SEQ ID NO: 55 consists of from 5' end to 3' end: 5' UTR SEQ ID NO: 77, mRNA ORF SEQ ID NO: 56, and 3' UTR SEQ ID NO: 78. | | 55 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGACCCCGGCGCCGCCACC | 77 |
| ORF of mRNA Construct (excluding the stop codon) | AUGGAGCUGCUGAUUCUGAAGGCCAACGCCAUUACCACC<br>AUUCUGACCGCCGUGACCUUCUGCUUCGCCAGCGGCCAGA<br>AUAUUACCGAGGAGUUCUACCAGUCAACCUGCAGCGCCG<br>UGAGCAAGGGCUACCUGAGCGCCCUACGGACCCGGUGGU<br>ACACCUCCGUGAUCACCAUUGAGCUGAGCAAUAUUAAGG<br>AGAAUAAGUGCAACGGGACCGACGCCAAGGUGAAGCUCA<br>UCAAGCAGGAGCUGGAUAAGUACAAGAACGCCGUGACCG<br>AGCUGCAGCUGCUGAUGCAGAGCACACCGGCCACGGGCU<br>CCGGCAGCGCCAUUUGCUCAGGCGUGGCCGUGUGCAAGG<br>UGCUGCACCUCGAGGGCGAGGUCAAUAAGAUUAAGAGCG<br>CCCUGUUGAGCACCAAUAAGGCCGUGGUGAGCCUGAGCA<br>ACGGCGUGAGCGUGCUGACCUUCAAGGUGCUGGAUCUCA<br>AGAAUUACAUUGAUAAGCAGCUGCUGCCAAUUCUCAAUA<br>AGCAGAGCUGCAGCAUUAGCAAUAUCGAAACCGUGAUUG<br>AGUUCCAGCAGAAGAAUAAUCGCCUGCUGGAGAUUACCC<br>GCGAGUUCAGCGUCAACGCCGGGGUGACCACCCCAGUCA<br>GCACCUACAUGCUGACCAAUAGCGAGCUGCUGAGCCUGA<br>UUAACGAUAUGCCCAUUACCAACGACCAGAAGAAGCUGA<br>UGAGCAAUAACGUGCAGAUUGUGCGCCAGCAGAGCUACA<br>GCAUUAUGUGCAUUAUUAAGGAGGAGGUGCUGGCCUACG<br>UGGUGCAGCUGCCCCUCUACGGCGUGAUUGAUACGCCCU<br>GCUGGAAGCUGCACACCAGCCCACUGUGCACCACCAAUAC<br>CAAGGAGGGCAGCAAUAUUUGCCUGACCCGCACCGAUCG<br>CGGGUGGUACUGCGAUAACGCCGGCAGCGUGAGCUUCUU<br>CCCACAGGCCGAAACAUGCAAGGUGCAGUCCAAUCGCGU<br>GUUCUGCGAUACCAUGAACAGCCGCACCCUGCCCAGCGAG<br>GUGAAUCUCUGCAACGUGGAUAUUUUCAAUCCAAAGUAC<br>GAUUGCAAGAUUAUGACCAGCAAGACCGACGUGAGCUCC<br>AGCGUGAUUACCUCACUCGGCGCCAUUGUGAGCUGCUAC<br>GGCAAGACCAAGUGCACCGCCUCAAAUAAGAAUCGCGGC<br>AUUAUUAAGACCUUCAGCAACGGCUGCGAUUACGUGAGC<br>AAUAAGGGCGUGGAUACCGUGAGCGUGGGAAAUACCCUG | 56 |

TABLE 7-continued

| | | |
|---|---|---|
| | UACUGCGUGAAUAAGCAGGAGGGCAAGAGCCUGUACGUG | |
| | AAGGGCGAGCCAAUUAUUAAUUUCUACGAUCCCCUGGUG | |
| | UUCCCCAGCGACGAGUUCGACGCCAGCAUUAGCCAGGUG | |
| | AACGAGAAGAUUAAUCAGAGCCUGGCCUUCAUUCGCAAG | |
| | UCCGACGAGCUCCUGCACAACGUGAACGCCGGCAAGAGC | |
| | ACCACCAACAUCAUGAUUACCACCAUCAUCAUUGUGAUU | |
| | AUCGUGAUCCUCCUCAGCCUCAUUGCCGUGGGCCUCCUCC | |
| | UGUACUGCAAGGCCCGCAGCACUCCUGUGACCCUCAGCAA | |
| | GGAUCAGCUGAGCGGCAUCAAUAAUAUCGCCUUCAGCAAU | |
| 3' UTR | UGAUAAUAGGCUGGAGCCUCGGUGGCCUAGCUUCUUGCC | 78 |
| | CCUUGGGCCUCCCCCCAGCCCCUCCUCCCCUUCCUGCACC | |
| | CGUACCCCCGUGGUCUUUGAAUAAAGUCUGAGUGGGCGGC | |
| Corresponding amino acid sequence | MELLILKANAITTILTAVTECRASGQNITEEFYQSTCSAVSKGY | 5 |
| | LSALRTGWYTSVITIELSNIKENKCNGTDAKVKLIKQELDKYK | |
| | NAVTELQLLMQSTPATGSGSAICSGVAVCKVLHLEGEVNKIK | |
| | SALLSTNKAVVSLSNGVSVLTFKVLDLKNYIDKQLLPILNKQS | |
| | CSISNIETVIEFQQKNNRLLEITREFSVNAGVTTPVSTYMLINSE | |
| | LLSLINDMPITNDQKKLMSNNVQIVRQQSYSIMCIIKEEVLAY | |
| | VVQLPLYGVIDTPCWKLHTSPLCTINTKEGSNICLTRTDRGW | |
| | YCDNAGSVSFFPQAETCKVQSNRVFCDTMNSRTLPSEVNLCN | |
| | VDIFNPKYDCKIMTSKTDVSSSVITSLGAIVSCYGKTKCTASNK | |
| | NRGIIKTFSNGCDYVSNKGVDTVSVGNTLYCVNKQEGKSLYV | |
| | KGEPIINFYDPLVFPSDEFDASISQVNEKINQSLAFIRKSDELLH | |
| | NVNAGKSTTNIMITTIVIVILLSLIAVGLLLYCKARSTPVTLS | |
| | KDQLSGINNIAFSN | |
| PolyA tail | 100 nt | |

MRK_RSVF mVRC1(v2)_SE_003

| | | |
|---|---|---|
| SEQ ID NO: 57 consists of from 5' end to 3' end: 5' UTR SEQ ID NO: 77, mRNA ORF SEQ ID NO: 58, and 3' UTR SEQ ID NO: 78. | | 57 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA | 77 |
| | AGACCCCGGCGCCGCCACC | |
| ORF of mRNA Construct (excluding the stop codon) | AUGGAGCUGCUGAUCCUGAAGGCCAACGCCAUCACCACC | 58 |
| | AUCCUGACCGCCGUGACCUUCUGCUUCGCCAGCGGCCAGA | |
| | ACAUUACCGAGGAGUUCUACCAGUCCACCUGCAGCGCCG | |
| | UGAGCAAGGGCUACCUGAGCGCCCUGCGCACCGGGUGGU | |
| | ACACCAGCCUGAUCACCAUCGAGCUGUCCAACAUCAAGG | |
| | AGAACAAGUGCAACGGCACAGACGCCAAGGUGAAGCUGA | |
| | UCAAGCAGGAGCUGGACAAGUACAAGAACGCCGUGACCG | |
| | AGCUCCAGCUGCUGAUGCAGUCCACCCCGGCCACCGGCAG | |
| | UGGAAGUGCUAUCUGCAGCGGGGUGGCCGUGUGCAAGGU | |
| | GCUGCACCUGGAGGGCGAGGUGAACAAGAUCAAGAGCGC | |
| | CCUGCUGAGCACCAACAAGGCCGUGGUGAGCCUGAGCAA | |
| | CGGGGUGUCCGUGCUGACAUUCAAGGUGCUGGACCUGAA | |
| | GAACUACAUCGACAAGCAGCUGCUGCCCAUCCUCAACAA | |
| | GCAGAGCUGCUCCAUCUCCAAUAUCGAAACCGUGAUCGA | |
| | GUUUCAGCAGAAGAACAACCGGCUGCUGGAGAUCACCCG | |
| | GGAGUUCUCCGUGAACGCCGGGGUGACCACCCCAGUGAG | |
| | CACCUACAUGCUGACCAACUCCGAGCUGCUGAGCCUGAUC | |
| | AACGAUAUGCCAAUCACAAACGAUCAGAAGAAGCUGAUG | |
| | AGCAACAACGUGCAGAUCGUGCGGCAGCAGUCCUACAGC | |
| | AUCAUGUGCAUCAUCAAGGAGGAGGUGCUGCCCUACGUG | |
| | GUGCAGCUGCCCCUGUACGCCGUGAUCGACACUCCUUGC | |
| | UGGAAGCUGCACACCUCACCGCUGUGCACCACGAACACUA | |
| | AGGAGGGCAGCAACAUCUGCCUGACCCGGACCGACCGAG | |
| | GCUGGUACUGCGACAACGCCGGCAGCGUCUCUUUCUUUC | |
| | CGCAGGCCGAGACGUGCAAGGUGCAGUCCAACCGGGUGU | |
| | UCUGCGACACCAUGAACUCCCGGACCCUGCCCUCCGAGGU | |
| | GAACCUGUGCAACGUGGACAUUUUCAACCCCAAGUACGA | |
| | CUGCAAGAUCAUGACCAGUAAGACCGACGUGUCCAGCUC | |
| | CGUAAUCACCAGCCUGGGCGCCAUCGUGUCCUGUUACGG | |
| | CAAGACCAAGUGUACCGCCUCCAACAAGAACCGAGGUAU | |
| | CAUCAAGACCUUCUCCAACGGGUGCGACUACGUGUCCAA | |
| | CAAGGGCGUGGACACCGUGAGCGUGGGAAAUACCCUCUA | |
| | CUGCGUGAACAAGCAGGAGGGGAAGUCCCUGUACGUGAA | |
| | GGGUGAGCCCAUCAUCAACUUUUACGAUCCCCUGGUGUU | |
| | CCCCAGCGACGAGUUCGACGCAUCCAUUAGCCAGGUGAA | |
| | CGAGAAGAUCAACCAGAGUCUGGCCUUCAUCCGCAAGUC | |
| | CGACGAGCUGCUGCACAACGUGAACGCUGGCAAGUCAAC | |
| | AACCAACAUCAUGAUCACGACCAUCAUUAUCGUGAUCAU | |
| | CGUGAUCCUGCUGUCCCUGAUCGCAGUGGGCCUGCUCCU | |
| | GUACUGCAAGGCCCGCAGCACACCCGUGACCCUCAGCAAG | |
| | GAUCAGCUCAGCGGCAUCAACAACAUCGCCUUCAGCAAC | |
| 3' UTR | UGAUAAUAGGCUGGAGCCUCGGUGCCCUAGCUUCUUGCC | 78 |
| | CCUUGGGCCUCCCCCCAGCCCCUCCUCCCCUUCCUGCACC | |
| | CGUACCCCCGUGGUCUUUGAAUAAAGUCUGAGUGGGCGGC | |

TABLE 7-continued

| | | |
|---|---|---|
| Corresponding amino acid sequence | MELLILKANAITTILTAVTECFASGQNITEEFYQSTCSAVSKGY<br>LSALRTGWYTSVITIELSNIKENKCNGTDAKVKLIKQELDKYK<br>NAVTELQLLMQSTPATGSGSAICSGVAVCKVLHLEGEVNKIK<br>SALLSTNKAVVSLSNGVSVLTFKVLDLKNYIDKQLLPILNKQS<br>CSISNIETVIEFQQKNNRLLEITREFSVNAGVTTPVSTYMLINSE<br>LLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>NRGIIKTESNGCDYVSNKGVDTVSVGNTLYCVNKQEGKSLYV<br>KGEPIINFYDPLVFPSDEFDASISQVNEKINQSLAFIRKSDELLH<br>NVNAGKSTTNIMITTIIVIIVILLSLIAVGLLLYCKARSTPVTLS<br>KDQLSGINNIAFSN | 5 |
| PolyA tail | 100 nt | |

MRK sLZE129

| | | |
|---|---|---|
| SEQ ID NO: 59 consists of from 5' end to 3' end: 5' UTR SEQ ID NO: 2, mRNA ORF SEQ ID NO: 60, and 3' UTR SEQ ID NO: 4. | | 59 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC<br>GAGCUGCAGUUAUUGAUGGGAGGCGGUAGCGGUGGCGGA<br>UCCGGCGGUGGAAGCGGCUCUGCCAUUGCUUCCGGCGUG<br>GCUGUAUGUAAAGUUCUCCACCUCGAGGGAGAGGUUAAU<br>AAGAUUAAGUCGGCCCUGCUGAGUACUAACAAAGCAGUG<br>GUGUCGCUGAGUAACGGAGUAAGUGUGUUAACAUUUAAG<br>GUGCUGGACCUCAAGAAUUAUAUUGACAAACAGUUGCUU<br>CCUAUUCUAAACAAACAGAGCUGUUCAAUAAGUAAUAUU<br>GAAACUGUUAUUGAGUUUCAGCAGAAGAACAACAGGCUU<br>CUUGAGAUUACACGCGAGUUCAGUGUCAAUGCCGGCGUU<br>ACAACACCCGUGUCUACCUACAUGCUGACGAAUUCUGAG<br>CUUCUCUCUCUCAUAAACGACAUGCCCAUUACGAAUGAC<br>CAAAAGAAACUUAUGUCCAACAACGUGCAGAUUGUGCGA<br>CAGCAAUCCUAUAGCAUUAUGUGUAUCAUCAAGGAAGAG<br>GUACUCGCUUAUGUUGUGCAGCUACCACUCUAUGGUGUG<br>AUUGACACCCCCUGUUGGAAGCUGCAUACCAGUCCACUC<br>UGCACCACUAACACAAAGGAAGGGAGCAAUAUUUGCCUC<br>ACUCGAACCGACAGGGGGUGGUAUUGCGAUAAUGCGGGC<br>UCCGUGUCCUUCUUUCCACAGGCUGAAACUUGUAAGGUA<br>CAGUCAAACCGCGUGUUCUGUGAUACUAUGAAUUCUCUG<br>ACUCUUCCCAGCGAGGUUAAUCUCUGCAACGUCGACAUU<br>UUCAAUCCUAAAUAUGACUGCAAGAUCAUGACCAGCAAG<br>ACCGACGUCUCCAGCUCAGUAAUCACUAGCCUAGGGGCC<br>AUUGUAAGCUGCUAUGGCAAAACCAAGUGUACUGCCUCU<br>AAUAAGAACAGAGGCAUAAUUAAAACCUUUUCAAAUGGC<br>UGUGACUAUGUGUCGAAUAAGGGCGUCGACACGGUCUCA<br>GUAGGGAAUACCCUCUACUACGUUAACAAACAGGAAGGC<br>AAAUCCCUUUAUGUAAAGGGCGAGCCCAUCAUAAAUUUC<br>UACGACCCACUUUCCGCCAUCGGUGGCUAUAUCCCAGAA<br>GCCCCAAGAGACGGACAAGCGUACGUCCGGAAAGAUGCU<br>GAGUGGGUCCUCCUCUCUACCUUUCUU | 60 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGGC | 4 |
| Corresponding amino acid sequence | MELLILKANAITTILTAVTECEASGQNITEEFYQSTCSAVSKGY<br>LSALRTGWYTSVITIELSNIKENKCNGTDAKVKLIKQELDKYK<br>NAVTELQLLMGGGSGGGSGGGSGSAIASGVAVCKVLHLEGE<br>VNKIKSALLSTNKAVVSLSNGVSVLTFKVLDLKNYIDKQLLPI<br>LNKQSCSISNIETVIEFQQKNNRLLEITREFSVNAGVTTPVSTY<br>MLTNSELLSLINDMPITNDQKKLMSNNVQIVRQQSYSIMCHIKE<br>EVLAYVVQLPLYGVIDTPCWKLHTSPLCTTNTKEGSNICLTRT<br>DRGWYCDNAGSVSFFPQAETCKVQSNRVFCDTMNSLTLPSEV<br>NLCNVDIFNPKYDCKIMTSKTDVSSSVITSLGAIVSCYGKTKCT<br>ASNKNRGIIKTESNGCDYVSNKGVDTVSVGNTLYYVNKQEGK<br>SLYVKGEPIINFYDPLSAIGGYIPEAPRDGQAYVRKDGEWVLL<br>STFL | 61 |
| PolyA tail | 100 nt | |

TABLE 7-continued

| MRK SLZF128 | | |
|---|---|---|
| SEQ ID NO: 62 consists of from 5' end to 3' end: 5' UTR SEQ ID NO: 2, mRNA ORF SEQ ID NO: 63, and 3' UTR SEQ ID NO: 4. | | 62 |
| Chemistry | 1-methylpseudouridine | |
| Cap | 7mG(5')ppp(5')NimpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC<br>GAGCUGCAGUUAUUGAUGCAGAGUACACCUGCCACCAAU<br>AACAGAGCUAGGAGGGAGUUGCCUAGGUUUAUGAACUAC<br>ACUCUCAACAACGCGAAGAAAACCAAUGUGACGCUAUCC<br>AAGAAACGGAAGAGGAGGUUCCUGGGGUUUUUUUAGGG<br>GUGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>AACGGAGUAAGUGUGUUAACAUUUAAGGUGCUGGACCUC<br>AAGAAUUAUAUUGACAAACAGUUGCUUCCUAUUCUAAAC<br>AAACAGAGCUGUUCAAUAAGUAAUAUUGAAACUGUUAUU<br>GAGUUUCAGCAGAAGAACAACAGGCUUCUUGAGAUUACA<br>CGCGAGUUCAGUGUCAAUGCCGGCGUUACAACACCCGUG<br>UCUACCUACAUGCUGACGAAUUCUGAGCUUCUCUCUCUC<br>AUAAACGACAUGCCCAUUACGAAUGACCAAAAGAAACUU<br>AUGUCCAACAACGUGCAGAUUGUGCGACAGCAAUCCUAU<br>AGCAUUAUGUGUAUCAUCAAGGAAGAGGUACUCGCUUAU<br>GUUGUGCAGCUACCACUCUAUGGUGUGAUUGACACCCCC<br>UGUUGGAAGCUGCAUACCAGUCCACUCUGCACCACUAAC<br>ACAAAGGAAGGGAGCAAUAUUUGCCUCACUCGAACCGAC<br>AGGGGGUGGUAUUGCGAUAAUGCGGGCUCCGUGUCCUUC<br>UUUCCACAGGCUGAAACUUGUAAGGUACAGUCAAACCGC<br>GUGUUCUGUGAUACUAUGAAUUCUCUGACUCUUCCCAGC<br>GAGGUUAAUCUCUGCAACGUCGACAUUUUCAAUCCUAAA<br>UAUGACUGCAAGAUCAUCACCAGCAAGACCGACGUCUCC<br>AGCUCAGUAAUCACUAGCCUAGGGGCCAUUGUAAGCUGC<br>UAUGGCAAAACCAAGUGUACUGCCUCUAAUAAGAACAGA<br>GGCAUAAUUAAAACCUUUUCAAAUGGCUGUGACUAUGUG<br>UCGAAUAAGGGCGUCGACACGGUCUCAGUAGGGAAUACC<br>CUCUACUACGUUAACAAACAGGAAGGCAAAUCCCUUUAU<br>GUAAAGGGCGAGCCCAUCAUAAAUUUCUACGACCCACUU<br>UCCGCCAUCGGUGGCUAUAUCCCAGAAGCCCCAAGAGAC<br>GGACAAGCGUACGUCCGGAAAGAUGGUGAGUGGGUCCUC<br>CUCUCUACCUUUCUU | 63 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGGGC | 4 |
| Corresponding amino acid sequence | MELLILKANAITTILTAVTECFASGQNITEEFYQSTCSAVSKGY<br>LSALRTGWYTSVITIELSNIKENKCNGTDAKVKLIKQELDKYK<br>NAVTELQLLMQSTPATNNRARRELPREMNYTLNNAKKTNVT<br>LSKKRKRRFLGFLLGVGSAIASGVAVCKVLHLEGEVNKIKSAL<br>LSTNKAVVSLSNGVSVLTFKVLDLKNYIDKQLLPILNKQSCSIS<br>NIETVIEFQQKNNRLLEITREFSVNAGVTTPVSTYMLINSELLS<br>LINDMPITNDQKKLMSNNVQIVRQQSYSIMCIIKEEVLAYVVQ<br>LPLYGVIDTPCWKLHTSPLCTTNTKEGSNICLTRTDRGWYCD<br>NAGSVSFFPQAETCKVQSNRVFCDTMNSLTLPSEVNLCNVDIF<br>NPKYDCKIMTSKTDVSSSVITSLGAIVSCYGKTKCTASNKNRG<br>IIKTESNGCDYVSNKGVDTVSVGNTLYYVNKQEGKSLYVKGE<br>PIINFYDPLSAIGGYIPEAPRDGQAYVRKDGEWVLLSTFL | 64 |
| PolyA tail | 100 nt | |

| MRK_sLZF125 | | |
|---|---|---|
| SEQ ID NO: 65 consists of from 5' end to 3' end: 5' UTR SEQ ID NO: 2, mRNA ORF SEQ ID NO: 66, and 3' UTR SEQ ID NO: 4. | | 65 |
| Chemistry | 1-methylpseudouridine | |
| Cap | 7mG(5')ppp(5 )NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU | 66 |

TABLE 7-continued

| | | |
|---|---|---|
| | AUCAAGCAGGAACUCGACAAAUAUAAGAACGCUGUGACC<br>GAGCUGCAGUUAUUGAUGCAGAGUACACCUGCCACCAAU<br>AACAGAGCUAGGAGGGAGUUGCCUAGGUUUAUGAACUAC<br>ACUCUCAACAACGCGAAGAAAACCAAUGUGACGCUAUCC<br>AAGAAACGGAAGAGGAGGUUCCUGGGGUUUCUUUUAGGG<br>GUGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>AACGGAGUAAGUGUGUUAACAUUUAAGGUGCUGGACCUC<br>AAGAAUUAUAUUGACAAACAGUUGCUUCCUAUUCUAAAC<br>AAACAGAGCUGUUCAAUAAGUAAUAUUGAAACUGUUAUU<br>GAGUUUCAGCAGAAGAACAACAGGCUUCUUGAGAUUACA<br>CGCGAGUUCAGUGUCAAUGCCGGCGUUACAACACCCGUG<br>UCUACCUACAUGCUGACGAAUUCUGAGCUUCUCUCUCUC<br>AUAAACGACAUGCCCAUUACGAAUGACCAAAAGAAACUU<br>AUGUCCAACAACGUGCAGAUUGUGCGACAGCAAUCCUAU<br>AGCAUUAUGUGUAUCAUCAAGGAAGAGGUACUCGCUUAU<br>GUUGUGCAGCUACCACUCUAUGGUGUGAUUGACACCCCC<br>UGUUGGAAGCUGCAUACCAGUCCACUCUGCACCACUAAC<br>ACAAAGGAAGGGAGCAAUAUUUGCCUCACUCGAACCGAC<br>AGGGGGUGGUAUUGCGAUAAUGCGGGCUCCGUGUCCUUC<br>UUUCCACAGGCUGAAACUUGUAAGGUACAGUCAAACCGC<br>GUGUUCUGUGAUACUAUGAAUUCUCUGACUCUUCCCAGC<br>GAGGUUAAUCUCUGCAACGUCGACAUUUUCAAUCCUAAA<br>UAUGACUGCAAGAUCAUGACCAGCAAGACCGACGUCUCC<br>AGCUCAGUAAUCACUAGCCUAGGGGCCAUUGUAAGCUGC<br>UAUGGCAAAACCAAGUGUACUGCCUCUAAUAAGAACAGA<br>GGCAUAAUUAAAACCUUUUCAAAUGGCUGUGACUAUGUG<br>UCGAAUAAGGGCGUCGACACGGUCUCAGUAGGGAAUACC<br>CUCUACUACGUUAACAAACAGGAAGGCAAAUCCCUUUAU<br>GUAAAGGGCGAGCCCAUCAUAAAUUUCUACGACCCACUU<br>GUGUUCCCCAGUUGCGAAUUCUGCGCAUCAAUCUCCCAG<br>GUGAACGAAAAGAUCAAUCAAUCCCUUGCUUUUAUACGA<br>AAGUCAGAUGAACUCCUGUCCGCCAUCGGUGGCUAUAUC<br>CCAGAAGCCCCAAGAGACGGACAAGCGUACGUCCGGAAA<br>GAUGGUGAGUGGGUCCUCCUCUCUACCUUUCUU | |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGGG | 4 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSTPATNNRARRELPREMNYTLNNAKKTNVT<br>LSKKRKRRFLGFLLGVGSAIASGVAVCKVLHLEGEVNKIKSAL<br>LSTNKAVVSLSNGVSVLTFKVLDLKNYIDKQLLPILNKQSCSIS<br>NIETVIERQQKNNRLLEITREFSVNAGVTTPVSTYMLTNSELLS<br>LINDMPITNDQKKLMSNNVQIVRQQSYSIMCIIKEEVLAYVVQ<br>LPLYGVIDTPCWKLHTSPLCTTNTKEGSNICLTRTDRGWYCD<br>NAGSVSFFPQAETCKVQSNRVFCDTMNSLTLPSEVNLCNVDIF<br>NPKYDCKIMTSKTDVSSSVITSLGAIVSCYGKTKCTASNKNRG<br>IIKTFSNGCDYVSNKGVDTVSVGNTLYYVNKQEGKSLYVKGE<br>PIINFYDPLVFPSCEFCASISQVNEKINQSLAFIRKSDELLSAIGG<br>YIPEAPRDGQAYVRKDGEWVLLSTFL | 67 |
| PolyA tail | 100 nt | |

MRK_sLZF111

| | | |
|---|---|---|
| SEQ ID NO: 68 consists of from 5' end to 3' end: 5' UTR SEQ ID NO: 2, mRNA ORF SEQ ID NO: 69, and 3' UTR SEQ ID NO: 4. | | 68 |
| Chemistry | 1-methylpseudouridine | |
| Cap | 7mG(5')ppp(5')NimpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC<br>GAGCUGCAGUUAUUGAUGGGAGGCGGUAGCGGUGGCGGA<br>UCCGGCGGUGGAAGCGGCUCUGCCAUUGCUUCCGGCGUG<br>GCUGUAUGUAAAGUUCUCCACCUCGAGGGAGAGGUUAAU<br>AAGAUUAAGUCGGCCCUGCUGAGUACUAACAAAGCAGUG<br>GUGUCGCUGAGUAACGGAGUAAGUGUGUUAACAUUUAAG<br>GUGCUGGACCUCAAGAAUUAUAUUGACAAACAGUUGCUU<br>CCUAUUCUAAACAAACAGAGCUGUUCAAUAAGUAAUAUU<br>GAAACUGUUAUUGAGUUUCAGCAGAAGAACAACAGGCUU<br>CUUGAGAUUACACGCGAGUUCAGUGUCAAUGCCGGCGUU<br>ACAACACCCGUGUCUACCUACAUGCUGACGAAUUCUGAG<br>CUUCUCUCUCUCAUAAACGACAUGCCCAUUACGAAUGAC | 69 |

TABLE 7-continued

| | | |
|---|---|---|
| | CAAAAGAAACUUAUGUCCAACAACGUGCAGAUUGUGCGA<br>CAGCAAUCCUAUAGCAUUAUGUGUAUCAUCAAGGAAGAG<br>GUACUCGCUUAUGUUGUGCAGCUACCACUCUAUGGUGUG<br>AUUGACACCCCCUGUUGGAAGCUGCAUACCAGUCCACUC<br>UGCACCACUAACACAAAGGAAGGGAGCAAUAUUUGCCUC<br>ACUCGAACCGACAGGGGGUGGUAUUGCGAUAAUGCGGGC<br>UCCGUGUCCUUCUUUCCACAGGCUGAAACUUGUAAGGUA<br>CAGUCAAACCGCGUGUUCUGUGAUACUAUGAAUUCUCUG<br>ACUCUUCCCAGCGAGGUUAAUCUCUGCAACGUCGACAUU<br>UUCAAUCCUAAAUAUGACUGCAAGAUCAUGACCAGCAAG<br>ACCGACGUCUCCAGCUCAGUAAUCACUAGCCUAGGGGCC<br>AUUGUAAGCUGCUAUGGCAAAACCAAGUGUACUGCCUCU<br>AAUAAGAACAGAGGCAUAAUUAAAACCUUUUCAAAUGGC<br>UGUGACUAUGUGUCGAAUAAGGGCGUCGACACGGUCUCA<br>GUAGGGAAUACCCUCUACUACGUUAACAAACAGGAAGGC<br>AAAUCCCUUUAUGUAAAGGGCGAGCCCAUCAUAAAUUUC<br>UACGACCCACUUGUGUUCCCCAGUUGCGAAUUCUGCGCA<br>UCAAUCUCCCAGGUGAACGAAAAGAUCAAUCAAUCCCUU<br>GCUUUUAUACGAAAGUCAGAUGAACUCCUGUCCGCCAUC<br>GGUGGCUAUAUCCCAGAAGCCCCAAGAGACGGACAAGCG<br>UACGUCCGGAAAGAUGGUGAGUGGGUCCUCCUCUCUACC<br>UUUCUU | |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGGGC | 4 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK.<br>NAVTELQLLMGGGSGGGSGGGSGSAIASGVAVCKVLHLEGE<br>VNKIKSALLSTNKAVVSLSNGVSVLTFKVLDLKNYIDKQLLPI<br>LNKQSCSISNIETVIEFQQKNNRLLEITREFSVNAGVTTPVSTY<br>MLTNSELLSLINDMPITNDQKKLMSNNVQIVRQQSYSIMCIIKE<br>EVLAYVVQLPLYGVIDTPCWKLHTSPLCTTNTKEGSNICLTRT<br>DRGWYCDNAGSVSFFPQAETCKVQSNRVFCDTMNSLTLPSEV<br>NLCNVDIFNPKYDCKIMTSKTDVSSSVITSLGAIVSCYGKTKCT<br>ASNKNRGIIKTFSNGCDYVSNKGVDTVSVGNTLYYVNKQEGK<br>SLYVKGEPINFYDPLVFPSCEFCASISQVNEKINQSLAFIRKSD<br>ELLSAIGGYIPEAPRDGQAYVRKDGEWVLLSTFL | 70 |
| PolyA tail | 100 nt | |
| | MRK_mLZF125 | |
| SEQ ID NO: 71 consists of from 5' end to 3' end: 5' UTR SEQ ID NO: 2, mRNA ORF SEQ ID NO: 72, and 3' UTR SEQ ID NO: 4. | | 71 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC<br>GAGCUGCAGUUAUUGAUGCAGAGUACACCUGCCACCAAU<br>AACAGAGCUAGGAGGGAGUUGCCUAGGUUUAUGAACUAC<br>ACUCUCAACAACGCGAAGAAAACCAAUGUGACGCUAUCC<br>AAGAAACGGAAGAGGAGGUUCCUGGGGUUUCUUUUAGGG<br>GUGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>AACGGAGUAAGUGUGUUAACAUUUAAGGUGCUGGACCUC<br>AAGAAUUAUAUUGACAAACAGUUGCUUCCUAUUCUAAAC<br>AAACAGAGCUGUUCAAUAAGUAAUAUUGAAACUGUUAUU<br>GAGUUUCAGCAGAAGAACAACAGGCUUCUUGAGAUUACA<br>CGCGAGUUCAGUGUCAAUGCCCGCGUUACAACACCCGUG<br>UCUACCUACAUGCUGACGAAUUCUGAGCUUCUCUCUCUC<br>AUAAACGACAUGCCCAUUACGAAUGACCAAAAGAAACUU<br>AUGUCCAACAACGUGCAGAUUGUGCGACAGCAAUCCUAU<br>AGCAUUAUGUGUAUCAUCAAGGAAGAGGUACUCGCUUAU<br>GUUGUGCAGCUACCACUCUAUGGUGUGAUUGACACCCCC<br>UGUUGGAAGCUGCAUACCAGUCCACUCUGCACCACUAAC<br>ACAAAGGAAGGGAGCAAUAUUUGCCUCACUCGAACCGAC<br>AGGGGGUGGUAUUGCGAUAAUGCGGGCUCCGUGUCCUUC<br>UUUCCACAGGCUGAAACUUGUAAGGUACAGUCAAACCGC<br>GUGUUCUGUGAUACUAUGAAUUCUCUGACUCUUCCCAGC<br>GAGGUUAAUCUCUGCAACGUCGACAUUUUCAAUCCUAAA<br>UAUGACUGCAAGAUCAUGACCAGCAAGACCGACGUCUCC<br>AGCUCAGUAAUCACUAGCCUAGGGGCCAUUGUAAGCUGC<br>UAUGGCAAAACCAAGUGUACUCCCUCUAAUAAGAACAGA | 72 |

TABLE 7-continued

| | | |
|---|---|---|
| | GGCAUAAUUAAAACCUUUUCAAAUGGCUGUGACUAUGUG<br>UCGAAUAAGGGCGUCGACACGGUCUCAGUAGGGAAUACC<br>CUCUACUACGUUAACAAACAGGAAGGCAAAUCCCUUUAU<br>GUAAAGGGCGAGCCCAUCAUAAAUUUCUACGACCCACUU<br>GUGUUCCCCAGUUGCGAAUUCUGCGCAUCAAUCUCCCAG<br>GUGAACGAAAAGAUCAAUCAAUCCCUUGCUUUUAUACGA<br>AAGUCAGAUGAACUCCUGCAUAACGUGAAUGCUGGGAAA<br>UCUACAACCAACAUCAUGAUCACUACCAUCAUUAUUGUG<br>AUUAUCGUAAUUCUGCUAUCCUUGAUUGCUGUCGGGCUG<br>CUUCUGUACUGUAAGGCCAGAUCGACGCCUGUGACCCUU<br>UCAAAAGACCAACUUAGCGGUAUCAAUAAUAUUGCCUUU<br>AGCAAU | |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGGGC | 4 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSTPATNNRARRELPRFMNYTLNNAKKTNVT<br>LSKKRKRRELGELLGVGSAIASGVAVCKVLHLEGEVNKIKSAL<br>LSTNKAVVSLSNGVSVLTFKVLDLKNYIDKQLLPILNKQSCSIS<br>NIETVIERQQKNNRLLEITREFSVNAGVTTPVSTYMLINSELLS<br>LINDMPITNDQKKLMSNNVQIVRQQSYSIMCIIKEEVLAYVVQ<br>LPLYGVIDTPCWKLHTSPLCTTNTKEGSNICLTRTDRGWYCD<br>NAGSVSFFPQAETCKVQSNRVFCDTMNSLTLPSEVNLCNVDIF<br>NPKYDCKIMTSKTDVSSSVITSLGAIVSCYGKTKCTASNKNRG<br>IIKTFSNGCDYVSNKGVDTVSYGNTLYYVNKQEGKSLYVKGE<br>PIINFYDPLVFPSCEFCASISQVNEKINQSLAFIRKSDELLHNVN<br>AGKSTTNIMITTIIIVIIVILLSLIAVGLLLYCKARSTPVTLSKDQ<br>LSGINNIAFSN | 73 |
| PolyA tail | 100 nt | |

MRK_mLZFI11

| | | |
|---|---|---|
| SEQ ID NO: 74 consists of from 5' end to 3' end: 5' UTR SEQ ID NO: 2, mRNA ORF SEQ ID NO: 75, and 3' UTR SEQ ID NO: 4 | | 74 |
| Chemistry | 1-methylpseudouridine | |
| Cap | 7mG(5')ppp(5')NimpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC<br>GAGCUGCAGUUAUUGAUGGGAGGCGGUAGCGGUGGCGGA<br>UCCGGCGGUGGAAGCGGCUCUGCCAUUGCUUCCGGCGUG<br>GCUGUAUGUAAAGUUCUCCACCUCGAGGGAGAGGUUAAU<br>AAGAUUAAGUCGGCCCUGCUGAGUACUAACAAAGCAGUG<br>GUGUCGCUGAGUAACGGAGUAAGUGUGUUAACAUUUAAG<br>GUGCUGGACCUCAAGAAUUAUAUUGACAAACAGUUGCUU<br>CCUAUUCUAAACAAACAGAGCUGUUCAAUAAGUAAUAUU<br>GAAACUGUUAUUGAGUUUCAGCAGAAGAACAACAGGCUU<br>CUUGAGAUUACACGCGAGUUCAGUGUCAAUGCCGGCGUU<br>ACAACACCCGUGUCUACCUACAUGCUGACGAAUUCUGAG<br>CUUCUCUCUCUCAUAAACGACAUGCCCAUUACGAAUGAC<br>CAAAAGAAACUUAUGUCCAACAACGUGCAGAUUGUGCGA<br>CAGCAAUCCUAUAGCAUUAUGUGUAUCAUCAAGGAAGAG<br>GUACUCGCUUAUGUUGUGCAGCUACCACUCUAUGGUGUG<br>AUUGACACCCCCUGUUGGAAGCUGCAUACCAGUCCACUC<br>UGCACCACUAACACAAAGGAAGGGAGCAAUAUUUGCCUC<br>ACUCGAACCGACAGGGGGUGGUAUUGCGAUAAUGCGGGC<br>UCCGUGUCCUUCUUUCCACAGGCUGAAACUUGUAAGGUA<br>CAGUCAAACCGCGUGUUCUGUGAUACUAUGAAUUCUCUG<br>ACUCUUCCCAGCGAGGUUAAUCUCUGCAACGUCGACAUU<br>UUCAAUCCUAAAUAUGACUGCAAGAUCAUGACCAGCAAG<br>ACCGACGUCUCCAGCUCAGUAAUCACUAGCCUAGGGGCC<br>AUUGUAAGCUGCUAUGGCAAAACCAAGUGUACUGCCUCU<br>AAUAAGAACAGAGGCAUAAUUAAAACCUUUUCAAAUGGC<br>UGUGACUAUGUGUCGAAUAAGGGCGUCGACACGGUCUCA<br>GUAGGGAAUACCCUCUACUACGUUAACAAACAGGAAGGC<br>AAAUCCCUUUAUGUAAAGGGCGAGCCCAUCAUAAAUUUC<br>UACGACCCACUUGUGUUCCCCAGUUGCGAAUUCUGCGCA<br>UCAAUCUCCCAGGUGAACGAAAAGAUCAAUCAAUCCCUU | 75 |

TABLE 7-continued

| | | |
|---|---|---|
| | GCUUUUAUACGAAAGUCAGAUGAACUCCUGCAUAACGUG<br>AAUGCUGGGAAAUCUACAACCAACAUCAUGAUCACUACC<br>AUCAUUAUUGUGAUUAUCGUAAUUCUGCUAUCCUUGAUU<br>GCUGUCGGGCUGCUUCUGUACUGUAAGGCCAGAUCGACG<br>CCUGUGACCCUUUCAAAAGACCAACUUAGCGGUAUCAAU<br>AAUAUUGCCUUUAGCAAU | |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGGC | 1 |
| Corresponding amino acid sequence | MELLILKANAITTILTAVTECFASGQNITEEFYQSTCSAVSKGY<br>LSALRTGWYTSVITIELSNIKENKCNGTDAKVKLIKQELDKYK<br>NAVTELQLLMGGGSGGGSGGGSGSAIASGVAVCKVLHLEGE<br>VNKIKSALLSTNKAVVSLSNGVSVLTFKVLDLKNYIDKQLLPI<br>LNKQSCSISNIETVIEFQQKNNRLLEITREFSVNAGVTTPVSTY<br>MLINSELLSLINDMPITNDQKKLMSNNVQIVRQQSYSIMCHIKE<br>EVLAYVVQLPLYGVIDTPCWKLHTSPLCTTNTKEGSNICLTRT<br>DRGWYCDNAGSVSFFPQAETCKVQSNRVFCDTMNSLTLPSEV<br>NLCNVDIFNPKYDCKIMTSKTDVSSSVITSLGAIVSCYGKTKCT<br>ASNKNRGIIKTESNGCDYVSNKGVDTVSVGNTLYYVNKQEGK<br>SLYVKGEPIINFYDPLVFPSCEFCASISQVNEKINQSLAFIRKSD<br>ELLHNVNAGKSTTNIMITTIIIVIIVILLSLIAVGLLLYCKARSTP<br>VTLSKDQLSGINNIAFSN | 76 |
| PolyA tail | 100 nt | |

MRK-04 membrane-bound DS-CAV1 (stabilized prefusion F protein)

| | | |
|---|---|---|
| SEQ ID NO: 90 consists of from 5' end to 3' end: 5' UTR SEQ ID NO: 2, mRNA ORF SEQ ID NO: 88, and 3' UTR SEQ ID NO: 4. | | 90 |
| Chemistry | 1-methylpseudouridine | |
| Cap | 7mG(5')ppp(5')NimpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAAAACGCUGUGACC<br>GAGCUGCAGUUAUUGAUGCAGAGUACACCUGCCACCAAU<br>AACAGAGCUAGGAGGGAGUUGCCUAGGUUUAUGAACUAC<br>ACUCUCAACAACGCGAAAAAAACCAAUGUGACGCUAUCC<br>AAGAAACGGAAGAGGAGGUUCCUGGGGUUUCUUUUAGGG<br>GUGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>AACGGAGUAAGUGUGUUAACAUUUAAGGUGCUGGACCUC<br>AAGAAUUAUAUUGACAAACAGUUGCUUCCUAUUCUAAAC<br>AAACAGAGCUGUUCAAUAAGUAAUAUUGAAACUGUUAUU<br>GAGUUUCAGCAGAAGAACAACAGGCUUCUUGAGAUUACA<br>CGCGAGUUCAGUGUCAAUGCCGGCGUUACAACACCCGUG<br>UCUACCUACAUGCUGACGAAUUCUGAGCUUCUCUCUCUC<br>AUAAACGACAUGCCCAUUACGAAUGACCAAAAAAAACUU<br>AUGUCCAACAACGUGCAGAUUGUGCGACAGCAAUCCUAU<br>AGCAUUAUGUGUAUCAUCAAGGAAGAGGUACUCGCUUAU<br>GUUGUGCAGCUACCACUCUAUGGUGUGAUUGACACCCCC<br>UGUUGGAAGCUGCAUACCAGUCCACUCUGCACCACUAAC<br>ACAAAGGAAGGGAGCAAUAUUUGCCUCACUCGAACCGAC<br>AGGGGGUGGUAUUGCGAUAAUGCGGGCUCCGUGUCCUUC<br>UUUCCACAGGCUGAAACUUGUAAGGUACAGUCAAACCGC<br>GUGUUCUGUGAUACUAUGAAUUCUCUGACUCUUCCCAGC<br>GAGGUUAAUCUCUGCAACGUCGACAUUUUCAAUCCUAAA<br>UAUGACUGCAAGAUCAUGACCAGCAAGACCGACGUCUCC<br>AGCUCAGUAAUCACUAGCCUAGGGGCCAUUGUAAGCUGC<br>UAUGGCAAAACCAAGUGUACUCCCUCUAAUAAGAACAGA<br>GGCAUAAUUAAAACCUUUUCAAAUGGCUGUGACUAUGUG<br>UCGAAUAAGGGCGUCGACACGGUCUCAGUAGGGAAUACC<br>CUCUACUACGUUAACAAACAGGAAGGCAAAUCCCUUUAU<br>GUAAAGGGCGAGCCCAUCAUAAAUUUCUACGACCCACUU<br>GUGUUCCCCAGUGAUGAAUUCGAUGCAUCAAUCUCCCAG<br>GUGAACGAAAAGAUCAAUCAAUCCCUUGCUUUUAUACGA<br>AAGUCAGAUGAACUCCUGCAUAACGUGAAUGCUGGGAAA<br>UCUACAACCAACAUCAUGAUCACUACCAUCAUUAUUGUG<br>AUUAUCGUAAUUCUGCUAUCCUUGAUUGCUGUCCGGCUG<br>CUUCUGUACUGUAAGGCCAGAUCGACGCCUGUGACCCUU<br>UCAAAAGACCAACUUAGCGGUAUCAAUAAUAUUGCCUUU<br>AGCAAU | 88 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGGC | 4 |

TABLE 7-continued

| | | |
|---|---|---|
| Corresponding amino acid sequence | MELLILKANAITTILTAVTICIASGQNITEEFYQSTCSAVSKGY<br>LSALRTGWYTSVITIELSNIKENKCNGTDAKVKLIKQELDKYK<br>NAVTELQLLMQSTPATNNRARRELPREMNYTLNNAKKTNVT<br>LSKKRKRRFLGFLLGVGSAIASGVAVCKVLHLEGEVNKIKSAL<br>LSTNKAVVSLSNGVSVLTFKVLDLKNYIDKQLLPILNKQSCSIS<br>NIETVIEFQQKNNRLLETTREFSVNAGVTTPVSTYMLINSELLS<br>LINDMPITNDQKKLMSNNVQIVRQQSYSIMCIKEEVLAYVVQ<br>LPLYGVIDTPCWKLHTSPLCTTNTKEGSNICLTRTDRGWYCD<br>NAGSVSFFPQAETCKVQSNRVFCDTMNSLTLPSEVNLCNVDIF<br>NPKYDCKIMTSKTDVSSSVITSLGAIVSCYGKTKCTASNKNRG<br>IIKTFSNGCDYVSNKGVDTVSVGNTLYYVNKQEGKSLYVKGE<br>PIINFYDPLVFPSDEFDASISQVNEKINQSLAFIRKSDELLHNVN<br>AGKSTTNIMITTHIVIIVILLSLIAVGLLLYCKARSTPVTLSKDQ<br>LSGINNIAFSN | 89 |
| PolyA tail | 100 nt | |

MRK_04_nopolyA_3mut

| | | |
|---|---|---|
| SEQ ID NO: 92 consists of from 5' end to 3' end: 5' UTR SEQ ID NO: 2, mRNA ORF SEQ ID NO: 91, and 3' UTR SEQ ID NO: 4. | | 92 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCCACGCUAAAGUCAAACUU<br>AUCAAGCAGGAACUCGACAAAUAUAAGAACGCUGUGACC<br>GAGCUGCAGUUAUUGAUGCAGAGUACACCUGCCACCAAU<br>AACAGAGCUAGGAGGGAGUUGCCUAGGUUUAUGAACUAC<br>ACUCUCAACAACGCGAAGAAAACCAAUGUGACGCUAUCC<br>AAGAAACGGAAGAGGAGGUUCCUGGGGUUUCUUUUAGGG<br>GUGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>AACGGAGUAAGUGUGUUAACAUUUAAGGUGCUGGACCUC<br>AAGAAUUAUAUUGACAAACAGUUGCUUCCUAUUCUAAAC<br>AAACAGAGCUGUUCAAUAAGUAAUAUUGAAACUGUUAUU<br>GAGUUUCAGCAGAAGAACAACAGGCUUCUUGAGAUUACA<br>CGCGAGUUCAGUGUCAAUGCCGGCGUUACAACACCCGUG<br>UCUACCUACAUGCUGACGAAUUCUGAGCUUCUCUCUCUC<br>AUAAACGACAUGCCCAUUACGAAUGACCAAAAGAAACUU<br>AUGUCCAACAACGUGCAGAUUGUGCGACAGCAAUCCUAU<br>AGCAUUAUGUGUAUCAUCAAGGAAGAGGUACUCGCUUAU<br>GUUGUGCAGCUACCACUCUAUGGUGUGAUUGACACCCCC<br>UGUUGGAAGCUGCAUACCAGUCCACUCUGCACCACUAAC<br>ACAAAGGAAGGGAGCAAUAUUUGCCUCACUCGAACCGAC<br>AGGGGGUGGUAUUGCGAUAAUGCGGGCUCCGUGUCCUUC<br>UUUCCACAGGCUGAAACUUGUAAGGUACAGUCAAACCGC<br>GUGUUCUGUGAUACUAUGAAUUCUCUGACUCUUCCCAGC<br>GAGGUUAAUCUCUGCAACGUCGACAUUUUCAAUCCUAAA<br>UAUGACUGCAAGAUCAUGACCAGCAAGACCGACGUCUCC<br>AGCUCAGUAAUCACUAGCCUAGGGGCCAUUGUAAGCUGC<br>UAUGGCAAAACCAAGUGUACUCCCUCUAAUAAGAACAGA<br>GGCAUAAUUAAAACCUUUUCAAAUGGCUGUGACUAUGUG<br>UCGAAUAAGGGCGUCGACACGGUCUCAGUAGGGAAUACC<br>CUCUACUACGUUAACAAACAGGAAGGCAAAUCCCUUUAU<br>GUAAAGGGCGAGCCCAUCAUAAAUUUCUACGACCCACUU<br>GUGUUCCCCAGUGAUGAAUUCGAUGCAUCAAUCUCCCAG<br>GUGAACGAAAAGAUCAAUCAAUCCCUUGCUUUUAUACGA<br>AAGUCAGAUGAACUCCUGCAUAACGUGAAUGCUGGGAAA<br>UCUACAACCAACAUCAUGAUCACUACCAUCAUUAUUGUG<br>AUUAUCGUAAUUCUGCUAUCCUUGAUUGCUGUCGGGCUG<br>CUUCUGUACUGUAAGGCCAGAUCGACGCCUGUGACCCUU<br>UCAAAAGACCAACUUAGCGGUAUCAAUAAUAUUGCCUUU<br>AGCAAU | 91 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGGC | 4 |
| Corresponding amino acid sequence | MELLILKANAITTILTAVTECFASGQNITEEFYQSTCSAVSKGY<br>LSALRTGWYTSVITIELSNIKENKCNGTDAKVKLIKQELDKYK<br>NAVTELQLLMQSTPATNNRARRELPRFMNYTLNNAKKTNVT<br>LSKKRKRRFLGFLLGVGSAIASGVAVCKVLHLEGEVNKIKSAL<br>LSTNKAVVSLSNGVSVLTFKVLDLKNYIDKQLLPILNKQSCSIS<br>NIETVIEFQQKNNRLLEITREFSVNAGVTTPVSTYMLINSELLS<br>LINDMPITNDQKKLMSNNVQIVRQQSYSIMCIIKEEVLAYVVQ<br>LPLYGVIDTPCWKLHTSPLCTTNTKEGSNICLTRTDRGWYCD | 89 |

TABLE 7-continued

| | | |
|---|---|---|
| | NAGSVSFFPQAETCKVQSNRVFCDTMNSLTLPSEVNLCNVDIF<br>NPKYDCKIMTSKTDVSSSVITSLGAIVSCYGKTKCTASNKNRG<br>IIKTFSNGCDYVSNKGVDTVSVGNTLYYVNKQEGKSLYVKGE<br>PIINFYDPLVFPSDEFDASISQVNEKINQSLAFIRKSDELLHNVN<br>AGKSTTNIMITTIVIIVILLSLIAVGLLLYCKARSTPVTLSKDQ<br>LSGINNIAFSN | |
| | VRC-4A | |
| SEQ ID NO: 98 consists of from 5' end to 3' end: 5' UTR SEQ ID NO: 2, mRNA ORF SEQ ID NO: 96, and 3' UTR SEQ ID NO: 4. | | 98 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGGGCGCGCUCCGCACAGGAUGG<br>UACACCUCCGUGAUCACCAUCGAGCUCAGCAAUAUUAAA<br>GAGAUCAAGUGCAAUGGUACCGACGCUAAAGUCAAACUU<br>AUCAAGCAGGAACUCGACAAAUAUAAGAACGCUGUGACC<br>GACCUGCAGUUAUUGAUGCAGAGUACACCUGCCACCGGG<br>UCGGGCUCUGCCAUUUGCUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>AACGGAGUAAGUGUGUUAACAUUUAAGGUGCUGGACCUC<br>AAGAAUUAUAUUGACAAACAGUUGCUUCCUAUUCUAAAC<br>AAACAGAGCUGUUCAAUACCCAAUAUUGAAACUGUUAUU<br>GAGUUUCAGCAGAAGAACAACAGGCUUCUUGAGAUUACA<br>CGCGAGUUCAGUGUCAAUGCCGGCGUUACAACACCCGUG<br>UCUACCUACAUGCUGACGAAUUCUGAGCUUCUCUCUCUC<br>AUAAACGACAUGCCCAUUACGAAUGACCAAAAGAAACUU<br>AUGUCCAACAACGUGCAGAUUGUGCGACAGCAAUCCUAU<br>AGCAUUAUGUGUAUCAUCAAGGAAGAGGUACUCGCUUAU<br>GUUGUGCAGCUACCACUCUAUGGUGUGAUUGACACCCCC<br>UGUUGGAAGCUGCAUACCAGUCCACUCUGCACCACUAAC<br>ACAAAGGAAGGGAGCAAUAUUUGCCUCACUCGAACCGAC<br>AGGGGGUGGUAUUGCGAUAAUGCGGGCUCCGUGUCCUUC<br>UUUCCACAGGCUGAAACUUGUAAGGUACAGUCAAACCGC<br>GUGUUCUGUGAUACUAUGAAUUCUCGUACUCUUCCCAGC<br>GAGGUUAAUCUCUGCAACGUCGACAUUUUCAAUCCUAAA<br>UAUGACUGCAAGAUCAUGACCAGCAAGACCGACGUCUCC<br>AGCUCAGUAAUCACUAGCCUAGGGGCCAUUGUAAGCUGC<br>UAUGGCAAAACCAAGUGUACUCCCUCUAAUAAGAACAGA<br>GGCAUAAUUAAAACCUUUUCAAAUGGCUGUGACUAUGUG<br>UCGAAUAAGGGCGUCGACACGGUCUCAGUAGGGAAUACC<br>CUCUACUGCGUUAACAAACAGGAAGGCCAGUCCCUUUAU<br>GUAAAGGGCGAGCCCAUCAUAAAUUUCUACGACCCACUU<br>GUGUUCCCCAGUGAUGAAUUCGAUGCAUCAAUCUCCCAG<br>GUGAACGAAAAGAUCAAUCAAUCCCUUGCUUUUAUACGA<br>AAGUCAGAUGAACUCCUGUCCGCCAUCGGUGGCUAUAUC<br>CCAGAAGCCCCAAGAGACGGACAAGCGUACGUCCGGAAA<br>GAUGGUGAGUGGGUCCUCCUCUCUACCUUUCUU | 96 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGGC | 4 |
| Corresponding amino acid sequence | MELLILKANAITTILTAVTECFASGQNITEEFYQSTCSAVSKGY<br>LGALRTGWYTSVITIELSNIKEIKCNGTDAKVKLIKQELDKYK<br>NAVTDLQLLMQSTPATGSGSAICSGVAVCKVLHLEGEVNKIK<br>SALLSTNKAVVSLSNGVSVLTFKVLDLKNYIDKQLLPILNKQS<br>CSIPNIETVIEFQQKNNRLLEITREFSVNAGVTTPVSTYMLINSE<br>LLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>NRGIIKTFSNGCDYVSNKGVDTVSVGNTLYCVNKQEGQSLYV<br>KGEPIINFYDPLVFPSDEFDASISQVNEKINQSLAFIRKSDELLS<br>AIGGYIPEAPRDGQAYVRKDGEWVLLSTFL | 44 |
| PolyA tail | 100 nt | |

TABLE 7-continued

| VRC-5A | | |
|---|---|---|
| SEQ ID NO: 99 consists of from 5' end to 3' end: 5' UTR SEQ ID NO: 2, mRNA ORF SEQ ID NO: 97, and 3' UTR SEQ ID NO: 4. | | 99 |
| Chemistry | 1-methylpseudouridine | |
| Cap | 7mG(5')ppp(5*)NImpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGGGCGCGCUCCGCACAGGAUGG<br>UACACCUCCGUGAUCACCAUCGAGCUCAGCAAUAUUAAA<br>GAGAUCAAGUGCAAUGGUACCGACGCUAAAGUCAAACUU<br>AUCAAGCAGGAACUCGACAAAUAUAAGAACGCUGUGACC<br>GACCUGCAGUUAUUGAUGCAGAGUACACCUGCCACCGGG<br>UCGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>GGCUGCGGAGUAAGUGUGUUAACAUUUAAGGUGCUGGAC<br>CUCAAGAAUUAUAUUGACAAACAGUUGCUUCCUAUUCUA<br>AACAAACAGAGCUGUUCAAUACCCAAUAUUGAAACUGUU<br>AUUGAGUUUCAGCAGAAGAACAACAGGCUUCUUGAGAUU<br>ACACGCGAGUUCAGUGUCAAUGCCGGCGUUACAACACCC<br>GUGUCUACCUACAUGCUGACGAAUUCUGAGCUUCUCUCU<br>CUCAUAAACGACAUGCCCAUUACGAAUGACCAAAAGAAA<br>CUUAUGUCCAACAACGUGCAGAUUGUGCGACAGCAAUCC<br>UAUAGCAUUAUGUGUAUCAUCAAGGAAGAGGUACUCGCU<br>UAUGUUGUGCAGCUACCACUCUAUGGUGUGAUUGACACC<br>CCCUGUUGGAAGCUGCAUACCAGUCCACUCUGCACCACUA<br>ACACAAAGGAAGGGAGCAAUAUUUGCCUCACUCGAACCG<br>ACAGGGGGUGGUAUUGCGAUAAUGCGGGCUCCGUGUCCU<br>UCUUUCCACAGGCUGAAACUUGUAAGGUACAGUCAAACC<br>GCGUGUUCUGUGAUACUAUGAAUUCUCGUACUCUUCCCA<br>GCGAGGUUAAUCUCUGCAACGUCGACAUUUUCAAUCCUA<br>AAUAUGACUGCAAGAUCAUGACCAGCAAGACCGACGUCU<br>CCAGCUCAGUAAUCACUAGCCUAGGGGCCAUUGUAAGCU<br>GCUAUGGCAAAACCAAGUGUACUGCCUCUAAUAAGUGCA<br>GAGGCAUAAUUAAAACCUUUUCAAAUGGCUGUGACUAUG<br>UGUCGAAUAAGGGCGUCGACACGGUCUCAGUAGGGAAUA<br>CCCUCUACUACGUUAACAAACAGGAAGGCCAGUCCCUUU<br>AUGUAAAGGGCGAGCCCAUCAUAAAUUUCUACGACCCAC<br>UUGUGUUCCCCAGUGAUGAAUUCGAUGCAUCAAUCUCCC<br>AGGUGAACGAAAAGAUCAAUCAAUCCCUUGCUUUUAUAC<br>GAAAGUCAGAUGAACUCCUGUCCGCCAUCGGUGGCUAUA<br>UCCCAGAAGCCCCAAGAGACGGACAAGCGUACGUCCGGA<br>AAGAUGGUGAGUGGGUCCUCCUCUCUACCUUUCUU | 97 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGGG<br>C | 4 |
| Corresponding amino acid sequence | MELLILKANAITTILTAVTECEASGQNITEEFYQSTCSAVSKGY<br>LGALRTGWYTSVITIELSNIKEIKCNGTDAKVKLIKQELDKYK<br>NAVTDLQLLMQSTPATGSGSAIASGVAVCKVLHLEGEVNKIK<br>SALLSTNKAVVSLSGCGVSVLTFKVLDLKNYIDKQLLPILNKQ<br>SCSIPNIETVIEFQQKNNRLLEITREFSVNAGVTTPVSTYMLTNS<br>ELLSLINDMPITNDQKKLMSNNVQIVRQQSYSIMCIIKEEVLAY<br>VVQLPLYGVIDTPCWKLHTSPLCTINTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>CRGIIKTFSNGCDYVSNKGVDTVSVGNTLYYVNKQEGQSLYV<br>KGEPINFYDPLVFPSDEFDASISQVNEKINQSLAFIRKSDELLS<br>AIGGYIPEAPRDGQAYVRKDGEWVLLSTFL | 47 |
| PolyA tail | 100 nt | |

*The underlined sequences above are signal sequences. It should be understood that any one of the open reading frames and/or corresponding amino acid sequences described in Table 7 may include or exclude the underlined signal sequence. It should also be understood that the underlined sequence may be replaced by a different signal sequence, for example, any one of SEQ ID NOs: 79-84.

EQUIVALENTS

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as “comprising.” “including,” “carrying,” “having,” “containing,” “involving,” “holding,” “composed of,” and the like are to be understood to be open-ended, i.e., to mean including but not limited to. Only the transitional phrases “consisting of” and “consisting essentially of” shall be closed or semi-closed transitional phrases, respectively, as set forth in the United States Patent Office Manual of Patent Examining Procedures, Section 2111.03.

The terms “about” and “substantially” preceding a numerical value mean±10% of the recited numerical value.

Where a range of values is provided, each value between the upper and lower ends of the range are specifically contemplated and described herein.

The entire contents of International Application Nos. PCT/US2015/02740, PCT/US2016/043348, PCT/US2016/043332, PCT/US2016/058327, PCT/US2016/058324, PCT/US2016/058314, PCT/US2016/058310. PCT/US2016/058321, PCT/US2016/058297, PCT/US2016/058319, and PCT/US2016/058314 are incorporated herein by reference.

What is claimed is:

1. A messenger ribonucleic acid (mRNA) comprising an open reading frame (ORF) encoding a prefusion respiratory syncytial virus (RSV) F protein, wherein the ORF encodes an amino acid sequence having at least 95% identity to the amino acid sequence of SEQ ID NO: 5, wherein identity defines the percentage of amino acid residues in the RSV F protein that are identical to residues of SEQ ID NO: 5 after introducing any necessary gaps to align the two full-length sequences.

2. The mRNA of claim 1, wherein the mRNA is chemically modified.

3. The mRNA of claim 2, wherein the ORF comprises 1-methyl-pseudouridine, adenosine, guanosine, and cytosine.

4. A vaccine comprising the mRNA of claim 3 formulated in a lipid nanoparticle.

5. The vaccine of claim 4, wherein the lipid nanoparticle comprises 20-60 mol % ionizable cationic lipid, 5-25 mol % neutral lipid, 25-55 mol % sterol, and 0.5-15 mol % polyethylene glycol (PEG)-modified lipid.

6. The vaccine of claim 5, wherein the ionizable cationic lipid is a compound of Formula (I):

(Formula (I))

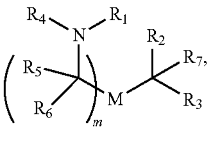

$R_1$ is selected from the group consisting of $C_{5-30}$ alkyl, $C_{5-20}$ alkenyl, and —R"M'R';

$R_2$ and $R_3$ are independently selected from the group consisting of $C_{1-14}$ alkyl and $C_{2-14}$ alkenyl;

$R_4$ is-$(CH_2)_n$Q, wherein Q is —OR, and n is selected from 1, 2, 3, 4, and 5;

each $R_5$ is H;

each $R_6$ is H;

M and M' are independently selected from —C(O)O— and —OC(O)—;

$R_7$ is H;

R is H;

R' is selected from the group consisting of $C_{1-18}$ alkyl and $C_{2-18}$ alkenyl;

R" is selected from the group consisting of $C_{3-14}$ alkyl and $C_{3-14}$ alkenyl; and m is selected from 5, 6, 7, 8, 9, 10, 11, 12, and 13.

7. The vaccine of claim 6, wherein:

$R_1$ is R"M'R';

$R_2$ and $R_3$ are each independently $C_{1-14}$ alkyl;

$R_4$ is $(CH_2)$,Q, wherein Q is OH and n is 4;

M and M' are each independently —OC(O)—;

$R_5$, $R_6$, and $R_7$ are each H;

R' is $C_{1-12}$ alkyl substituted with $C_{6-9}$ alkyl;

R" is $C_{3-14}$ alkyl; and m is 6.

8. The vaccine of claim 6, wherein:

$R_1$ is $C_{5-20}$ alkenyl;

$R_2$ and $R_3$ are each independently $C_{1-14}$ alkyl;

$R_4$ is $(CH_2)_n$Q, wherein Q is OH and n is 3;

M is-C(O)O—;

$R_5$, $R_6$, and $R_7$ are each H; and m is 6.

9. The vaccine of claim 6, wherein the compound of Formula (I) comprises a compound of Formula (IId), (IId)

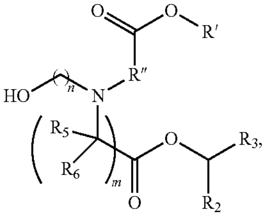

or a salt thereof, wherein n is 2, 3, or 4.

10. The vaccine of claim 6, wherein the compound of Formula (I) is Compound 1:

(Compound 1)

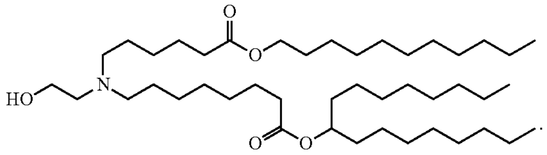

11. The vaccine of claim 6, wherein the neutral lipid is 1,2 distearoyl-sn-glycero-3-phosphocholine (DSPC) and the PEG-modified lipid is 1,2 dimyristoyl-sn-glycerol, methoxypolyethyleneglycol (PEG2000 DMG).

12. A method comprising administering to a subject the vaccine of claim 11 in a therapeutically effective amount to induce in the subject an RSV F protein neutralizing antibody titer.

13. A method comprising administering to a subject the vaccine of claim 4 in a therapeutically effective amount to induce in the subject an RSV F protein neutralizing antibody titer.

14. The method of claim 13, wherein the mRNA is administered intramuscularly.

* * * * *